United States Patent
Chasset et al.

(10) Patent No.: US 9,604,900 B2
(45) Date of Patent: Mar. 28, 2017

(54) INHIBITORS OF VIRAL REPLICATION, THEIR PROCESS OF PREPARATION AND THEIR THERAPEUTICAL USES

(75) Inventors: Sophie Chasset, Nandy (FR); Francis Chevreuil, Chantilly (FR); Benoit Ledoussal, Pommerit Jaudy (FR); Frédéric Le Strat, Gagny (FR); Richard Benarous, Paris (FR)

(73) Assignee: LABORATOIRE BIODIM, Paris (FR)

( * ) Notice: Subject to any disclaimer, the term of this patent is extended or adjusted under 35 U.S.C. 154(b) by 0 days.

(21) Appl. No.: 14/111,157

(22) PCT Filed: Apr. 13, 2012

(86) PCT No.: PCT/EP2012/056851
§ 371 (c)(1),
(2), (4) Date: Oct. 10, 2013

(87) PCT Pub. No.: WO2012/140243
PCT Pub. Date: Oct. 18, 2012

(65) Prior Publication Data
US 2014/0031338 A1 Jan. 30, 2014

Related U.S. Application Data

(60) Provisional application No. 61/476,051, filed on Apr. 15, 2011.

(30) Foreign Application Priority Data

Apr. 15, 2011 (EP) .................... 11305458

(51) Int. Cl.
| | | |
|---|---|---|
| A01N 43/16 | (2006.01) |
| A61K 31/35 | (2006.01) |
| C07D 311/00 | (2006.01) |
| C07C 57/38 | (2006.01) |
| C07C 59/66 | (2006.01) |
| C07D 215/14 | (2006.01) |
| C07D 311/58 | (2006.01) |
| C07D 405/04 | (2006.01) |
| C07D 407/04 | (2006.01) |
| A61K 31/192 | (2006.01) |
| A61K 31/352 | (2006.01) |
| A61K 31/473 | (2006.01) |
| C07C 215/14 | (2006.01) |
| A61K 31/353 | (2006.01) |
| A61K 31/357 | (2006.01) |
| A61K 31/47 | (2006.01) |
| A61K 31/4709 | (2006.01) |
| A61K 31/553 | (2006.01) |
| A61K 45/06 | (2006.01) |

(Continued)

(52) U.S. Cl.
CPC ............ *C07C 57/38* (2013.01); *A61K 31/192* (2013.01); *A61K 31/352* (2013.01); *A61K 31/353* (2013.01); *A61K 31/357* (2013.01); *A61K 31/47* (2013.01); *A61K 31/473* (2013.01); *A61K 31/4709* (2013.01); *A61K 31/553* (2013.01); *A61K 45/06* (2013.01); *C07C 59/66* (2013.01); *C07C 215/14* (2013.01); *C07D 215/14* (2013.01); *C07D 215/54* (2013.01); *C07D 311/58* (2013.01); *C07D 311/74* (2013.01); *C07D 405/04* (2013.01); *C07D 407/04* (2013.01); *C07D 413/04* (2013.01)

(58) Field of Classification Search
None
See application file for complete search history.

(56) References Cited

U.S. PATENT DOCUMENTS

| 2,842,559 A | 7/1958 | William et al. |
| 4,736,057 A | 4/1988 | Guildford et al. |

(Continued)

FOREIGN PATENT DOCUMENTS

| GB | 942 663 | 11/1963 |
| WO | WO 2007/106469 A2 | 9/2007 |

(Continued)

OTHER PUBLICATIONS

International Search Report; issued Aug. 22, 2012, in International Application No. PCT/EP2012/056851.
Adachi et al., "Production of Acquired Immunodeficiency Syndrome-Associated Retrovirus in Human and Nonhuman Cells Transfected with an Infectious Molecular Clone",*J. Virol.*, 59: 284-91 (1986).
Bradsher et al., "Aromatic Cyclodehydration, XXVIII.[1] 9, 10-2Dialkylphenanthrenes by Cyclization of Ketones", *J. Am. Chem. Soc.*, 76: 4140-4143 (1954).

(Continued)

*Primary Examiner* — Jeffrey H Murray
(74) *Attorney, Agent, or Firm* — Hunton & Williams LLP

(57) ABSTRACT

The present invention relates to aromatic carbocycle or heterocycle compounds comprising an acid function and being of formula (5),

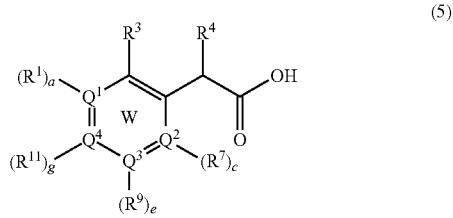

wherein W, $Q^1$, $Q^2$, $Q^3$, $Q^4$, $R^1$, $R^3$, $R^4$, $R^7$, $R^9$, $R^{11}$, a, c, e, and g are as described in the description; and the use of such compounds in the treatment or the prevention of viral disorders, including HIV.

10 Claims, No Drawings

(51) Int. Cl.
    C07D 215/54    (2006.01)
    C07D 311/74    (2006.01)
    C07D 413/04    (2006.01)

(56)         References Cited

U.S. PATENT DOCUMENTS 4,872,918  A    10/1989  Podraza et al.
    6,339,097  B1    1/2002  Festal et al.
    9,199,959  B2   12/2015  Iwaki et al.
2011/0224304  A1    9/2011  Iwama et al.
2012/0142771  A1    6/2012  Iwama et al.

FOREIGN PATENT DOCUMENTS

WO    WO 2007/131350 A1    11/2007
WO     WO2007/140940  *    12/2007  ............... C08G 8/04
WO    WO 2008/128344 A1    10/2008
WO    WO 2009/062285 A1     5/2009
WO    WO 2009/062288 A1     5/2009
WO    WO 2009/062289 A1     5/2009
WO    WO 2009/062308 A1     5/2009
WO    WO 2010/007120 A1     1/2010
WO    WO 2010/055911 A1     5/2010
WO    WO 2010/130034 A1    11/2010
WO    WO 2010/130842 A1    11/2010
WO    WO 2011/015641 A1     2/2011
WO    WO 2012/003497 A1     1/2012
WO    WO 2012/003498 A1     1/2012

OTHER PUBLICATIONS

Buchta, V. and H. Maar, "Uber Tri-Tetra- Und Pentacyclische Verbindungen, Die In Beziehung Zum Steranthren Stehen", *Liebigs Annalen der Chemie*, 674: 129-152 (1964).
Butera et al., "Computer-assisted Design and Synthesis of Novel Aldose Reductase Inhibitors", *Journal of Medicinal Chemistry*, 32:757-765 (1989).
Cervia et al, "Enfuvirtide (T-20): A Novel Human Immunodeficiency Virus Type 1 Fusion Inhibitor", *Clin. Infect. Dis.*, 37: 1102-06 (2003).
Christ et al., "Rational design of small-molecule inhibitors of the LEDGF/p75-integrase interaction and HIV replication" *Nat. Chem. Biol.*, 6:442-448 (2010).
Daar Es, "Emerging Resistance Profiles of Newly Approved Antiretroviral Drugs", *Topics HIV Med.*, 16: 110-6 (2008).
De Clercq, E., "Emerging Antiviral Drugs", *Expert Opin. Emerg. Drugs*, 13:393-416 (2008).
Dostert et al., "Synthese d'analogues partiellement saturés des neuroleptiques tricycliques clothiapine et octoclothépine", *Helvetica Chimica Acta*, 53: 1813- 1827 (1970).
Gutsche, D., "The Stereochemistry of the 2-Phenylcyclohexanecarboxylic Acids and the β-(2-Phenylcyclohexane)-propionic Acids", *Journal of the Chemical Society*, 70:4150-4154 (1948).
Hughes et al., "New treatment options for HIV salvage patients: An overview of second generation PIs, NNRTIs, integrase inhibitors and CCR5 antagonists", *J. Infect.*, 57:1-10 (2008).
Iida et al., "Stereochemical Studies of Alkyl Methylcyclohexaneacetatesz with 13C NMR Spectroscopy in Relation to Their Attractiveness to the German Cockroach", *Agric. Biol. Chem.*, 45:1553-159 (1981).
Jones et al., "Preclinical Evaluation of GS-9160, a Novel Inhibitor of Human Immunodeficiency Virus Type 1 Integrase", *Antimicrobials Agents and Chemiotherapy*, 53:1194-1203 (2009).
Lopez-Verges et al., "Tail-interacting protein TIP47 is a connector between Gag and Env and is required for Env incorporation into HIV-1 virions", *Proc. Natl. Acad. Sci. USA*, 103:14947-52 (2006).
Medarde et al., "Synthesis and evaluation of cardiotonic activity of simple butenolides II*", *Eur. J. Med. Chem.*, 28: 887-892 (1993).

Newman, M., "The Synthesis of 5-Methylchrysene and Related Compounds", *Journal of the Chemical Society*, 62: 870-874 (1940).
Nicolaou et al., "Total Synthesis of Sporolide B and 9-epi-Sporolide B", *J. Am. Chem. Soc.*, 132: 11350-11363 (2010).
Parmar et al., "Synthesis, antimicrobial and antiviral activities of novel polypheolic compounds", *Indian Journal of Chemistry*, vol. 35B: 220-232 (1996).
Ryabukhin et al., "Chlorotirmehtylsilane-Mediated Friedlander Synthesis of Polysubstituted Quinolines", *Synthesis*, 8:1214-1224 (2007).
Sayer et al., "Conformational Effects in the Hydrolyses of Rigid Benzylic Expoxides: Implications for Diol Epoxides of Polycyclic Hydrocarbons",*J Am. Chem. Soc.*, 104: 1972-1978 (1982).
Suginome et al., "Protoinduced Transforamtions. Part 28. Photoreactions of 17-Ehtoxycarbonylmethylene-etiojerva-5,13(17)- and -5, 16-diene-3β, 11β, 20E- triol 3,20-Diacetate 11-Nitrites", *Journal of the Chemical Society, Perkin Trans.* 1, 612-618 (1978).
Touzin et al., "Reaction D'Hydroxyalkylation Dee Enolates D'Ester α-Heterosubstitues Synthese D'Ethers D'enol D'α Cetoesters et de β-Cetoesteres Alkoxyles", *Tetrahedon Letters*, 18:1477-1480 (1975).
Turner, "Cyclized Products from the Stobbe Condensation with δ-Keto-esters",*Journal of the Chemical Society*, 73: 1284-1287 (1951).
Turner et al., "The Structure and Total Synthesis of Cassaic Acid", *Journal of the American Chemcial Society*, 88:1766-1775 (1966).
Wang et al., "Versatile Pd(II)-Catalyzed C-H Activation/Aryl-Aryl Coupling of Benzoic and Phenyl Acetic Acids",*J. Am. Chem. Soc.*, 130:17676-17677 (2008).
Database Medline [Online] US National Library of Medicine (NLM), Bethesda, MD, US; Jul. 1998 (Jul. 1998), Gordon Y J et al: "The effects of topical nonsteroidal anti-inflammatory drugs on adenoviral replication.", XP002663374, Database accession No. NLM9682703 & Gordon Y J et al: "The effects of topical nonsteroidal anti-inflammatory drugs on adenoviral replication.", Archives of Ophthalmology Jul. 1998 LNKD-PUBMED:9682703, vol. 116, No. 7, Jul. 1998 (Jul. 1998), pp. 900-905, ISSN: 0003-9950.
Database WPI Week 200602 Thomson Scientific, London, GB; AN 2006-013202 XP002663375, & IN DEL 200500540 A1 (Singh G) Aug. 26, 2005 (Aug. 26, 2005).
Database CA [Online] Chemical Abstracts Service, Columbus, Ohio, US; 1966, Lutsenko, V. V.: "Some .alpha.-methozyacetic acids of cyclohexane and 3-cyclohexane series", XP002663376, retrieved from STN Database accession No. 1967:411258 & Lutsenko, V. V.: "Some .alpha.-methozyacetic acids of cyclohexane and 3-cyclohexane series", Lietuvos TSR Mokslu Akademijos Darbai, Serija B: Chemija, Technika, Fizine Geografija , (3), 69-76 Coden: LMDBAL; ISSN: 0132-2729, 1966.
Database CA [Online] Chemical Abstracts Service, Columbus, Ohio, US; 1973, Berlin, Yu. A. et al: "Olivomycin and related antibiotics. XXVI. Absolute configuration of olivin and chromomycinone", XP002663377, retrieved from STN Database accession No. 1973:4473 & Berlin, Yu. A. et al: "Olivomycin and related antibiotics. XXVI. Absolute configuration of olivin and chromomycinone", Khimiya Prirodnykh Soedinenii , 8(4), 526-34 Coden: KPSUAR; ISSN: 0023-1150, 1972.
Database CA [Online] Chemical Abstracts Service, Columbus, Ohio, US; 1974, Berlin, Yu. A. et al: "Olivomycin and related antibiotics. XXXI. Stereochemistry of chromocycline", XP002663378, retrieved from STN Database accession No. 1974:3304 & Berlin, Yu. A. et al: "Olivomycin and related antibiotics. XXXI. Stereochemistry of chromocycline", Khimiya Prirodnykh Soedinenii , 9(4), 532-9 Coden: KPSUAR; ISSN: 0023-1150, 1973.
Database Medline [Online] US National Library of Medicine (NLM), Bethesda, MD, US; 2002, Zhang Guo-Gang et al: "A new compound from Forsythia suspensa (Thunb.) Vahl with antiviral effect on RSV.", XP002663386, Database accession No. NLM15277088 & Zhang Guo-Gang et al: "A new compound from Forsythia suspensa (Thunb.) Vahl with antiviral effect on RSV.",

(56) References Cited

OTHER PUBLICATIONS

Journal of Herbal Pharmacotherapy 2002 LNKD-PUBMED:15277088, vol. 2, No. 3, 2002, pp. 35-40, ISSN: 1522-8940.
Database CA [Online] Chemical Abstracts Service, Columbus, Ohio, US; 1995, Assy, M. G. et al: "The synthesis of pyridazine and fused pyridazine", XP002669328, retrieved from STN Database accession No. 1995:769330.
Database Registry [Online] Chemical Abstracts Service, Columbus, Ohio, US; Jan. 24, 2010 (Jan. 24, 2010), XP002669330, retrieved from STN.
Database Registry [Online] Chemical Abstracts Service, Columbus, Ohio, US; Jul. 29, 2009 (Jul. 29, 2009), XP002669331, retrieved from STN.
Database Registry [Online] Chemical Abstracts Service, Columbus, Ohio, US; Apr. 23, 2008 (Apr. 23, 2008), XP002669332, retrieved from STN.
Database Registry [Online] Chemical Abstracts Service, Columbus, Ohio, US; Feb. 3, 2011 (Feb. 3, 2011), XP002669333, retrieved from STN.
Database Registry [Online] Chemical Abstracts Service, Columbus, Ohio, US; Feb. 2, 2011 (Feb. 2, 2011), XP002669334, retrieved from STN.
Partial European Search Report; issued Dec. 2, 2011, in EP11305458.
Partial European Search Report; issued Feb. 29, 2012, in EP11305458.
European Search Opinion; issued Feb. 29, 2012, in EP11305458.

\* cited by examiner

INHIBITORS OF VIRAL REPLICATION, THEIR PROCESS OF PREPARATION AND THEIR THERAPEUTICAL USES

CROSS-REFERENCE TO RELATED APPLICATIONS

This application is the U.S. National Phase of International Application No. PCT/IB2012/056851, filed Apr. 13, 2012, which claims priority to European Application No. EP 11305458.9, filed Apr. 15, 2011, and U.S. provisional Application No. 61/476,051, filed Apr. 15, 2011. The contents of each are hereby incorporated by reference in their entireties.

BACKGROUND OF THE INVENTION

The present invention relates to compounds, their use in the treatment or the prevention of viral disorders, including HIV. The present invention also relates to methods for the preparation of such compounds. The present invention also relates to pharmaceutical compositions comprising such compounds. The present invention also relates to the treatment of viral infections by the administration of a therapeutically efficient amount of such compounds.

The Acquired Immuno Deficiency Syndrome (AIDS) is a disease due to infection by the Human Immunodeficiency Virus (HIV). HIV is a retrovirus, belonging to the subclass of primate lentiviruses. Two types of HIV have been identified, HIV-1 and HIV-2. HIV-1 is responsible for the larger part of the AIDS global epidemic in the world, with virtually every country reporting cases.

Currently HIV infected patients are treated with Highly Active Anti Retroviral Therapies (HAART) that rely on a combination of several drugs belonging to different classes. Up to 2003, all approved anti-HIV drugs were inhibitors of the catalytic activity of two viral enzymes, Reverse Transcriptase (RT) inhibitors and Protease (PR) inhibitors. Reverse Transcriptase inhibitors include two different classes, Nucleoside/Nucleotide RT Inhibitors (NRTI) and Non Nucleoside RT Inhibitors (NNRTI). In 2003 a new class of Anti-retroviral drug (ARV), Fusion inhibitor (Enfuvirtide) was introduced (Cervia et al, Clin Infect Dis., 2003, 37(8): 1102-6). And lately, in 2007, two other classes of ARV were approved, Entry inhibitors (Maraviroc (Pfizer)) targeting the CCR5 co-receptor, and Integrase inhibitors (Raltegravir (Merck)) (Hughes et al, J Infect., 2008, 57(1):1-10.). Although these three novel drugs were very useful to treat patients in therapeutic failure due to multiresistance to RT and PR inhibitors, resistance mutations against these drugs have already been reported.

Although the development of these potent anti-HIV drugs, has allowed HIV-infected people to live longer and to benefit of a higher quality of life, it is clear that these drugs do not cure the HIV infection. Moreover, their prolonged use often results in significant toxicity and in the emergence of drug-resistant viruses. Importantly, the ability of HIV to establish latent reservoirs early in the course of infection ensures the persistence of the virus even in the face of intensive drug therapy and vigorous antiviral immune response.

Thus, there is a continuous need for the development of novel anti-HIV therapies or a 2008, 13(3):393-416.).

Document of Christ et al (Christ et al, Nat. Chem. Biol., 2010, 6: 442.) and documents WO 2007/131350, WO 2009/062285, WO 2009/062288, WO 2009/062289, WO 2009/062308, WO 2010/130034, WO 2010/130842, WO 2011/015641, WO2011/076765, WO 2012/003498 and WO 2012/0033735 describe partially or totally unsaturated heterocyclic derivatives as anti-HIV agents.

Document WO 2012/003497 describes napthyl derivatives as anti-HIV agents.

However, these compounds are different from the compounds according to the invention.

SUMMARY OF THE INVENTION

The present invention relates to compounds that are able to totally or partially solve the above-mentioned problems and drawbacks.

The present invention provides new antiviral agents, especially anti-retroviral agents, and more particularly anti-HIV compounds.

The compounds according the invention are inhibitors of HIV replication as assessed by HIV-1 replication assay as herein-detailed. These compounds are thus useful agents for treating or preventing virus, such as HIV, or other viral pathogenic diseases or disorders, by inhibiting replication of the virus into the host infected cells.

Therefore, the compounds according to the invention constitute a useful class of new potent antiviral compounds that can be used in the treatment and/or prevention of viral infections in animals, mammals and humans, more specifically for the treatment and/or prevention of HIV in humans.

The present invention further relates to such compounds for their use as a medicine, to the use of such compounds as medicines, more specifically as antiviral agents, and to their use for the manufacture of medicaments for treating and/or preventing viral infections, in particular retroviral infections such as, but not limited to, HIV in humans.

The invention also relates to pharmaceutical compositions comprising such compounds in an antiviral effective amount, optionally in combination with at least one further antiviral agent.

The present invention further relates to such pharmaceutical composition for its use for the treatment of an HIV infection in a mammal being infected or having a risk to be infected by the HIV.

The present invention also relates to a method of treatment or prevention of viral infections, in particular retroviral infections such as, but not limited to HIV in humans by the administration of one or more such compounds, optionally in combination with one or more other antiviral agents, to a patient in need thereof.

The present invention also relates to a method of inhibiting the replication of HIV comprising exposing the virus to an effective amount of one or more such compounds under conditions where replication of HIV is inhibited.

In a first aspect, the invention provides compounds comprising a 6-membered carbocycle or heterocycle, said compounds having a structure according to formula (A):

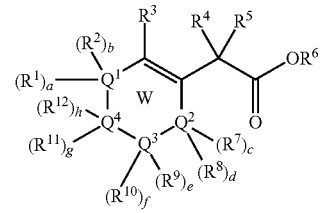

wherein:
W represents a substituted, partially or totally unsaturated, aromatic or non-aromatic carbo- or heterocycle;
a, b, c, d, e, f, g and h independently represent 0 or 1;

$Q^1$ represents $CR^1$, $CR^2$, $CR^1R^2$, N, $NR^1$, $NR^2$, S, O, C=O, C=S, N=O, S=O, $S(O)_2$;

$Q^2$ represents $CR^7$, $CR^8$, $CR^7R^8$, N, $NR^7$, $NR^8$, S, O, C=O, C=S, N=O, S=O, $S(O)_2$;

$Q^3$ represents $CR^9$, $CR^{10}$, $CR^9R^{10}$, N, $NR^9$, $NR^{10}$, S, O, C=O, C=S, N=O, S=O, $S(O)_2$;

$Q^4$ represents $CR^{11}$, $CR^{12}$, $CR^{11}R^{12}$, N, $NR^{11}$, $NR^{12}$, S, O, C=O, C=S, N=O, S=O, $S(O)_2$;

$R^1$, $R^2$, $R^7$, $R^8$, $R^9$, $R^{10}$, $R^{11}$ and $R^{12}$ independently represent hydrogen, —CN, —OH, —O-cycloalkyl, —O-cycloalkenyl, —O-cycloalkynyl, —$NH_2$, —$NR^{13}$-cycloalkyl, —$NR^{13}$-cycloalkenyl, —$NR^{13}$-cycloalkynyl, —S-cycloalkyl, —S-cycloalkenyl, —S-cycloalkynyl, —COOH, —$C(O)NH_2$, —$CF_3$, —$SO_2NH_2$, —$NHSO_2NH_2$, —$NHC(O)NH_2$, —$OC(O)NH_2$, halogen, alkyl, alkenyl, alkynyl, heteroalkyl, heteroalkenyl, heteroalkynyl, aryl, —O-aryl, —$NR^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;

and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$R^3$ represents —O-cycloalkyl, —O-cycloalkenyl, —O-cycloalkynyl, —$NR^{13}$-cycloalkyl, —$NR^{13}$-cycloalkenyl, —$NR^{13}$-cycloalkynyl, —S-cycloalkyl, —S-cycloalkenyl, —S-cycloalkynyl, $C_4$-$C_{20}$ alkyl, $C_4$-$C_{20}$ alkenyl, $C_4$-$C_{20}$ alkynyl, heteroalkyl, heteroalkenyl, heteroalkynyl, aryl, —O-aryl, —$NR^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be fused with at least one further cycle, and wherein alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$R^4$ or $R^5$ identical, or different, independently represent hydrogen halogen, —CN, —O-cycloalkyl, —O-cycloalkenyl, —O-cycloalkynyl, —S-cycloalkyl, —S-cycloalkenyl, —S-cycloalkynyl, $C_3$-$C_{20}$ alkyl, alkenyl, alkynyl, heteroalkyl, heteroalkenyl, heteroalkynyl, aryl, —O-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^2$, and wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety, $R^4$ and $R^5$ form a group of formula (i)

(i)

wherein Z represents hydrogen, alkyl or heteroalkyl and wherein a carbon atom or heteroatom of said alkyl, can be oxidized to form a C=O, C=S, N=O, N=S, S=O or $S(O)_2$;

$R^6$ represents hydrogen, alkyl, aryl or arylalkyl, $R^{13}$ represents hydrogen, alkyl, aryl or arylalkyl, wherein a carbon atom of said alkyl or aryl can be oxidized to form a C=O or C=S;

$R^1$, $Q^1$, $Q^4$ and $R^{11}$ form a saturated, partially or totally unsaturated 5, 6 or 7 membered carbo- or hetero-cycle or a saturated, partially or totally unsaturated 10, 11, 12, 13 or 14-membered polycarbo- or polyheterocycle;

$R^1$, $Q^1$, $Q^4$ and $R^{12}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle $R^2$, $Q^1$, $Q^4$ and $R^{11}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^2$, $Q^1$, $Q^4$ and $R^{12}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle $R^9$, $Q^3$, $Q^4$ and $R^{11}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^9$, $Q^3$, $Q^4$ and $R^{12}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^{10}$, $Q^3$, $Q^4$ and $R^{11}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^{10}$, $Q^3$, $Q^4$ and $R^{12}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^7$, $Q^2$, $Q^3$ and $R^9$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^7$, $Q^2$, $Q^3$ and $R^{10}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^8$, $Q^2$, $Q^3$ and $R^9$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$R^8$, $Q^2$, $Q^3$ and $R^{10}$ form a saturated, partially or totally unsaturated 5, 6 or 7 membered carbocycle or heterocycle or a saturated, partially or totally unsaturated 10, 11, 12, 13 or 14 membered polycarbocycle or polyheterocycle;

$T^1$ represents hydrogen, halogen, —$OT^3$, —$OCF_3$, =O, —$ST^3$, =S, —$S(O)T^4$, —$S(O)_2T^4$, —$S(O)_2NT^5T^6$, $CF_3$, $NO_2$, —$NT^3S(O)_2T^4$, CN, —$NT^3C(O)T^4$, —$NT^3C(O)NT^5T^8$, —$C(O)OT^3$, —$C(O)NT^5T^6$, —$C(O)T^4$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be substituted with one or more $T^7$, wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$;

$T^2$ represents hydrogen, halogen, —$OT^8$, —$OCF_3$, =O, —$ST^8$, =S, —$S(O)T^8$, —$S(O)_2T^9$, —$S(O)_2NT^{10}T^{11}$, —$CF_3$, —$NO_2$, —$NT^{10}T^{11}$, —$NT^8S(O)_2T^9$, —CN, —$NT^8C(O)T^9$, —$NT^8C(O)NT^{10}T^{11}$, —$C(O)OT^8$, —$C(O)NT^{10}T^{11}$, —$C(O)T^9$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be substituted with one or more $T^7$, wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$;

$T^3$ represents hydrogen, alkyl, alkenyl, alkynyl, heteroalkyl, heteroalkenyl, heteroalkynyl, aryl, heterocycle, wherein said alkyl, alkenyl, alkynyl, heteroalkyl, heteroalkenyl, heteroalkynyl, aryl, heterocycle can be substituted or non substituted with one or more —OH, =O, halogen, —SH, =S, —$CF_3$, —O-alkyl, —$OCF_3$, —CN, —$NO_2$, —C(O)OH, —$NH_2$ or $C(O)NH_2$, and wherein a carbon atom or heteroatom of said alkyl, alkenyl, alkynyl, heteroalkyl, heteroalkenyl, heteroalkynyl, aryl, heterocycle can be oxidized to form a C=O, C=S, N=O, N=S, S=O or $S(O)_2$;

$T^4$ represents —OH, alkyl, alkenyl, alkynyl, heteroalkyl, heteroalkenyl, heteroalkynyl, aryl, heterocycle, wherein said alkyl, alkenyl, alkynyl, heteroalkyl, heteroalkenyl, heteroalkynyl, aryl, heterocycle, can be substituted or non substituted with one or more —OH, =O, halogen, —SH, =S, —$CF_3$, —O-alkyl, —$OCF_3$, —CN, —NO2, —C(O)OH, —$NH_2$ or $C(O)NH_2$, and wherein a carbon atom or heteroatom of said alkyl, alkenyl, alkynyl, heteroalkyl, heteroalkenyl, heteroalkynyl aryl, heterocycle can be oxidized to form a C=O, C=S, N=O, N=S, S=O or $S(O)_2$;

T⁵ or T⁶ independently represent hydrogen, alkyl, alkenyl, alkynyl, heteroalkyl, heteroalkenyl, heteroalkynyl, aryl, heterocycle
  wherein said alkyl, alkenyl, alkynyl, heteroalkyl, heteroalkenyl, heteroalkynyl, aryl, heterocycle can be substituted or non substituted with one or more —OH, =O, halogen, —SH, =S, —CF₃, —O-alkyl, —OCF₃, —CN, —NO₂, —C(O)OH, —NH₂ or C(O)NH₂,
  and wherein a carbon atom or heteroatom of said alkyl, alkenyl, alkynyl, heteroalkyl, heteroalkenyl, heteroalkynyl aryl, heterocycle can be oxidized to form a C=O, C=S, N=O, N=S, S=O or S(O)₂,
  or T⁵ or T⁶ can be taken together to form a 4, 5, 6 or 7 membered heterocycle substituted or non substituted with an alkyl, alkenyl, alkynyl, heteroalkyl, heteroalkenyl, heteroalkynyl, —OH, halogen, —SH, —CF₃, —O-alkyl, —OCF₃, —CN, —NO₂, —C(O)OH, —NH₂ or —C(O)NH₂;
T⁷ independently represents an alkyl, alkenyl, alkynyl, heteroalkyl, heteroalkenyl, heteroalkynyl, —OH, =O, halogen, —SH, =S, —CF₃, —CN, —NO₂, —COOH, —NH₂, —C(O)NH₂;
T⁸ represents hydrogen, alkyl, alkenyl, alkynyl, heteroalkyl, heteroalkenyl, heteroalkynyl,
  wherein said alkyl, alkenyl, alkynyl, heteroalkyl, heteroalkenyl, heteroalkynyl, can be substituted or non substituted with one or more —OH, =O, halogen, —SH, =S, —CF₃, —O-alkyl, —OCF₃, —CN, —NO2, —C(O)OH, —NH₂ or —C(O)NH₂,
  and wherein a carbon atom or heteroatom of said alkyl, alkenyl, alkynyl, heteroalkyl, heteroalkenyl, heteroalkynyl can be oxidized to form a C=O, C=S, N=O, N=S, S=O or S(O)₂;
T⁹ represents —OH, alkyl, alkenyl, alkynyl, heteroalkyl, heteroalkenyl, heteroalkynyl, wherein said alkyl, alkenyl, alkynyl, heteroalkyl, heteroalkenyl, heteroalkynyl, can be substituted or non substituted with one or more —OH, =O, halogen, —SH, =S, —CF₃, —O-alkyl, —OCF₃, —CN, —NO₂, —C(O)OH, —NH₂ or —C(O)NH₂,
  and wherein a carbon atom or heteroatom of said alkyl, alkenyl, alkynyl, heteroalkyl, heteroalkenyl, heteroalkynyl can be oxidized to form a C=O, C=S, N=O, N=S, S=O or S(O)₂;
T¹⁰ or T¹¹ independently represent hydrogen, alkyl, alkenyl, alkynyl, heteroalkyl, heteroalkenyl, heteroalkynyl,
  wherein said alkyl, alkenyl, alkynyl, heteroalkyl, heteroalkenyl, heteroalkynyl, can be substituted or non substituted with one or more —OH, =O, halogen, —SH, =S, —CF₃, —O-alkyl, —OCF₃, —CN, —NO₂, —C(O)OH, —NH₂ or —C(O)NH₂,
  and wherein a carbon atom or heteroatom of said alkyl, alkenyl, alkynyl, heteroalkyl, heteroalkenyl, heteroalkynyl can be oxidized to form a C=O, C=S, N=O, N=S, S=O or S(O)₂,
  or T¹⁰ or T¹¹ can be taken together to form a 4, 5, 6 or 7 membered heterocycle substituted or non substituted with an alkyl, alkenyl, alkynyl, heteroalkyl, heteroalkenyl, heteroalkynyl, —OH, halogen, —SH, —CF₃, O-alkyl, —OCF₃, —CN, —NO2, —C(O)OH, —NH₂ or —C(O)NH₂;
and a racemate, enantiomer, isomer, atropoisomer or diastereoisomer or a phamaceutically acceptable salt thereof, provided that
i) W does not represent a substituted 1,3 pyrimidine moiety wherein Q¹ and Q³ simultaneously represent N;

ii) if R³ represents an aryl or an heterocycle and R⁶ represents hydrogen, W does not represent a substituted pyridine moiety wherein Q³ represents N;
iii) if R³ represents an aryl or an heterocycle and R⁶ represents hydrogen, W does not represent a substituted quinoline moiety wherein b and h simultaneously represent 0, R¹, Q¹, Q⁴ and R¹¹ form a substituted or non-substituted aromatic 6-membered carbocycle and Q³ represents N;
iv) if R³ represents an aryl or an heterocycle and R⁶ represents hydrogen, W does not represent a substituted 3,4-dihydro-2H-1-benzopyran-2-one wherein b and h simultaneously represent 0, R¹, Q¹, Q⁴ and R¹¹ form a substituted or non-substituted aromatic 6-membered carbocycle, Q³ represents 0 and Q² represents C=O;
v) if R³ represents an aryl or an heterocycle and R⁶ represents hydrogen, W does not represent a substituted 1,2-dihydroquinolin-2-one wherein b and h simultaneously represent 0, R¹, Q¹, Q⁴ and R¹¹ form a substituted or non-substituted aromatic 6-membered carbocycle, Q³ represents N and Q² represents C=O;
vi) if R³ represents an aryl or an heterocycle, R⁶ represents hydrogen, Q¹, Q² and Q⁴ simultaneously represent C, Q³ represents N and d represents 0:
  R¹, Q¹, Q⁴ and R¹¹ do not form a 5-membered saturated, partially or totally unsaturated heterocycle, substituted or not substituted,
  R¹, Q¹, Q⁴ and R¹² do not form a 5-membered saturated, partially or totally unsaturated heterocycle, substituted or not substituted;
  R², Q¹, Q⁴ and R¹¹ do not form a 5-membered saturated, partially or totally unsaturated heterocycle, substituted or not substituted;
  R², Q¹, Q⁴ and R¹² do not form a 5-membered saturated, partially or totally unsaturated heterocycle, substituted or not substituted;
  R¹, Q¹, Q⁴ and R¹¹ do not form a 5-membered saturated, partially or totally unsaturated heterocycle, substituted or not substituted, comprising at least one further heteroatom selected from O, N or S;
  R¹, Q¹, Q⁴ and R¹² do not form a 5-membered saturated, partially or totally unsaturated heterocycle, substituted or not substituted, comprising at least one further heteroatom selected from O, N or S;
  R², Q¹, Q⁴, and R¹¹ do not form a 5-membered saturated, partially or totally unsaturated heterocycle, substituted or not substituted, comprising at least one further heteroatom selected from O, N or S;
  R², Q¹, Q⁴ and R¹² do not form a 5-membered saturated, partially or totally unsaturated heterocycle, substituted or not substituted, comprising at least one further heteroatom selected from O, N or S;
vii) W does not represent a compound of formula (vii)

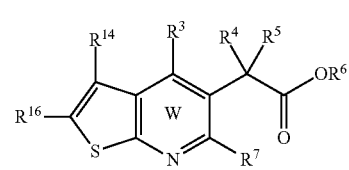

(vii)

wherein R¹⁴ or R¹⁶ independently represent hydrogen, —CN, —OH, —O-cycloalkyl, —O-cycloalkenyl, —O-cycloalkynyl, —NH₂, —NR¹³-cycloalkyl, —NR¹³-cycloalkenyl, —NR¹³-cycloalkynyl, —S-cycloalkyl, —S-cycloalkenyl, —S-cycloalkynyl, —COOH, —C(O)NH₂, —CF₃, —SO₂NH₂, —NHSO₂NH₂, —NHC(O)NH₂, —OC(O)NH₂, halogen, alkyl, alkenyl, alkynyl, heteroalkyl, heteroalkenyl, heteroalkynyl, aryl, —O-aryl, —NR¹³-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR¹³-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one T¹, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)₂, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

and R³, R⁴, R⁵, R⁶, R⁷ and T¹ are defined as for the compound of formula (A);

viii) W does not represent a compound of formula (viii)

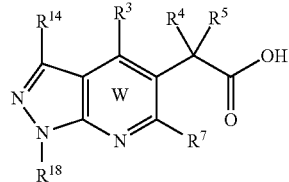

(viii)

wherein:
R³ represents an aryl or an heterocycle;
R¹⁴ or R¹⁸ independently represent hydrogen, —CN, —OH, —O-cycloalkyl, —O-cycloalkenyl, —O-cycloalkynyl, —NH₂, —NR¹³-cycloalkyl, —NR¹³-cycloalkenyl, —NR¹³-cycloalkynyl, —S-cycloalkyl, —S-cycloalkenyl, —S-cycloalkynyl, —COOH, —C(O)NH₂, —CF₃, —SO₂NH₂, —NHSO₂NH₂, —NHC(O)NH₂, —OC(O)NH₂, halogen, alkyl, alkenyl, alkynyl, heteroalkyl, heteroalkenyl, heteroalkynyl, aryl, —O-aryl, —NR¹³-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR¹³-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one T¹, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)₂, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

and R⁴, R⁵, R⁷, R¹³ and T¹ are defined as for the compound of formula (A);

ix) if R⁴ represents a hydrogen atom or a halogen atom, R⁵ does not represent a hydrogen atom or a halogen atom;

x) if R⁵ represents a hydrogen atom or a halogen atom, R⁴ does not represent a hydrogen atom or a halogen atom;

xi) R⁴ or R⁵ does not represent —OMe;

xii) W does not represent 2-(4-chloro-2-phenylphenyl)-3-methylbutanoïc acid;

xiii) W does not represent a compound of formula (xiii)

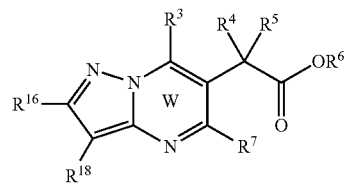

(xiii)

wherein:
R¹⁶ or R¹⁸ independently represent hydrogen, —CN, —OH, —O-cycloalkyl, —O-cycloalkenyl, —O-cycloalkynyl, —NH₂, —NR¹³-cycloalkyl, —NR¹³-cycloalkenyl, —NR¹³-cycloalkynyl, —S-cycloalkyl, —S-cycloalkenyl, —S-cycloalkynyl, —COON, —C(O)NH₂, —CF₃, —SO₂NH₂, —NHSO₂NH₂, —NHC(O)NH₂, —OC(O)NH₂, halogen, alkyl, alkenyl, alkynyl, heteroalkyl, heteroalkenyl, heteroalkynyl, aryl, —O-aryl, —NR¹³-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR¹³-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one T¹, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

and $R^3$, $R^4$, $R^5$, $R^6$, $R^7$, $R^{13}$ and $T^1$ are defined as for the compound of formula (A);

xiv) W does not represent a compound of formula (xiv)

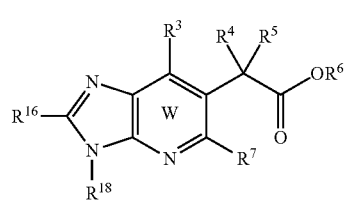

(xiv)

wherein:

$R^{18}$ and $R^{18}$ independently represent hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COOH, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

and $R^3$, $R^4$, $R^5$, $R^6$, $R^7$, $R^{13}$ and $T^1$ are defined as for the compound of formula (A);

xv) W does not represent a compound of formula (xv)

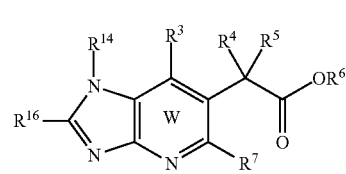

(xv)

wherein:

$R^{14}$ and $R^{16}$ independently represent hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COOH, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety, and $R^3$, $R^4$, $R^5$, $R^6$, $R^7$, $R^{13}$ and $T^1$ are defined as for the compound of formula (A);

xvi) W does not represent a compound of formula (xvi)

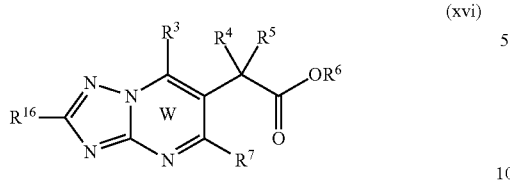

wherein:

R$^{16}$ represents hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COON, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one T$^1$, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C═O, C═S, N═O, N═S, S═O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

and R$^3$, R$^4$, R$^5$, R$^6$, R$^7$, R$^{13}$ and T$^1$ are defined as for the compound of formula (A);

xvii) W does not represent a compound of formula (xvii)

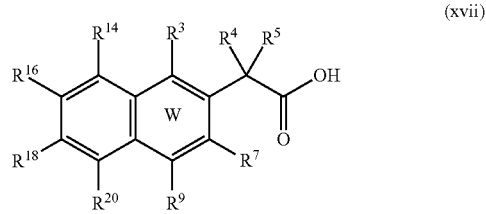

wherein:

R$^{14}$, R$^{16}$, R$^{18}$ and R$^{20}$ independently represent hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COOH, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one T$^1$, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C═O, C═S, N═O, N═S, S═O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

and R$^3$, R$^4$, R$^5$, R$^7$, R$^9$, R$^{13}$ and T$^1$ are defined as for the compound of formula (A);

xviii) W does not represent a compound of formula (xviii), (xix) or (xx)

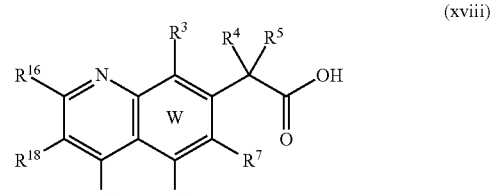

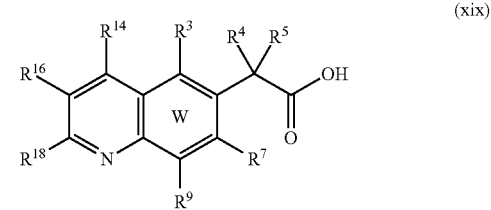

-continued

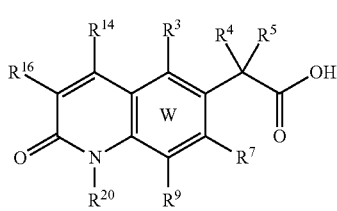

(xx)

wherein:
$R^{14}$, $R^{16}$, $R^{18}$ and $R^{20}$ independently represent hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COOH, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one T$^1$, And wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle, and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

and $R^3$, $R^4$, $R^5$, $R^7$, $R^9$, $R^{13}$ and T$^1$ are defined as for the compound of formula (A).

DETAILED DESCRIPTION OF THE INVENTION

Even if described in particular or preferred embodiments, the present invention is not to be understood as being limited to such particular or preferred embodiments.

The term "alkyl" as used herein, either alone or in combination with another radical, refers to acyclic, straight or branched chain alkyl radicals.

The term "alkenyl", as used herein, either alone or in combination with another radical, refers to an unsaturated, acyclic straight or branched chain hydrocarbon radicals, at least two of carbon atoms are bonded to each other by a double bond.

The term "alkynyl", as used herein, either alone or in combination with another radical, refers to an unsaturated, acyclic straight or branched chain hydrocarbon radicals, at least two of carbon atoms are bonded to each other by a triple bond.

The term "cycloalkyl", as used herein, either alone or in combination with another radical, refers to a monocyclic or polycyclic saturated hydrocarbon radical.

The term "cycloalkenyl", as used herein, alone or in combination with another radical, refers to a monocyclic or polycyclic non-aromatic hydrocarbon radical with at least one site of unsaturation, namely a carbon-carbon double bond The term "cycloalkynyl", as used herein, alone or in combination with another radical, refers to a monocyclic or polycyclic non-aromatic hydrocarbon radical with at least one site of unsaturation, namely a carbon-carbon triple bond The term "heteroalkyl" as used herein, alone or in combination with another radical, refers to an acyclic alkyl wherein one or more carbon atoms are replaced by an oxygen, nitrogen or sulphur atom.

The term "heteroalkenyl" as used herein, alone or in combination with another radical, refers to an acyclic alkenyl wherein one or more carbon atoms are replaced by an oxygen, nitrogen or sulphur atom.

The term "heteroalkynyl" as used herein, alone or in combination with another radical, refers to an acyclic alkynyl wherein one or more carbon atoms are replaced by an oxygen, nitrogen or sulphur atom.

The term "aryl", as used herein, either alone or in combination with another radical, refers to a carbocyclic aromatic monocyclic group containing 6 carbon atoms which can be fused with at least another saturated, unsaturated or aromatic carbocycle.

The term "arylakyl", as used herein, either alone or in combination with another radical, refers to an acyclic alkyl radical in which one of the hydrogen atoms bonded to a carbon atom is replaced with an aryl radical.

The term "arylalkenyl" as used herein, alone or in combination with another radical, refers to an acyclic alkenyl radical in which one of the hydrogen atoms bonded to a carbon atom, is replaced with an aryl radical.

The term "arylalkynyl" as used herein, alone or in combination with another radical, refers to an acyclic alkynyl radical in which one of the hydrogen atoms bonded to a carbon atom, is replaced with an aryl radical.

The term "arylheteroalkyl" as used herein, alone or in combination with another radical, refers to a heteroalkyl radical in which one of the hydrogen atoms bonded to a carbon atom is replaced with an aryl radical.

The term "arylheteroalkenyl" as used herein, alone or in combination with another radical, refers to a heteroalkenyl radical in which one of the hydrogen atoms bonded to a carbon atom, is replaced with an aryl radical.

The term "arylheteroalkynyl" as used herein, alone or in combination with another radical, refers to a heteroalkynyl radical in which one of the hydrogen atoms bonded to a carbon atom, is replaced with an aryl radical.

The term "carbocycle", as used herein and unless specified otherwise, either alone or in combination with another radical, refers to a 3- to 8 membered saturated, unsaturated or aromatic cyclic radical in which all of the ring members are carbon atoms and which can be fused with at least another carbocycle.

The term "heterocycle" as used herein means a saturated, unsaturated or aromatic ring system of 3 to 18 atoms including at least one N, O or S and which can be fused with at least another carbocycle or heterocycle.

The term "heterocyclyl-alkyl" as used herein, alone or in combination with another radical, refers to an acyclic alkyl radical in which one of the hydrogen atoms bonded to a carbon atom is replaced with an heterocycle radical.

The term "heterocyclyl-alkenyl" as used herein, alone or in combination with another radical, refers to an acyclic alkenyl radical in which one of the hydrogen atoms bonded to a carbon atom is replaced with an heterocycle radical.

The term "heterocyclyl-alkynyl" as used herein, alone or in combination with another radical, refers to an acyclic alkynyl radical in which one of the hydrogen atoms bonded to a carbon atom is replaced with an heterocycle radical.

The term "heterocyclyl-heteroalkyl" as used herein, alone or in combination with another radical, refers to a heteroalkyl radical in which one of the hydrogen atoms bonded to a carbon atom is replaced with an heterocycle radical.

The term "heterocycle-heteroalkenyl" as used herein, alone or in combination with another radical, refers to a heteroalkenyl radical in which one of the hydrogen atoms bonded to a carbon atom, is replaced with an heterocycle radical.

The term "heterocycle-heteroalkynyl" as used herein, alone or in combination with another radical, refers to a heteroalkynyl radical in which one of the hydrogen atoms bonded to a carbon atom is replaced with an heterocycle radical.

The expression "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, "pharmaceutically acceptable salts" refer to derivatives of the disclosed compounds wherein the parent compound is modified by making acid or base salts thereof. Examples of pharmaceutically acceptable salts include, but are not limited to, mineral or organic acid salts of basic residues such as amines; alkali or organic salts of acidic residues such as carboxylic acids; and the like.

The pharmaceutically acceptable salts of the present invention can be synthesized from the parent compound which contains a basic or acidic moiety by conventional chemical methods.

The term "treatment" as used herein is intended to mean the administration of a compound or composition according to the present invention to alleviate or eliminate symptoms of HIV infection and/or to reduce viral load in a patient. The term "treatment" also encompasses the administration of a compound or composition according to the present invention post-exposure of the individual to the virus but before the appearance of symptoms of the disease, and/or prior to the detection of the virus in the blood, to prevent the appearance of symptoms of the disease and/or to prevent the virus from reaching detectable levels in the blood, and the administration of a compound or composition according to the present invention to prevent perinatal transmission of HIV from mother to baby, by administration to the mother before giving birth and to the child within the first days of life.

The expression "therapeutically effective amount" refers to an amount of a compound according to the invention, which when administered to a patient in need thereof, is sufficient to effect treatment for disease-states, conditions, or disorders for which the compounds have utility. Such an amount would be sufficient to elicit the biological or medical response of a tissue system, or patient that is sought by a researcher or clinician. The amount of a compound according to the invention which constitutes a therapeutically effective amount will vary depending on such factors as the compound and its biological activity, the composition used for administration, the time of administration, the route of administration, the rate of excretion of the compound, the duration of the treatment, the type of disease-state or disorder being treated and its severity, drugs used in combination with or coincidentally with the compounds of the invention, and the age, body weight, general health, sex and diet of the patient Such a therapeutically effective amount can be determined routinely by one of ordinary skill in the art having regard to their own knowledge, the state of the art, and this disclosure The term "mammal" as used herein is intended to encompass humans, as well as non-human mammals which are susceptible to infection by HIV or non human equivalents of HIV. Non-human mammals include but are not limited to domestic animals, such as cows, pigs, dogs, cats, rabbits, rats and mice, and non domestic animals.

The compounds according to the invention are compounds of formula (A) as defined and including the embodiments described in the summary of the invention.

Particularly, the compounds according to the invention are compounds of formula (A) wherein $R^6$ represents hydrogen.

More particularly, the compounds according to the invention are compounds of formula (A) wherein $R^5$ represents hydrogen.

Advantageously, the invention provides compounds of formula (1) to (5):

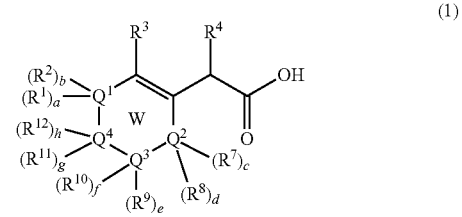

(1)

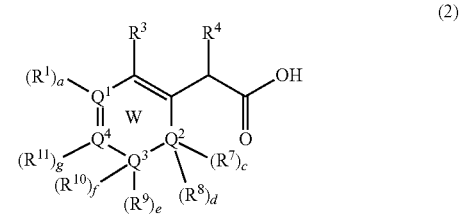

(2)

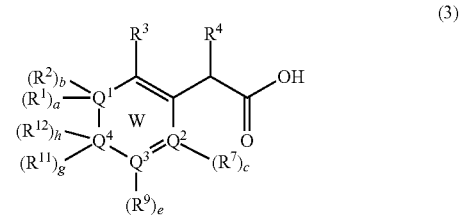

(3)

-continued (4)
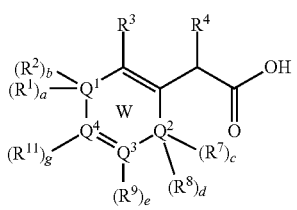

(5)
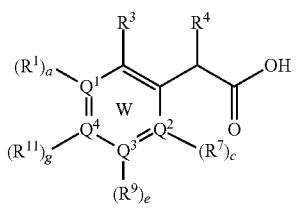

wherein:

W represents a substituted, partially or totally unsaturated, aromatic or non-aromatic carbo- or heterocycle;

a, b, c, d, e, f, g and h independently represent 0 or 1;

$Q^1, Q^2, Q^3, Q^4, R^1, R^2, R^3, R^4, R^7, R^8, R^9, R^{10}, R^{11}, R^{12}, R^{13}, T^1, T^2, T^3, T^4, T^5, T^6, T^7, T^8, T^9$ and $T^{10}$ are defined as for the compounds of formula (A) including the relevant proviso.

Preferably, the invention provides compounds of formula (1A), (2A), (3A), (4A) or (5A):

(1A)
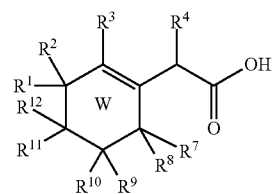

(2A)
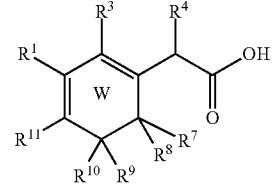

(3A)
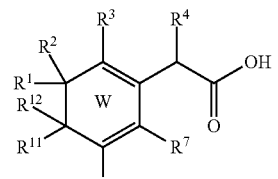

(4A)
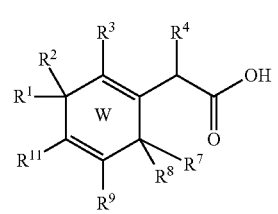

(5A)
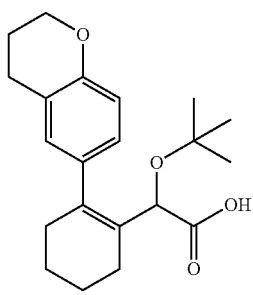

wherein:

W represents a substituted, partially or totally unsaturated or aromatic carbocycle;

$Q^1, Q^2, Q^3, Q^4, R^1, R^2, R^3, R^4, R^7, R^8, R^9, R^{10}, R^{11}, R^{12}, R^{13}, T^1, T^2, T^3, T^4, T^5, T^6, T^7, T^8, T^9$ and $T^{10}$ are defined as for the compounds of formula (A).

As examples of compounds of formula (1A), the invention provides compounds of formula (1A-1) and (1A-2):

(1A-1)
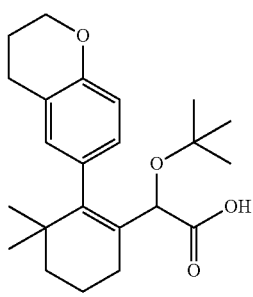

(1A-2)
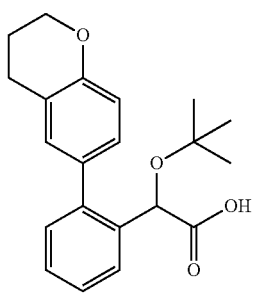

As examples of compounds (5A), the invention provides compounds of formula (5A-1), (5A-2), (5A-3), (5A-4), (5A-5), (5A-6), (5A-7), (5A-8), (5A-9), (5A-10), (5A-11), (5A-12), (5A-13), (5A-14), (5A-15), (5A-16), (5A-17), (5A-18), (5A-19) or (5A-20):

(5A-1)
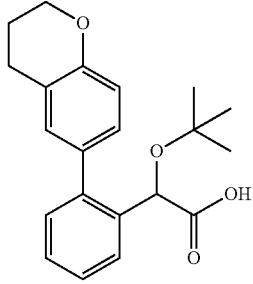

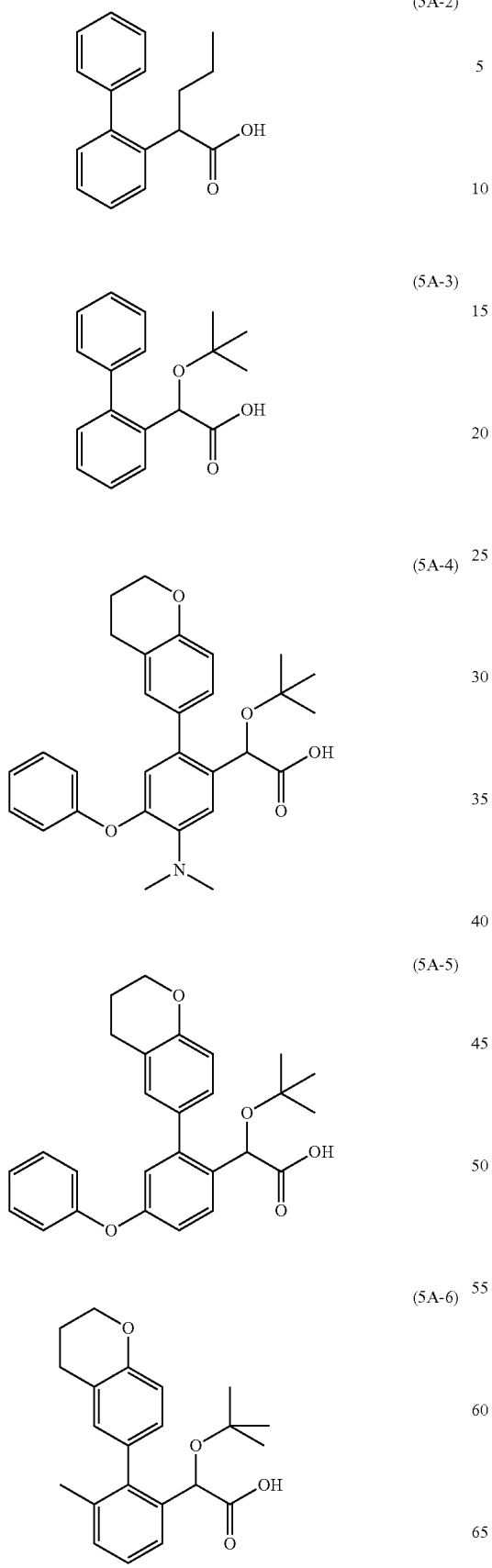
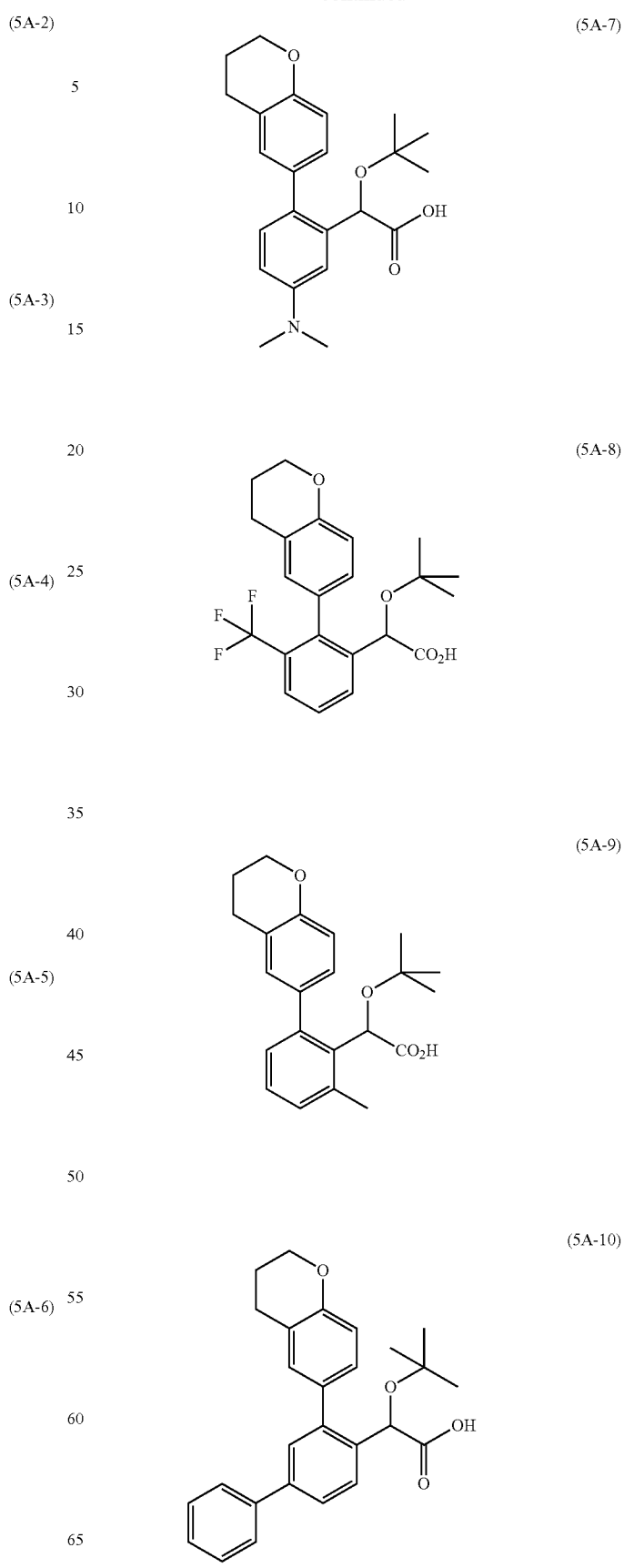

(5A-11)
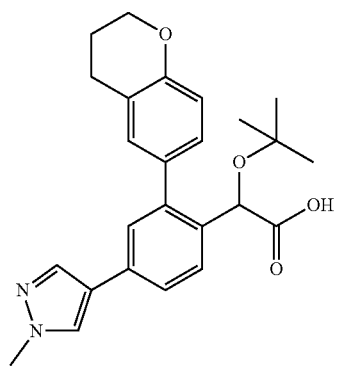
(5A-12)
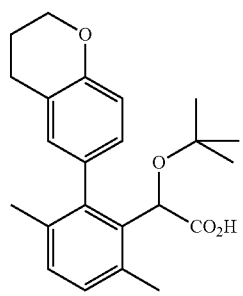
(5A-13)
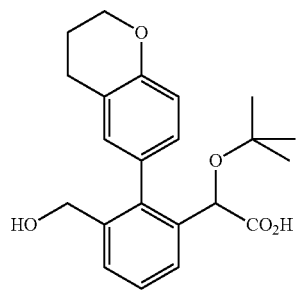
(5A-14)
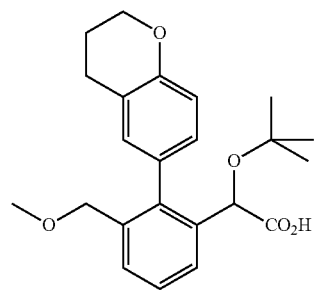
(5A-15)
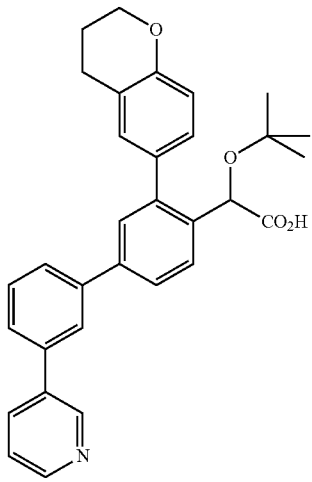
(5A-16)
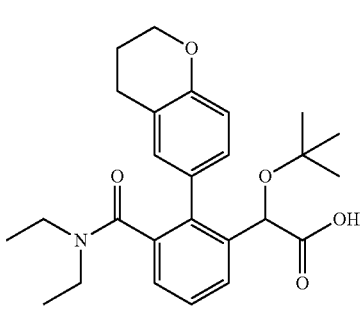
(5A-17)
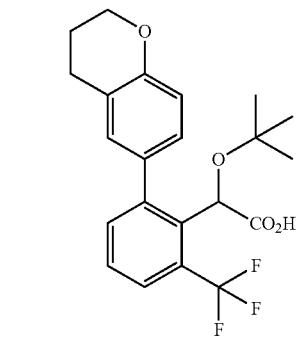
(5A-18)
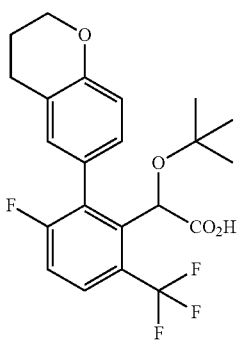

-continued
(5A-19)
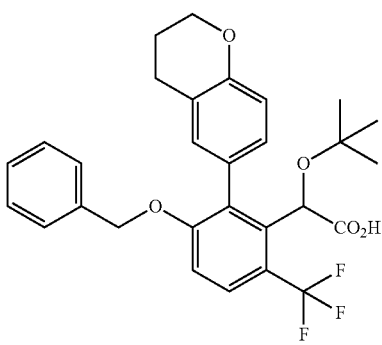
(5A-20)
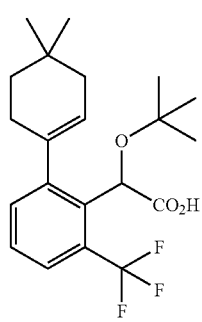
Preferably, the invention also provides compounds of formula (5B) to (5J)
(5B)
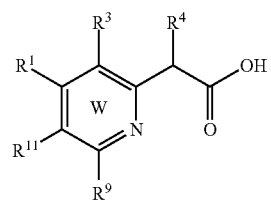
(5C)
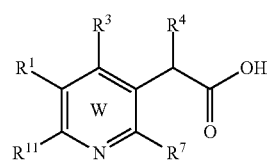
(5D)
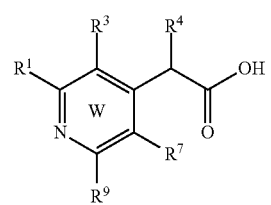
(5E)
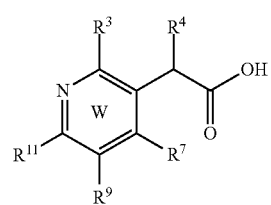
(5F)
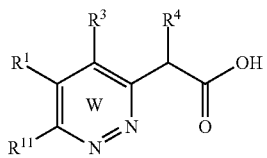
(5G)
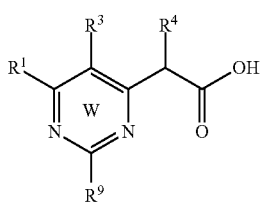
(5H)
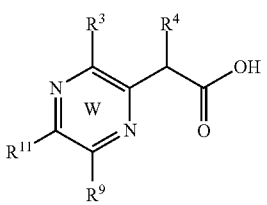
(5I)
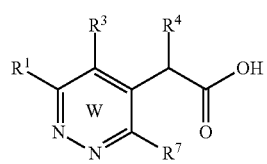
(5J)
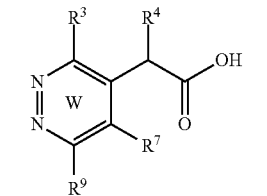
wherein:
W represents a substituted aromatic heterocycle;
$R^1, R^3, R^4, R^7, R^9, R^{11}, R^{13}, T^1, T^2, T^3, T^4, T^5, T^6, T^7, T^8, T^9$ and $T^{10}$ are defined as for the compounds of formula (A) including the relevant proviso.
Also advantageously, the invention provides compounds of formula (6) to (12)
(6)
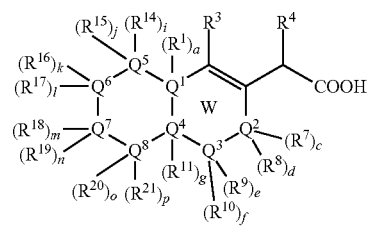

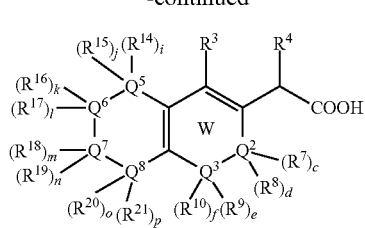 (7)

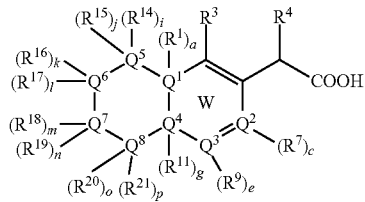 (8)

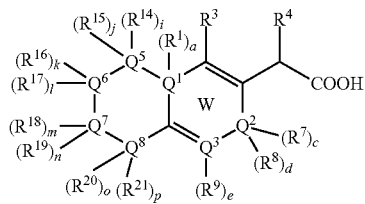 (9)

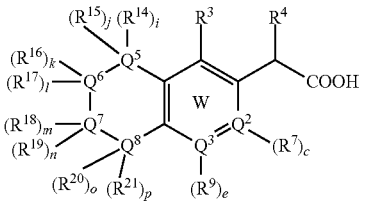 (10)

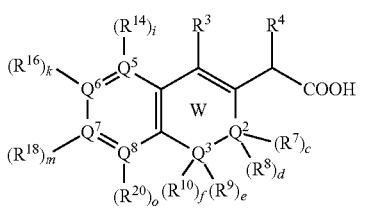 (11)

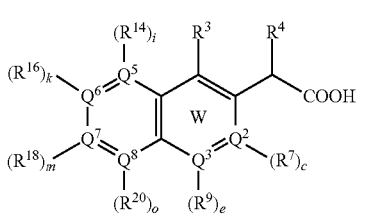 (12)

wherein:

W represents a fused, substituted, partially or totally unsaturated or aromatic carbo- or heterocycle;

a, c, d, e, f, g, i, j, k, l, m, n, o and p independently represent 0 or 1;

$Q^1$ represents $CR^1$, N;

$Q^4$ represents $CR^{11}$, N;

$Q^5$ represents $CR^{14}$, $CR^{15}$, $CR^{14}R^{15}$, N, $NR^{14}$, $NR^{15}$, S, O, C=O, C=S, N=O, S=O, $S(O)_2$;

$Q^6$ represents $CR^{16}$, $CR^{17}$, $CR^{16}R^{17}$, N, $NR^{16}$, $NR^{17}$, S, O, C=O, C=S, N=O, S=O, $S(O)_2$;

$Q^7$ represents $CR^{18}$, $CR^{19}$, $CR^{18}R^{19}$, N, $NR^{18}$, $NR^{19}$, S, O, C=O, C=S, N=O, S=O, $S(O)_2$;

$Q^8$ represents $CR^{20}$, $CR^{21}$, $CR^{20}R^{21}$, N, $NR^{20}$, $NR^{21}$, S, O, C=O, C=S, N=O, S=O, $S(O)_2$;

$R^{14}$, $R^{15}$, $R^{16}$, $R^{17}$, $R^{18}$, $R^{19}$, $R^{20}$ et $R^{21}$, independently represent hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COON, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;

and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$Q^2$, $Q^3$, $R^1$, $R^3$, $R^4$, $R^7$, $R^8$, $R^9$, $R^{10}$, $R^{11}$, $R^{13}$, $T^1$, $T^2$, $T^3$, $T^4$, $T^5$, $T^6$, $T^7$, $T^9$ and $T^{10}$ are defined as for the compounds of formula (A) including the relevant proviso.

As examples of compounds of formula (10), the invention provides compounds of formula (10A) or (10B):

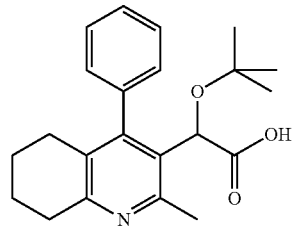 (10A)

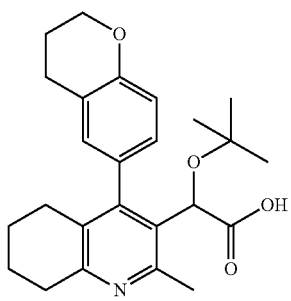
(10B)
As an example of compounds of formula (11), the invention provides a compound of formula (11A):
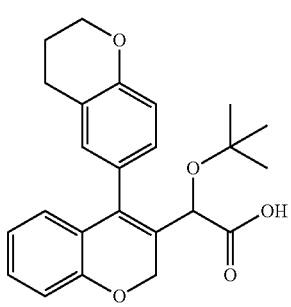
(11A)
As examples of compounds of formula (12), the invention provides compounds of formula (12A) or (12B):
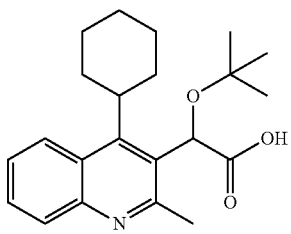
(12A)
(12B)
Also advantageously, the invention provides compounds of formula (13) to (20):
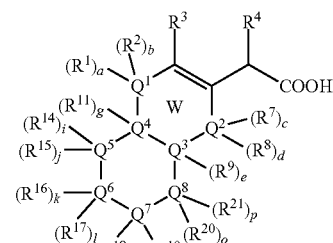
(13)
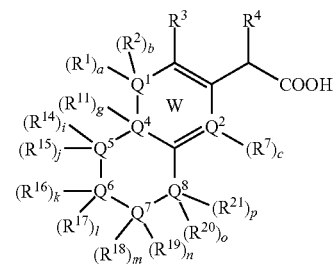
(14)
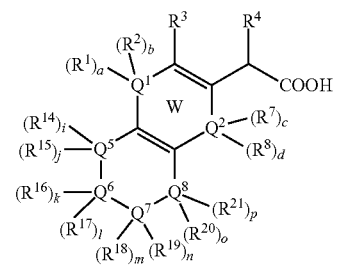
(15)
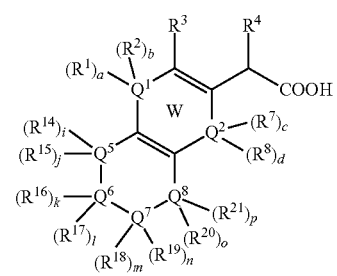
(16)
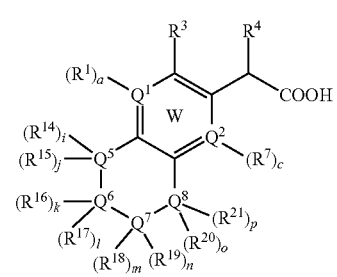
(17)
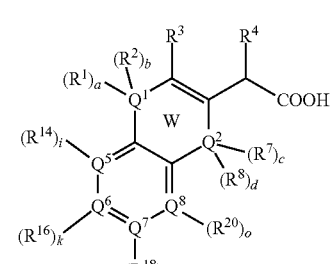
(18)

-continued

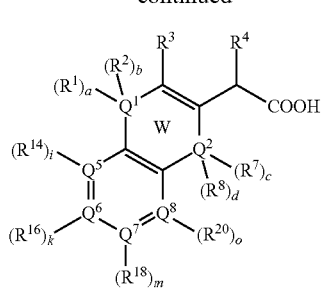
(19)

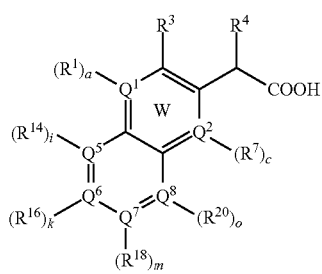
(20)

wherein:
- W represents a fused, substituted, partially or totally unsaturated or aromatic carbo- or heterocycle;
- a, b, c, d, e, g, i, j, k, l, m, n, o and p independently represent 0 or 1;
- $Q^3$ represents $CR^9$, N;
- $Q^4$ represents $CR^{11}$, N;
- $Q^5$ represents $CR^{14}$, $CR^{15}$, $CR^{14}R^{15}$, N, $NR^{14}$, $NR^{15}$, S, O, C=O, C=S, N=O, S=O, $S(O)_2$;
- $Q^6$ represents $CR^{16}$, $CR^{17}$, $CR^{16}R^{17}$, N, $NR^{16}$, $NR^{17}$, S, O, C=O, C=S, N=O, S=O, $S(O)_2$;
- $Q^7$ represents $CR^{18}$, $CR^{19}$, $CR^{18}R^{19}$, N, $NR^{18}$, $NR^{19}$, S, O, C=O, C=S, N=O, S=O, $S(O)_2$;
- $Q^8$ represents $CR^{20}$, $CR^{21}$, $CR^{20}R^{21}$, N, $NR^{20}$, $NR^{21}$, S, O, C=O, C=S, N=O, S=O, $S(O)_2$;
- $R^{14}$, $R^{15}$, $R^{16}$, $R^{17}$, $R^{18}$, $R^{19}$, $R^{20}$ et $R^{21}$, independently represent hydrogen, —CN, —OH, —O-cycloalkyl, —O-cycloalkenyl, —O-cycloalkynyl, —NH₂, —NR¹³-cycloalkyl, —NR¹³-cycloalkenyl, —NR¹³-cycloalkynyl, —S-cycloalkyl, —S-cycloalkenyl, —S-cycloalkynyl, —COON, —C(O)NH₂, —CF₃, —SO₂NH₂, —NHSO₂NH₂, —NHC(O)NH₂, —OC(O)NH₂, halogen, alkyl, alkenyl, alkynyl, heteroalkyl, heteroalkenyl, heteroalkynyl, aryl, —O-aryl, —NR¹³-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR¹³-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$,
- wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$,
- and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;
- and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;
- $Q^1$, $Q^2$, $R^1$, $R^2$, $R^3$, $R^4$, $R^7$, $R^8$, $R^9$, $R^{11}$, $R^{13}$, $T^1$, $T^2$, $T^3$, $T^4$, $T^5$, $T^6$, $T^7$, $T^8$, $T^9$ and $T^{10}$ are defined as for the compounds of formula (A).

Also advantageously, the invention provides compounds of formula (21) to (27):

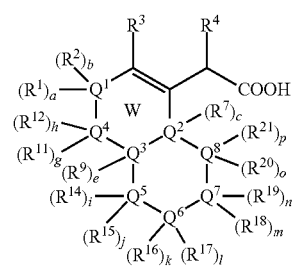
(21)

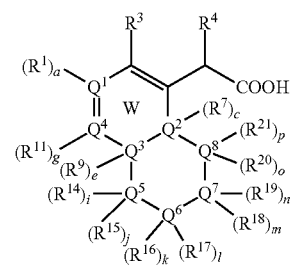
(22)

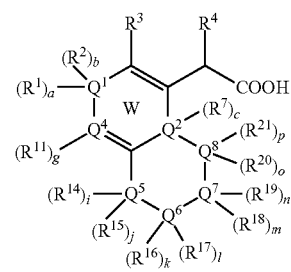
(23)

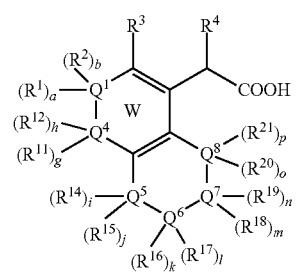
(24)

-continued (25)

(26)

(27)

wherein:
W represents a fused, substituted, partially or totally unsaturated or aromatic carbo- or heterocycle;
a, b, c, e, g, h, i, j, k, l, m, n, o and p independently represent 0 or 1;
$Q^2$ represents $CR^7$, N;
$Q^3$ represents $CR^9$, N;
$Q^5$ represents $CR^{14}$, $CR^{15}$, $CR^{14}R^{15}$, N, $NR^{14}$, $NR^{15}$, S, O, C=O, C=S, N=O, S=O, $S(O)_2$;
$Q^6$ represents $CR^{16}$, $CR^{17}$, $CR^{16}R^{17}$, N, $NR^{16}$, $NR^{17}$, S, O, C=O, C=S, N=O, S=O, $S(O)_2$;
$Q^7$ represents $CR^{18}$, $CR^{19}$, $CR^{18}R^{19}$, N, $NR^{18}$, $NR^{19}$, S, O, C=O, C=S, N=O, S=O, $S(O)_2$;
$Q^8$ represents $CR^{20}$, $CR^{21}$, $CR^{20}R^{21}$, N, $NR^{20}$, $NR^{21}$, S, O, C=O, C=S, N=O, S=O, $S(O)_2$;
$R^{14}$, $R^{15}$, $R^{16}$, $R^{17}$, $R^{18}$, $R^{19}$, $R^{20}$ et $R^{21}$, independently represent hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COON, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$, wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;

and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$Q^1$, $Q^4$, $R^1$, $R^2$, $R^3$, $R^4$, $R^7$, $R^9$, $R^{11}$, $R^{12}$, $R^{13}$, $T^1$, $T^2$, $T^3$, $T^4$, $T^5$, $T^6$, $T^7$, $T^8$, $T^9$ and $T^{10}$ are defined as for the compounds of formula (A) including the relevant proviso.

Preferably, the invention also provides compounds of formula (10A), (17A), (20A), (25A) or (27A):

(10A)

(17A)

(20A)

-continued

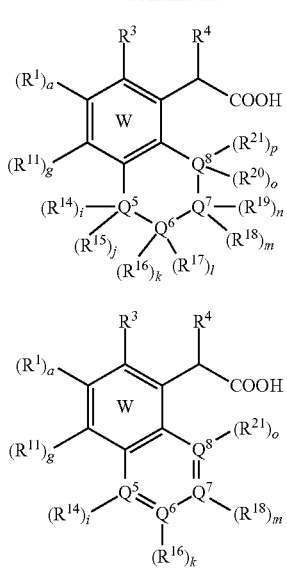

(25A)

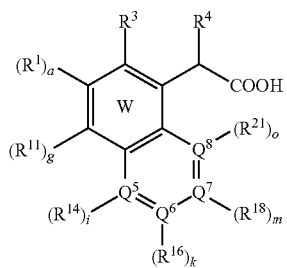

(27A)

wherein:
W represents a fused, substituted, aromatic carbo- or heterocycle;
a, c, e, g, i, j, k, l, m, n, o and p independently represent 0 or 1;
$Q^5$ represents $CR^{14}$, $CR^{15}$, $CR^{14}R^{15}$, N, $NR^{14}$, $NR^{15}$, S, O, C=O, C=S, N=O, S=O, $S(O)_2$;
$Q^6$ represents $CR^{16}$, $CR^{17}$, $CR^{16}R^{17}$, N, $NR^{16}$, $NR^{17}$, S, O, C=O, C=S, N=O, S=O, $S(O)_2$;
$Q^7$ represents $CR^{18}$, $CR^{19}$, $CR^{18}R^{19}$, N, $NR^{18}$, $NR^{19}$, S, O, C=O, C=S, N=O, S=O, $S(O)_2$;
$Q^8$ represents $CR^{20}$, $CR^{21}$, $CR^{20}R^{21}$, N, $NR^{20}$, $NR^{21}$, S, O, C=O, C=S, N=O, S=O, $S(O)_2$;
$R^{14}$, $R^{15}$, $R^{16}$, $R^{17}$, $R^{18}$, $R^{19}$, $R^{20}$ et $R^{21}$, independently represent hydrogen, —CN, —OH, —O-cycloalkyl, —O-cycloalkenyl, —O-cycloalkynyl, —$NH_2$, —$NR^{13}$-cycloalkyl, —$NR^{13}$-cycloalkenyl, —$NR^{13}$-cycloalkynyl, —S-cycloalkyl, —S-cycloalkenyl, —S-cycloalkynyl, —COOH, —$C(O)NH_2$, —$CF_3$, —$SO_2NH_2$, —$NHSO_2NH_2$, —$NHC(O)NH_2$, —$OC(O)NH_2$, halogen, alkyl, alkenyl, alkynyl, heteroalkyl, heteroalkenyl, heteroalkynyl, aryl, —O-aryl, —$NR^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$,
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$,
and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;
and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;
$R^1$, $R^7$, $R^9$, $R^{11}$, $R^{13}$, $T^1$, $T^2$, $T^3$, $T^4$, $T^5$, $T^6$, $T^7$, $T^8$, $T^9$ and $T^{10}$ are defined as for the compounds of formula (A).

As an example of compounds (17), the invention provides a compound of formula (17A-1)

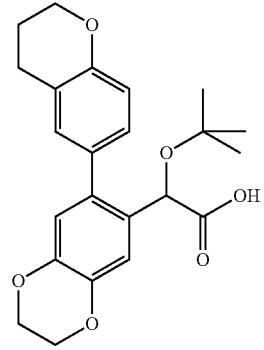

(17A-1)

As examples of compounds (20), the invention provides compounds of formula (20A-1) or (20A-2):

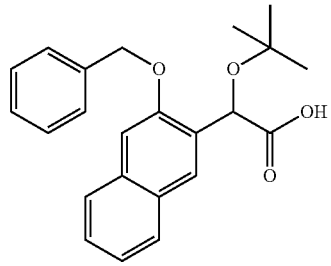

(20A-1)

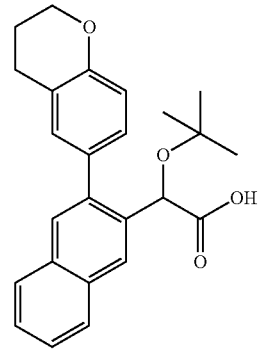

(20A-2)

As compounds of formula (27), the invention provides compounds of formula (27A-1), (27A-2), (27A-3) or (27A-4):

Also advantageously, the invention provides compounds of formula (28) to (43):

wherein:
W represents a fused, substituted, partially or totally unsaturated or aromatic carbo- or heterocycle;
a, c, d, e, f, g, i, j, k, l, m and n independently represent 0 or 1;
$Q^1$ represents $CR^1$, N;
$Q^4$ represents $CR^{11}$, N;
$Q^5$ represents $CR^{14}$, $CR^{15}$, $CR^{14}R^{15}$, N, $NR^{14}$, $NR^{15}$, S, O, C=O, C=S, N=O, S=O, $S(O)_2$;
$Q^6$, represents $CR^{16}$, $CR^{17}$, $CR^{16}R^{17}$, N, $NR^{16}$, $NR^{17}$, S, O, C=O, C=S, N=O, S=O, $S(O)_2$;
$Q^7$ represents $CR^{18}$, $CR^{19}$, $CR^{18}R^{19}$, N, $NR^{18}$, $NR^{19}$, S, O, C=O, C=S, N=O, S=O, $S(O)_2$;
$R^{14}$, $R^{15}$, $R^{16}$, $R^{17}$, $R^{18}$ et $R^{19}$, independently represent hydrogen, —CN, —OH, —O-cycloalkyl, —O-cycloalkenyl, —O-cycloalkynyl, —$NH_2$, —$NR^{13}$-cycloalkyl, —$NR^{13}$-cycloalkenyl, —$NR^{13}$-cycloalkynyl, —S-cycloalkyl, —S-cycloalkenyl, —S-cycloalkynyl, —COOH, —C(O)$NH_2$, —$CF_3$, —$SO_2NH_2$, —$NHSO_2NH_2$, —NHC(O)$NH_2$, —OC(O)$NH_2$, halogen, alkyl, alkenyl, alkynyl, heteroalkyl, heteroalkenyl, heteroalkynyl, aryl, —O-aryl, —$NR^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$,
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$,
and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;

and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

$Q^2$, $Q^3$, $R^1$, $R^3$, $R^4$, $R^7$, $R^8$, $R^9$, $R^{10}$, $R^{11}$, $R^{13}$, $T^1$, $T^2$, $T^3$, $T^4$, $T^5$, $T^6$, $T^7$, $T^8$, $T^9$ and $T^{10}$ are defined as for the compounds of formula (A) including the relevant proviso.

Also advantageously, the invention provides compounds of formula (44) to (56):

(44)
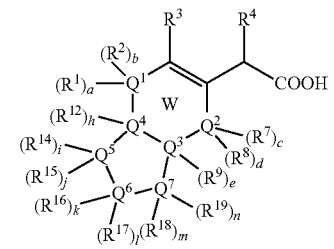

(45)
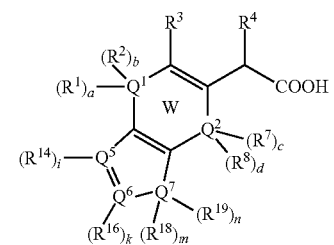

(46)
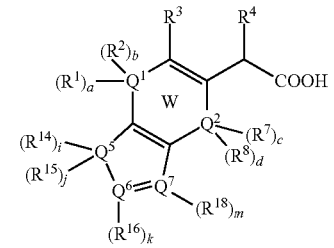

(47)
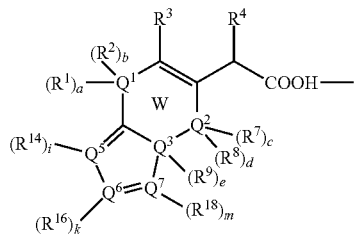

(48)
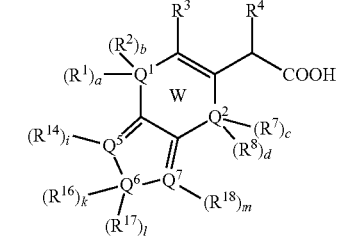

(49)
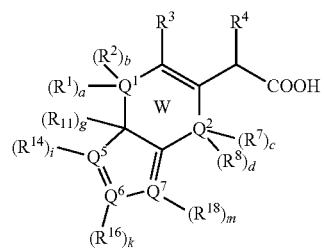

(50)
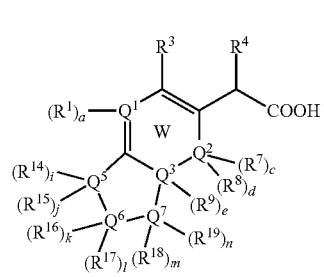

(51)
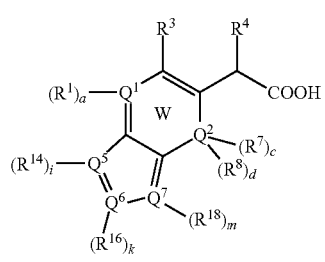

(52)
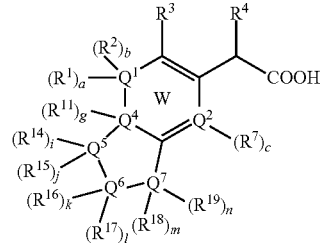

(53)
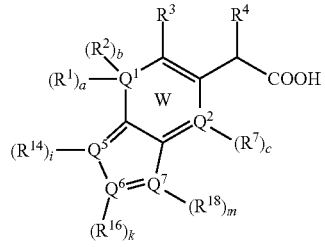

(54)
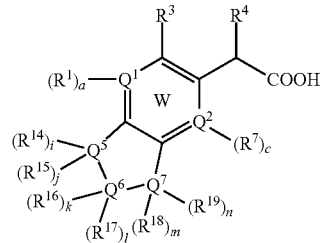

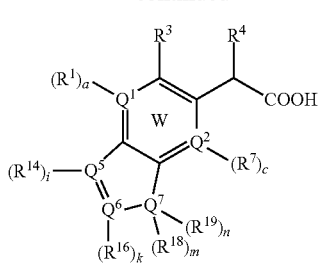

(55)

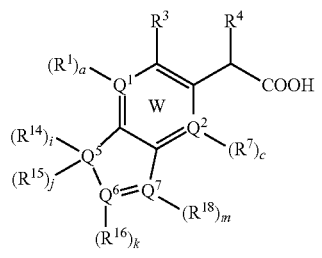

(56)

wherein:
W represents a fused, substituted, partially or totally unsaturated or aromatic carbo- or heterocycle;
a, b, c, d, e, g, i, j, k, l, m and n independently represent 0 or 1;
$Q^3$ represents $CR^9$, N;
$Q^4$ represents $CR^{11}$, N;
$Q^5$ represents $CR^{14}$, $CR^{15}$, $CR^{14}R^{15}$ $NR^{14}$, $NR^{15}$, S, O, C=O, C=S, N=O, S=O, $S(O)_2$;
$Q^6$, represents $CR^{16}$, $CR^{17}$, $CR^{16}R^{17}$, N, $NR^{16}$, $NR^{17}$, S, O, C=O, C=S, N=O, S=O, $S(O)_2$;
$Q^7$ represents $CR^{18}$, $CR^{19}$, $CR^{18}R^{19}$, N, $NR^{18}$, $NR^{19}$, S, O, C=O, C=S, N=O, S=O, $S(O)_2$;
$R^{14}$, $R^{15}$, $R^{16}$, $R^{17}$, $R^{18}$ et $R^{19}$, independently represent hydrogen, —CN, —OH, —O-cycloalkyl, —O-cycloalkenyl, —O-cycloalkynyl, —$NH_2$, —$NR^{13}$-cycloalkyl, —$NR^{13}$-cycloalkenyl, —$NR^{13}$-cycloalkynyl, —S-cycloalkyl, —S-cycloalkenyl, —S-cycloalkynyl, —COOH, —C(O)$NH_2$, —$CF_3$, —$SO_2NH_2$, —$NHSO_2NH_2$, —NHC(O)$NH_2$, —OC(O)$NH_2$, halogen, alkyl, alkenyl, alkynyl, heteroalkyl, heteroalkenyl, heteroalkynyl, aryl, —O-aryl, —$NR^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$,
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$,
and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;
and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;
$Q^1$, $Q^2$, $R^1$, $R^2$, $R^3$, $R^4$, $R^7$, $R^8$, $R^9$, $R^{11}$, $R^{13}$, $T^1$, $T^2$, $T^3$, $T^5$, $T^6$, $T^7$, $T^8$, $T^9$ and $T^{10}$ are defined as for the compounds of formula (A).

Also advantageously, the invention provides compounds of formula (57) to (72):

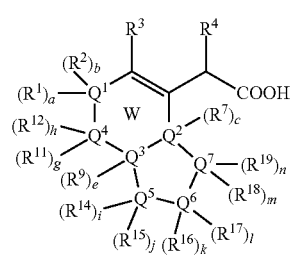

(57)

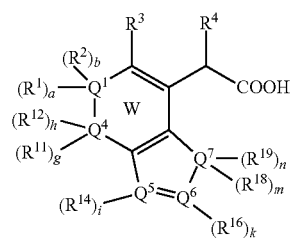

(58)

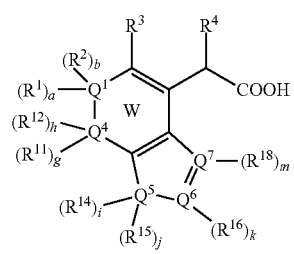

(59)

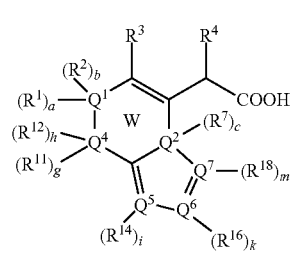

(60)

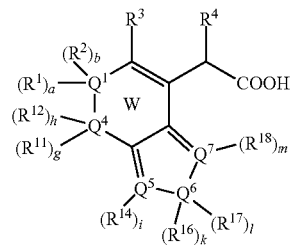

(61)

-continued

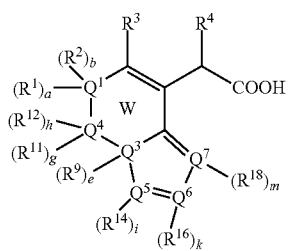
(62)

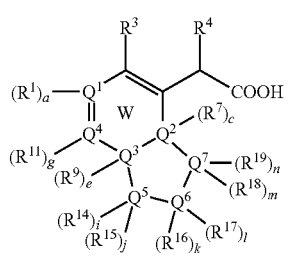
(63)

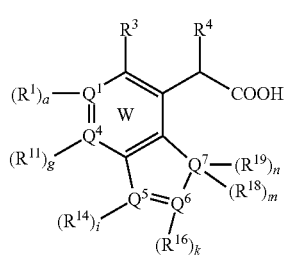
(64)

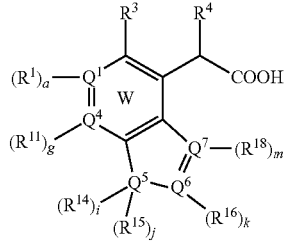
(65)

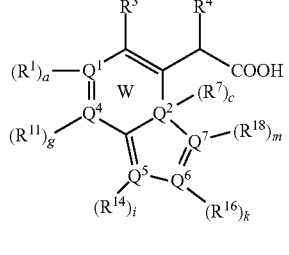
(66)

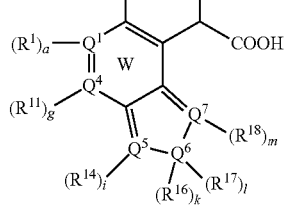
(67)

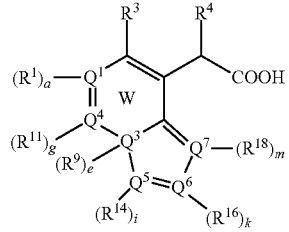
(68)

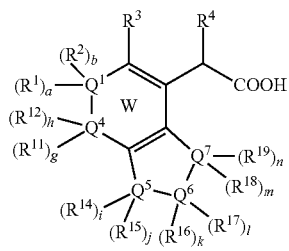
(69)

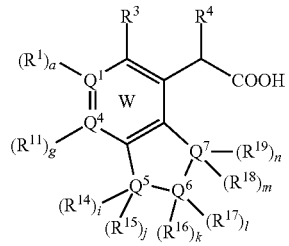
(70)

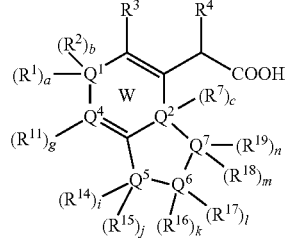
(71)

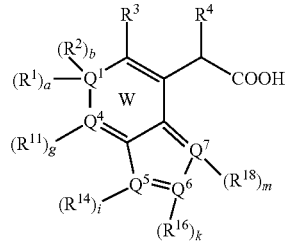
(72)

wherein:
W represents a fused, substituted, partially or totally unsaturated or aromatic carbo- or heterocycle;
a, b, c, e, g, h, i, j, k, l, m and n independently represent 0 or 1;
$Q^2$ represents $CR^7$, N;
$Q^3$ represents $CR^9$, N;
$Q^5$ represents $CR^{14}$, $CR^{15}$, $CR^{14}R^{15}$, N, $NR^{14}$, $NR^{15}$, S, O, C=O, C=S, N=O, S=O, $S(O)_2$;
$Q^6$, represents $CR^{16}$, $CR^{17}$, $CR^{16}R^{17}$, N, $NR^{16}$, $NR^{17}$, S, O, C=O, C=S, N=O, S=O, $S(O)_2$;
$Q^7$ represents $CR^{18}$, $CR^{19}$, $CR^{18}R^{19}$, N, $NR^{18}$, $NR^{19}$, S, O, C=O, C=S, N=O, S=O, $S(O)_2$;
$R^{14}$, $R^{15}$, $R^{16}$, $R^{17}$, $R^{18}$ et $R^{19}$, independently represent hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COON, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one T$^1$, wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or S(O)$_2$, and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;

and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;

Q$^1$, Q$^4$, R$^1$, R$^2$, R$^3$, R$^4$, R$^7$, R$^9$, R$^{11}$, R$^{12}$, R$^{13}$, T$^1$, T$^2$, T$^3$, T$^4$, T$^5$, T$^6$, T$^7$, T$^9$ and T$^{10}$ are defined as for the compounds of formula (A).

Preferably, the invention also provides compounds of formula (39A), (40A), (41A), (54A), (55A), (56A), (64A), (65A) or (70A)

(39A)

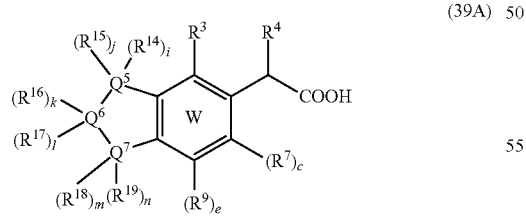

(40A)

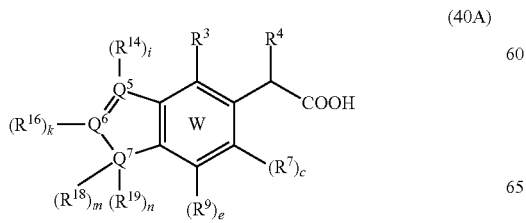

(41A)

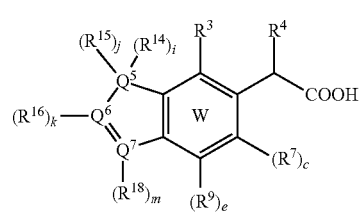

(54A)

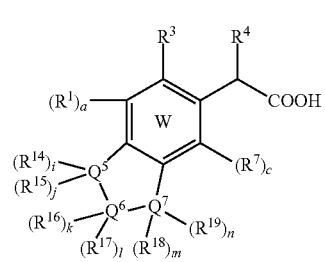

(55A)

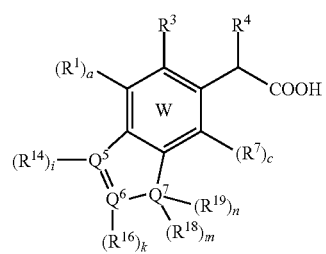

(56A)

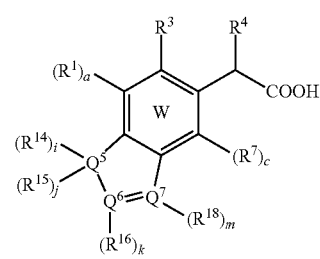

(64A)

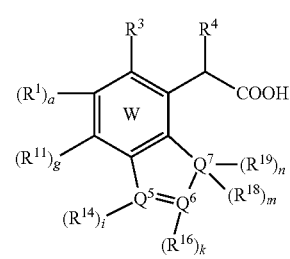

(65A)

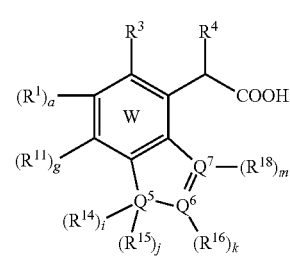

-continued

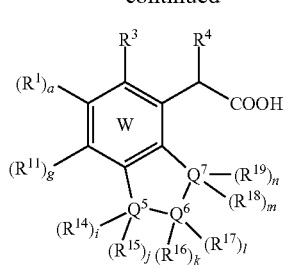

(70A)

wherein:
W represents a fused, substituted, aromatic carbo- or heterocycle;
a, c, e, g, i, j, k, l, m and n independently represent 0 or 1;
$Q^5$ represents $CR^{14}$, $CR^{15}$, $CR^{14}R^{15}$, $NR^{14}$, $NR^{15}$, S, O, C=O, C=S, N=O, S=O, $S(O)_2$;
$Q^6$, represents $CR^{16}$, $CR^{17}$, $CR^{16}R^{17}$, N, $NR^{16}$, $NR^{17}$, S, O, C=O, C=S, N=O, S=O, $S(O)_2$;
$Q^7$ represents $CR^{18}$, $CR^{19}$, $CR^{18}R^{19}$, N, $NR^{18}$, $NR^{19}$, S, O, C=O, C=S, N=O, S=O, $S(O)_2$;
$R^{14}$, $R^{15}$, $R^{16}$, $R^{17}$, $R^{18}$ et $R^{19}$, independently represent hydrogen, —CN, —OH, —O-cycloalkyl, —O-cycloalkenyl, —O-cycloalkynyl, —$NH_2$, —$NR^{13}$-cycloalkyl, —$NR^{13}$-cycloalkenyl, —$NR^{13}$-cycloalkynyl, —S-cycloalkyl, —S-cycloalkenyl, —S-cycloalkynyl, —COON, —C(O)$NH_2$, —$CF_3$, —$SO_2NH_2$, —$NHSO_2NH_2$, —NHC(O)$NH_2$, —OC(O)$NH_2$, halogen, alkyl, alkenyl, alkynyl, heteroalkyl, heteroalkenyl, heteroalkynyl, aryl, —O-aryl, —$NR^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —$NR^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl, non-substituted or substituted by at least one $T^1$,
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, heterocyclyl-heteroalkynyl can be oxidized to form a C=O, C=S, N=O, N=S, S=O or $S(O)_2$,
and wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one further cycle;
and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, heterocyclyl-alkynyl group can include one or more heteroatoms, selected from O, S and N, in the alkyl, alkenyl, alkynyl moiety;
$R^1$, $R^3$, $R^4$, $R^7$, $R^9$, $R^{11}$, $R^{13}$, $T^1$, $T^2$, $T^3$, $T^4$, $T^5$, $T^6$, $T^7$, $T^8$, $T^9$ and $T^{10}$ are defined as for the compounds of formula (A).

As an example of formula (40), the invention provides a compound of formula (40A-1):

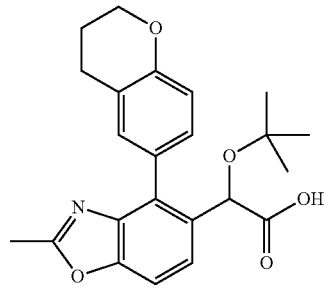

(39A-1)

Combination Therapy

Combination therapy is contemplated wherein a compound according to the invention, or a pharmaceutically acceptable salt thereof, is co-administered with at least one further antiviral agent. The additional agents may be combined with compounds according to the invention to create a single dosage form. Alternatively these additional agents may be separately administered, concurrently or sequentially, as part of a multiple dosage form.

When the pharmaceutical composition of this invention comprises a combination of a compound according to the invention, or a pharmaceutically acceptable salt thereof, and at least one further antiviral agent, both the compound and the additional agent should be present at dosage levels of between about 10 to 100%, and more preferably between about 10 and 80% of the dosage normally administered in a monotherapy regimen.

In the case of a synergistic interaction between the compound according to the invention and the additional antiviral agent or agents, the dosage of any or all of the active agents in the combination may be reduced compared to the dosage normally administered in a monotherapy regimen.

Antiviral agents contemplated for use in such combination therapy include agents (compounds or biologicals) that are effective to inhibit the formation and/or replication of a virus in a mammal, including but not limited to agents that interfere with either host or viral mechanisms necessary for the formation and/or replication of a virus in a mammal. Such agents can be selected from:

NRTIs (nucleoside or nucleotide reverse transcriptase inhibitors; including but not limited to zidovudine, didanosine, zalcitabine, stavudine, lamivudine, emtricitabine, abacavir, and tenofovir);

NNRTIs (non-nucleoside reverse transcriptase inhibitors; including but not limited to nevirapine, delavirdine, efavirenz, etravirine, rilpivirine and BILR 355);

protease inhibitors (including but not limited to ritonavir, tipranavir, saquinavir, nelfinavir, indinavir, amprenavir, fosamprenavir, atazanavir, lopinavir, darunavir and brecanavir);

entry inhibitors including but not limited to CCR5 antagonists, such as maraviroc (UK-427,857), vicriviroc (SCH-D, SCH-417690) and TAK-652), CXCR4 antagonists such as AMD-11070, fusion inhibitors (including but not limited to enfuvirtide (T-20)) and others (including but not limited to BMS-488043);

integrase inhibitors (including but not limited to MK-0518, c-1605, BMS-538158 and GS 9137);

TAT inhibitors;

maturation inhibitors (including but not limited to bevirimat (PA-457)); and immunomodulating agents (including but not limited to levamisole).

Furthermore, a compound according to the invention can be used with at least one other compound according to the invention or with one or more antifungal or antibacterial agents (including but not limited to fluconazole).

Therefore, according to one embodiment, the pharmaceutical composition of this invention further comprises one or more antiviral agents.

A further embodiment provides the pharmaceutical composition of this invention wherein the additional antiviral agent comprises at least one NNRTI.

According to another embodiment of the pharmaceutical composition of this invention, the additional antiviral agent comprises at least one NRTI.

According to yet another embodiment of the pharmaceutical composition of this invention, the additional antiviral agent comprises at least one protease inhibitor.

According to still another embodiment of the pharmaceutical composition of this invention, the additional antiviral agent comprises at least one entry inhibitor.

According to a further embodiment of the pharmaceutical composition of this invention, the additional antiviral agent comprises at least one integrase inhibitor.

EXAMPLES

The following examples are provided for the purpose of illustrating the present invention and by no means should be interpreted to limit the scope of the present invention.

The first part represents the preparation of the compounds (intermediates and final compounds) whereas the second part describes the evaluation of antiviral activity of compounds according to the invention.

Abbreviations or symbols used herein include:
DMSO: dimethylsulfoxide
MS: Mass Spectrometry
NMR: Nuclear Magnetic Resonance Spectroscopy
s: singlet
d: doublet
t: triplet
q: quadruplet
dd: doubled doublet
dt: doubled triplet
m: massif
TLC: Thin Layer Chromatography Example 1: Synthesis of 2-(tert-butoxy)-2-[2-(3,4-dihydro-2H-1-benzopyran-6-yl)phenyl]acetic acid

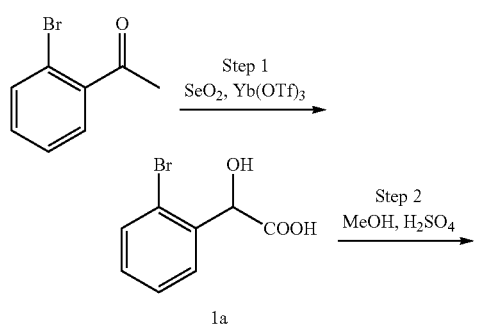

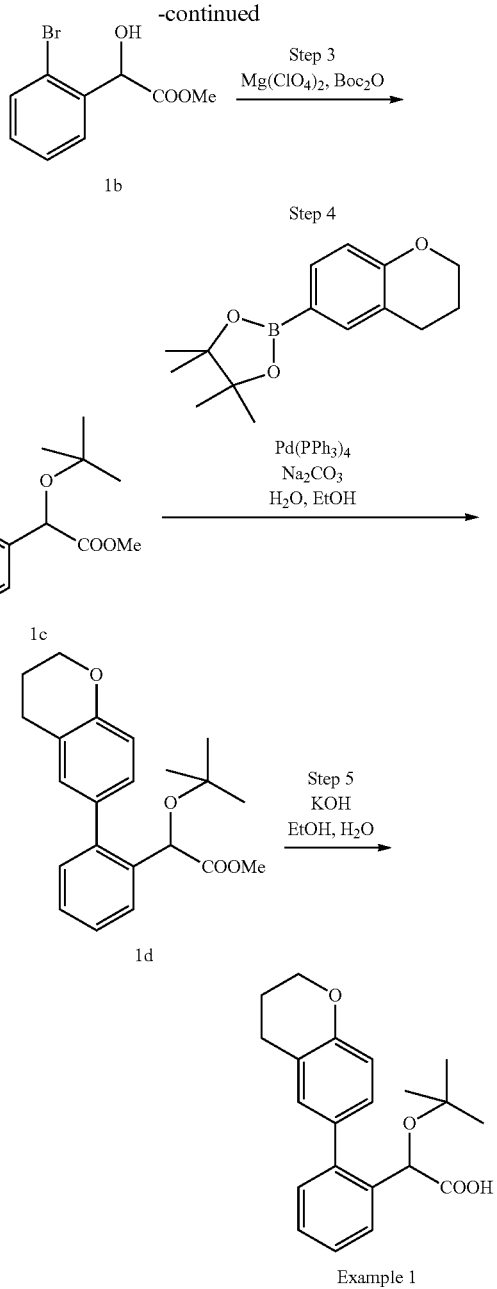

Example 1

Step 1: Preparation of intermediate 2-(2-bromophenyl)-2-hydroxyacetic acid (1a)

To a solution of 2-bromoacetophenone (3.0 g, 15 mmol) in 1,4-dioxane (45 mL) and water (15 mL) was added selenium dioxide (3.34 g, 30.1 mmol) and ytterbium(III) trifluoromethanesulfonate hydrate (0.61 g, 0.98 mmol). The mixture was heated at 90° C. for 18 hours. The mixture was filtered at room temperature through Celite®. The filtrate was concentrated in vacuo. To the residue was added a 0.25M aqueous solution of sodium hydroxide (150 mL). The resulting solution was extracted with dichloromethane (2×60 mL). The aqueous layer was acidified with concentrated hydrochloric acid until pH 1 and extracted with ethyl acetate (2×60 mL). This organic layer was dried over sodium sulfate and evaporated to dryness to provide 2-(2-bromophenyl)-2-hydroxyacetic acid (1a) (2.32 g, 10 mmol, 66%) as a yellow solid which was used without further purification.

¹H NMR (300 MHz, CDCl₃) δ 5.67 (s, 1H), 7.21 (dt, J=1.8, 7.2 Hz, 1H), 7.34 (dt, J=1.2, 7.5 Hz, 1H), 7.42 (dd, J=1.8, 7.8 Hz, 1H), 7.59 (dd, J=1.2, 8.1 Hz, 1H).

Step 2: Preparation of intermediate methyl 2-(2-bromophenyl)-2-hydroxyacetate (1b)

A solution of 2-(2-bromophenyl)-2-hydroxyacetic acid (1a) (2.32 g, 10 mmol) and sulfuric acid (54 µL, 1 mmol) in methanol (50 mL) was refluxed for 3.5 hours. The mixture was concentrated in vacuo. A saturated aqueous solution of sodium bicarbonate (30 mL) was added to the residue and the product was extracted with ethyl acetate (2×20 mL). The organic layer was washed with brine, dried over sodium sulfate and evaporated to dryness. The residue was purified by flash chromatography on silica gel (cyclohexane/ethyl acetate 85/15) to provide methyl 2-(2-bromophenyl)-2-hydroxyacetate (1b) (2.07 g, 8.44 mmol, 84%) as a pale yellow solid.

¹H NMR (300 MHz, CDCl₃) δ 3.56 (d, J=4.8 Hz, 1H), 3.77 (s, 3H), 5.58 (d, J=4.8 Hz, 1H), 7.19 (dt, J=2.1, 7.2 Hz, 1H), 7.30-7.40 (m, 2H), 7.58 (dd, J=1.0, 8.1 Hz, 1H).

Step 3: Preparation of intermediate methyl 2-(2-bromophenyl)-2-(tert-butoxy)acetate (1c)

To a solution of methyl 2-(2-bromophenyl)-2-hydroxyacetate (1b) (256 mg, 1.04 mmol) in anhydrous dichloromethane (3 mL) under nitrogen atmosphere were added magnesium perchlorate (23 mg, 0.1 mmol) and di-tert-butyl dicarbonate (520 mg, 2.38 mmol). The mixture was refluxed for 24 hours. Water (10 mL) was added and layers were separated. The organic layer was extracted with dichloromethane (2×10 mL). The organic layers were dried over sodium sulfate and concentrated in vacuo. The residue was purified by flash chromatography on silica gel (cyclohexane/ethyl acetate 90/10) to provide methyl 2-(2-bromophenyl)-2-(tert-butoxy)acetate (1c) (84 mg, 0.28 mmol, 26%) as a white solid.

¹H NMR (300 MHz, CDCl₃) δ 1.23 (s, 9H), 3.69 (s, 3H), 5.48 (s, 1H), 7.15 (dt, J=1.8, 7.8 Hz, 1H), 7.33 (t, J=7.8 Hz, 1H), 7.52 (d, J=8.1 Hz, 1H), 7.65 (dd, J=1.5, 7.8 Hz, 1H).

Step 4: Preparation of intermediate methyl 2-(tert-butoxy)-2-[2-(3,4-dihydro-2H-1-benzopyran-6-yl)phenyl]acetate (1d)

To a solution of methyl 2-(2-bromophenyl)-2-(tert-butoxy)acetate (1c) (60 mg, 0.20 mmol) in toluene (1.1 mL) was added sodium carbonate (84 mg, 0.79 mmol), water (0.48 mL), palladium tetrakis(triphenylphospine) (12 mg, 0.01 mmol) and a solution of 6-(4,4,5,5-tetramethyl-1,3,2-dioxaborolan-2-yl)chroman (93 mg, 0.36 mmol) in ethanol (0.55 mL). The mixture was refluxed for 18 hours. The mixture was then cooled at room temperature and water (5 mL) was added. The aqueous layer was extracted with toluene (2×5 mL). The organic layers were washed with a 1M sodium hydroxide aqueous solution (5 mL), dried over sodium sulfate and concentrated in vacuo. The residue was purified by flash chromatography on silica gel (cyclohexane/ethyl acetate 90/10) to provide methyl 2-(tert-butoxy)-2-[2-(3,4-dihydro-2H-1-benzopyran-6-yl)phenyl]acetate (1d) (43 mg, 0.12 mmol, 60%) as a white solid. ¹H NMR (400 MHz, CDCl₃) 50.99 (s, 9H), 2.04-2.07 (m, 2H), 2.80-2.86 (m, 2H), 3.68 (s, 3H), 4.24 (dd, J=4.8, 6.0 Hz, 2H), 5.21 (s, 1H), 6.85 (d, J=8.4 Hz, 1H), 7.07 (d, J=1.6 Hz, 1H), 7.12 (dd, J=1.6, 8.4 Hz, 1H), 7.21 (dd, J=1.6, 7.2 Hz, 1H), 7.28-7.36 (m, 2H), 7.66 (dd, J=1.6, 7.2 Hz, 1H).

MS m/z ([M+Na]⁺) 377.

Step 5: Preparation of 2-(tert-butoxy)-2-[2-(3,4-dihydro-2H-1-benzopyran-6-yl)phenyl]acetic acid A solution of methyl 2-(tert-butoxy)-2-[2-(3,4-dihydro-2H-1-benzopyran-6-yl)phenyl]acetate (1d) (42 mg, 0.12 mmol) and potassium hydroxide (27 mg, 0.47 mmol) in ethanol (6 mL) and water (2 mL) was refluxed for 90 minutes. The mixture was concentrated in vacuo. Water (10 mL) was added to the residue and the solution was extracted with diethyl ether (10 mL). The aqueous layer was acidified with concentrated hydrochloric acid until pH 1 and was extracted with dichloromethane (2×5 mL). The organic layer was dried over sodium sulfate and evaporated to dryness to provide 2-(tert-butoxy)-2-[2-(3,4-dihydro-2H-1-benzopyran-6-yl)phenyl]acetic acid (example 1) (35 mg, 0.10 mmol, 87%) as a white solid.

¹H NMR (400 MHz, DMSO-d₆) δ 0.90 (s, 9H), 1.93-1.96 (m, 2H), 2.74-2.80 (m, 2H), 4.17 (t, J=5.2 Hz, 2H), 5.06 (s, 1H), 6.82 (d, J=8.4 Hz, 1H), 7.09-7.13 (m, 2H), 7.17-7.20 (m, 1H), 7.30-7.35 (m, 2H), 7.50-7.52 (m, 1H), 12.61 (broad s, 1H).

MS m/z ([M−H]⁻) 339.

Example 2: Synthesis of 2-(tert-butoxy)-2-(4-cyclohexyl-2-methylquinolin-3-yl)acetic acid

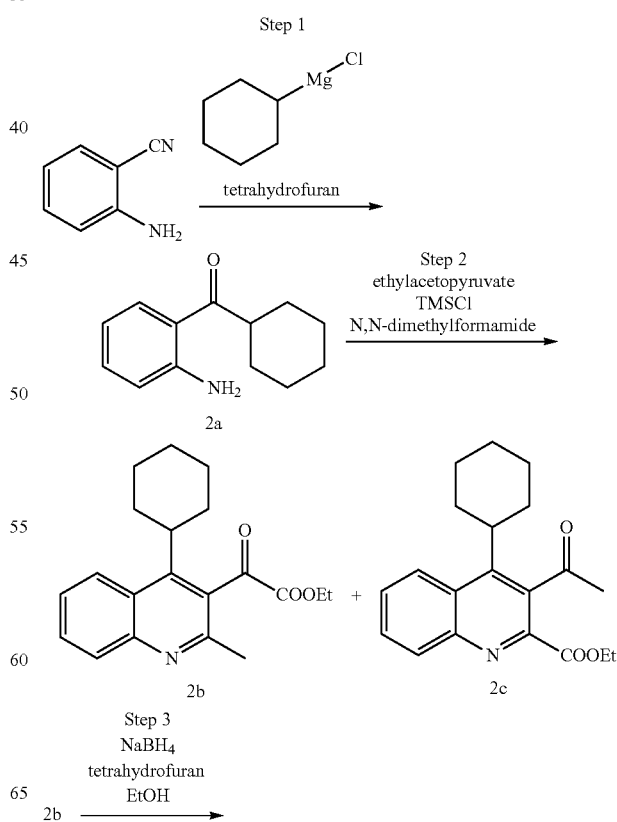

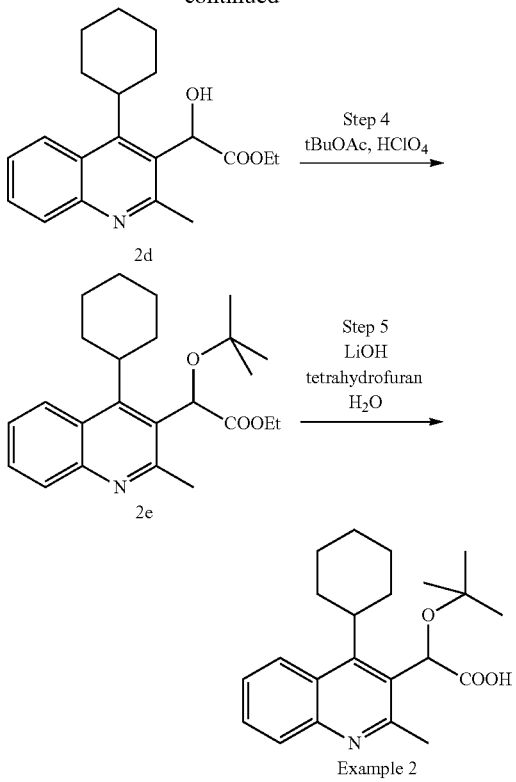

Example 2

Step 1: Preparation of Intermediate 2-Cyclohexanecarbonylaniline (2a)

Cyclohexylmagnesium chloride (21.16 mL, 1M in methyltetrahydrofuran, 21.16 mmol) was added to a solution of 2-aminobenzonitrile (1 g, 8.46 mmol) in tetrahydrofuran (17 mL) at −10° C. over 45 minutes. Then the reaction was allowed to warm to room temperature and to stir at this temperature for 18 hours. The reaction was quenched by slow addition of a 6N hydrochloric acid aqueous solution at 0° C. and made basic by the addition of a 5N sodium hydroxide aqueous solution at room temperature. The organic layer was separated and the aqueous layer was extracted with ethyl acetate for three times. The combined organic layers were washed with brine, dried over sodium sulfate and concentrated in vacuo. The crude product was purified by flash chromatography on silica gel (cyclohexane/ethyl acetate 95/5) to afford the desired product (2a) as a light orange powder (981.2 mg, 4.83 mmol, 57%).

$^1$H NMR (400 MHz, DMSO-$d_6$) δ 1.19-1.25 (m, 1H), 1.29-1.47 (m, 4H), 1.62-1.80 (m, 5H), 3.28-3.37 (m, 1H), 6.53 (t, J=7.0 Hz, 1H), 6.75 (d, J=8.4 Hz, 1H), 7.15-7.25 (m, 3H), 7.78 (d, J=8.2 Hz, 1H).

MS m/z [M+H]$^+$) 204.

Step 2: Preparation of intermediate ethyl 2-(4-cyclohexyl-2-methylquinolin-3-yl)-2-oxoacetate (2b)

2-cyclohexanecarbonylaniline (2a) (544 mg, 2.68 mmol) and ethylacetopyruvate (423.2 mg, 2.68 mmol) were placed in a tube and dissolved in N,N-dimethylformamide (6.5 mL). Trimethylsilyl chloride (1.36 mL, 10.70 mmol) was added dropwise to the solution under an argon atmosphere. The tube was thoroughly closed and heated on a reactor at 100° C. for 1 hour. After cooling to room temperature (CAUTION: excessive pressure inside), a saturated sodium bicarbonate aqueous solution and water were added and the mixture was extracted three times with ethyl acetate. The combined organic extracts were washed with brine, dried over sodium sulfate, filtered and concentrated in vacuo. The residue was purified by 4 preparative TLC, using dichloromethane/methanol (99/1) as the eluent, to afford the desired product (2b) (with a small quantity of by-product (2c)) as a colorless oil (201 mg, 0.62 mmol, 23%).

$^1$H NMR (400 MHz, CDCl$_3$) δ 1.38-1.47 (m, 7H), 1.81-2.00 (m, 5H), 2.18-2.40 (m, 1H), 2.60 (s, 3H), 4.45 (q, J=7.2 Hz, 2H), 7.52-7.61 (m, 1H), 7.75 (t, J=7.5 Hz, 1H), 8.08 (d, J=8.2 Hz, 1H), 8.31 (d, J=8.3 Hz, 1H).

MS m/z [M+H]$^+$ 326

Step 3: Preparation of intermediate ethyl 2-(4-cyclohexyl-2-methylquinolin-3-yl)-2-hydroxyacetate (2d)

To a solution of ethyl 2-(4-cyclohexyl-2-methylquinolin-3-yl)-2-oxoacetate (2b) (190.8 mg, 0.586 mmol) in a mixture of tetrahydrofuran (4.7 mL) and ethanol (1.1 mL) at 0° C. was added sodium borohydride (19.85 mg, 0.525 mmol). The mixture was stirred at 0° C. for 2 hours. The mixture was partitioned between water and ethyl acetate, and the aqueous phase was acidified with a 1N hydrochloric acid aqueous solution until pH 5-6. The organic layer was washed with brine, dried over sodium sulfate, filtered and concentrated in vacuo. The residue was purified by preparative TLC, using dichloromethane/methanol (95/5) as the eluent to afford ethyl 2-(4-cyclohexyl-2-methylquinolin-3-yl)-2-hydroxyacetate (2d) as a yellow oil (134.3 mg, 0.41 mmol, 37%).

$^1$H NMR (400 MHz, CDCl$_3$) δ 1.23 (t, J=7.1 Hz, 3H), 1.31-1.70 (m, 4H), 1.82-2.10 (m, 5H), 2.22-2.38 (m, 1H), 2.86 (s, 3H), 3.24-3.36 (m, 1H), 4.17-4.38 (m, 2H), 5.79 (s, 1H), 7.43-7.51 (m, 1H), 7.63-7.72 (m, 1H), 8.03 (d, J=8.1 Hz, 1H), 8.46 (d, J=8.1 Hz, 1H).

MS m/z [M+H]$^+$ 328.

Step 4: Preparation of intermediate ethyl 2-(tert-butoxy)-2-(4-cyclohexyl-2-methylquinolin-3-yl) acetate (2e)

To a suspension of ethyl 2-(4-cyclohexyl-2-methylquinolin-3-yl)-2-hydroxyacetate (3d) (134 mg, 0.409 mmol) in tert-butylacetate (4.5 mL) at −10° C. was added perchloric acid (103 μL). The mixture was stirred at −5° C. for 2 hours. The mixture was then basified with a saturated aqueous solution of sodium bicarbonate (5 mL) until pH 6. The aqueous layer was extracted with ethyl acetate. The organic layer was washed with brine, dried over sodium sulfate, filtered and concentrated in vacuo. The residue was purified by preparative TLC, using cyclohexane/ethyl acetate (70/30) to afford ethyl 2-(tert-butoxy)-2-(4-cyclohexyl-2-methylquinolin-3-yl)acetate (3e) as a solid (27 mg, 0.07 mmol, 17.2%).

$^1$H NMR (400 MHz, CDCl$_3$) δ 1.20 (t, J=7.12 Hz, 3H), 8.48 (d, J=8.6 Hz, 1H), 8.01 (d, J=8.3 Hz, 1H), 7.64 (t, J=8.2 Hz, 1H), 7.46 (t, J=8.3 Hz, 1H), 4.16 (m, 2H), 3.85 (m, 1H), 2.94 (s, 3H), 2.26 (m, 2H), 1.95 (m, 4H), 1.53 (m, 5H), 1.26 (s, 9H).

MS m/z [M+H]$^+$ 384.

Step 5: Preparation of 2-(tert-butoxy)-2-(4-cyclohexyl-2-methylquinolin-3-yl)acetic acid Lithium hydroxide (10.1 mg, 0.42 mmol) was added to a solution of ethyl 2-(tert-butoxy)-2-(4-cyclohexyl-2-methylquinolin-3-yl)acetate (2e) (27 mg, 0.07 mmol) in a mixture of tetrahydrofuran (0.91 mL) and water (0.73 mL). The mixture was heated at 70° C. for 4 hours. Additional lithium hydroxide (5 mg, 0.2 mmol) was added and the heating continued at 70° C. overnight. The mixture was concentrated in vacuo. The residue was partitioned between water and dichloromethane. The aqueous layer was acidified with a 1N hydrochloric acid solution and extracted with dichloromethane three times. The organic layer was washed with brine (10 mL), dried over sodium sulfate, filtered and evaporated to dryness to afford the desired product (example 2) as a white powder (26 mg, 0.07 mmol, 99%).

$^1$H NMR (400 MHz, CDCl$_3$) δ 1.28 (s, 9H), 1.39-1.59 (m, 3H), 1.62-2.07 (m, 4H), 2.10-2.42 (m, 3H), 2.95 (s, 3H), 3.39 (broad s, 1H), 5.68 (s, 1H), 7.47 (t, J=7.7 Hz, 1H), 7.66 (t, J=7.9 Hz, 1H), 8.04 (d, J=8.5 Hz, 1H), 8.46 (d, J=8.6 Hz, 1H).

MS m/z [M+H]$^+$ 356.

Example 3: Synthesis of 2-(tert-butoxy)-2-(4-tert-butyl-2-methylquinolin-3-yl)acetic acid

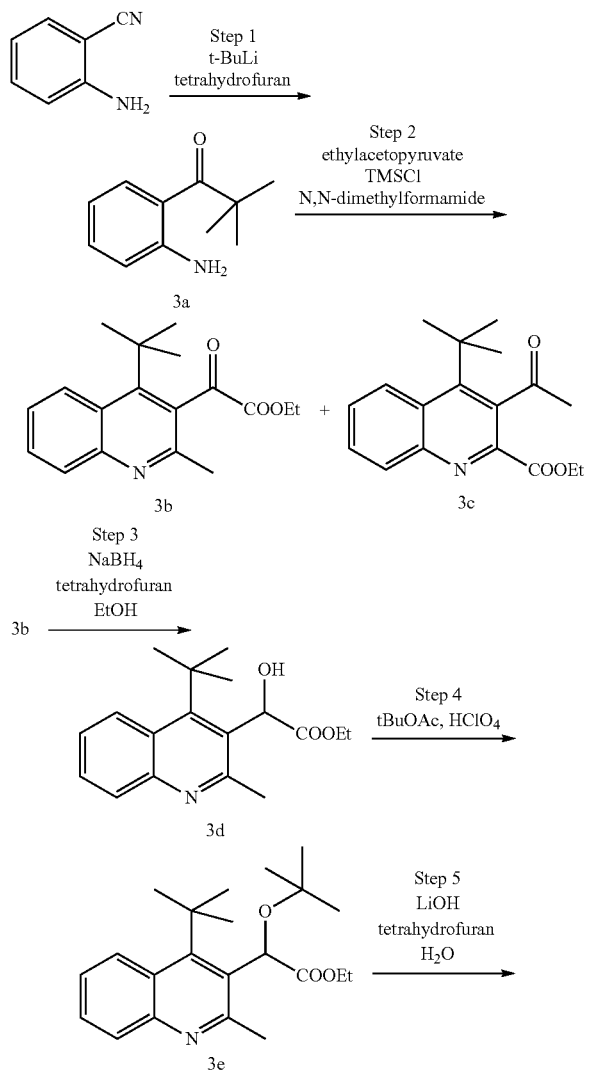

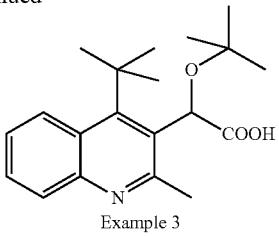

Example 3

Step 1: Preparation of intermediate 1-(2-aminophenyl)-2,2-dimethylpropan-1-one (3a)

Tert-butyllithium (13.23 mL, 1.6M in pentane, 21.16 mmol) was added to a solution of 2-aminobenzonitrile (1 g, 8.46 mmol) in anhydrous tetrahydrofuran (20 mL) at −5° C. over 30 minutes. Then the reaction was allowed to warm to room temperature and to stir at this temperature for 18 hours. The reaction was quenched by slow addition of a 6N hydrochloric acid aqueous solution at 0° C. and made basic by the addition of a 1N sodium hydroxide aqueous solution at room temperature. The organic layer was separated and the aqueous layer was extracted with ethyl acetate for three times. The combined organic layers were washed with brine, dried over sodium sulfate and concentrated in vacuo. The residue was purified by 4 preparative TLC, using cyclohexane/ethyl acetate (80/20) as the eluent, to afford the desired ketone (3a) as a yellow oil (329 mg, 1.86 mmol, 22%).

$^1$H NMR (400 MHz, CDCl$_3$) δ 1.39 (s, 9H), 5.66 (broad s, 2H), 6.67 (dt, J=1.2, 7.2 Hz, 1H), 6.71 (dd, J=1.0, 8.2 Hz, 1H), 7.23 (dt, J=1.5, 7.1 Hz, 1H), 7.82 (dd, J=1.4, 8.1 Hz, 1H).

MS m/z [M+H]$^+$ 178.

Step 2: Preparation of intermediate ethyl 2-(4-tert-butyl-2-methylquinolin-3-yl)-2-oxoacetate (3b)

1-(2-Aminophenyl)-2,2-dimethylpropan-1-one (3a) (329 mg, 1.86 mmol) and ethylaceto-pyruvate (293.5 mg, 1.86 mmol) were placed in a tube and dissolved in N,N-dimethylformamide (4.4 mL). Trimethylsilyl chloride (0.942 mL, 7.42 mmol) was added dropwise to the solution under an argon atmosphere. The tube was thoroughly closed and heated on a reactor at 100° C. for 1 hour. After cooling to room temperature (CAUTION: excessive pressure inside),), a saturated sodium bicarbonate aqueous solution and water were added and the mixture was extracted three times with ethyl acetate. The combined organic extracts were washed with brine, dried over sodium sulfate, filtered and concentrated in vacuo. The residue was purified by 2 preparative TLC, using cyclohexane/ethyl acetate (70/30) as the eluent, to afford the mixture of the 2 isomeric compounds (3b) and (3c) with a respective ratio 40/60 as an orange oil (318.8 mg, 1.06 mmol, 57.3%).

$^1$H NMR (400 MHz, CDCl$_3$) isomer (3b) S 1.41 (t, J=7.1 Hz, 3H), 1.65 (s, 9H), 2.52 (s, 3H), 4.46 (q, J=7.1 Hz, 2H), 7.55 (dt, J=1.4, 7.1 Hz, 1H), 7.71 (dt, J=1.2, 7.0 Hz, 1H), 8.08 (dd, J=1.0, 8.2 Hz, 1H), 8.48 (d, J=8.2 Hz, 1H).

MS m/z [M+H]$^+$ 300.

$^1$H NMR (400 MHz, CDCl$_3$) isomer (3c) δ 1.47 (t, J=7.1 Hz, 3H), 1.73 (s, 9H), 2.79 (s, 3H), 4.50 (q, J=7.1 Hz, 2H), 7.64 (dt, J=1.5, 7.2 Hz, 1H), 7.75 (dt, J=1.2, 7.0 Hz, 1H), 8.25 (dd, J=1.1, 8.4 Hz, 1H), 8.52 (d, J=8.2 Hz, 1H).

MS m/z [M+H]$^+$ 300.

Step 3: Preparation of intermediate ethyl 2-(4-tert-butyl-2-methylquinolin-3-yl)-2-hydroxyacetate (3d)

To a solution of ethyl 2-(4-tert-butyl-2-methylquinolin-3-yl)-2-oxoacetate (3b) (318.8 mg, 1.065 mmol) in a mixture of tetrahydrofuran (7.8 mL) and ethanol (2 mL) at 0° C. was added sodium borohydride (36.3 mg, 0.958 mmol). The mixture was stirred at 0° C. for 1 hour. The mixture was partitioned between water and ethyl acetate. The aqueous phase was acidified with a 1N hydrochloric acid aqueous solution until pH 5-6. The organic layer was washed with brine, dried over sodium sulfate, filtered and concentrated in vacuo. The residue was purified by 2 preparative TLC, using dichloromethane/methanol (96/4) to afford ethyl 2-(4-tert-butyl-2-methylquinolin-3-yl)-2-hydroxyacetate (3d) (82.5 mg, 0.27 mmol, 65%).

$^1$H NMR (400 MHz, CDCl$_3$) δ 1.15 (t, J=7.1 Hz, 3H), 1.84 (s, 9H), 2.67 (s, 3H), 4.15-4.25 (m, 2H), 5.99 (s, 1H), 7.43 (dt, J=1.4, 7.1 Hz, 1H), 7.62 (dt, J=1.1, 7.0 Hz, 1H), 7.99 (d, J=8.6 Hz, 1H), 8.41 (d, J=8.8 Hz, 1H).

MS m/z [M+H]$^+$ 302.

Step 4: Preparation of intermediate ethyl 2-(tert-butoxy)-2-(4-tert-butyl-2-methylquinolin-3-yl)acetate (3e)

To a suspension of ethyl 2-(4-tert-butyl-2-methylquinolin-3-yl)-2-hydroxyacetate (3d) (82.5 mg, 0.274 mmol) in tert-butylacetate (2 mL) at −10° C. was added perchloric acid (54 μL). The reaction mixture was stirred at −10° C. for 3 hours. The mixture was then basified with a saturated aqueous solution of sodium bicarbonate (6 mL) until pH7. The aqueous layer was extracted with ethyl acetate. The organic layer was washed with brine, dried over sodium sulfate, filtered and concentrated in vacuo. The residue was purified by preparative TLC, using cyclohexane/ethyl acetate (70/30) to afford ethyl 2-(tert-butoxy)-2-(4-tert-butyl-2-methylquinolin-3-yl)acetate (3e) as a solid (31.1 mg, 0.09 mmol, 31.7%).

$^1$H NMR (400 MHz, CDCl$_3$) δ 1.11 (s, 9H), 1.32 (t, J=7.1 Hz, 3H), 1.79 (broad s, 9H), 2.80 (broad s, 3H), 4.31 (m, 2H), 6.20 (broad s, 1H), 7.42 (t, J=7.2 Hz, 1H), 7.59 (t, J=7.2 Hz, 1H), 7.98 (d, J=7.8 Hz, 1H), 8.41 (d, J=8.5 Hz, 1H).

MS m/z [M+H]$^+$ 358.

Step 5: Preparation of 2-(tert-butoxy)-2-(4-tert-butyl-2-methylquinolin-3-yl)acetic acid A solution of ethyl 2-(tert-butoxy)-2-(4-tert-butyl-2-methylquinolin-3-yl)acetate (3e) (11 mg, 0.031 mmol) and potassium hydroxide (34.5 mg, 0.62 mmol) in a mixture of water (0.6 mL) and ethanol (0.2 mL) was stirred at 85° C. overnight. The reaction mixture was partitioned between water and dichloromethane. The aqueous layer was acidified with a 1N hydrochloric acid solution and extracted with dichloromethane three times. The organic layer was washed with brine, dried over sodium sulfate, filtered and evaporated to dryness to afford the desired acid (example 3) as a yellow powder (5 mg, 0.015 mmol, 50%).

$^1$H NMR (400 MHz, CDCl$_3$) δ 0.87 (s, 9H), 1.44 (s, 9H), 2.21 (s, 3H), 5.28 (s, 1H), 6.77 (d, J=7.9 Hz, 1H), 7.05 (t, J=7.8 Hz, 1H), 7.20 (t, J=7.9 Hz, 1H), 7.43 (d, J=7.8 Hz, 1H).

MS m/z [M+H]$^+$ 330.

Example 4: Synthesis of 2-(tert-butoxy)-2-[2-(3,4-dihydro-2H-1-benzopyran-6-yl)-5-(dimethylamino)-4-phenoxyphenyl]acetic acid

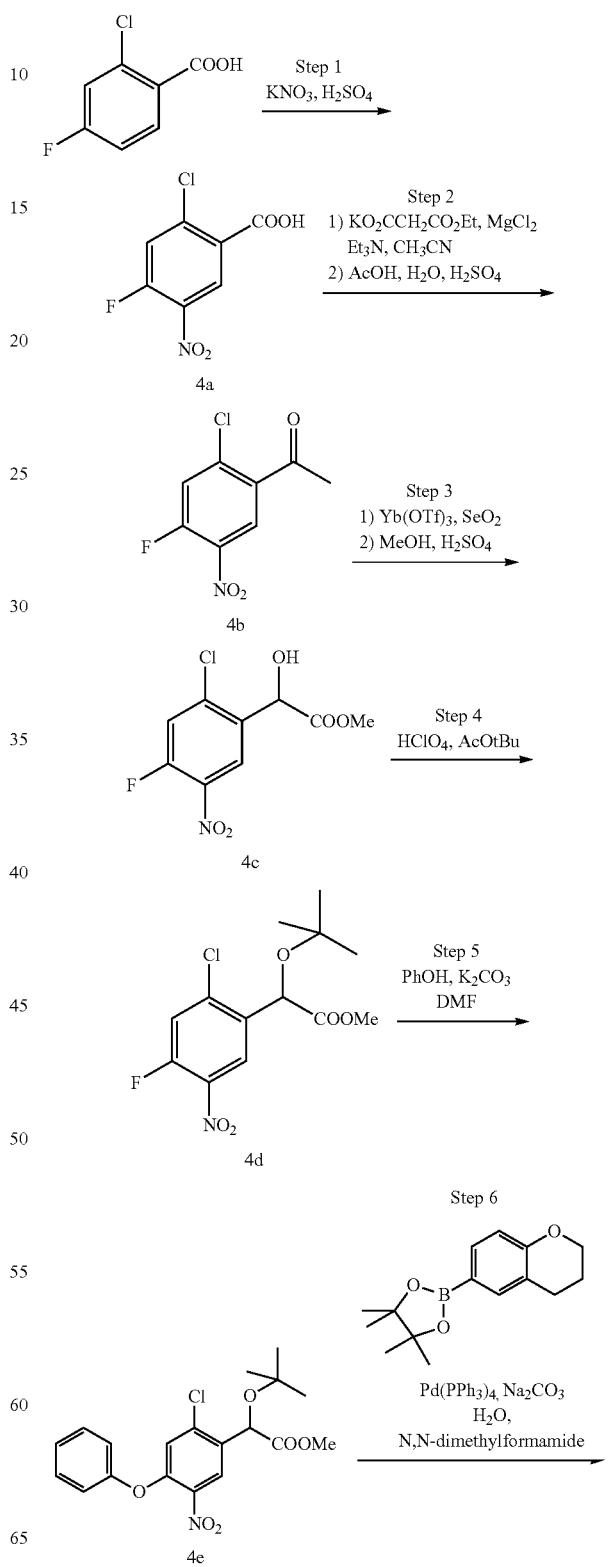

-continued

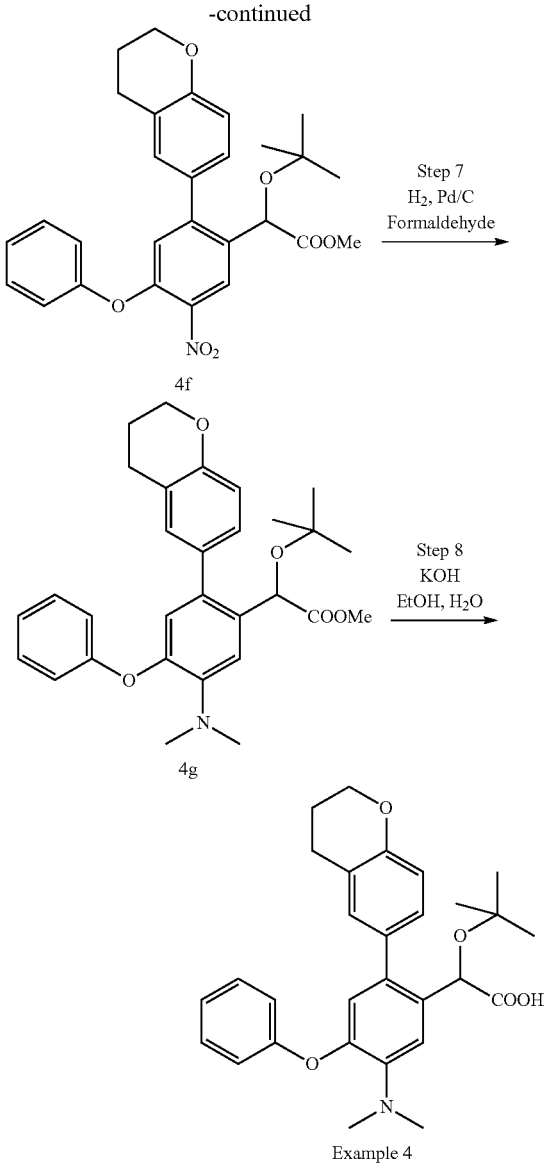

Example 4

Step 1: Preparation of intermediate 2-chloro-4-fluoro-5-nitrobenzoic acid (4a)

To a suspension of 2-chloro-4-fluorobenzoic acid (2.0 g, 11.46 mmol) in sulfuric acid (8 mL) was added potassium nitrate (1.27 g, 12.6 mmol) at 0° C. The mixture was stirred at room temperature for 4 hours then added to ice (150 mL). The mixture was stirred for 2 hours and filtered. The solid was washed with water and dried under reduce pressure over phosphorous pentoxide to provide 2-chloro-4-fluoro-5-nitrobenzoic acid (4a) as a white solid.

$^1$H NMR (400 MHz, DMSO-$d_6$) δ 8.03 (d, J=11.1 Hz, 1H), 8.55 (d, J=8.2 Hz, 1H).

MS m/z ([M–H]$^-$) 218, 220, ([2M–H]$^-$) 437.

Step 2: Preparation of intermediate 1-(2-chloro-4-fluoro-5-nitrophenyl)ethan-1-one (4b)

A suspension of 2-chloro-4-fluoro-5-nitrobenzoic acid (4a) (1.61 g, 7.33 mmol) in thionyl chloride (10 mL) was refluxed for 2 hours. After cooling to room temperature, the mixture was concentrated in vacuo. Toluene (2×10 mL) was added and the mixture was concentrated again to provide acyl chloride. To a suspension of potassium ethyl malonate (2.62 g, 15.4 mmol) in anhydrous acetonitrile (20 mL) under nitrogen atmosphere at 0° C. were successively added triethylamine (3.3 mL, 23.8 mmol) and magnesium chloride (1.61 g, 16.9 mmol). The mixture was stirred at room temperature for 2.5 hours and re-cooled before adding dropwise a solution of acyl chloride in acetonitrile (6 mL). The mixture was stirred at room temperature overnight, cooled at 0° C. and a 13% hydrochloric acid aqueous solution (10 mL) was added. Layers were separated. The organic layer was concentrated in vacuo to remove acetonitrile. The aqueous layer was extracted with ethyl acetate (2×15 mL). The combined organic layers extracts were washed with a saturated solution of sodium bicarbonate (20 mL), brine (20 mL), dried over sodium sulfate and concentrated in vacuo. The residue was then refluxed in a mixture of acetic acid (12 mL), water (7.5 mL) and sulfuric acid (1.5 mL) for 6 hours. After cooling to room temperature, the mixture was concentrated in vacuo to remove acetic acid. The residue was poured into ice water (50 mL) and extracted with ethyl acetate (3×15 mL). The organic layer was washed with a saturated solution of sodium bicarbonate (20 mL), a 2M sodium hydroxide aqueous solution (20 mL), dried over sodium sulfate and evaporated to dryness to provide 1-(2-chloro-4-fluoro-5-nitrophenyl)ethan-1-one (4b) (1.11 g, 5.1 mmol, 70%) as a yellow oil which was used without further purification.

$^1$H NMR (300 MHz, CDCl$_3$) δ 2.70 (s, 3H), 7.43 (d, J=10.2 Hz, 1H), 8.38 (d, J=8.1 Hz, 1H).

Step 3: Preparation of intermediate methyl 2-(2-chloro-4-fluoro-5-nitrophenyl)-2-hydroxyacetate (4c)

A mixture of 1-(2-chloro-4-fluoro-5-nitrophenyl)ethan-1-one (4b) (301 mg, 1.38 mmol), selenium dioxide (307 mg, 2.77 mmol) and ytterbium(III) trifluoromethanesulfonate (86 mg, 0.14 mmol) in a mixture of 1,4-dioxane (4 mL) and water (1.4 mL) was stirred at 90° C. for 24 hours. Selenium dioxide (307 mg, 2.77 mmol) and ytterbium(III) trifluoromethanesulfonate (86 mg, 0.14 mmol) were added again and the mixture was stirred at 90° C. for 24 hours. After cooling to room temperature, the mixture was filtered on Celite®. The filtrate was concentrated in vacuo. The residue was dissolved in 0.25M NaOH (15 mL) and extracted with diethyl ether (2×10 mL). The aqueous layer was acidified with 1M hydrochloric acid until pH 1 and extracted with ethyl acetate (2×15 mL). The organic layer was dried over sodium sulfate and concentrated in vacuo. The residue was refluxed in methanol (10 mL) in the presence of two drops of sulfuric acid for 3 hours. The mixture was concentrated in vacuo. The residue was partitioned between ethyl acetate (10 mL) and a saturated aqueous solution of sodium bicarbonate (10 mL). The aqueous layer was extracted with ethyl acetate (2×10 mL). The organic layer was dried over sodium sulfate and evaporated to dryness. The residue was purified by flash chromatography on silica gel (cyclohexane/ethyl acetate 80/20) to provide methyl 2-(2-chloro-4-fluoro-5-nitrophenyl)-2-hydroxyacetate (4c) (154 mg, 0.58 mmol, 42%) as a yellow oil.

$^1$H NMR (300 MHz, CDCl$_3$) δ 3.70 (d, J=3.9 Hz, 1H), 3.80 (s, 3H), 5.56 (d, J=3.9 Hz, 1H), 7.38 (d, J=10.2 Hz, 1H), 8.21 (d, J=7.8 Hz, 1H).

Step 4: Preparation of intermediate methyl 2-(tert-butoxy)-2-(2-chloro-4-fluoro-5-nitrophenyl)acetate (4d)

To a solution of methyl 2-(2-chloro-4-fluoro-5-nitrophenyl)-2-hydroxyacetate (4c) (154 mg, 0.58 mmol) in tert-butyl acetate (10 mL) at −20° C. was added perchloric acid (1.4 mL). The mixture was stirred at −20° C. for 2 hours and at room temperature for 1 hour before being poured into a saturated aqueous solution of sodium bicarbonate (30 mL). Water (60 mL) was added. The layers were separated and the aqueous layer was extracted with ethyl acetate (2×20 mL). The organic layers were dried over sodium sulfate and concentrated in vacuo. The residue was purified by flash chromatography on silica gel (cyclohexane/ethyl acetate: 90/10) to provide methyl 2-(tert-butoxy)-2-(2-chloro-4-fluoro-5-nitrophenyl)acetate (4d) (59 mg, 0.18 mmol, 31%) as a yellow oil.

$^1$H NMR (300 MHz, CDCl$_3$) δ 1.25 (s, 9H), 3.72 (s, 3H), 5.41 (s, 1H), 7.33 (d, J=10.2 Hz, 1H), 8.41 (d, J=8.1 Hz, 1H).

Step 5: Preparation of intermediate methyl 2-(tert-butoxy)-2-(2-chloro-5-nitro-4-phenoxy phenyl)acetate (4e)

To a solution of methyl 2-(tert-butoxy)-2-(2-chloro-4-fluoro-5-nitrophenyl)acetate (4d) (58 mg, 0.18 mmol) in anhydrous N,N-dimethylformamide (2 mL) were successively added phenol (18 mg, 0.19 mmol) and potassium carbonate (28 mg, 0.2 mmol). The mixture was heated at 75° C. for 4 hours. After cooling to room temperature, the mixture was poured into water (10 mL) and extracted with ethyl acetate (2×10 mL). The organic layer was washed with a 2M sodium hydroxide aqueous solution (10 mL), brine (10 mL), dried over sodium sulfate and concentrated in vacuo to provide methyl 2-(tert-butoxy)-2-(2-chloro-5-nitro-4-phenoxyphenyl)acetate (4e) (69 mg, 0.175 mmol, 97%) as a yellow oil which was used without further purification.

$^1$H NMR (300 MHz, CDCl$_3$) δ 1.25 (s, 9H), 3.73 (s, 3H), 5.39 (s, 1H), 6.91 (s, 1H), 7.09 (d, J=7.6 Hz, 2H), 7.23-7.27 (m, 1H), 7.43 (t, J=7.6 Hz, 2H), 8.27 (s, 1H).

Step 6: Preparation of intermediate methyl 2-(tert-butoxy)-2-[2-(3,4-dihydro-2H-1-benzopyran-6-yl)-5-nitro-4-phenoxyphenyl]acetate (4f)

A mixture of methyl 2-(tert-butoxy)-2-(2-chloro-5-nitro-4-phenoxyphenyl)acetate (4e) (69 mg, 0.175 mmol), sodium carbonate (74 mg, 0.7 mmol), 6-(4,4,5,5-tetramethyl-1,3,2-dioxaborolan-2-yl)chroman (68 mg, 0.26 mmol) and palladium tetrakis(triphenylphospine) (10 mg, 0.08 mmol) in degassed N,N-dimethylformamide (1.5 mL) and water (0.5 mL) was heated at 100° C. for 4 hours. After cooling to room temperature, the mixture was poured into water (10 mL). The aqueous layer was extracted with ethyl acetate (2×5 mL). The organic layer was washed with brine (2×5 mL), dried over sodium sulfate and concentrated in vacuo. The residue was purified by flash chromatography on silica gel (cyclohexane/ethyl acetate: 90/10) to provide methyl 2-(tert-butoxy)-2-[2-(3,4-dihydro-2H-1-benzopyran-6-yl)-5-nitro-4-phenoxyphenyl]acetate (4f) (29 mg, 0.059 mmol, 33%) as a yellow oil.

$^1$H NMR (300 MHz, CDCl$_3$) δ 1.03 (s, 9H), 1.99-2.07 (m, 2H), 2.76-2.81 (m, 2H), 3.72 (s, 3H), 4.20-4.24 (m, 2H), 5.12 (s, 1H), 6.81-6.84 (m, 2H), 6.95 (d, J=2.0 Hz, 1H), 7.00 (dd, J=2.0 8.2 Hz, 1H), 7.06-7.09 (m, 2H), 7.13-7.18 (m, 1H), 7.33-7.38 (m, 2H), 8.30 (s, 1H).

Step 7: Preparation of intermediate methyl 2-(tert-butoxy)-2-[2-(3,4-dihydro-2H-1-benzopyran-6-yl)-5-(dimethylamino)-4-phenoxyphenyl]acetate (4g)

A mixture of methyl 2-(tert-butoxy)-2-[2-(3,4-dihydro-2H-1-benzopyran-6-yl)-5-nitro-4-phenoxyphenyl]acetate (4f) (29 mg, 0.059 mmol), 37% aqueous formaldehyde (0.10 mL, 1.36 mmol) and palladium on charcoal (10 mg) in methanol (5 mL) was stirred at room temperature under hydrogen atmosphere for 4 hours. The mixture was filtered on Celite® (washed with methanol) and the filtrate was concentrated in vacuo. The residue was purified by flash chromatography on silica gel (cyclohexane/ethyl acetate: 90/10) to provide methyl 2-(tert-butoxy)-2-[2-(3,4-dihydro-2H-1-benzopyran-6-yl)-5-(dimethylamino)-4-phenoxyphenyl] acetate (4g) (17 mg, 0.034 mmol, 58%) as a colorless oil.

$^1$H NMR (300 MHz, CDCl$_3$) δ 1.01 (s, 9H), 1.97-2.04 (m, 2H), 2.75-2.80 (m, 2H), 2.86 (s, 6H), 3.72 (s, 3H), 4.18-4.22 (m, 2H), 5.16 (s, 1H), 6.70 (s, 1H), 6.78 (d, J=8.1 Hz, 1H), 6.79-7.06 (m, 5H), 7.24-7.31 (m, 3H).

Step 8: Preparation of 2-(tert-butoxy)-2-[2-(3,4-dihydro-2H-1-benzopyran-6-yl)-5-(dimethylamino)-4-phenoxyphenyl]acetic acid A mixture of methyl 2-(tert-butoxy)-2-[2-(3,4-dihydro-2H-1-benzopyran-6-yl)-5-(dimethylamino)-4-phenoxyphenyl]acetate (4g) (17 mg, 0.034 mmol) and potassium hydroxide (12 mg, 0.21 mmol) in a mixture of ethanol (3 mL) and water (1 mL) was refluxed for 2 hours. The mixture was concentrated in vacuo. Water (5 mL) was added to the residue and an extraction was performed with diethyl ether (2×5 mL). The aqueous layer was acidified with 1M hydrochloric acid until pH 5 and extracted with ethyl acetate (2×5 mL). The organic layer was dried over sodium sulfate and concentrated in vacuo. The residue was triturated in pentane and evaporated to dryness to provide 2-(tert-butoxy)-2-[2-(3,4-dihydro-2H-1-benzopyran-6-yl)-5-(dimethylamino)-4-phenoxyphenyl]acetic acid (example 4) (15 mg, 0.031 mmol, 93%) as a white solid.

$^1$H NMR (400 MHz, CDCl$_3$) δ 1.00 (s, 9H), 1.99-2.05 (m, 2H), 2.76-2.81 (m, 2H), 2.84 (s, 6H), 4.20 (t, J=8.1 Hz, 2H), 5.21 (s, 1H), 6.74 (s, 1H), 6.78 (d, J=8.4 Hz, 1H), 6.99-7.06 (m, 4H), 7.16-7.18 (m, 2H), 7.26-7.31 (m, 2H).

MS m/z ([M−H]$^-$) 474.

Example 5: Synthesis of 2-[2-(benzyloxy)naphthalen-1-yl]-2-(tert-butoxy)acetic acid

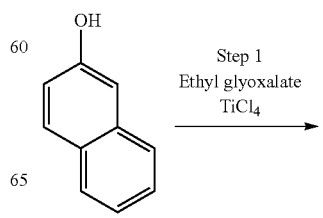

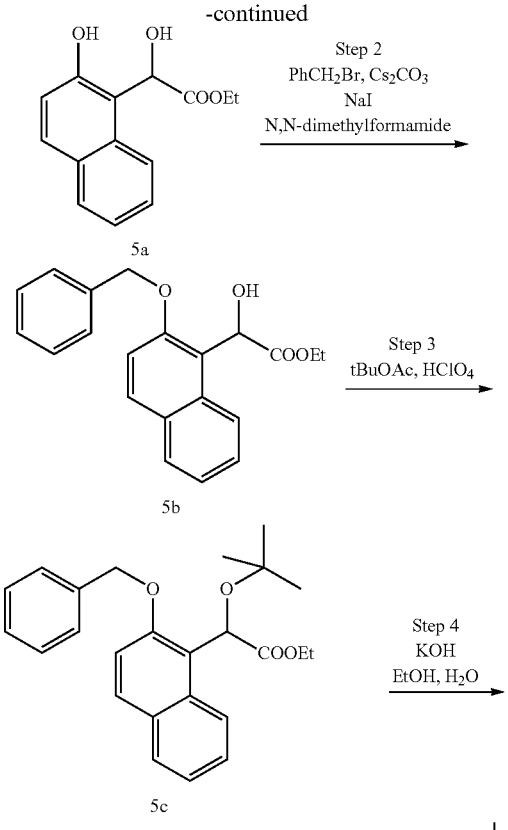

Example 5

Step 1: Preparation of intermediate ethyl 2-hydroxy-2-(2-hydroxynaphthalen-1-yl)acetate (5a)

Titanium chloride (0.4 mL, 3.64 mmol) was dropwise added to a solution of 2-naphthol (500 mg, 3.47 mmol) and ethyl glyoxalate 50% in toluene (1.0 mL, 5.2 mmol) in anhydrous dichloromethane (10 mL) at 0° C. under nitrogen atmosphere. The mixture was stirred at 0° C. for 30 minutes and poured into ice water (50 mL). The mixture was stirred for 30 minutes. Layers were separated and the aqueous layer was extracted with dichloromethane (2×20 mL). The combined organic layers were dried over sodium sulfate and concentrated in vacuo. The residue was purified by flash chromatography on silica gel (cyclohexane/ethyl acetate: 60/40) to provide ethyl 2-hydroxy-2-(2-hydroxynaphthalen-1-yl)acetate (5a) (0.84 g, 3.41 mmol, 98%).

$^1$H NMR (300 MHz, CDCl$_3$) δ 1.13 (t, J=7.1 Hz, 3H), 3.69 (broad s, 1H), 4.12 (q, J=7.1 Hz, 2H), 6.16 (s, 1H), 7.11 (d, J=8.8 Hz, 1H), 7.35 (dt, J=0.8, 7.9 Hz, 1H), 7.50 (dt, J=1.3, 6.9 Hz, 1H), 7.74 (d, J=8.8 Hz, 1H), 7.78 (d, J=7.9 Hz, 1H), 7.9 (broad s, 1H), 7.92 (d, J=8.6 Hz, 1H).

MS m/z ([M−H]$^−$) 245.

Step 2: Preparation of intermediate ethyl 2-hydroxy-2-[2-(benzyloxy)naphthalen-1-yl]acetate (5b)

To a solution of ethyl 2-hydroxy-2-(2-hydroxynaphthalen-1-yl)acetate (5a) (0.73 g, 2.96 mmol) in anhydrous N,N-dimethylformamide (10 mL) at 0° C. under nitrogen atmosphere were successively added benzyl bromide (1.1 mL, 8.9 mmol), cesium carbonate (1.93 g, 5.93 mmol) and sodium iodide (0.44 g, 2.96 mmol). The mixture was stirred at room temperature for 4 hours and poured into water (50 mL). The aqueous layer was extracted with ethyl acetate (2×20 mL). The combined organic layers were washed with brine (2×20 mL), dried over sodium sulfate and concentrated in vacuo. The residue was purified by flash chromatography on silica gel (cyclohexane/ethyl acetate 90/10 then 80/20) to provide a solid which was triturated in cylohexane and filtered to provide ethyl 2-hydroxy-2-[2-(benzyloxy)naphthalen-1-yl]acetate (5b) (0.70 g, 2.08 mmol, 70%) as a white solid.

$^1$H NMR (300 MHz, CDCl$_3$) δ 1.11 (t, J=7.1 Hz, 3H), 3.68 (d, J=5.5 Hz, 1H), 4.06-4.20 (m, 2H), 5.22 (d, J=12.0 Hz, 1H), 5.28 (d, J=12.0 Hz, 1H), 6.11 (d, J=5.5 Hz, 1H), 7.29 (d, J=9.0 Hz, 1H), 7.33-7.54 (m, 7H), 7.78-7.84 (m, 2H), 8.06 (d, J=8.5 Hz, 1H).

MS m/z ([M+H−H$_2$O]$^+$) 319.

Step 3: Preparation of intermediate ethyl 2-[2-(benzyloxy)naphthalen-1-yl]-2-(tert-butoxy)acetate (5c)

To a solution of ethyl 2-hydroxy-2-[2-(benzyloxy)naphthalen-1-yl]acetate (5b) (0.70 g, 2.08 mmol) in tert-butyl acetate (34 mL) at −20° C. was added perchloric acid (4.5 mL). The mixture was stirred at −20° C. for 2 hours and at room temperature for 30 minutes before being poured into a saturated solution of sodium bicarbonate (100 mL). Water (150 mL) was added. The layers were separated and the aqueous layer was extracted with ethyl acetate (2×30 mL). The organic layers were dried over sodium sulfate and concentrated in vacuo. The residue was purified by flash chromatography on silica gel (cyclohexane/ethyl acetate: 90/10) to provide ethyl 2-[2-(benzyloxy)naphthalen-1-yl]-2-(tert-butoxy)acetate (5c) (0.39 g, 0.99 mmol, 48%) as a yellow oil.

$^1$H NMR (300 MHz, CDCl$_3$) δ 1.07 (t, J=7.1 Hz, 3H), 1.20 (s, 9H), 4.00-4.18 (m, 2H), 5.29 (s, 2H), 6.27 (s, 1H), 7.25-7.52 (m, 7H), 7.72-7.76 (m, 2H), 8.44 (d, J=8.5 Hz, 1H).

MS m/z ([M+Na]$^+$) 415.
MS m/z ([M−H]$^−$) 391.

Step 4: Preparation of 2-[2-(benzyloxy)naphthalen-1-yl]-2-(tert-butoxy)acetic acid A mixture of ethyl 2-[2-(benzyloxy)naphthalen-1-yl]-2-(tert-butoxy)acetate (5c) (50 mg, 0.13 mmol) and potassium hydroxide (29 mg, 0.51 mmol) in a mixture of ethanol (3 mL) and water (1 mL) was refluxed for 2 hours. The mixture was concentrated in vacuo. Water (5 mL) was added to the residue and an extraction was performed with diethyl ether (2×5 mL). The aqueous layer was acidified with 1M hydrochloric acid until pH 1 and extracted with ethyl acetate (2×5 mL). The organic layer was dried over sodium sulfate and concentrated in vacuo. The residue was triturated in pentane and evaporated to dryness to provide 2-[2-(benzyloxy)naphthalen-1-yl]-2-(tert-butoxy)acetic acid (example 5) (30 mg, 0.082 mmol, 65%) as a white solid.

$^1$H NMR (400 MHz, CDCl$_3$) δ 1.20 (s, 9H), 5.26 (d, J=11.9, 1H), 5.30 (d, J=11.9, 1H), 6.24 (s, 1H), 7.29 (d, J=9.0 Hz, 1H), 7.34-7.50 (m, 7H), 7.77 (d, J=8.0 Hz, 1H), 7.81 (d, J=9.0 Hz, 1H), 8.02 (d, J=8.6 Hz, 1H).

MS m/z ([M–H]$^-$) 363.

Example 6: Synthesis of 2-(tert-butoxy)-2-[7-(3,4-dihydro-2H-1-benzopyran-6-yl)-2,3-dihydro-1,4-benzodioxin-6-yl]acetic acid

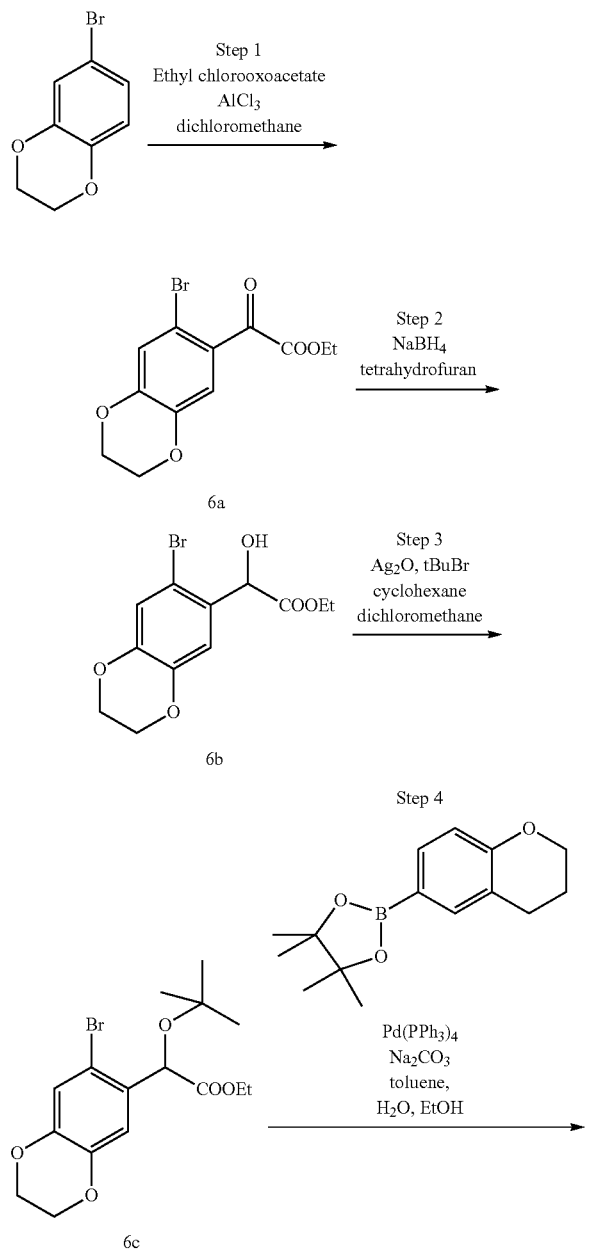

Step 1: Preparation of intermediate ethyl 2-(7-bromo-2,3-dihydro-1,4-benzodioxin-6-yl)-2-oxoacetate (6a)

Aluminium chloride (0.49 g, 3.7 mmol) was added to a solution of 6-bromo-1,4-benzodioxane (0.50 g, 2.3 mmol) and ethyl chlorooxoacetate (0.35 g, 2.5 mmol) in anhydrous dichloromethane (10 mL) previously cooled with an ice bath. The reaction mixture was stirred at room temperature overnight and poured into ice water. The mixture was extracted with dichloromethane (2×20 mL) and the organic layer was dried over sodium sulfate, filtered and evaporated to dryness to provide ethyl 2-(7-bromo-2,3-dihydro-1,4-benzodioxin-6-yl)-2-oxoacetate (6a) (0.71 g, 2.3 mmol, 97%) as a yellow oil which was used without further purification.

$^1$H NMR (300 MHz, CDCl$_3$) δ 1.40 (t, J=7.2 Hz, 3H), 4.25-4.34 (m, 4H), 4.40 (q, J=7.2 Hz, 2H), 7.13 (s, 1H), 7.33 (s, 1H).

Step 2: Preparation of intermediate ethyl 2-(7-bromo-2,3-dihydro-1,4-benzodioxin-6-yl)-2-hydroxyacetate (6b)

A solution of 2-(7-bromo-2,3-dihydro-1,4-benzodioxin-6-yl)-2-oxoacetate (6a) (0.60 g, 1.9 mmol) in anhydrous tetrahydrofuran (10 mL) was cooled to −10° C. and sodium borohydride (0.22 g, 5.7 mmol) was added portionwise under a nitrogen atmosphere. After 30 minutes stirring, a few drops of 1N hydrochloric acid solution were added and the resulting precipitate was filtered. The filtrate was concentrated in vacuo. The residue was diluted with brine and extracted with ethyl acetate (2×20 mL). The organic layer was dried over sodium sulfate, filtered and evaporated to dryness to provide ethyl 2-(7-bromo-2,3-dihydro-1,4-benzodioxin-6-yl)-2-hydroxyacetate (6b) (0.61 g, 1.9 mmol, 100%) which was used without further purification.

$^1$H NMR (300 MHz, CDCl$_3$) δ 1.24 (t, J=7.2 Hz, 3H), 4.15-4.30 (m, 6H), 5.41 (s, 1H), 6.87 (s, 1H), 7.08 (s, 1H).

Step 3: Preparation of intermediate ethyl 2-(7-bromo-2,3-dihydro-1,4-benzodioxin-6-yl)-2-(tert-butoxy)acetate (6c)

Silver oxide (0.22 g, 0.94 mmol) and tert-butyl bromide (0.26 g, 1.90 mmol) were successively added to a solution of ethyl 2-(7-bromo-2,3-dihydro-1,4-benzodioxin-6-yl)-2-hydroxyacetate (6b) (0.10 g, 0.31 mmol) in a mixture of cyclohexane (2 mL) and dichloromethane (0.5 mL). The reaction mixture was stirred at room temperature for 48 hours with addition of an equivalent of silver oxide and tert-butyl bromide at t=16 h/21 h/24 h. Upon completion of the reaction, the mixture was filtered over Celite® and the filtrate was concentrated in vacuo. The residue was purified by flash chromatography on silica gel (cyclohexane/ethyl acetate: 80/20) to provide ethyl 2-(7-bromo-2,3-dihydro-1,4-benzodioxin-6-yl)-2-(tert-butoxy)acetate (6c) (85 mg, 0.23 mmol, 73%).

$^1$H NMR (300 MHz, CDCl$_3$) δ 1.20-1.25 (m, 12H), 4.08-4.18 (m, 2H), 4.23 (s, 4H), 5.31 (s, 1H), 7.02 (s, 1H), 7.17 (s, 1H).

Step 4: Preparation of intermediate ethyl 2-(tert-butoxy)-2-[7-(3,4-dihydro-2H-1-benzopyran-6-yl)-2,3-dihydro-1,4-benzodioxin-6-yl]acetate (6d)

To a solution of ethyl 2-(7-bromo-2,3-dihydro-1,4-benzodioxin-6-yl)-2-(tert-butoxy)acetate (6c) (85 mg, 0.23 mmol) in mixture of ethanol (0.6 mL), toluene (1.26 mL) and water (0.5 mL) were added sodium carbonate (96 mg, 0.91 mmol) and 6-(4,4,5,5-tetramethyl-1,3,2-dioxaborolan-2-yl)chroman (106 mg, 0.41 mmol). After 5 minutes of nitrogen bubbling, tetrakis(triphenylphosphine)palladium (13 mg, 0.01 mmol) was added and the mixture was heated at 95° C. overnight. The mixture was then cooled at room temperature and water (5 mL) was added. The aqueous layer was extracted with toluene (3×10 mL). The combined organic layers were washed with a saturated aqueous solution of sodium bicarbonate, dried over sodium sulfate and concentrated in vacuo. The residue was purified by flash chromatography on silica gel (cyclohexane/ethyl acetate: 80/20) to provide ethyl 2-(tert-butoxy)-2-[7-(3,4-dihydro-2H-1-benzopyran-6-yl)-2,3-dihydro-1,4-benzodioxin-6-yl]acetate (6d) (52 mg, 0.12 mmol, 53%).

$^1$H NMR (300 MHz, CDCl$_3$) δ 0.99 (s, 9H), 1.23 (t, J=7.2 Hz, 3H), 1.99-2.08 (m, 2H), 2.76-2.84 (m, 2H), 4.07-4.17 (m, 4H), 4.26 (s, 4H), 5.05 (s, 1H), 6.71 (s, 1H), 6.80 (d, J=8.2 Hz, 1H), 7.04-7.10 (m, 2H), 7.18 (s, 1H).

Step 5: Preparation of 2-(tert-butoxy)-2-[7-(3,4-dihydro-2H-1-benzopyran-6-yl)-2,3-dihydro-1,4-benzodioxin-6-yl]acetic acid A solution of 2-(tert-butoxy)-2-[7-(3,4-dihydro-2H-1-benzopyran-6-yl)-2,3-dihydro-1,4-benzodioxin-6-yl]acetate (6d) (50 mg, 0.12 mmol) and potassium hydroxide (57 mg, 0.47 mmol) in a mixture of ethanol (2 mL) and water (6 mL) was refluxed for 60 minutes. The mixture was concentrated in vacuo. Water (10 mL) was added to the residue and the solution was extracted with diethyl ether (10 mL). The aqueous layer was acidified with concentrated hydrochloric acid until pH 2 and was extracted with ethyl acetate (2×10 mL). The organic layer was dried over sodium sulfate and evaporated to dryness to provide 2-(tert-butoxy)-2-[7-(3,4-dihydro-2H-1-benzopyran-6-yl)-2,3-dihydro-1,4-benzodioxin-6-yl]acetic acid (example 6) (33 mg, 0.08 mmol, 69%) as a white solid.

$^1$H NMR (300 MHz, CDCl$_3$) δ 0.99 (s, 9H), 1.99-2.07 (m, 2H), 2.79-2.85 (m, 2H), 4.21-4.25 (m, 2H), 4.27 (s, 4H), 5.13 (s, 1H), 6.75 (s, 1H), 6.82 (d, J=8.6 Hz, 1H), 6.92 (s, 1H), 7.15-7.23 (m, 2H).

Example 7: Synthesis of 2-(tert-butoxy)-2-[7-(3,4-dihydro-2H-1-benzopyran-6-yl)-2,3-dihydro-1,4-benzodioxin-6-yl]acetic acid

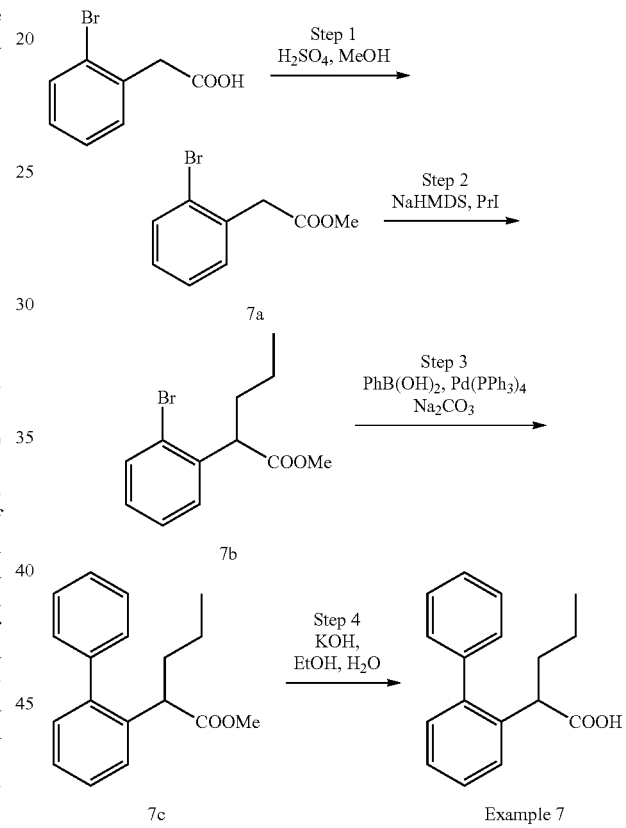

Step 1: Preparation of intermediate methyl 2-(2-bromophenyl)acetate (7a)

To a solution of (2-bromophenyl)acetic acid (3.0 g, 14.0 mmol) and sulfuric acid (75 µL, 1.4 mmol) in methanol (60 mL) was refluxed for 3.5 hours before being cooled to room temperature and concentrated in vacuo. A saturated solution of sodium hydrogenocarbonate (20 mL) was added to the residue and extracted with ethyl acetate (2×25 mL). The organic layer was dried over sodium sulfate and concentrated in vacuo to provide methyl 2-(2-bromophenyl)acetate (7a) (3.09 g, 13.5 mmol, 96%) as a colorless oil.

$^1$H NMR (300 MHz, CDCl$_3$) δ 3.68 (s, 3H), 3.76 (s, 2H), 7.07-7.13 (m, 1H), 7.21-25 (m, 2H), 7.53 (d, J=8.0 Hz, 1H).

Step 2: Preparation of intermediate methyl 2-(2-bromophenyl)pentanoate (7b)

To a solution of methyl 2-(2-bromophenyl)acetate (7a) (300 mg, 1.31 mmol) in anhydrous tetrahydrofurane (5 mL) under nitrogen atmosphere at 0° C. was dropwise added a 1 M solution of sodium bis(trimethylsilyl)amide in tetrahydrofurane (1.31 mL, 1.31 mmol). The mixture was stirred at room temperature for 45 minutes and iodopropane (128 µL, 1.31 mmol) was added. The mixture was stirred at room temperature for 3 hours and water (5 mL) was added. Layers were separated. The aqueous layer was extracted with ethyl acetate (2×10 mL). The organic layers were dried over sodium sulfate and concentrated in vacuo. The residue was purified by flash chromatography on silica gel (cyclohexane/ethyl acetate 90/10) to provide methyl 2-(2-bromophenyl)pentanoate (7b) (261 mg, 0.92 mmol, 73%) as a colorless oil.

$^1$H NMR (300 MHz, CDCl$_3$) δ 0.93 (t, J=7.2 Hz, 3H), 1.24-1.41 (m, 2H), 1.69-1.81 (m, 1H), 1.98-2.11 (m, 1H), 3.68 (s, 3H), 4.19 (t, J=7.5 Hz, 1H), 7.11 (dt, J=1.7 Hz, J=7.9 Hz, 1H), 7.29 (dt, J=1.2 Hz, J=7.9 Hz, 1H), 7.38 (dd, J=1.7 Hz, J=7.9 Hz, 1H), 7.53 (dd, J=1.2 Hz, J=7.9 Hz, 1H).

Step 3: Preparation of intermediate methyl 2-(2-phenylphenyl)pentanoate (7c)

A mixture of methyl 2-(2-bromophenyl)pentanoate (7b) (149 mg, 0.55 mmol), sodium carbonate (233 mg, 2.2 mmol), phenylboronic acid (100 mg, 0.82 mmol) and palladium tetrakis(triphenylphosphine) (32 mg, 0.027 mmol) in a mixture of toluene (2.5 mL), ethanol (1.25 mL) and water (1.1 mL) was refluxed overnight. The mixture diluted with toluene (10 mL), washed with a 1 M solution of sodium hydroxide (5 mL), dried over sodium sulfate and concentrated in vacuo. The residue was purified by flash chromatography on silica gel (cyclohexane/ethyl acetate 80/20) to provide methyl 2-(2-phenylphenyl)pentanoate (7c) (97 mg, 0.36 mmol, 66%) as a yellow oil.

$^1$H NMR (300 MHz, CDCl$_3$) δ 0.70 (t, J=7.2 Hz, 3H), 0.99-1.09 (m, 2H), 1.58-1.70 (m, 1H), 1.89-2.01 (m, 1H), 3.65 (s, 3H), 3.79 (t, J=7.5 Hz, 1H), 7.22-7.48 (m, 9H).

Step 4: Preparation of 2-(2-phenylphenyl)pentanoic acid

A solution of methyl 2-(2-phenylphenyl)pentanoate (7c) (87 mg, 0.32 mmol) and potassium hydroxide (73 mg, 1.3 mmol) in a mixture of ethanol (6 mL) and water (2 mL) was stirred at 90° C. for 90 minutes. Ethanol was evaporated in vacuo. The residue was diluted with water (10 mL) and washed with diethyl ether (5 mL). The aqueous layer was acidified with 1M hydrochloric acid was added until pH 1 and extracted with ethyl acetate (2×5 mL). The organic layer was dried over sodium sulfate and concentrated in vacuo to provide the desired acid (example 7) (69 mg, 0.27 mmol, 84%) as a white solid.

$^1$H NMR (300 MHz, DMSO-d$_6$) δ 0.63 (t, J=7.2 Hz, 3H), 0.89-1.04 (m, 2H), 1.48-1.60 (m, 1H), 1.79-1.91 (m, 1H), 3.62 (t, J=7.5 Hz, 1H), 7.20 (dd, J=1.3 Hz, J=7.4 Hz, 1H), 7.27-7.49 (m, 8H), 12.34 (s, 1H).

MS m/z ([M−H]$^−$) 253.

Example 8: Synthesis of 2-(tert-butoxy)-2-(2-phenylphenyl)acetic acid

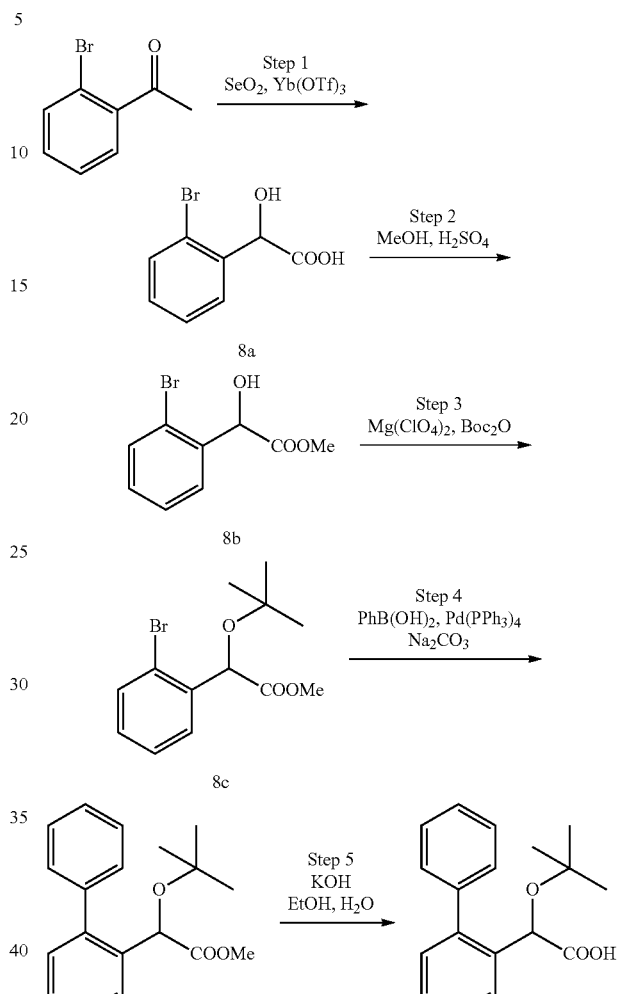

Step 1: Preparation of intermediate 2-(2-bromophenyl)-2-hydroxyacetic acid (8a)

To a solution of 2-bromoacetophenone (3.0 g, 15 mmol) in 1,4-dioxane (45 mL) and water (15 mL) was added selenium dioxide (3.34 g, 30.1 mmol) and ytterbium(III) trifluoromethanesulfonate hydrate (0.61 g, 0.98 mmol). The mixture was heated at 90° C. for 18 hours. The mixture was filtered at room temperature on celite. The filtrate was concentrated under vacuum. To the residue was added a 0.25M aqueous solution of sodium hydroxide (150 mL). The resulting solution was extracted with dichloromethane (2×60 mL). The aqueous layer was acidified with concentrated hydrochloric acid until pH 1 and extracted with ethyl acetate (2×60 mL). This organic layer was dried with sodium hydroxide and concentrated under vacuum to provide 2-(2-bromophenyl)-2-hydroxyacetic acid (8a) (2.32 g, 10 mmol, 66%) as a yellow solid which was used without further purification.

$^1$H NMR (300 MHz, CDCl$_3$) δ 5.67 (s, 1H), 7.21 (dt, J=1.8 Hz, J=7.2 Hz, 1H), 7.34 (dt, J=1.2 Hz, J=7.5 Hz, 1H), 7.42 (dd, J=1.8 Hz, J=7.8 Hz, 1H), 7.59 (dd, J=1.2 Hz, J=8.1 Hz, 1H).

Step 2: Preparation of intermediate methyl 2-(2-bromophenyl)-2-hydroxyacetate (8b)

A solution of 2-(2-bromophenyl)-2-hydroxyacetic acid (8a) (2.32 g, 10 mmol) and sulfuric acid (54 μL, 1 mmol) in methanol (50 mL) was refluxed for 3.5 hours. The mixture was concentrated under vacuum. A saturated aqueous solution of sodium bicarbonate (30 mL) was added to the residue and the product was extracted with ethyl acetate (2×20 mL). The organic layer was washed with brine, dried with sodium sulfate and concentrated under vacuum. The residue was purified by flash chromatography on silica gel (cyclohexane/ethyl acetate 85/15) to provide methyl 2-(2-bromophenyl)-2-hydroxyacetate (2.07 g, 8.44 mmol, 84%) as a pale yellow solid.

$^1$H NMR (300 MHz, CDCl$_3$) δ 3.56 (d, J=4.8 Hz, 1H), 3.77 (s, 3H), 5.58 (d, J=4.8 Hz, 1H), 7.19 (dt, J=2.1 Hz, J=7.2 Hz, 1H), 7.30-7.40 (m, 2H), 7.58 (dd, J=1.0 Hz, J=8.1 Hz, 1H).

Step 3: Preparation of intermediate methyl 2-(2-bromophenyl)-2-(tert-butoxy)acetate (8c)

To a solution of methyl 2-(2-bromophenyl)-2-hydroxyacetate (8b) (256 mg, 1.04 mmol) in anhydrous dichloromethane (3 mL) under nitrogen atmosphere were added magnesium perchlorate (23 mg, 0.1 mmol) and di-tert-butyl dicarbonate (520 mg, 2.38 mmol). The mixture was refluxed for 24 hours. Water (10 mL) was added and layers were separated. The organic layer was extracted with dichloromethane (2×10 mL). The organic layers were dried with sodium sulfate and concentrated under vacuum. The residue was purified by flash chromatography on silica gel (cyclohexane/ethyl acetate 90/10) to provide compound methyl 2-(2-bromophenyl)-2-(tert-butoxy)acetate (8c) (84 mg, 0.28 mmol, 26%) as a white solid.

$^1$H NMR (300 MHz, CDCl$_3$) δ 1.23 (s, 9H), 3.69 (s, 3H), 5.48 (s, 1H), 7.15 (dt, J=1.8 Hz, J=7.8 Hz, 1H), 7.33 (t, J=7.8 Hz, 1H), 7.52 (d, J=8.1 Hz, 1H), 7.65 (dd, J=1.5 Hz, J=7.8 Hz, 1H).

Step 4: Preparation of intermediate methyl 2-(tert-butoxy)-2-(2-phenylphenyl)acetate (8d)

To a solution of methyl 2-(2-bromophenyl)-2-(tert-butoxy)acetate (8c) (60 mg, 0.20 mmol) in toluene (1.1 mL) was added sodium carbonate (84 mg, 0.79 mmol), water (0.48 mL), palladium tetrakis(triphenylphosphine) (12 mg, 0.01 mmol) and a solution of phenylboronic acid (44 mg, 0.36 mmol) in ethanol (0.55 mL). The mixture was refluxed for 18 hours. The mixture was then cooled at room temperature and water (5 mL) was added. The aqueous layer was extracted with toluene (2×5 mL). The organic layers were washed with a 1M sodium hydroxide aqueous solution (5 mL), dried with sodium sulfate and concentrated under vacuum. The residue was purified by flash chromatography on silica gel (cyclohexane/ethyl acetate 90/10) to provide methyl 2-(tert-butoxy)-2-(2-phenylphenyl)acetate (8d) (52 mg, 0.17 mmol, 88%) as a colorless oil.

$^1$H NMR (300 MHz, CDCl$_3$) δ 0.97 (s, 9H), 3.69 (s, 3H), 5.19 (s, 1H), 7.23-7.45 (m, 8H), 7.67-7.70 (m, 1H).

MS m/z ([M+Na]$^+$) 321.

Step 5: Preparation of 2-(tert-butoxy)-2-(2-phenylphenyl)acetic acid

A solution of methyl 2-(tert-butoxy)-2-(2-phenylphenyl) acetate (8d) (49 mg, 0.16 mmol) and potassium hydroxide (37 mg, 0.66 mmol) in a mixture of ethanol (6 mL) and water (2 mL) was refluxed for 90 minutes. The mixture was concentrated under vacuum. Water (10 mL) was added to the residue and the solution was extracted with diethyl ether (10 mL). The aqueous layer was acidified with concentrated hydrochloric acid until pH 1 and was extracted with dichloromethane (2×5 mL). The organic layer was dried with sodium sulfate and concentrated under vacuum to provide the desired acid (example 8) (37 mg, 0.13 mmol, 78%) as a white solid.

$^1$H NMR (300 MHz, DMSO-d$_6$) δ 0.85 (s, 9H), 5.03 (s, 1H), 7.22-7.24 (m, 1H), 7.35-7.45 (m, 5H), 7.47-7.55 (m, 3H), 12.67 (broad s, 1H).

MS m/z ([M−H]$^−$) 283.

Example 9: Synthesis of 2-(tert-butoxy)-2-[2-(3,4-dihydro-2H-1-benzopyran-6-yl)-4-phenoxyphenyl] acetic acid

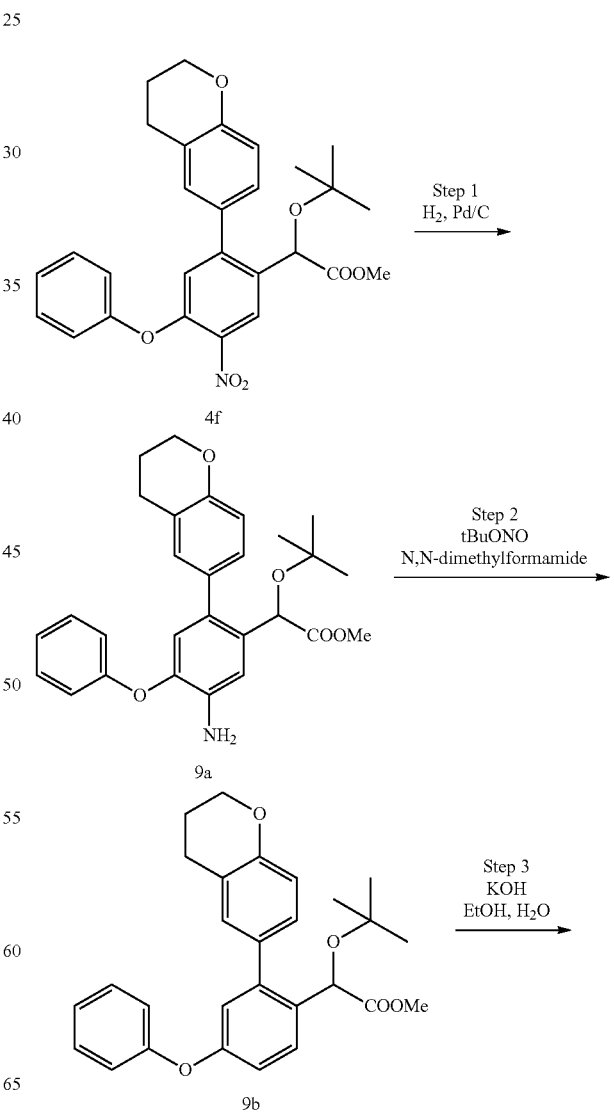

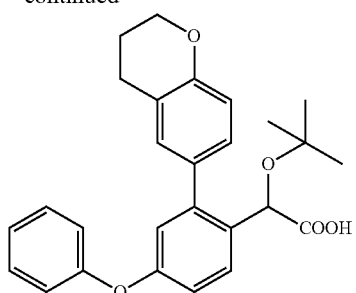

Example 9

Step 1: Preparation of intermediate methyl 2-[5-amino-2-(3,4-dihydro-2H-1-benzopyran-6-yl)-4-phenoxy phenyl]-2-(tert-butoxy)-acetate (9a)

A mixture of methyl 2-(tert-butoxy)-2-[2-(3,4-dihydro-2H-1-benzopyran-6-yl)-5-nitro-4-phenoxyphenyl]acetate (4f) (124 mg, 0.25 mmol) and palladium on charcoal (24 mg) in methanol (7 mL) was stirred at room temperature under hydrogen atmosphere for 1 hour. The mixture was filtered on Celite® (washed with methanol) and the filtrate was concentrated under vacuum to provide the desired aniline (9a) (101 mg, 0.22 mmol, 87%) as a brown oil which was used without further purification.

$^1$H NMR (300 MHz, CDCl$_3$) δ 1.01 (s, 9H), 1.98-2.06 (m, 2H), 2.74-2.81 (m, 2H), 3.71 (s, 3H), 4.19-4.22 (m, 2H), 5.13 (s, 1H), 6.68 (s, 1H), 6.78 (d, J=8.1 Hz, 1H), 6.98-7.07 (m, 5H), 7.26-7.33 (m, 3H).

MS m/z ([M+H]$^+$) 462.

Step 2: Preparation of intermediate methyl 2-(tert-butoxy)-2-[2-(3,4-dihydro-2H-1-benzopyran-6-yl)-4-phenoxyphenyl]acetate (9b)

To a solution of tert-butyl nitrite (26 µL, 0.22 mmol) in anhydrous N,N-dimethylformamide (1 mL) under nitrogen atmosphere at 60° C. was dropwise added a solution of methyl 2-[5-amino-2-(3,4-dihydro-2H-1-benzopyran-6-yl)-4-phenoxyphenyl]-2-(tert-butoxy)-acetate (9a) (50 mg, 0.11 mmol) in anhydrous N,N-dimethylformamide (0.5 mL). Stirring was maintained at 60° C. for 30 minutes then cooled at room temperature and poured in water (10 mL). The aqueous layer was extracted with ethyl acetate (2×10 mL). The organic layer was washed with a 1M hydrochloric acid solution (10 mL), brine (10 mL), dried with sodium sulfate and concentrated under vacuum. The residue was purified by flash chromatography on silica gel (cyclohexane/ethyl acetate 90/10) to provide methyl 2-(tert-butoxy)-2-[2-(3,4-dihydro-2H-1-benzopyran-6-yl)-4-phenoxyphenyl]acetate (9b) (22 mg, 0.049 mmol, 46%).

$^1$H NMR (400 MHz, CDCl$_3$) δ 1.00 (s, 9H), 2.01-2.07 (m, 2H), 2.79-2.84 (m, 2H), 3.71 (s, 3H), 4.21-4.24 (m, 2H), 5.17 (s, 1H), 6.82-6.85 (m, 2H), 6.96 (dd, J=2.6 Hz, J=8.6 Hz, 1H), 7.04-7.12 (m, 5H), 7.31-7.35 (m, 2H), 7.61 (d, J=8.6 Hz, 1H).

Step 3: Preparation of 2-(tert-butoxy)-2-[2-(3,4-dihydro-2H-1-benzopyran-6-yl)-4-phenoxyphenyl] acetic acid A mixture of methyl 2-(tert-butoxy)-2-[2-(3,4-dihydro-2H-1-benzopyran-6-yl)-4-phenoxyphenyl]acetate (9b) (22 mg, 0.049 mmol) and potassium hydroxide (11 mg, 0.2 mmol) in a mixture of ethanol (3 mL) and water (1 mL) was refluxed for 1 hour. The mixture was concentrated under vacuum. Water (5 mL) was added to the residue followed by 1M hydrochloric acid until pH 1. The aqueous layer was extracted with ethyl acetate (2×5 mL). The organic layer was dried with sodium sulfate and concentrated under vacuum. The residue was triturated in pentane and concentrated under vacuum to provide the desired acid (example 9) (16 mg, 0.037 mmol, 76%) as a white solid.

$^1$H NMR (400 MHz, CDCl$_3$) δ 0.99 (s, 9H), 2.00-2.06 (m, 2H), 2.77-2.87 (m, 2H), 4.22 (t, J=5.2 Hz, 2H), 5.21 (s, 1H), 6.83 (d, J=8.5 Hz, 1H), 6.88 (d, J=2.6 Hz, 1H), 6.96 (dd, J=2.6 Hz, J=8.5 Hz, 1H), 7.03-7.06 (m, 2H), 7.11 (t, J=7.4 Hz, 1H), 7.22-7.26 (m, 3H), 7.31-7.36 (m, 3H).

MS m/z ([M–H]$^-$) 431.

Example 10: Synthesis of 2-[3-(benzyloxy)naphthalen-2-yl]-2-(tert-butoxy)acetic acid

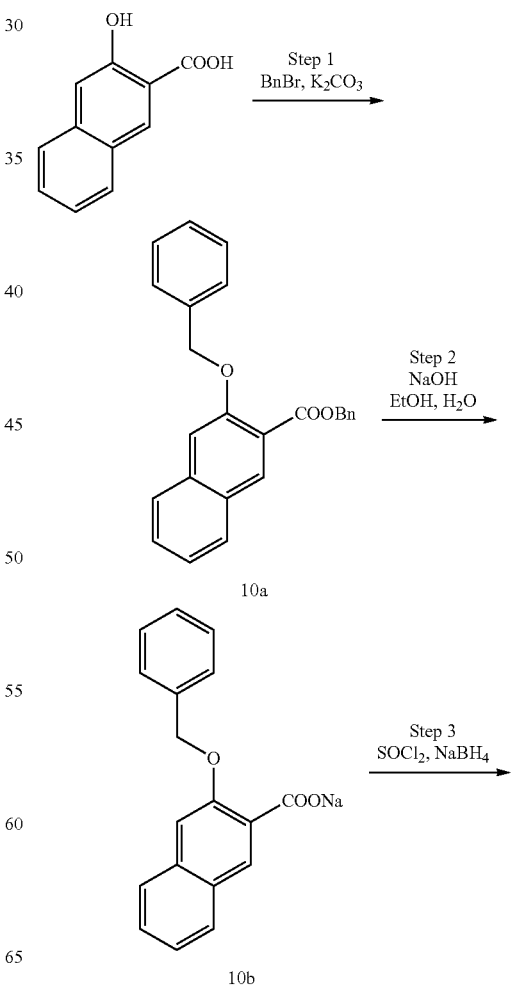

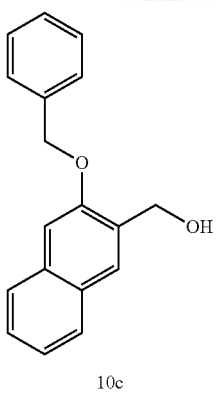

10c

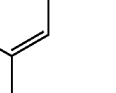

10d

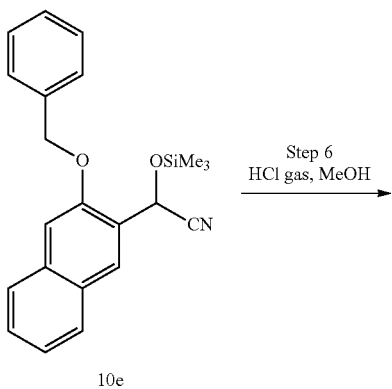

10e

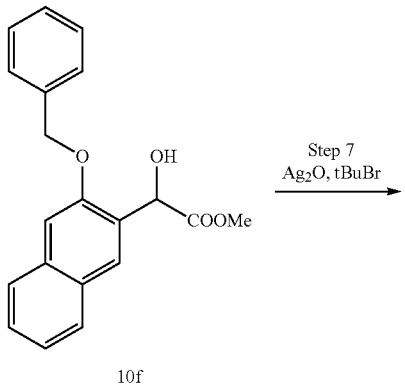

10f

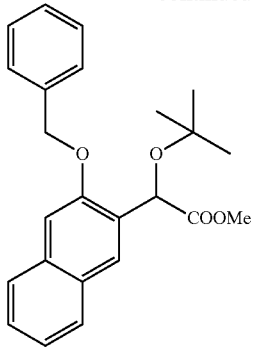

10g

[structure with COOH]

Example 10

Step 1-2: Preparation of intermediate sodium 3-(benzyloxy)naphthalene-2-carboxylate (10b)

Benzyl bromide (1.4 mL, 11.7 mmol) was added to a solution of 3-hydroxy-2-naphtoic acid (1.0 g, 5.3 mmol) and potassium carbonate (1.6 g, 11.7 mmol) in acetone (10 mL). The reaction mixture was refluxed overnight and then, concentrated in vacuo. The residue was diluted with water (20 mL) and extracted with ethyl acetate (2×20 mL) The combined organic layers were washed with 2M sodium hydroxide (20 mL), dried over sodium sulfate, filtered and evaporated to dryness to provide benzyl 3-(benzyloxy)naphthalene-2-carboxylate (10a) (2.16 g). A mixture of the crude and sodium hydroxide (0.85 g, 21.2 mmol) in a mixture of ethanol (30 mL) and water (10 mL) was refluxed for 30 minutes. After cooling to room temperature, the precipitate was filtered and washed with ethanol. The solid was dissolved in toluene and evaporated to dryness to provide sodium 3-(benzyloxy)naphthalene-2-carboxylate (10b) (0.82 g, 2.7 mmol, 51% over two steps) as a white solid.

$^1$H NMR (300 MHz, DMSO-$d_6$) δ 5.21 (s, 2H), 7.25-7.40 (m, 6H), 7.55-7.57 (m, 2H), 7.64 (s, 1H), 7.67-7.75 (m, 2H).

Step 3: Preparation of intermediate [3-(benzyloxy)naphthalen-2-yl]methanol (10c)

A solution of sodium 3-(benzyloxy)naphthalene-2-carboxylate (10b) (0.49 g, 1.65 mmol) in water (5 mL) was acidified with 1M hydrochloric acid until pH 2 and extracted with ethyl acetate (2×15 mL). The organic layer was dried over sodium sulfate and concentrated in vacuo. A mixture of the crude and thionyl chloride (5 mL) was refluxed for 60 minutes. The reaction mixture was concentrated in vacuo and coevaporated with toluene to provide an oil which was slowly added to a solution of sodium borohydride (0.15 g, 1.65 mmol) in anhydrous dimethoxyethane (10 mL) under a nitrogen atmosphere at 10° C. After stirring at room temperature for 90 minutes, the reaction mixture was concentrated in vacuo. Water (10 mL) was added to the residue, followed by acetic acid (2 mL) to ensure sodium borohydride decomposition. The mixture was basified with ammonium hydroxide until pH 8 and extracted with ethyl acetate (2×20 mL). The organic layer was dried over sodium sulfate, filtered and evaporated to dryness to provide the desired alcohol (10c) (0.44 g, 1.65 mmol, 100%) as an oil, which was used without further purification.

$^1$H NMR (300 MHz, CDCl$_3$) δ 4.89 (s, 2H), 5.24 (s, 2H), 7.23 (s, 1H), 7.33-7.51 (m, 7H), 7.71-7.80 (m, 3H).

Step 4: Preparation of intermediate 3-(benzyloxy)naphthalene-2-carbaldehyde (10d)

A solution of [3-(benzyloxy)naphthalen-2-yl]methanol (10c) (0.44 g, 1.65 mmol) and manganese dioxide (1.45 g, 16.5 mmol) in dichloromethane (6 mL) was stirred at room temperature overnight. The reaction mixture was filtered over Celite® and the filtrate was evaporated to dryness to provide 3-(benzyloxy)naphthalene-2-carbaldehyde (10d) (0.43 g, 1.64 mmol, 99%) as a yellow solid, which was used without further purification.

$^1$H NMR (300 MHz, CDCl$_3$) δ 5.29 (s, 2H), 7.29 (s, 1H), 7.34-7.47 (m, 4H), 7.49-7.57 (m, 3H), 7.73 (d, J=8.2 Hz, 1H), 7.90 (d, J=8.2 Hz, 1H), 8.40 (s, 1H), 10.67 (s, 1H).

Step 5: Preparation of intermediate ({1-[3-(benzyloxy)naphthalen-2-yl]prop-2-yn-1-yl}oxy) trimethylsilane (10e)

To a solution of 3-(benzyloxy)naphthalene-2-carbaldehyde (10d) (430 mg, 1.65 mmol) in anhydrous dichloromethane (5 mL) at 0° C. under nitrogen atmosphere were successively added zinc iodide (53 mg, 0.16 mmol) and trimethylsilylcyanide (0.24 mL, 1.99 mmol). The mixture was stirred for 2 hours, allowed to reach room temperature. A saturated solution of sodium bicarbonate (10 mL) was added. The aqueous layer was extracted with dichloromethane (2×10 mL). The combined organic layers were dried over sodium sulfate and evaporated to dryness to provide ({1-[3-(benzyloxy)naphthalen-2-yl]prop-2-yn-1-yl}oxy) trimethylsilane (10e) (450 mg, 1.24 mmol, 75%) which was used without further purification.

$^1$H NMR (300 MHz, CDCl$_3$) δ 0.23 (s, 9H), 5.23 (d, J=11.6 Hz, 1H), 5.29 (d, J=11.6 Hz, 1H), 5.91 (s, 1H), 7.23 (s, 1H), 7.35-7.55 (m, 7H), 7.73 (d, J=8.1 Hz, 1H), 7.84 (d, J=8.1 Hz, 1H), 8.08 (s, 1H).

Step 6: Preparation of intermediate methyl 2-[3-(benzyloxy)naphthalen-2-yl]-2-hydroxyacetate (10f)

Anhydrous methanol (5 mL) was cooled at 0° C. and bubbled for 5 min with hydrogen chloride. ({1-[3-(benzyloxy)naphthalen-2-yl]prop-2-yn-1-yl}oxy)trimethylsilane (10e) (100 mg, 0.28 mmol) was added and the mixture was then warmed at room temperature for 30 minutes and concentrated in vacuo. The residue, dissolved in 1M hydrochloric acid (5 mL), was stirred at room temperature for 2 hours. The mixture was extracted with ethyl acetate (2×10 mL) and the organic layer was dried over sodium sulfate and evaporated to dryness to provide methyl 2-[3-(benzyloxy) naphthalen-2-yl]-2-hydroxyacetate (10f) (87 mg, 0.27 mmol, 97%) which was used without further purification.

$^1$H NMR (300 MHz, CDCl$_3$) δ 3.67 (s, 3H), 5.21 (d, J=12.3 Hz, 1H), 5.25 (d, J=12.3 Hz, 1H), 5.46 (s, 1H), 7.23 (s, 1H), 7.32-7.48 (m, 7H), 7.69-7.80 (m, 3H).

Step 7: Preparation of intermediate methyl 2-[3-(benzyloxy)naphthalen-2-yl]-2-(tert-butoxy)acetate (10g)

Silver oxide (194 mg, 0.84 mmol) and tert-butyl bromide (0.19 mL, 1.67 mmol) were successively added to a solution of methyl 2-[3-(benzyloxy)naphthalen-2-yl]-2-hydroxyacetate (10f) (90 mg, 0.28 mmol) in a mixture of cyclohexane (2 mL) and dichloromethane (0.5 mL). The reaction mixture was stirred at room temperature for 4 days, with addition of silver oxide and tert-butyl bromide every hour of working day until the reaction stopped evolution. The mixture was filtered over Celite®, and the filtrate was concentrated in vacuo. The residue was purified by flash chromatography on silica gel (cyclohexane/ethyl acetate 75/25) to provide methyl 2-[3-(benzyloxy)naphthalen-2-yl]-2-(tert-butoxy)acetate (10g) (64 mg, 0.17 mmol, 60%).

$^1$H NMR (300 MHz, CDCl$_3$) δ 1.27 (s, 9H), 3.64 (s, 3H), 5.25 (s, 2H), 5.64 (s, 1H), 7.18 (s, 1H), 7.31-7.51 (m, 7H), 7.69 (d, J=8.1 Hz, 1H), 7.80 (d, J=7.9 Hz, 1H), 8.04 (s, 1H).

Step 8: Preparation of 2-[3-(benzyloxy)naphthalen-2-yl]-2-(tert-butoxy)acetic acid A solution of methyl 2-[3-(benzyloxy)naphthalen-2-yl]-2-(tert-butoxy)acetate (10g) (30 mg, 0.08 mmol) and potassium hydroxide (39 mg, 0.32 mmol) in a mixture of ethanol (1 mL) and water (3 mL) was refluxed for 60 minutes. The mixture was concentrated in vacuo. Water (5 mL) was added to the residue and the solution was extracted with diethyl ether (10 mL). The aqueous layer was acidified with concentrated hydrochloric acid until pH 2 and was extracted with ethyl acetate (2×10 mL). The organic layer was dried over sodium sulfate and evaporated to dryness to provide 2-[3-(benzyloxy)naphthalen-2-yl]-2-(tert-butoxy)acetic acid (example 10) (26 mg, 0.07 mmol, 89%) as a white solid.

$^1$H NMR (300 MHz, CDCl$_3$) δ 1.26 (s, 9H), 5.22 (d, J=11.8 Hz, 1H), 5.28 (d, J=11.8 Hz, 1H), 5.55 (s, 1H), 7.21 (s, 1H), 7.31-7.53 (m, 7H), 7.69 (d, J=8.1 Hz, 1H), 7.76 (d, J=8.1 Hz, 1H), 7.85 (s, 1H).

Example 11: Synthesis of 2-(tert-butoxy)-2-[2-(3,4-dihydro-2H-1-benzopyran-6-yl)-3-methylphenyl]acetic acid

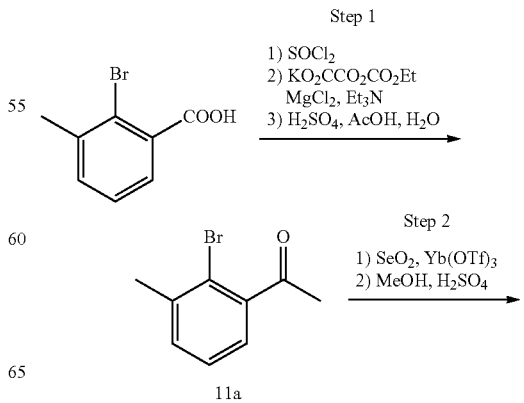

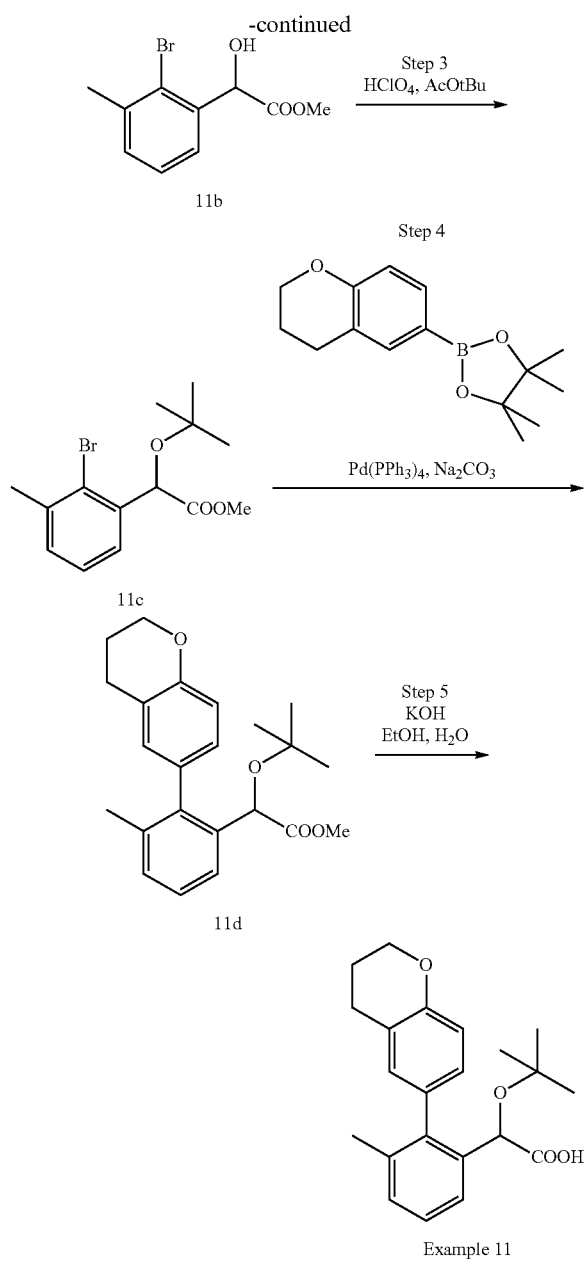

Step 1: Preparation of intermediate 1-(2-bromo-3-methylphenyl)ethan-1-one (11a)

A suspension of 2-bromo-3-methylbenzoic acid (1.00 g, 4.65 mmol) in thionyl chloride (10 mL) was refluxed for 2 hours. After cooling to room temperature, the mixture was concentrated in vacuo. Toluene (2×10 mL) was added and the mixture was concentrated again to provide acyl chloride. To a suspension of potassium ethyl malonate (1.66 g, 9.77 mmol) in anhydrous acetonitrile (15 mL) under nitrogen atmosphere at 0° C. were successively added triethylamine (2.1 mL, 15.1 mmol) and magnesium chloride (1.02 g, 10.7 mmol). The mixture was stirred at room temperature for 2.5 hours and re-cooled before adding dropwise a solution of acyl chloride in acetonitrile (5 mL). The mixture was stirred at room temperature overnight, cooled at 0° C. and a 13% hydrochloric acid aqueous solution (10 mL) was added. Layers were separated. The organic layer was concentrated in vacuo to remove acetonitrile. The aqueous layer was extracted with ethyl acetate (2×15 mL). The combined organic layers extracts were washed with a saturated solution of sodium bicarbonate (20 mL), brine (20 mL), dried over sodium sulfate and concentrated in vacuo. The residue was then refluxed in a mixture of acetic acid (8 mL), water (5 mL) and sulfuric acid (1.0 mL) for 3 hours. After cooling to room temperature, the mixture was concentrated in vacuo to remove acetic acid. The residue was poured into ice water (50 mL) and extracted with ethyl acetate (2×15 mL). The organic layer was washed with a saturated solution of sodium bicarbonate (2×20 mL), brine (20 mL), dried over sodium sulfate and evaporated to dryness to provide 1-(2-bromo-3-methylphenyl)ethan-1-one (11a) (586 mg, 2.75 mmol, 59%) as a yellow oil which was used without further purification.

$^1$H NMR (300 MHz, CDCl$_3$) δ 2.48 (s, 3H), 2.64 (s, 3H), 7.19 (dd, J=1.8 Hz, J=7.2 Hz, 1H), 7.28-7.38 (m, 2H).

Step 2: Preparation of intermediate methyl 2-(2-bromo-3-methylphenyl)-2-hydroxyacetate (11b)

A mixture of 1-(2-bromo-3-methylphenyl)ethan-1-one (11a) (570 mg, 2.68 mmol), selenium dioxide (594 mg, 5.35 mmol) and ytterbium(III) trifluoromethanesulfonate (166 mg, 0.27 mmol) in a mixture of 1,4-dioxane (9 mL) and water (3 mL) was stirred at 90° C. overnight. After cooling to room temperature, the mixture was filtered on Celite®. The filtrate was concentrated in vacuo. The residue was dissolved in ethyl acetate (30 mL) and washed with 0.5M NaOH (2×30 mL). The aqueous layer was acidified with 37% hydrochloric acid until pH 3 and extracted with ethyl acetate (2×30 mL). The organic layer was dried over sodium sulfate and concentrated in vacuo. The residue was refluxed in methanol (10 mL) in the presence of two drops of sulfuric acid for 1 hour. The mixture was concentrated in vacuo. The residue was partitioned between ethyl acetate (10 mL) and water (10 mL). The aqueous layer was extracted with ethyl acetate (2×10 mL). The combined organic extracts were washed with a saturated aqueous solution of sodium bicarbonate (20 mL), dried over sodium sulfate and evaporated to dryness. The residue was purified by flash chromatography on silica gel (cyclohexane/ethyl acetate 80/20) to provide methyl 2-(2-bromo-3-methylphenyl)-2-hydroxyacetate (11b) (296 mg, 1.14 mmol, 42%) as a yellow oil.

$^1$H NMR (300 MHz, CDCl$_3$) δ 2.49 (s, 3H), 3.58 (d, J=5.2 Hz, 1H), 3.81 (s, 3H), 5.70 (d, J=5.2 Hz, 1H), 7.22-7.30 (m, 3H).

Step 3: Preparation of intermediate methyl 2-(2-bromo-3-methylphenyl)-2-(tert-butoxy)acetate (11c)

To a solution of methyl 2-(2-bromo-3-methylphenyl)-2-hydroxyacetate (11b) (296 mg, 1.14 mmol) in tert-butyl acetate (20 mL) at −20° C. was added perchloric acid (2.7 mL). The mixture was stirred at −20° C. for 2 hours before being poured into a saturated aqueous solution of sodium bicarbonate (50 mL). Water (100 mL) was added. The layers were separated and the aqueous layer was extracted with ethyl acetate (2×30 mL). The organic layers were dried over sodium sulfate and concentrated in vacuo. The residue was purified by flash chromatography on silica gel (cyclohexane/ethyl acetate 90/10) to provide methyl 2-(2-bromo-3-methylphenyl)-2-(tert-butoxy)acetate (11c) (231 mg, 0.73 mmol, 64%) as a yellow oil.

¹H NMR (300 MHz, CDCl₃) δ 1.23 (s, 9H), 2.42 (s, 3H), 3.68 (s, 3H), 5.56 (s, 1H), 7.16-7.25 (m, 2H), 7.48 (dd, J=2.0 Hz, J=7.3 Hz, 1H).

Step 4: Preparation of intermediate methyl 2-(tert-butoxy)-2-[2-(3,4-dihydro-2H-1-benzopyran-6-yl)-3-methylphenyl]acetate (11d)

A mixture of methyl 2-(2-bromo-3-methylphenyl)-2-(tert-butoxy)acetate (11c) (72 mg, 0.23 mmol), sodium carbonate (97 mg, 0.91 mmol), 6-(4,4,5,5-tetramethyl-1,3,2-dioxaborolan-2-yl)chroman (104 mg, 0.41 mmol) and palladium tetrakis(triphenylphosphine) (13 mg, 0.011 mmol) in a mixture of toluene (1.1 mL), water (0.55 mL) and ethanol (0.48 mL) was heated at 85° C. overnight. After cooling to room temperature, the mixture was poured into water (10 mL). The aqueous layer was extracted with toluene (2×5 mL). The organic layer was washed with brine (10 mL), dried over sodium sulfate and concentrated in vacuo. The residue was purified by flash chromatography on silica gel (cyclohexane/ethyl acetate 95/5) to provide methyl 2-(tert-butoxy)-2-[2-(3,4-dihydro-2H-1-benzopyran-6-yl)-3-methylphenyl]acetate (11d) (66 mg, 0.18 mmol, 78%) as a colorless oil.

¹H NMR (300 MHz, CDCl₃) δ 1.02 and 1.03 (s, 9H), 2.04-2.09 (m, 5H), 2.76-2.85 (m, 2H), 3.61 and 3.62 (s, 3H), 4.22-4.26 (m, 2H), 4.89 and 4.90 (s, 1H), 6.83-6.94 (m, 3H), 7.17-7.27 (m, 2H), 7.50 (t, J=8.1 Hz, 1H).

MS m/z ([M+Na]⁺) 391.

Step 5: Preparation of 2-(tert-butoxy)-2-[2-(3,4-dihydro-2H-1-benzopyran-6-yl)-3-methyl phenyl] acetic acid A mixture of methyl 2-(tert-butoxy)-2-[2-(3,4-dihydro-2H-1-benzopyran-6-yl)-3-methylphenyl] acetate (11d) (63 mg, 0.17 mmol) and potassium hydroxide (38 mg, 0.68 mmol) in a mixture of ethanol (6 mL) and water (2 mL) was refluxed for 1 hour. The mixture was concentrated in vacuo. Water (2 mL) was added to the residue and the resulting solution was acidified with 1M hydrochloric acid until pH 3 and extracted with ethyl acetate (2×5 mL). The organic layer was dried over sodium sulfate and concentrated in vacuo. The residue was triturated in petroleum ether and evaporated to dryness to provide the desired acid (example 11) (50 mg, 0.14 mmol, 82%) as a white solid.

¹H NMR (400 MHz, CDCl₃) δ 1.09 and 1.10 (s, 9H), 2.08-2.11 (m, 5H), 2.76-2.90 (m, 2H), 4.27-4.30 (m, 2H), 4.97 and 4.98 (s, 1H), 6.85-6.93 (m, 2H), 7.26-7.35 (m, 4H).

MS m/z ([M−H]⁻) 353.

Example 12: Synthesis of 2-[2-(3,4-dihydro-2H-1-benzopyran-6-yl)naphthalen-1-yl]-2-ethoxyacetic acid

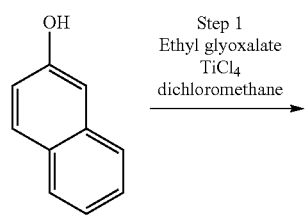

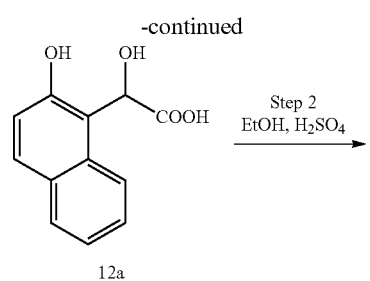

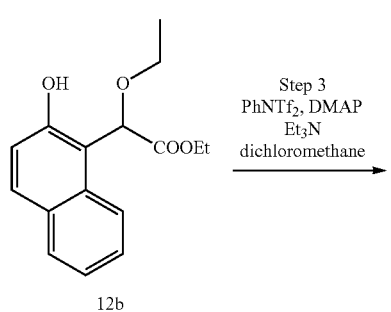

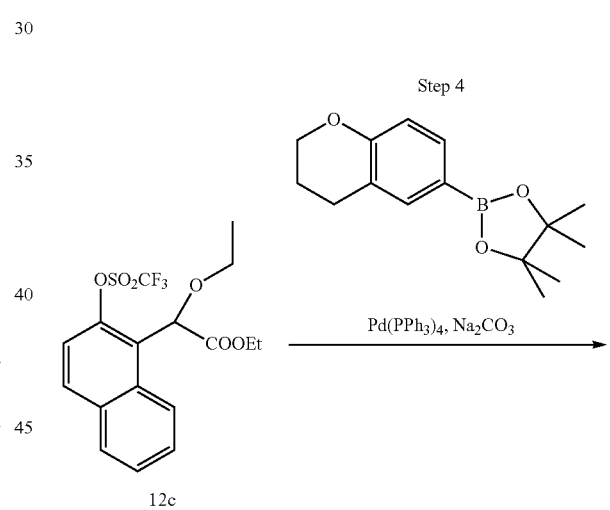

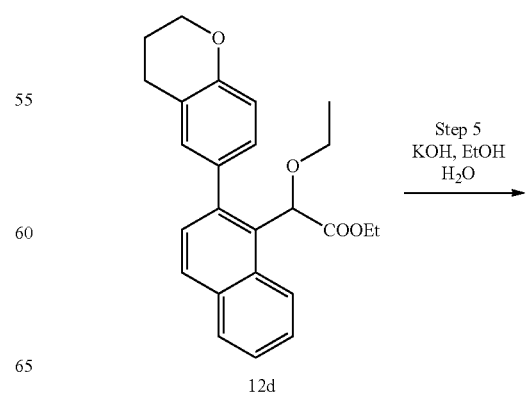

-continued

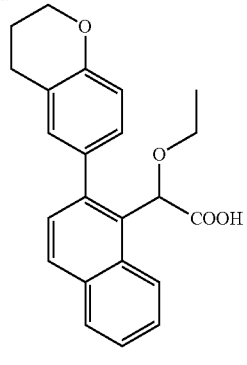

Example 12

Step 1-2: Preparation of intermediate ethyl 2-ethoxy-2-(2-hydroxynaphthalen-1-yl)acetate (12b)

To a solution of 2-naphthol (1.00g, 6.94 mmol) and ethyl glyoxalate 50% in toluene (2.06 mL, 10.4 mmol) in anhydrous dichloromethane (20 mL) at 0° C., under nitrogen atmosphere was dropwise added titanium chloride (0.80 mL, 7.28 mmol). The black mixture was stirred at 0° C. for 45 minutes then poured in ice (150 mL). The mixture was stirred for 30 min. The aqueous layer was extracted with ethyl acetate (3×50 mL). The organic layer was washed with 2 M sodium hydroxide (2×50 mL). The basic aqueous layer was acidified with 37% hydrochloric acid and extracted with ethyl acetate (2×50 mL). The organic layer was dried over sodium sulfate and concentrated in vacuo. The residue dissolved in ethanol (10 mL) and refluxed for 1 hour in the presence of 2 drops of sulfuric acid. The mixture was concentrated in vacuo. The residue was dissolved in water (10 mL) and extracted with ethyl acetate (2×10 mL). The organic layer was washed with brine, dried on sodium sulfate and concentrated in vacuo. The residue was purified by flash chromatography on silica gel (cyclohexane/ethyl acetate 70/30) to provide ethyl 2-ethoxy-2-(2-hydroxynaphthalen-1-yl)acetate (12b) (140 mg, 0.51 mmol, 7%) as a yellow solid.

$^1$H NMR (300 MHz, CDCl$_3$) δ 1.16 (t, J=7.2 Hz, 3H), 1.33 (t, J=7.2 Hz, 3H), 3.60-3.80 (m, 2H), 4.07-4.26 (m, 2H), 5.83 (s, 1H), 7.13 (d, J=8.7 Hz, 1H), 7.34 (t, J=7.5 Hz, 1H), 7.51 (t, J=7.2 Hz, 1H), 7.75 (t, J=8.7 Hz, 2H), 7.99 (d, J=8.7 Hz, 1H), 8.48 (s, 1H).

MS m/z ([M−H]$^−$) 273.

Step 3: Preparation of intermediate ethyl 2-ethoxy-2-{2-[(trifluoromethane)sulfonyloxy]naphthalen-1-yl}acetate (12c)

To a solution of ethyl 2-ethoxy-2-(2-hydroxynaphthalen-1-yl)acetate (12b) (135 mg, 0.49 mmol), N-phenyl-bis(trifluoromethanesulfonimide) (264 mg, 0.74 mmol) and 4-(dimethylamino)pyridine (6 mg, 0.05 mmol) in anhydrous dichloromethane (8 mL) at 0° C. under nitrogen atmosphere was added triethylamine (137 μL, 0.98 mmol). The mixture was stirred at room temperature for 3 hours. Water (10 mL) was added. The aqueous layer was extracted with dichloromethane (2×10 mL). The organic layers were dried over sodium sulfate and concentrated in vacuo. The residue was purified by flash chromatography on silica gel (cyclohexane/ethyl acetate 90/10) to provide ethyl 2-ethoxy-2-{2-[(trifluoromethane) sulfonyloxy]naphthalen-1-yl}acetate (12c) (195 mg, 0.48 mmol, 97%) as a yellow oil.

$^1$H NMR (300 MHz, CDCl$_3$) δ 1.08 (t, J=7.1 Hz, 3H), 1.24 (t, J=7.0 Hz, 3H), 3.50 (dq, J=9.0 7.0 Hz, 1H), 3.80 (dq, J=9.0 7.0 Hz, 1H), 4.04 (dq, J=10.7 7.1 Hz, 1H), 4.20 (dq, J=10.7 7.1 Hz, 1H), 5.72 (s, 1H), 7.40 (d, J=9.0 Hz, 1H), 7.55-7.60 (m, 2H), 7.86-7.93 (m, 2H), 8.53-8.56 (m, 1H).

MS m/z ([M−H]$^−$) 405.

Step 4: Preparation of intermediate ethyl 2-[2-(3,4-dihydro-2H-1-benzopyran-6-yl)naphthalen-1-yl]-2-ethoxyacetate (12d)

A mixture of ethyl 2-ethoxy-2-{2-[(trifluoromethane) sulfonyloxy]naphthalen-1-yl}acetate (12c) (82 mg, 0.20 mmol), sodium carbonate (86 mg, 0.81 mmol), 6-(4,4,5,5-tetramethyl-1,3,2-dioxaborolan-2-yl)chroman (94 mg, 0.36 mmol) and palladium tetrakis(triphenylphospine) (12 mg, 0.010 mmol) in toluene (1.1 mL), water (0.55 mL) and ethanol (0.48 mL) was heated at 85° C. overnight. After cooling to room temperature, the mixture was poured into water (10 mL). The aqueous layer was extracted with toluene (2×5 mL). The organic layer was washed with brine (10 mL), dried over sodium sulfate and concentrated in vacuo. The residue was purified by flash chromatography on silica gel (cyclohexane/ethyl acetate 95/5) to provide ethyl 2-[2-(3,4-dihydro-2H-1-benzopyran-6-yl)naphthalen-1-yl]-2-ethoxyacetate (12d) (55 mg, 0.14 mmol, 69%) as a colorless oil.

$^1$H NMR (300 MHz, CDCl$_3$) δ 1.08-1.13 (m, 6H), 2.04-2.10 (m, 2H), 2.84 (t, J=6.4 Hz, 2H), 3.28-3.35 (m, 1H), 3.46-3.54 (m, 1H), 4.04 (dq, J=10.7 7.1 Hz, 1H), 4.17-4.27 (m, 3H), 5.48 (s, 1H), 6.86 (d, J=8.3 Hz, 1H), 7.16 (broad s, 1H), 7.36 (d, J=8.4 Hz, 1H), 7.44-7.52 (m, 2H), 7.95-7.85 (m, 2H), 8.45 (d, J=8.2 Hz, 1H).

MS m/z ([M+Na]$^+$) 413.

Step 8: Preparation of 2-[2-(3,4-dihydro-2H-1-benzopyran-6-yl)naphthalen-1-yl]-2-ethoxyacetic acid A mixture of ethyl 2-[2-(3,4-dihydro-2H-1-benzopyran-6-yl)naphthalen-1-yl]-2-ethoxyacetate (55 mg, 0.14 mmol) and potassium hydroxide (12d) (32 mg, 0.56 mmol) in a mixture of ethanol (6 mL) and water (2 mL) was refluxed for 90 minutes. The mixture was concentrated in vacuo. Water (2 mL) was added to the residue and the aqueous layer was extracted with diethyl ether (5 mL). The aqueous layer was acidified with 1M hydrochloric acid until pH 3 and extracted with ethyl acetate (2×5 mL). The organic layer was dried over sodium sulfate and concentrated in vacuo to provide the desired acid (example 12) (38 mg, 0.10 mmol, 74%) as a white solid.

$^1$H NMR (300 MHz, CDCl$_3$) δ 1.04 (t, J=7.2 Hz, 3H), 2.02-2.10 (m, 2H), 2.80-2.86 (m, 2H), 3.25-3.34 (m, 2H), 4.23-4.27 (m, 1H), 5.62 (s, 1H), 6.86 (d, J=8.1 Hz, 1H), 7.09-7.26 (m, 1H), 7.38 (d, J=8.4 Hz, 1H), 7.46-7.54 (m, 2H), 7.82-7.88 (m, 2H), 8.14 (m, 1H).

MS m/z ([M−H]$^−$) 361.

Example 13: Synthesis of 2-(tert-butoxy)-2-[2-(3,4-dihydro-2H-1-benzopyran-6-yl)-5-(dimethylamino)phenyl]acetic acid

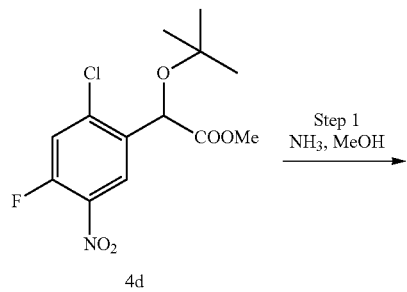

4d

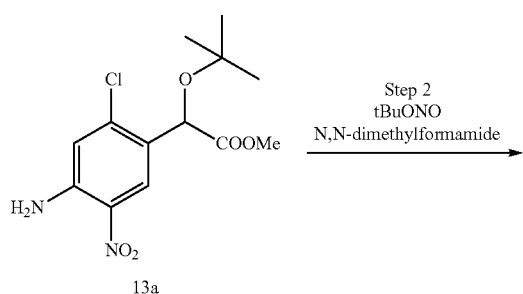

13a

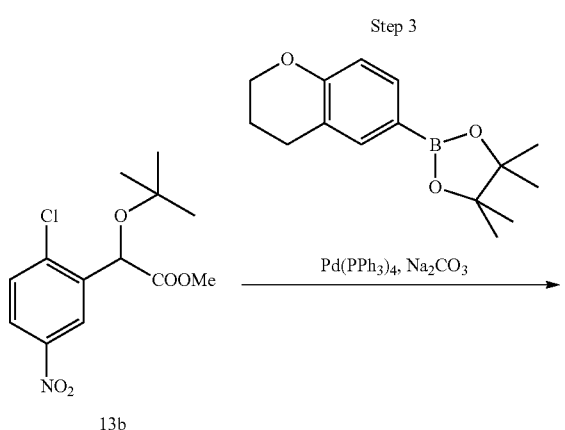

13b

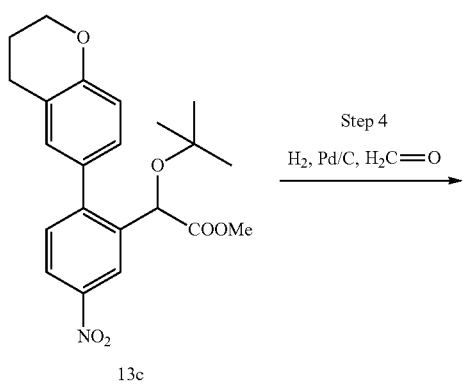

13c

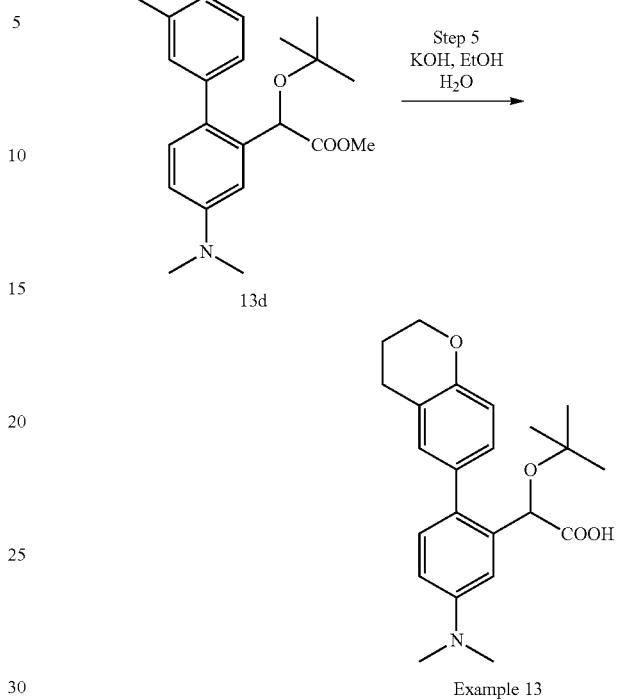

13d

Example 13

Step 1: Preparation of intermediate methyl 2-(4-amino-2-chloro-5-nitrophenyl)-2-(tert-butoxy)acetate (13a)

A solution of methyl 2-(tert-butoxy)-2-(2-chloro-4-fluoro-5-nitrophenyl)acetate (4d) (104 mg, 0.33 mmol) in $NH_3$ 7 M in methanol (2 mL) was stirred at 60° C. for 30 minutes. The mixture was concentrated in vacuo. The residue was purified by flash chromatography on silica gel (cyclohexane/ethyl acetate 80/20) to provide methyl 2-(4-amino-2-chloro-5-nitrophenyl)-2-(tert-butoxy)acetate (13a) (52 mg, 0.16 mmol, 50%) as a yellow oil.

$^1$H NMR (300 MHz, $CDCl_3$) δ 1.24 (s, 9H), 3.71 (s, 3H), 5.31 (s, 1H), 6.11 (broad s, 2H), 6.84 (s, 1H), 8.39 (s, 1H). MS m/z ([M−H]$^-$) 315.

Step 2: Preparation of intermediate methyl 2-(tert-butoxy)-2-(2-chloro-5-nitrophenyl)acetate (13b)

To a solution of tert-butyl nitrite (39 μL, 0.33 mmol) in N,N-dimethylformamide (1 mL) at 60° C. was dropwise added a solution of methyl 2-(4-amino-2-chloro-5-nitrophenyl)-2-(tert-butoxy)acetate (52 mg, 0.16 mmol) in N,N-dimethylformamide (0.5 mL). The mixture was stirred at 60° C. for 1 hour, poured in water (10 mL) and extracted with ethyl acetate (2×10 mL). The organic layer was washed with brine (2×5 mL), dried with sodium sulfate and concentrated in vacuo. The residue was dissolved in toluene (5 mL) and concentrated in vacuo to provide methyl 2-(tert-butoxy)-2-(2-chloro-5-nitrophenyl)acetate (13b) (48 mg, 0.16 mmol, 96%) as a yellow oil which was used without further purification.

$^1$H NMR (300 MHz, $CDCl_3$) δ 1.25 (s, 9H), 3.72 (s, 3H), 5.49 (s, 1H), 7.51 (d, J=8.7 Hz, 1H), 8.11 (dd, J=2.7 8.7 Hz, 1H), 8.55 (d, J=2.7 Hz, 1H).

Step 3: Preparation of intermediate methyl 2-(tert-butoxy)-2-[2-(3,4-dihydro-2H-1-benzopyran-6-yl)-5-nitrophenyl]acetate (13c)

A mixture of methyl 2-(tert-butoxy)-2-(2-chloro-5-nitrophenyl)acetate (13b) (48 mg, 0.16 mmol), sodium carbonate (67 mg, 0.64 mmol), 6-(4,4,5,5-tetramethyl-1,3,2-dioxaborolan-2-yl)chroman (74 mg, 0.29 mmol) and palladium tetrakis(triphenylphospine) (9 mg, 0.008 mmol) in toluene (1.1 mL), water (0.55 mL) and ethanol (0.48 mL) was heated at 85° C. overnight. After cooling to room temperature, the mixture was poured into water (10 mL). The aqueous layer was extracted with toluene (2×5 mL). The organic layer was washed with brine (10 mL), dried over sodium sulfate and concentrated in vacuo. The residue was purified by flash chromatography on silica gel (cyclohexane/ethyl acetate 90/10) to provide methyl 2-(tert-butoxy)-2-[2-(3,4-dihydro-2H-1-benzopyran-6-yl)-5-nitrophenyl]acetate (13c) (29 mg, 0.072 mmol, 45%) as a yellow oil.

$^1$H NMR (300 MHz, CDCl$_3$) δ 1.02 (s, 9H), 2.03-2.11 (m, 2H), 2.81-2.86 (m, 2H), 3.70 (s, 3H), 4.24-4.28 (m, 2H), 5.21 (s, 1H), 6.88 (d, J=8.4 Hz, 1H), 7.03 (d, J=2.4 Hz, 1H), 7.09 (dd, J=2.4 8.4 Hz, 1H), 7.37 (d, J=8.4 Hz, 1H), 8.14 (dd, J=2.4 8.4 Hz, 1H), 8.56 (d, J=2.4 Hz, 1H).

Step 4: Preparation of intermediate methyl 2-(tert-butoxy)-2-[2-(3,4-dihydro-2H-1-benzopyran-6-yl)-5-(dimethylamino)phenyl]acetate (13d)

A mixture of methyl 2-(tert-butoxy)-2-[2-(3,4-dihydro-2H-1-benzopyran-6-yl)-5-nitrophenyl] acetate (13c) (28 mg, 0.07 mmol), 37% aqueous formaldehyde (0.12 mL, 1.61 mmol) and palladium on charcoal (10 mg) in methanol (4 mL) was stirred at room temperature under hydrogen atmosphere for 2 hours. The mixture was filtered on millipore and the filtrate was concentrated in vacuo. The residue was purified by flash chromatography on silica gel (cyclohexane/ethyl acetate 80/20) to provide intermediate methyl 2-(tert-butoxy)-2-[2-(3,4-dihydro-2H-1-benzopyran-6-yl)-5-(dimethylamino)phenyl]acetate (13d) (23 mg, 0.058 mmol, 82%) as a colorless oil.

$^1$H NMR (300 MHz, CDCl$_3$) δ 1.00 (s, 9H), 2.01-2.09 (m, 2H), 2.79-2.85 (m, 2H), 2.97 (s, 6H), 3.68 (s, 3H), 4.21-4.25 (m, 2H), 5.20 (s, 1H), 6.71 (dd, J=2.7 8.4 Hz, 1H), 6.82 (d, J=8.4 Hz, 1H), 6.97 (d, J=2.7 Hz, 1H), 7.05-7.13 (m, 3H).
MS m/z ([M+H]$^+$) 398.

Step 5: Preparation of 2-(tert-butoxy)-2-[2-(3,4-dihydro-2H-1-benzopyran-6-yl)-5-(dimethylamino)phenyl]acetic acid A mixture of methyl 2-(tert-butoxy)-2-[2-(3,4-dihydro-2H-1-benzopyran-6-yl)-5-(dimethyl amino)phenyl]acetate (13d) (20 mg, 0.05 mmol) and potassium hydroxide (21 mg, 0.37 mmol) in a mixture of ethanol (3 mL) and water (1 mL) was refluxed for 90 minutes. The mixture was concentrated in vacuo. Water (2 mL) was added to the residue and the resulting solution was extracted with diethyl ether (5 mL). The aqueous layer was acidified with 1M hydrochloric acid until pH 4 and extracted with ethyl acetate (2×5 mL). The organic layer was dried over sodium sulfate and concentrated in vacuo. The residue was triturated in pentane and evaporated to dryness to provide 2-(tert-butoxy)-2-[2-(3,4-dihydro-2H-1-benzopyran-6-yl)-5-(dimethylamino)phenyl] acetic acid (example 13) (19 mg, 0.049 mmol, 99%) as a white solid.

$^1$H NMR (300 MHz, CDCl$_3$) δ 0.99 (s, 9H), 2.00-2.07 (m, 2H), 2.79-2.85 (m, 2H), 2.96 (s, 6H), 4.20-4.24 (m, 2H), 5.24 (s, 1H), 6.71-6.75 (m, 2H), 6.82 (d, J=8.7 Hz, 1H), 7.12 (d, J=8.7 Hz, 1H), 7.20-7.22 (m, 2H).

MS m/z ([M−H]$^-$) 382.

MS m/z ([M+H]$^+$) 384.

Example 14: Synthesis of 2-(tert-butoxy)-2-[3-(3,4-dihydro-2H-1-benzopyran-6-yl) naphthalene-2-yl] acetic acid

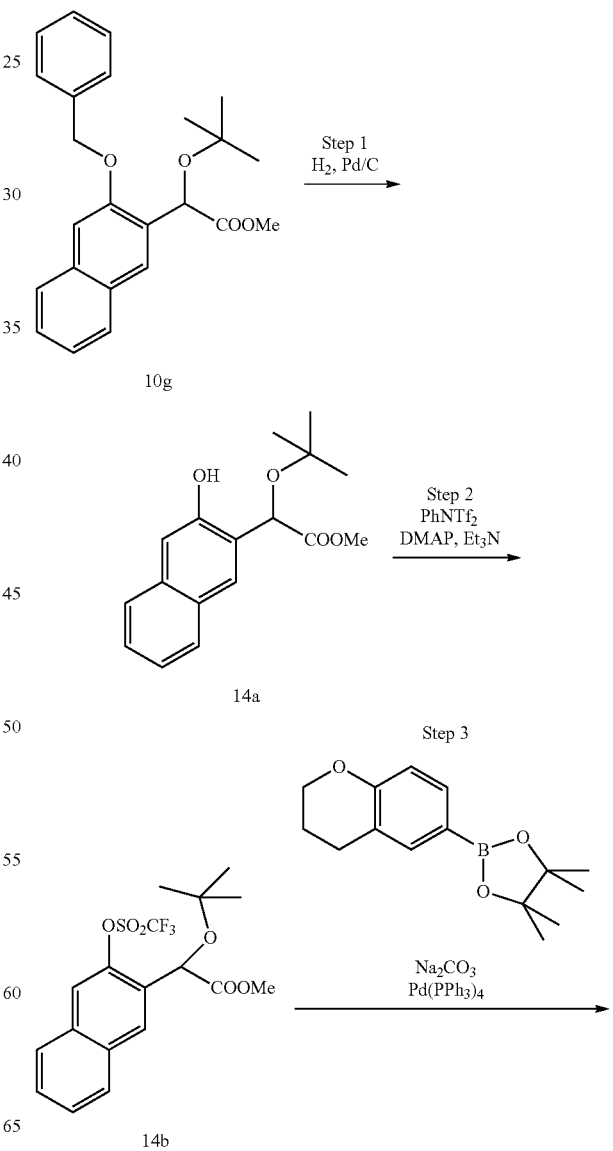

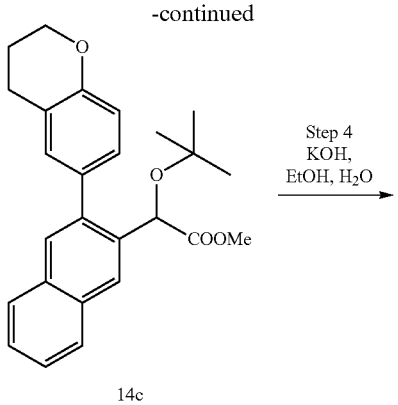

14c

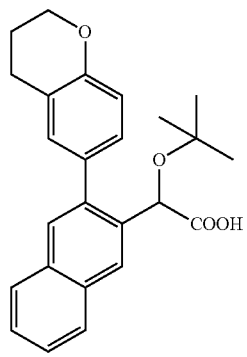

Example 14

Step 1: Preparation of intermediate methyl 2-(tert-butoxy)-2-(3-hydroxynaphthalen-2-yl) acetate (14a)

A mixture of methyl 2-[3-(benzyloxy)naphthalen-2-yl]-2-(tert-butoxy)acetate (10g) (120 mg, 0.32 mmol) and palladium on charcoal (12 mg) in ethyl acetate (2 mL) was stirred at room temperature under hydrogen atmosphere for 4 days. The mixture was filtered on millipore and the filtrate was concentrated in vacuo to provide methyl 2-(tert-butoxy)-2-(3-hydroxynaphthalen-2-yl)acetate (14a) (88 mg, 0.30 mmol, 96%).

$^1$H NMR (300 MHz, CDCl$_3$) δ 1.31 (s, 9H), 3.71 (s, 3H), 5.36 (s, 1H), 7.25 (s, 1H), 7.27-33 (m, 1H), 7.37-44 (m, 1H), 7.65-7.77 (m, 3H), 8.10 (s, 1H).

Step 2: Preparation of intermediate methyl 2-(tert-butoxy)-2-{3-[(trifluoromethane) sulfonyloxy]naphthalen-2-yl}acetate (14b)

To a solution of methyl 2-(tert-butoxy)-2-(3-hydroxynaphthalen-2-yl)acetate (14a) (90 mg, 0.31 mmol), N-phenyl-bis(trifluoromethanesulfonimide) (167 mg, 0.47 mmol) and 4-(dimethylamino)pyridine (4 mg, 0.03 mmol) in anhydrous dichloromethane (3 mL) at 0° C. under nitrogen atmosphere was added triethylamine (87 µL, 0.62 mmol). The mixture was stirred at room temperature for 1 hour. Water (5 mL) was added. The aqueous layer was extracted with dichloromethane (2×7 mL). The organic layers were successively washed with a saturated solution of sodium bicarbonate (5 mL) and 1N hydrochloric acid (5 mL), then dried over sodium sulfate and concentrated in vacuo. The residue was purified by flash chromatography on silica gel (cyclohexane/ethyl acetate 50/50) to provide methyl 2-(tert-butoxy)-2-{3-[(trifluoromethane)sulfonyloxy]naphthalen-2-yl}acetate (90 mg, 0.21 mmol, 69%).

$^1$H NMR (300 MHz, CDCl$_3$) δ 1.29 (s, 9H), 3.71 (s, 3H), 5.50 (s, 1H), 7.53-7.59 (m, 2H), 7.77 (s, 1H), 7.83-7.86 (m, 1H), 7.89-7.93 (m, 1H), 8.22 (s, 1H).

Step 3: Preparation of intermediate methyl 2-(tert-butoxy)-2-[3-(3,4-dihydro-2H-1-benzopyran-6-yl) naphthalen-2-yl]acetate (14c)

A mixture of methyl 2-(tert-butoxy)-2-{3-[(trifluoromethane)sulfonyloxy]naphthalen-2-yl}acetate (14b) (90 mg, 0.21 mmol), sodium carbonate (91 mg, 0.86 mmol), and 6-(4,4,5,5-tetramethyl-1,3,2-dioxaborolan-2-yl)chroman (100 mg, 0.39 mmol)) in a mixture of toluene (1.26 mL), ethanol (0.6 mL) and water (0.5 mL) was bubbled with nitrogen for 5 minutes. Palladium tetrakis(triphenylphospine) (12 mg, 0.01 mmol) was added and the reaction mixture was heated at 95° C. overnight. After cooling to room temperature, water (2 mL) was added. The aqueous layer was extracted with toluene (2×8 mL). The organic layers were washed with brine (5 mL), dried over sodium sulfate and concentrated in vacuo. The residue was purified by flash chromatography on silica gel (cyclohexane/ethyl acetate 80/20) to provide methyl 2-(tert-butoxy)-2-[3-(3,4-dihydro-2H-1-benzopyran-6-yl)naphthalen-2-yl] acetate (14c) (70 mg, 0.17 mmol, 81%).

$^1$H NMR (300 MHz, CDCl$_3$) δ 1.05 (s, 9H), 2.04-2.12 (m, 2H), 2.80-2.89 (m, 2H), 3.67 (s, 3H), 4.27 (t, J=5.2 Hz, 2H), 5.53 (s, 1H), 6.89 (d, J=8.3 Hz, 1H) 7.14-7.22 (m, 2H), 7.44-7.48 (m, 2H), 7.69 (s, 1H), 7.77-7.80 (m, 1H), 7.85-7.91 (m, 1H), 8.16 (s, 1H).

Step 4: Preparation of 2-(tert-butoxy)-2-[3-(3,4-dihydro-2H-1-benzopyran-6-yl) naphthalene-2-yl] acetic acid A solution of methyl 2-(tert-butoxy)-2-[3-(3,4-dihydro-2H-1-benzopyran-6-yl)naphthalen-2-yl]acetate (14c) (70 mg, 0.17 mmol) and potassium hydroxide (84 mg, 0.69 mmol) in a mixture of ethanol (2 mL) and water (6 mL) was refluxed for 60 minutes. The mixture was concentrated in vacuo. Water (8 mL) was added to the residue and the solution was washed with diethyl ether (10 mL). The aqueous layer was acidified with concentrated hydrochloric acid until pH 2 and was extracted with ethyl acetate (2×10 mL). The organic layer was dried with sodium sulfate and concentrated in vacuo. The residue was purified by preparative TLC (dichloromethane/methanol 95/5) to provide the desired acid (example 14) (20 mg, 0.05 mmol, 29%).

$^1$H NMR (300 MHz, CDCl$_3$) δ 1.03 (s, 9H), 2.02-2.11 (m, 2H), 2.81-2.89 (m, 2H), 4.26 (t, J=5.3 Hz, 2H) 5.37 (s, 1H), 6.89 (d, J=8.6 Hz, 1H) 7.29-7.32 (m, 2H), 7.44-7.51 (m, 2H), 7.73 (s, 1H), 7.78-7.87 (m, 2H), 7.99 (s, 1H).

MS m/z ([M−H]$^−$) 389.

Example 15: Synthesis of 2-(tert-butoxy)-2-[2-(3,4-dihydro-2H-1-benzopyran-6-yl) naphthalene-1-yl] acetic acid
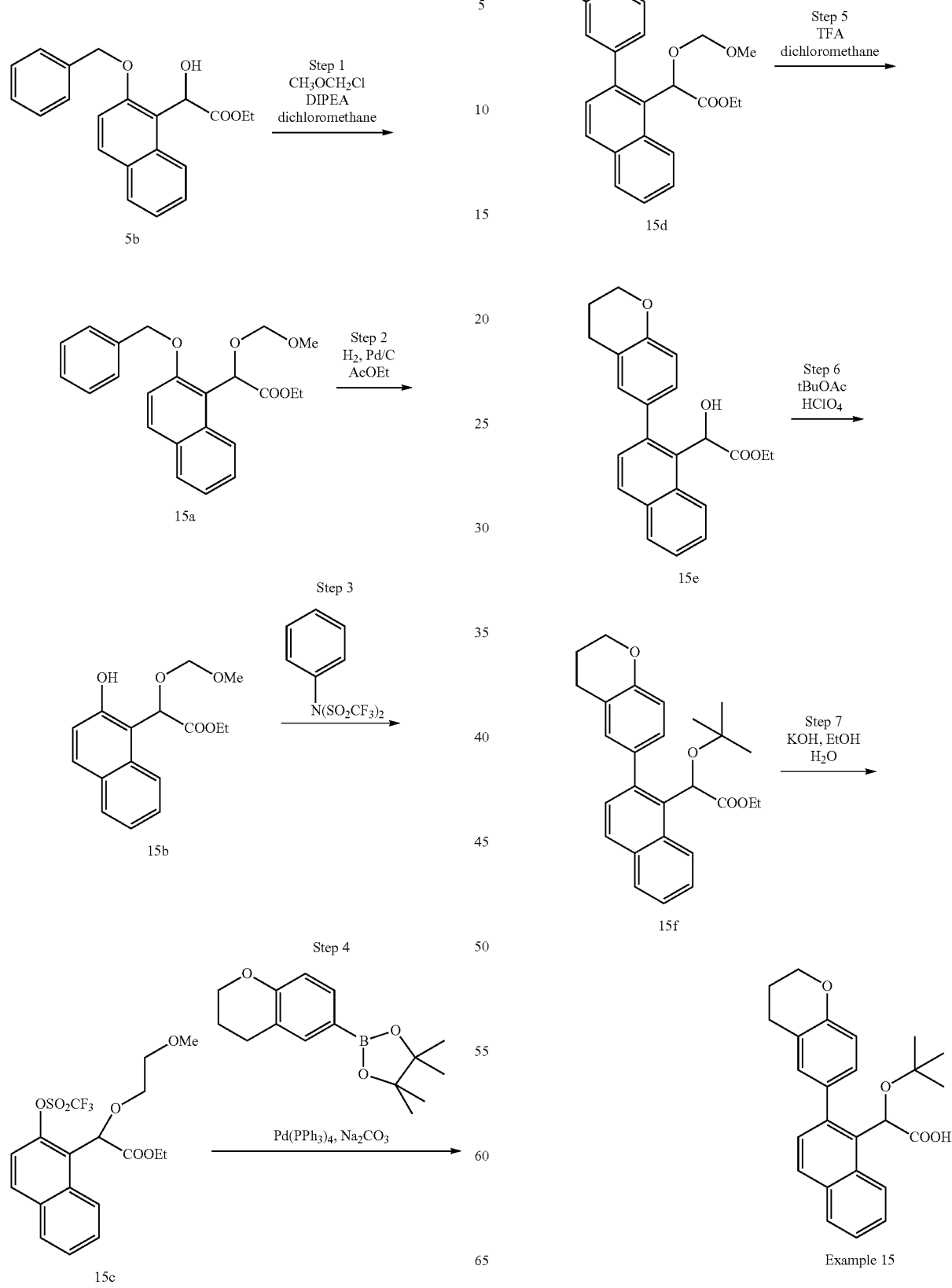

Step 1: Preparation of intermediate ethyl 2-[2-(benzyloxy)naphthalen-1-yl]-2-(methoxy methoxy)acetate (15a)

To a solution of ethyl 2-hydroxy-2-[2-(benzyloxy)naphthalen-1-yl]acetate (5b) (341 mg, 1.01 mmol) in anhydrous dichloromethane (5 mL) under nitrogen atmosphere at 0° C. was added disopropylethylamine (353 µL, 2.03 mmol) and chloromethyl methyl ether (154 µL, 2.03 mmol). The mixture was stirred at room temperature for 72 hours before adding water (5 mL). Layers were separated. The aqueous layer was extracted with dichloromethane (2×5 mL). The organic layers were dried over sodium sulfate and concentrated in vacuo. The residue was dissolved in ethyl acetate (10 mL), washed with brine (10 mL), dried over sodium sulfate and concentrated in vacuo to provide ethyl 2-[2-(benzyloxy)naphthalen-1-yl]-2-(methoxymethoxy)acetate (15a) (384 mg, 1.01 mmol, 99%) as a colorless oil.

$^1$H NMR (300 MHz, CDCl$_3$) δ 1.09 (t, J=7.2 Hz, 3H), 3.35 (s, 3H), 4.06-4.18 (m, 2H), 4.67 (d, J=6.6 Hz, 1H), 4.85 (d, J=6.6 Hz, 1H), 5.25 (d, J=12.0 Hz, 1H), 5.31 (d, J=12.0 Hz, 1H), 6.40 (s, 1H), 7.27-7.51 (m, 9H), 7.75-7.82 (m, 2H), 8.24 (d, J=8.7 Hz, 1H).

MS m/z ([M−H]$^−$) 379.

Step 2: Preparation of intermediate ethyl 2-(2-hydroxynaphthalen-1-yl)-2-(methoxy methoxy)acetate (15b)

A mixture of ethyl 2-[2-(benzyloxy)naphthalen-1-yl]-2-(methoxymethoxy)acetate (15a) (384 mg, 1.01 mmol) and palladium on charcoal (60 mg) in ethyl acetate (10 mL) was stirred at room temperature under hydrogen atmosphere for 48 hours. The mixture was filtered on millipore and the filtrate was concentrated in vacuo. The residue was purified by flash chromatography on silica gel (cyclohexane/ethyl acetate: 90/10) to provide the desired phenol (15b) (107 mg, 0.368 mmol, 36%) as a colorless oil.

$^1$H NMR (300 MHz, CDCl$_3$) δ 1.16 (t, J=7.1 Hz, 3H), 3.42 (s, 3H), 4.08-4.27 (m, 2H), 4.78 (d, J=6.8 Hz, 1H), 4.84 (d, J=6.8 Hz, 1H), 6.12 (s, 1H), 7.14 (d, J=8.9 Hz, 1H), 7.35 (t, J=7.8 Hz, 1H), 7.49-7.55 (m, 1H), 7.75-7.79 (m, 2H), 7.89 (broad s, 1H), 8.01 (d, J=8.6 Hz, 1H).

MS m/z ([M+Na]$^+$) 313.
MS m/z ([M−H]$^−$) 289.

Step 3: Preparation of ethyl 2-(methoxymethoxy)-2-{2-[(trifluoromethane)sulfonyloxy] naphthalen-1-yl}acetate (15c)

To a solution of ethyl 2-(2-hydroxynaphthalen-1-yl)-2-(methoxymethoxy)acetate (15b) (107 mg, 0.37 mmol), N-phenyl-trifluoromethanesulfonimide (198 mg, 0.55 mmol) and 4-(dimethylamino)pyridine (5 mg, 0.03 mmol) in anhydrous dichloromethane (8 mL) at 0° C. under nitrogen atmosphere was added triethylamine (103 µL, 0.74 mmol). The mixture was stirred at room temperature for 3 hours. Water (10 mL) was added. The aqueous layer was extracted with dichloromethane (2×10 mL). The organic layers were dried over sodium sulfate and concentrated in vacuo. The residue was purified by flash chromatography on silica gel (cyclohexane/ethyl acetate 90/10) to provide ethyl 2-(methoxymethoxy)-2-{2-[(trifluoromethane)sulfonyloxy] naphthalen-1-yl}acetate (15c) (151 mg, 0.357 mmol, 96%) as a yellow solid.

$^1$H NMR (300 MHz, CDCl$_3$) δ 1.10 (t, J=7.2 Hz, 3H), 3.31 (s, 3H), 4.02-4.27 (m, 2H), 4.69 (d, J=6.6 Hz, 1H), 4.89 (d, J=6.8 Hz, 1H), 6.03 (s, 1H), 7.43 (d, J=9.1 Hz, 1H), 7.52-7.63 (m, 2H), 7.87-7.95 (m, 2H), 8.43 (d, J=8.0 Hz, 1H).

MS m/z ([M−H]$^−$) 421.

Step 4: Preparation of ethyl 2-(methoxymethoxy)-2-[2-(3,4-dihydro-2H-1-benzopyran-6-yl)naphthalen-1-yl]acetate (15d)

A mixture of 2-(methoxymethoxy)-2-{2-[(trifluoromethane)sulfonyloxy]naphthalen-1-yl}acetate (15c) (150 mg, 0.36 mmol), sodium carbonate (151 mg, 1.42 mmol), 6-(4,4,5,5-tetramethyl-1,3,2-dioxaborolan-2-yl)chroman (166 mg, 0.64 mmol) and palladium tetrakis(triphenylphospine) (21 mg, 0.018 mmol) in a mixture of toluene (1.1 mL), water (0.55 mL) and ethanol (0.48 mL) was heated at 95° C. overnight. After cooling to room temperature, the mixture was poured into water (10 mL). The aqueous layer was extracted with toluene (2×5 mL). The organic layer was washed with brine (10 mL), dried over sodium sulfate and concentrated in vacuo. The residue was purified by flash chromatography on silica gel (cyclohexane/ethyl acetate: 90/10) to provide ethyl 2-(methoxymethoxy)-2-[2-(3,4-dihydro-2H-1-benzopyran-6-yl)naphthalen-1-yl]acetate (15d) (69 mg, 0.17 mmol, 48%) as a colorless oil.

$^1$H NMR (300 MHz, CDCl$_3$) δ 1.14 (t, J=7.1 Hz, 3H), 2.03-2.11 (m, 2H), 2.84 (t, J=6.4 Hz, 2H), 3.18 (s, 3H), 4.00-4.27 (m, 4H), 4.57 (d, J=6.6 Hz, 1H), 4.74 (d, J=6.6 Hz, 1H), 5.80 (s, 1H), 6.87 (d, J=8.4 Hz, 1H), 7.16-7.19 (m, 2H), 7.37 (d, J=8.4 Hz, 1H), 7.47-7.56 (m, 2H), 7.80-7.87 (m, 2H), 8.41 (d, J=8.3 Hz, 1H).

MS m/z ([M+Na]$^+$) 429.

Step 5: Preparation of ethyl 2-[2-(3,4-dihydro-2H-1-benzopyran-6-yl)naphthalen-1-yl]-2-hydroxyacetate (15e)

A solution of ethyl 2-(methoxymethoxy)-2-[2-(3,4-dihydro-2H-1-benzopyran-6-yl)naphthalen-1-yl]acetate (15d) (69 mg, 0.17 mmol) and trifluoroacetic acid (0.13 mL, 1.7 mmol) in dicholormethane was stirred at room temperature for 2 days. The mixture was concentrated in vacuo. An aqueous saturated solution of sodium bicarbonate (10 mL) was added to the residue. The aqueous layer was extracted with dichloromethane (2×10 mL). The organic layer was dried with sodium sulfate and concentrated in vacuo. The residue was purified by flash chromatography on silica gel (cyclohexane/ethyl acetate 80/20) to provide ethyl 2-[2-(3,4-dihydro-2H-1-benzopyran-6-yl)naphthalen-1-yl]-2-hydroxyacetate (15e) (46 mg, 0.12 mmol, 74%) as a colorless oil.

$^1$H NMR (300 MHz, CDCl$_3$) δ 1.08 (t, J=7.1 Hz, 3H), 2.02-2.10 (m, 2H), 2.85 (t, J=6.4 Hz, 2H), 3.44 (d, J=1.8 Hz, 1H), 4.06-4.26 (m, 4H), 5.73 (d, J=1.8 Hz, 1H), 6.87 (d, J=8.2 Hz, 1H), 7.19-7.24 (m, 2H), 7.41 (d, J=8.4 Hz, 1H), 7.39-7.53 (m, 2H), 7.82-7.88 (m, 2H), 8.10 (d, J=7.5 Hz, 1H).

MS m/z ([M+H−H$_2$O]$^+$) 345.

Step 6: Preparation of ethyl 2-(tert-butoxy)-2-[2-(3,4-dihydro-2H-1-benzopyran-6-yl)naphthalen-1-yl]acetate (15f)

To a solution of ethyl 2-[2-(3,4-dihydro-2H-1-benzopyran-6-yl)naphthalen-1-yl]-2-hydroxyacetate (15e) (45 mg, 0.12 mmol) in tert-butyl acetate (2.3 mL) at −20° C. was added perchloric acid (0.3 mL). The mixture was stirred at −20° C. for 2 hours before being poured into a saturated aqueous solution of sodium bicarbonate (10 mL). Water (10 mL) was added. The layers were separated and the aqueous layer was extracted with ethyl acetate (2×10 mL). The organic layers were dried over sodium sulfate and concentrated in vacuo. The residue was purified by flash chromatography on silica gel (cyclohexane/ethyl acetate 90/10) to provide ethyl 2-(tert-butoxy)-2-[2-(3,4-dihydro-2H-1-benzopyran-6-yl)naphthalen-1-yl]acetate (15f) (22 mg, 0.052 mmol, 42%) as a colorless oil.

$^1$H NMR (300 MHz, CDCl$_3$) δ 0.96 (s, 9H), 1.17 (t, J=7.1 Hz, 3H), 2.03-2.11 (m, 2H), 2.75-2.92 (m, 2H), 4.02-4.28 (m, 4H), 5.65 (s, 1H), 6.88 (d, J=8.3 Hz, 1H), 7.10-7.40 (broad s, 2H), 7.33 (d, J=8.4 Hz, 1H), 7.42-7.52 (m, 2H), 7.76-7.83 (m, 2H), 8.53 (d, J=9.2 Hz, 1H).

MS m/z ([M+Na]$^+$) 441.

Step 7: Preparation of 2-(tert-butoxy)-2-[2-(3,4-dihydro-2H-1-benzopyran-6-yl)naphthalen-1-yl]acetic acid A mixture of ethyl 2-(tert-butoxy)-2-[2-(3,4-dihydro-2H-1-benzopyran-6-yl)naphthalen-1-yl]acetate (15f) (21 mg, 0.05 mmol) and potassium hydroxide (23 mg, 0.4 mmol) in a mixture of ethanol (3 mL) and water (1 mL) was refluxed for 7 hours. The mixture was concentrated in vacuo. Water (2 mL) was added to the residue and the aqueous layer was extracted with diethyl ether (5 mL). The aqueous layer was acidified with 1M hydrochloric acid until pH 2 and extracted with diethyl ether (2×5 mL). The organic layer was dried over sodium sulfate and concentrated in vacuo. The residue was purified by preparative TLC (dichloromethane/methanol 95/5) to provide the desired acid (example 15) (8 mg, 0.02 mmol, 40%) as a white solid.

$^1$H NMR (300 MHz, CDCl$_3$) δ 0.89 (s, 9H), 2.03 (broad s, 2H), 2.82 (broad s, 2H), 4.24 (t, J=4.8 Hz, 2H), 5.79 (s, 1H), 6.87 (broad s, 1H), 7.12 (broad s, 1H), 7.35 (d, J=8.4 Hz, 1H), 7.44 (broad s, 3H), 7.78-7.81 (m, 2H), 8.14 (broad s, 1H).

MS m/z ([M−H]$^−$) 389.

Example 16: Synthesis of 2-(tert-butoxy)-2-[2-(3,4-dihydro-2H-1-benzopyran-6-yl)cyclohex-1-en-1-yl]acetic acid

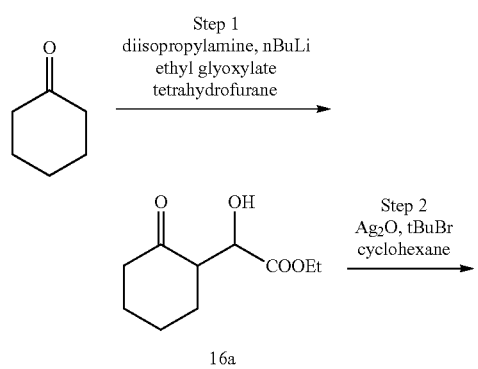

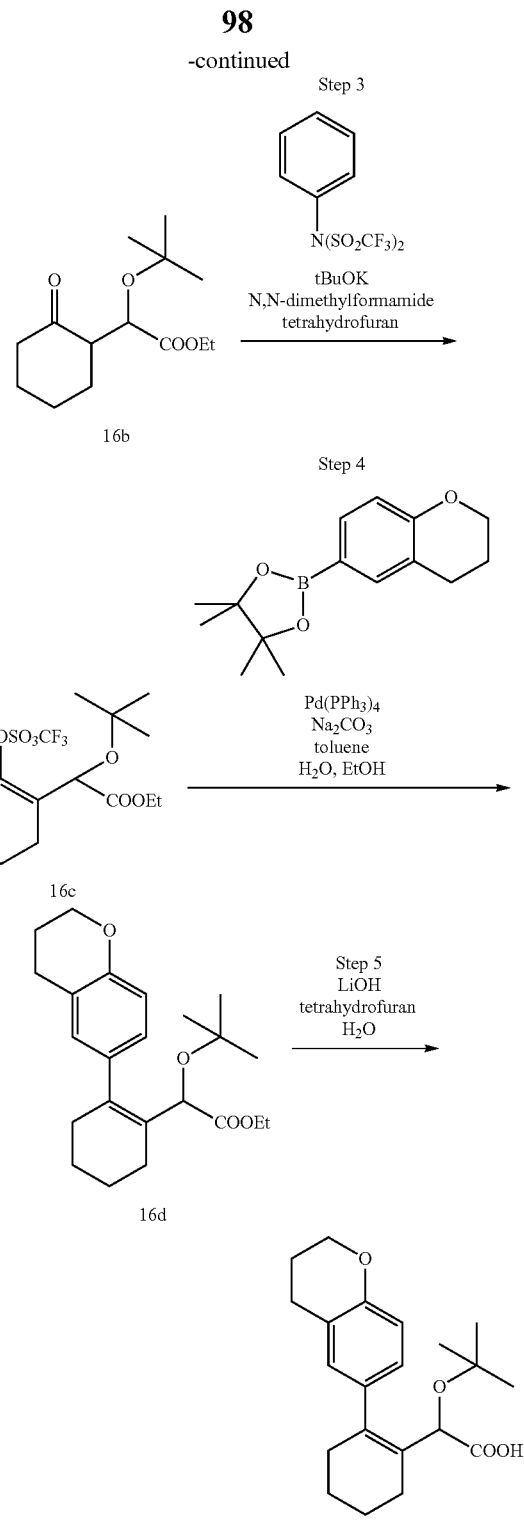

Step 1: Preparation of intermediate ethyl 2-hydroxy-2-(2-oxocyclohexyl)acetate (16a)

To a solution of diisopropylamine (0.857 mL, 6.11 mmol) in tetrahydrofuran (9 mL) was added dropwise n-butyllithium (1.6M in hexane, 3.82 mL, 6.11 mmol) at −78° C., under argon atmosphere. After 30 minutes at −78° C., a solution of cyclohexanone (500 mg, 5.09 mmol) in tetrahydrofuran (45 mL) was added. The mixture was stirred for 10 minutes and ethyl glyoxylate (50% in toluene, 1.22 mL, 6.11 mmol) was added to the reaction mixture at −78° C. The mixture was kept at −78° C. for 3 hours and 30 minutes, quenched with a saturated solution of sodium hydrogencarbonate and extracted with dichloromethane three times. The organic layer was washed with brine, dried over sodium sulfate, filtered and concentrated in vacuo. The residue was purified by flash chromatography on silica gel (cyclohexane/ethyl acetate 80/20) to provide ethyl 2-hydroxy-2-(2-oxocyclohexyl)acetate (16a) (412 mg, 2.06 mmol, 40%, mixture of both diastereoisomers) as a pale yellow liquid.

$^1$H NMR (400 MHz, CDCl$_3$) δ 1.34 (t, J=7.1 Hz, 3H), 1.68-1.77 (m, 2H), 1.90-2.18 (m, 4H), 2.32-2.54 (m, 2H), 2.81-3.01 (m, 1H), 4.26-4.32 (q, J=7.1 Hz, 2H), 4.70-4.72 (m, 1H).

MS m/z ([M+H]$^+$) 201.

Step 2: Preparation of intermediate ethyl 2-(tert-butoxy)-2-(2-oxocyclohexyl)acetate (16b)

Silver oxide (1.22 g, 5.27 mmol) and tert-butyl bromide (1.18 mL, 10.55 mmol) were successively added to a solution of ethyl 2-hydroxy-2-(2-oxocyclohexyl)acetate (16a) (352 mg, 1.76 mmol) in cyclohexane (17.5 mL). The reaction mixture was stirred at room temperature for 24 hours. During this time, two equivalents of silver oxide and tert-butyl bromide were added after 5 hours and 7 hours of the reaction time. Upon completion of the reaction, the mixture was filtered off and the filtrate was concentrated in vacuo. The residue was purified by flash chromatography on silica gel (cyclohexane/ethyl acetate 80/20) to provide ethyl 2-(tert-butoxy)-2-(2-oxocyclohexyl)acetate (16b) (303.7 mg, 1.18 mmol, 67%, mixture of both diastereoisomers).

$^1$H NMR (400 MHz, CDCl$_3$) δ 1.23 and 1.24 (s, 9H), 1.29-1.33 (m, 3H), 1.56-1.78 (m, 3H), 1.90-2.08 (m, 2H), 2.21-2.47 (m, 3H), 2.70-2.76 (m, 1H), 4.18-4.25 (m, 2H), 4.36-4.51 (m, 1H).

MS m/z ([M+Na]$^+$) 279.

Step 3: Preparation of intermediate ethyl 2-(tert-butoxy)-2-{2-[(trifluoromethane)sulfonyl oxy]cyclohex-1-en-1-yl}acetate (16c)

To a solution of ethyl 2-(tert-butoxy)-2-(2-oxocyclohexyl)acetate (16b) (272 mg, 1.06 mmol) in N,N-dimethylformamide (6.3 mL) and tetrahydrofuran (1.1 mL) was added a solution of potassium tert-butoxide (1M in tetrahydrofuran, 1.11 mL, 1.11 mmol) at −78° C. under argon atmosphere. After 1 hour at −78° C., a solution of N-phenyl-bis(trifluoromethanesulfonimide) (436 mg, 1.22 mmol) in tetrahydrofuran (1.45 mL) and N,N-dimethylformamide (0.3 mL) was slowly added to the mixture at −78° C. which was stirred at −78° C. for 1.5 hour. The reaction was quenched by addition of saturated sodium bicarbonate solution and the mixture was extracted with ethyl acetate twice. The combined organic layers were washed with brine, dried over anhydrous sodium sulfate, and concentrated in vacuo. The residue was purified by flash chromatography on silica gel (cyclohexane/ethyl acetate 95/5) to give a single isomer ethyl 2-(tert-butoxy)-2-{2-[(trifluoromethane)sulfonyloxy]cyclohex-1-en-1-yl}acetate (16c) (275 mg, 0.71 mmol, 67%).

$^1$H NMR (400 MHz, CDCl$_3$) δ 1.25 (s, 9H), 1.29 (t, J=7.1 Hz, 3H), 1.61-1.81 (m, 4H), 2.07-2.14 (m, 1H), 2.32-2.52 (m, 3H), 4.22 (q, J=7.1 Hz, 2H), 5.12 (s, 1H).

MS m/z ([M+Na]$^+$) 411.

Step 4: Preparation of intermediate ethyl 2-(tert-butoxy)-2-[2-(3,4-dihydro-2H-1-benzopyran-6-yl)cyclohex-1-en-1-yl]acetate (16d)

To a solution of ethyl 2-(tert-butoxy)-2-{2-[(trifluoromethane)sulfonyloxy]cyclohex-1-en-1-yl}acetate (16c) (265 mg, 0.682 mmol) in a mixture of toluene (2.65 mL) and ethanol (0.7 mL) was added a solution of sodium carbonate 2M (0.682 mL, 1.36 mmol), palladium tetrakis(triphenylphosphine) (39.4 mg, 0.05 mmol) and 6-(4,4,5,5-tetramethyl-1,3,2-dioxaborolan-2-yl)chroman (195.2 mg, 0.75 mmol). The mixture was heated at 80° C. for 20 hours. The mixture was then cooled at room temperature and water was added. The aqueous layer was extracted with ethyl acetate three times.

The combined organic layers were washed with brine, dried over sodium sulfate and concentrated in vacuo. The residue was purified by preparative TLC (cyclohexane/ethyl acetate 90/10) to give ethyl 2-(tert-butoxy)-2-[2-(3,4-dihydro-2H-1-benzopyran-6-yl)cyclohex-1-en-1-yl]acetate (16d) (131 mg, 0.352 mmol, 52%).

$^1$H NMR (400 MHz, CDCl$_3$) δ 1.01-1.02 (m, 9H), 1.31-1.36 (m, 4H), 1.65-1.74 (m, 3H), 1.96-2.44 (m, 6H), 2.78-2.85 (m, 2H), 4.17-4.27 (m, 4H), 4.70 (s, 1H), 6.78 (d, J=8.1 Hz, 1H), 6.97-6.99 (m, 2H).

MS m/z ([M+Na]$^+$) 395.

Step 5: Preparation of 2-(tert-butoxy)-2-[2-(3,4-dihydro-2H-1-benzopyran-6-yl)cyclohex-1-en-1-yl] acetic acid Lithium hydroxide (23.7 mg, 0.989 mmol) was added to a solution of 2-(tert-butoxy)-2-[2-(3,4-dihydro-2H-1-benzopyran-6-yl)cyclohex-1-en-1-yl]acetate (16d) (123 mg, 0.33 mmol) in a mixture of tetrahydrofuran (4.1 mL) and water (3.3 mL). The mixture was heated at 70° C. for 20 hours, during this time, 3 equivalents of lithium hydroxide were added after 7 hours of the reaction time. Upon completion of the reaction, the mixture was concentrated in vacuo. The residue was partitioned between water and dichloromethane. The product was extracted with dichloromethane. The organic layer was washed with brine, dried over sodium sulfate, filtered and concentrated in vacuo. The residue was purified by preparative TLC (dichloromethane/methanol 95/5) to give the desired acid (example 16) (72 mg, 0.21 mmol, 63%).

$^1$H NMR (400 MHz, CDCl$_3$) δ 1.07 (s, 9H), 1.67-2.47 (m, 10H), 2.77-2.87 (m, 2H), 4.23 (t, J=5.2 Hz, 2H), 4.88 (s, 1H), 6.79 (d, J=8.4 Hz, 1H), 7.09-7.13 (m, 2H).

MS m/z ([M+Na]$^+$) 367.

Example 17: Synthesis of 2-(tert-butoxy)-2-[4-(3,4-dihydro-2H-1-benzopyran-6-yl)-2H-chromen-3-yl] acetic acid

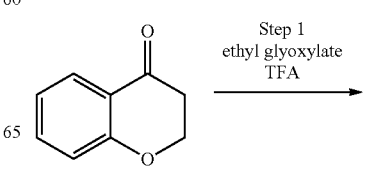

Step 1
ethyl glyoxylate
TFA

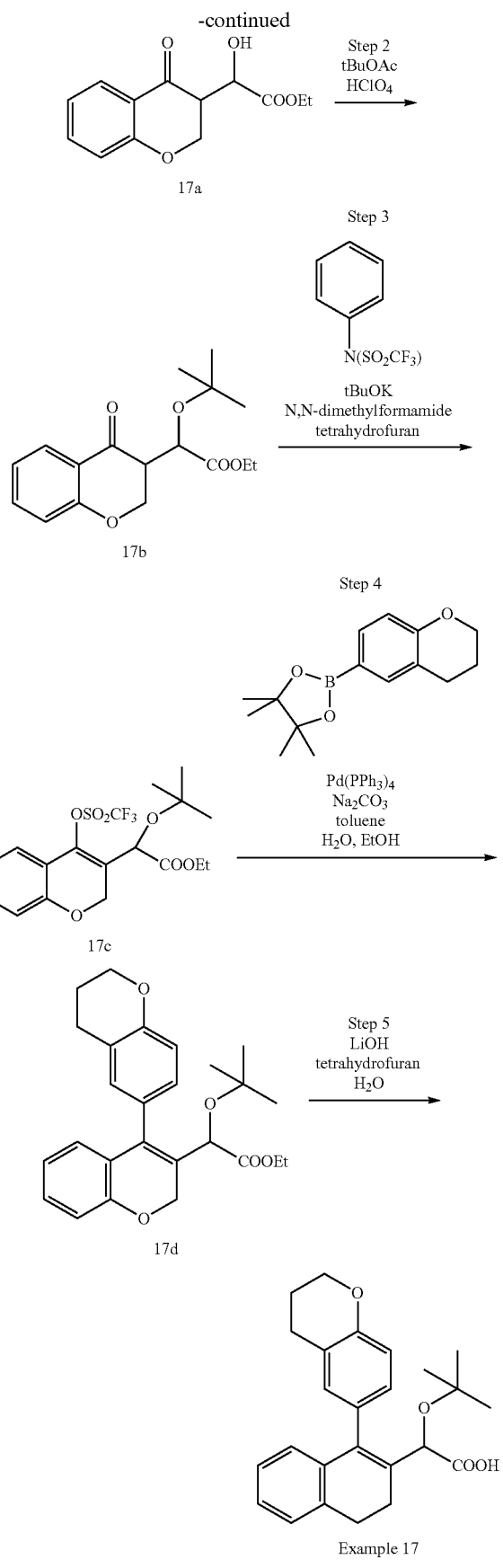

Step 1: Preparation of intermediate ethyl 2-hydroxy-2-(4-oxo-3,4-dihydro-2H-1-benzopyran-3-yl) acetate (17a)

Under nitrogen atmosphere, chromanone (768 mg, 5.18 mmol) was added at 0° C. to a solution of trifluoroacetic acid (3.8 µL, 0.05 mmol) and ethylglyoxylate (50% in toluene, 0.2 mL, 1 mmol). The mixture was stirred at 0° C. for 10 minutes then at room temperature overnight. The volatiles were evaporated and the crude material was purified by preparative TLC (cyclohexane/ethyl acetate 70/30) to afford ethyl 2-hydroxy-2-(4-oxo-3,4-dihydro-2H-1-benzopyran-3-yl)acetate as a colorless oil (17a) (235 mg, 0.94 mmol, 93%, mixture of diastereoisomers).

$^1$H NMR (400 MHz, CDCl$_3$) δ 1.24-1.37 (m, 3H), 3.28-3.53 (m, 1H), 4.29-4.36 (m, 3H), 4.48-4.98 (m, 3H), 7.01 (d, J=8.3 Hz, 1H), 7.03-7.10 (m, 1H), 7.50-7.54 (m, 1H), 7.90-7.97 (m, 1H).

MS m/z ([M+H]$^+$) 251.

Step 2: Preparation of intermediate ethyl 2-(tert-butoxy)-2-(4-oxo-3,4-dihydro-2H-1-benzopyran-3-yl)acetate (17b)

To a suspension of ethyl 2-hydroxy-2-(4-oxo-3,4-dihydro-2H-1-benzopyran-3-yl)acetate (17a) (235 mg, 0.939 mmol) in tert-butylacetate (5.6 mL) at −10° C. was added perchloric acid (70%, 168 µL). The mixture was stirred at −5° C. for 5 hours and then basified with a saturated aqueous solution of sodium bicarbonate until pH 8. The aqueous layer was extracted with ethyl acetate. The organic layer was washed with brine, dried over sodium sulfate, filtered and concentrated in vacuo. The residue was purified by preparative TLC (cyclohexane/ethyl acetate 70/30) to afford ethyl 2-(tert-butoxy)-2-(4-oxo-3,4-dihydro-2H-1-benzopyran-3-yl)acetate (17b) as a solid (135 mg, 0.44 mmol, 47%, mixture of diastereoisomers).

$^1$H NMR (400 MHz, CDCl$_3$) 1.17-1.34 (m, 12H), 2.99-3.19 (m, 1H), 4.10-4.28 (m, 2H), 4.57-4.72 (m, 3H), 6.98-7.08 (m, 2H), 7.47-7.54 (m, 1H), 7.92-7.95 (m, 1H).

MS m/z ([M+Na]$^+$) 329.

Step 3: Preparation of intermediate ethyl 2-(tert-butoxy)-2-{4-[(trifluoromethane)sulfonyloxy]-2H-chromen-3-yl}acetate (17c)

To a solution of ethyl 2-(tert-butoxy)-2-(4-oxo-3,4-dihydro-2H-1-benzopyran-3-yl)acetate (1b) (144 mg, 0.47 mmol) in a mixture of N,N-dimethylformamide (2.9 mL) and tetrahydrofuran (0.48 mL) was added a solution of potassium tert-butoxide (1 M in tetrahydrofuran, 0.5 mL, 0.5 mmol) at −78° C. under argon atmosphere, and the mixture was stirred at the same temperature for 1 hour. A solution of N-phenyl-bis(trifluoromethanesulfonimide) (193 mg, 0.54 mmol) in a mixture of tetrahydrofuran (0.6 mL) and dimethylformamide (0.14 mL) was slowly added to the mixture at −78° C. which was further stirred at the same temperature for 1 hour. The reaction was quenched by addition of saturated sodium bicarbonate solution and the mixture was extracted with ethyl acetate twice. The combined organic layers were washed with brine, dried over anhydrous sodium sulfate, and concentrated in vacuo. The residue was purified by preparative TLC (cyclohexane/ethyl acetate 90/10) to give ethyl 2-(tert-butoxy)-2-{4-[(trifluoromethane)sulfonyloxy]-2H-chromen-3-yl}acetate (17c) (175 mg, 0.40 mmol, 85%).

¹H NMR (400 MHz, CDCl₃) δ 1.28-1.33 (m, 12H), 4.25 (q, J=7.1 Hz, 2H), 5.05 (s, 2H), 5.16 (s, 1H), 6.92 (d, J=8.1 Hz, 1H), 7.03 (t, J=7.5 Hz, 1H), 7.27-7.31 (m, 1H), 7.35 (d, J=7.4 Hz, 1H).
MS m/z ([M+Na]⁺) 461.

Step 4: Preparation of intermediate ethyl 2-(tert-butoxy)-2-[4-(3,4-dihydro-2H-1-benzopyran-6-yl)-2H-chromen-3-yl]acetate (17d)

To a solution of ethyl 2-(tert-butoxy)-2-{4-[(trifluoromethane)sulfonyloxy]-2H-chromen-3-yl}acetate (17c) (171 mg, 0.39 mmol) in a mixture of toluene (1.60 mL) and ethanol (0.4 mL) was added a solution of sodium carbonate 2M (0.39 mL, 0.78 mmol), palladium tetrakis(triphenylphosphine) (22.5 mg, 0.05 mmol) and 6-(4,4,5,5-tetramethyl-1,3,2-dioxaborolan-2-yl)chroman (111.6 mg, 0.429 mmol). The mixture was refluxed for 20 hours. The mixture was then cooled at room temperature and water was added. The aqueous layer was extracted with ethyl acetate. The organic layers were washed with brine, dried over sodium sulfate and concentrated in vacuo. The residue was purified by preparative TLC (cyclohexane/ethyl acetate 90/10) to give ethyl 2-(tert-butoxy)-2-[4-(3,4-dihydro-2H-1-benzopyran-6-yl)-2H-chromen-3-yl]acetate (1d) (129 mg, 0.306 mmol, 78%).
¹H NMR (400 MHz, CDCl₃) δ 1.09 (s, 9H), 1.29-1.36 (m, 3H), 2.09 (m, 2H), 2.85 (m, 2H), 4.19-4.30 (m, 4H), 4.71 (s, 1H), 4.82 (d, J=14.8 Hz, 1H), 5.08 (d, J=14.0 Hz, 1H), 6.74-6.91 (m, 5H), 7.04-7.08 (m, 1H), 7.15 (dt, J=1.7, 6.3 Hz, 1H).
MS m/z ([M+Na]⁺) 445.

Step 5: Preparation of 2-(tert-butoxy)-2-[4-(3,4-dihydro-2H-1-benzopyran-6-yl)-2H-chromen-3-yl]acetic acid (example)

Lithium hydroxide (20.2 mg, 0.843 mmol) was added to a solution of ethyl 2-(tert-butoxy)-2-[4-(3,4-dihydro-2H-1-benzopyran-6-yl)-2H-chromen-3-yl]acetate (17d) (119 mg, 0.281 mmol) in a mixture of tetrahydrofuran (3.5 mL) and water (2.8 mL). The mixture was heated at 70° C. for 4 hours. The mixture was concentrated in vacuo. The residue was partitioned between water and dichloromethane. The aqueous layer was acidified with hydrochloric acid 1N and extracted with ethyl acetate twice. The organic layer was washed with brine, dried over sodium sulfate, filtered and concentrated in vacuo. The residue was purified by preparative TLC (dichloromethane/methanol 95/5) to give the desired acid (example 17) (67 mg, 0.169 mmol, 57%).
¹H NMR (400 MHz, CDCl₃) δ 1.16 (s, 9H), 2.07-2.10 (m, 2H), 2.74-2.89 (m, 2H), 4.28 (t, J=5.2 Hz, 2H), 4.71 (d, J=13.6 Hz, 1H), 4.88-4.95 (m, 2H), 6.78-6.93 (m, 5H), 7.16-7.20 (m, 1H), 7.39-7.44 (m, 1H).
MS m/z ([M−H]⁻) 393.

Example 18: Synthesis of 2-(tert-butoxy)-2-(2-methyl-4-phenyl-5,6,7,8-tetrahydro quinolin-3-yl) acetic acid Step 1
NaH
PMBCl, NaI
tetrahydrofuran

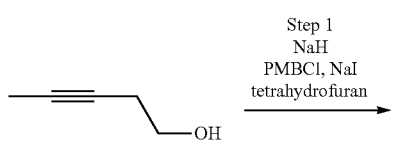

-continued

Step 2

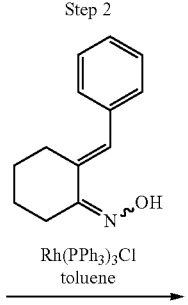

Rh(PPh₃)₃Cl
toluene

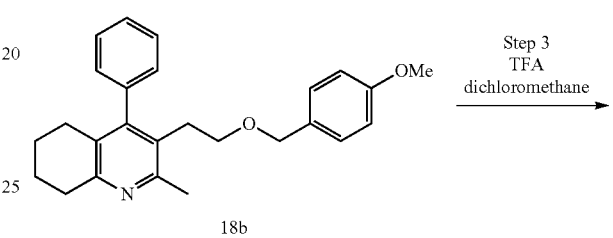

Step 3
TFA
dichloromethane

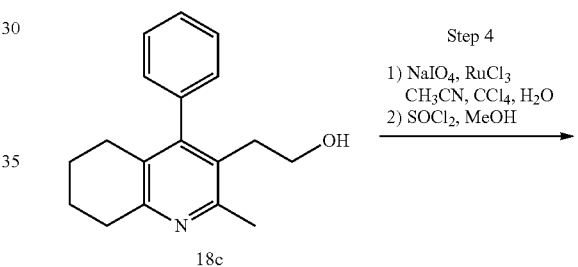

Step 4
1) NaIO₄, RuCl₃
   CH₃CN, CCl₄, H₂O
2) SOCl₂, MeOH

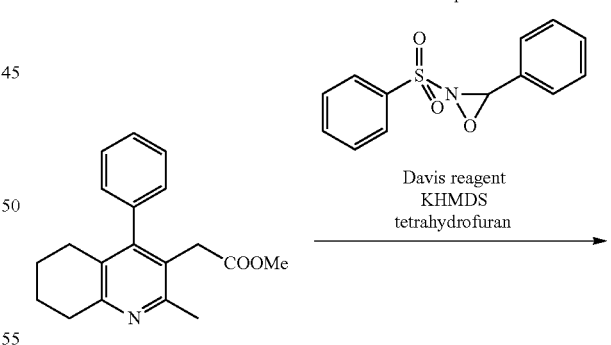

Davis reagent
KHMDS
tetrahydrofuran

Step 5

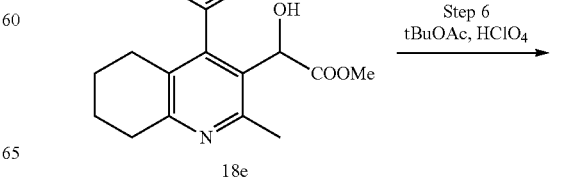

Step 6
tBuOAc, HClO₄

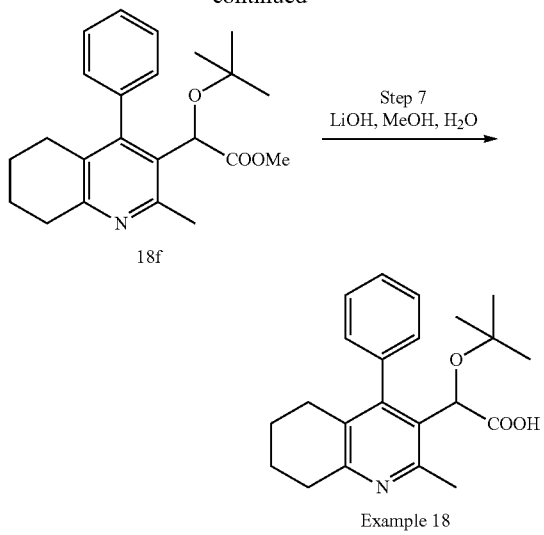

Example 18

Step 1: Preparation of intermediate 1-methoxy-4-[(pent-3-yn-1-yloxy)methyl]benzene (18a)

To a suspension of sodium hydride (60% in oil, 0.50 g, 14.85 mmol) in tetrahydrofuran (15 mL) under nitrogen atmosphere at 0° C. was added dropwise 3-pentyn-3-ol (0.50 g, 5.94 mmol). The mixture was stirred at 0° C. for 30 minutes and then, were added 1-(chloromethyl)-4-methoxybenzene (1.21 mL, 8.91 mmol) and sodium iodide (0.089 g, 0.59 mmol). After 24 hours at room temperature, the reaction mixture was quenched with water (100 mL) and extracted with ethyl acetate (2×50 mL). The combined organic extracts were washed with water (100 mL), brine (100 mL) and dried over sodium sulfate and evaporated to dryness. The residue was purified by flash chromatography on silica gel (cyclohexane/dichloromethane 30/70) to provide 1-methoxy-4-[(pent-3-yn-1-yloxy)methyl]benzene (18a) (1.03 g, 5.04 mmol, 85%) as a yellow oil.

$^{1}$H NMR (400 MHz, CDCl$_{3}$) δ 1.81 (t, J=2.5 Hz, 3H), 2.44-2.48 (m, 2H), 3.55 (t, J=7.1 Hz, 2H), 3.84 (s, 3H), 4.52 (s, 2H), 6.91 (d, J=8.7 Hz, 2H), 7.30 (d, J=8.2 Hz, 2H).

Step 2: Preparation of intermediate 3-{2-[(4-methoxyphenyl)methoxy]ethyl}-2-methyl-4-phenyl-5,6,7,8-tetrahydroquinoline (18b)

A sealed tube containing tris(triphénylphosphine)rhodium (I) chloride (0.420 g, 0.45 mmol) and anhydrous toluene (10 mL) was degassed with argon 3 times. 1-Methoxy-4-[(pent-3-yn-1-yloxy)methyl]benzene (18a) (0.949 g, 4.65 mmol) and N-[(2E)-2-(phenylmethylidene) cyclohexylidene] hydroxylamine (0.850 g, 4.22 mmol, prepared according to Parthasarathy et al., *J. Org. Chem.* 2009, 74, 9359-9364) were added sequentially and the reaction mixture was allowed to stir at 130° C. for 16 hours. The mixture was filtered through a short Celite® pad and washed with dichloromethane (3×10 mL). The filtrate was concentrated in vacuo and the residue was purified by flash chromatography on silica gel (cyclohexane/ethyl acetate 80/20) to provide 3-{2-[(4-methoxyphenyl)methoxy]ethyl}-2-methyl-4-phenyl-5,6,7,8-tetrahydroquinoline (18b) (0.561 g, 1.45 mmol, 34%) as a brown oil.

$^{1}$H NMR (400 MHz, CDCl$_{3}$) δ 1.65-1.71 (m, 2H), 1.81-1.88 (m, 2H), 2.23 (t, J=6.4 Hz 2H), 2.60 (s, 3H), 2.71 (t, J=7.8 Hz, 2H), 2.95 (t, J=6.4 Hz, 2H), 3.36 (t, J=7.8 Hz, 2H), 3.83 (s, 3H), 4.28 (s, 2H), 6.86 (d, J=8.7 Hz, 2H), 7.04 (dd, J=1.7, 7.7 Hz, 2H), 7.13 (d, J=8.7 Hz, 2H), 7.36-7.46 (m, 3H).

MS m/z ([M+H]$^{+}$) 388.

Step 3: Preparation of intermediate 2-(2-methyl-4-phenyl-5,6,7,8-tetrahydroquinolin-3-yl)ethan-1-ol (18c)

To a solution of 3-{2-[(4-methoxyphenyl)methoxy]ethyl}-2-methyl-4-phenyl-5,6,7,8-tetrahydroquinoline (18b) (0.560 g, 1.45 mmol) in anhydrous dichloromethane (25 mL) under nitrogen atmosphere was added trifluoroacetic acid (2.21 mL, 28.9 mmol). The mixture was stirred at room temperature for 2 hours. The mixture was slowly neutralized with saturated aqueous sodium hydrogencarbonate solution (final pH ca 8-9), extracted with dichloromethane (50 mL). The organic layers were dried over sodium sulfate and concentrated in vacuo. The residue was purified by flash chromatography on silica gel (ethyl acetate/methanol from 100/0 to 95/5) to afford 2-(2-methyl-4-phenyl-5,6,7,8-tetrahydroquinolin-3-yl)ethan-1-ol (18c) (0.223 g, 0.84 mmol, 58%) as a beige meringue.

$^{1}$H NMR (400 MHz, CDCl$_{3}$) δ 1.65-1.72 (m, 2H), 1.82-1.88 (m, 2H), 2.24 (t, J=6.4 Hz, 2H), 2.62 (s, 3H), 2.69 (t, J=7.7 Hz, 2H), 2.94 (t, J=6.4 Hz, 2H), 3.59 (t, J=7.7 Hz, 2H), 7.11 (dd, J=1.5, 6.8 Hz, 2H), 7.38-7.49 (m, 3H).

MS m/z ([M+H]$^{+}$) 268.

Step 4: Preparation of intermediate methyl 2-(2-methyl-4-phenyl-5,6,7,8-tetrahydroquinolin-3-yl)acetate (18d)

To a biphasic solution of 2-(2-methyl-4-phenyl-5,6,7,8-tetrahydroquinolin-3-yl)ethan-1-ol (18c) (0.187 g, 0.70 mmol) in a mixture of acetonitrile (4 mL), carbon tetrachloride (4 mL) and water (6 mL) were added sodium periodate (0.613 g, 2.87 mmol) and ruthenium (III) chloride hydrate (0.003g, 0.015 mmol). The mixture was vigorously stirred at room temperature for 45 minutes, diluted with water (20 mL) and extracted with dichloromethane (2×20 mL). The combined organic extracts were dried over sodium sulfate and concentrated in vacuo. This material was dissolved in methanol (7 mL), the mixture was cooled to 0° C. and thionyl chloride (0.051 mL, 0.7 mmol) was added dropwise. The mixture was allowed to stir at room temperature for 16 hours and was concentrated to dryness. The residue was taken up in ethyl acetate (20 mL) and washed with sodium hydroxide 2N aqueous solution (20 mL) and water (2×20 mL). The organic layer was dried over sodium sulfate and evaporated to dryness. The residue was purified by flash chromatography on silica gel (cyclohexane/ethyl acetate 70/30) to provide methyl 2-(2-methyl-4-phenyl-5,6,7,8-tetrahydroquinolin-3-yl)acetate (18d) (0.050 g, 0.168 mmol, 24%) as a colorless oil.

$^{1}$H NMR (400 MHz, CDCl$_{3}$) δ 1.67-1.73 (m, 2H), 1.84-1.90 (m, 2H), 2.30 (t, J=6.4 Hz, 2H), 2.52 (s, 3H), 2.98 (t, J=6.4 Hz, 2H), 3.40 (s, 2H), 3.64 (s, 3H), 7.10 (dd, J=1.5, 6.7 Hz, 2H), 7.39-7.49 (m, 3H).

MS m/z ([M+H]$^{+}$) 296.

Step 5: Preparation of intermediate methyl 2-hydroxy-2-(2-methyl-4-phenyl-5,6,7,8-tetrahydroquinolin-3-yl)acetate (18e)

To a solution of potassium bis(trimethylsilyl)amide (1M solution in tetrahydrofuran, 0.84 mL, 0.84 mmol) in anhydrous tetrahydrofuran (3 mL) at −78° C. under an argon atmosphere was added dropwise a solution of methyl 2-(2-methyl-4-phenyl-5,6,7,8-tetrahydroquinolin-3-yl)acetate (18d) (0.165 g, 0.56 mmol) in anhydrous tetrahydrofuran (2 ml). The solution was stirred at −78° C. for 30 minutes and then a solution of Davis reagent (0.219 g, 0.84 mmol, prepared according to Davis et al., *J. Org. Chem.* 1988, 53, 2087-2089) in anhydrous tetrahydrofuran (3 mL) was added. After 75 minutes at −78° C., the reaction mixture was quenched with a saturated solution of ammonium chloride (30 mL) and extracted with ethyl acetate (2×20 mL). The combined organic extracts were dried over sodium sulfate and evaporated to dryness. The residue was purified by flash chromatography on silica gel (cyclohexane/dichloromethane 50/50) to provide methyl 2-hydroxy-2-(2-methyl-4-phenyl-5,6,7,8-tetrahydroquinolin-3-yl)acetate (18e) (0.130 g, 0.42 mmol, 75%) as a white meringue.

$^1$H NMR (400 MHz, CDCl$_3$) δ 1.63-1.71 (m, 2H), 1.79-1.88 (m, 2H), 2.25 (t, J=6.4 Hz, 2H), 2.51 (s, 3H), 2.95 (t, J=6.4 Hz, 2H), 3.09 (d, J=2.5 Hz, 1H), 3.71 (s, 3H), 5.02 (d, J=2.5 Hz, 1H), 7.12-7.20 (m, 2H), 7.36-7.48 (m, 3H).

MS m/z ([M+H]$^+$) 312.

Step 6: Preparation of intermediate methyl 2-(tert-butoxy)-2-(2-methyl-4-phenyl-5,6,7,8-tetrahydroquinolin-3-yl)acetate (18f)

To a solution of methyl 2-hydroxy-2-(2-methyl-4-phenyl-5,6,7,8-tetrahydroquinolin-3-yl)acetate (18e) (0.090 g, 0.29 mmol) in tert-butyl acetate (3 mL) was added perchloric acid (0.057 mL, 0.95 mmol). The mixture was stirred for 90 minutes at room temperature. The reaction mixture was quenched with a saturated aqueous solution of sodium hydrogencarbonate (10 mL) and extracted with ethyl acetate (2×10 mL). The organic layers were dried over sodium sulfate and concentrated in vacuo. The residue was purified by flash chromatography on silica gel (cyclohexane/ethyl acetate 70/30) to provide methyl 2-(tert-butoxy)-2-(2-methyl-4-phenyl-5,6,7,8-tetrahydroquinolin-3-yl)acetate (18f) (90 mg, 0.24 mmol, 50%) as a yellow oil.

$^1$H NMR (400 MHz, CDCl$_3$) δ 0.95 (s, 9H), 1.50-1.90 (m, 4H), 2.11 (dt, J=17.0, 5.7 Hz, 1H), 2.30-2.45 (m, 1H), 2.61 (s, 3H), 2.95 (t, J=5.4 Hz, 2H), 3.68 (s, 3H), 4.89 (s, 1H), 7.11-7.17 (m, 1H), 7.24-7.30 (m, 1H), 7.39-7.50 (m, 3H).

MS m/z ([M+H]$^+$) 368.

Step 7: Preparation of 2-(tert-butoxy)-2-(2-methyl-4-phenyl-5,6,7,8-tetrahydro quinolin-3-yl)acetic acid An aqueous solution of lithium hydroxide (2N, 0.678 mL, 1.36 mmol) was added to a solution of methyl 2-(tert-butoxy)-2-(2-methyl-4-phenyl-5,6,7,8-tetrahydroquinolin-3-yl)acetate (18f) (0.083 g, 0.23 mmol) in methanol (4 mL). The mixture was stirred at 70° C. for 140 minutes. Methanol was evaporated in vacuo. The residue was diluted with water (5 mL) and washed with dichloromethane (5 mL). The pH of the aqueous layer was adjusted to approximately 5-6 with 1M hydrochloric acid. The aqueous layer was extracted with ethyl acetate (2×8 mL). The organic layer was dried over sodium sulfate and evaporated to dryness to provide the desired acid (example 18) (0.073 g, 0.021 mmol, 91%) as a white solid.

$^1$H NMR (400 MHz, CDCl$_3$) δ 0.98 (s, 9H), 1.51-1.63 (m, 1H), 1.70-1.94 (m, 3H), 2.13 (dt, J=17.0, 5.3 Hz, 1H), 2.39-2.51 (m, 1H), 2.63 (s, 3H), 3.01 (t, J=6.4 Hz, 2H), 4.98 (s, 1H), 7.16 (d, J=6.8 Hz, 1H), 7.38-7.55 (m, 4H).

MS m/z ([M+H]$^+$) 354.
MS m/z ([M−H]$^−$) 352.

Example 19: Synthesis of ethyl 2-(tert-butoxy)-2-[4-(3,4-dihydro-2H-1-benzopyran-6-yl)-2-methyl-1,3-benzoxazol-5-yl]acetic acid

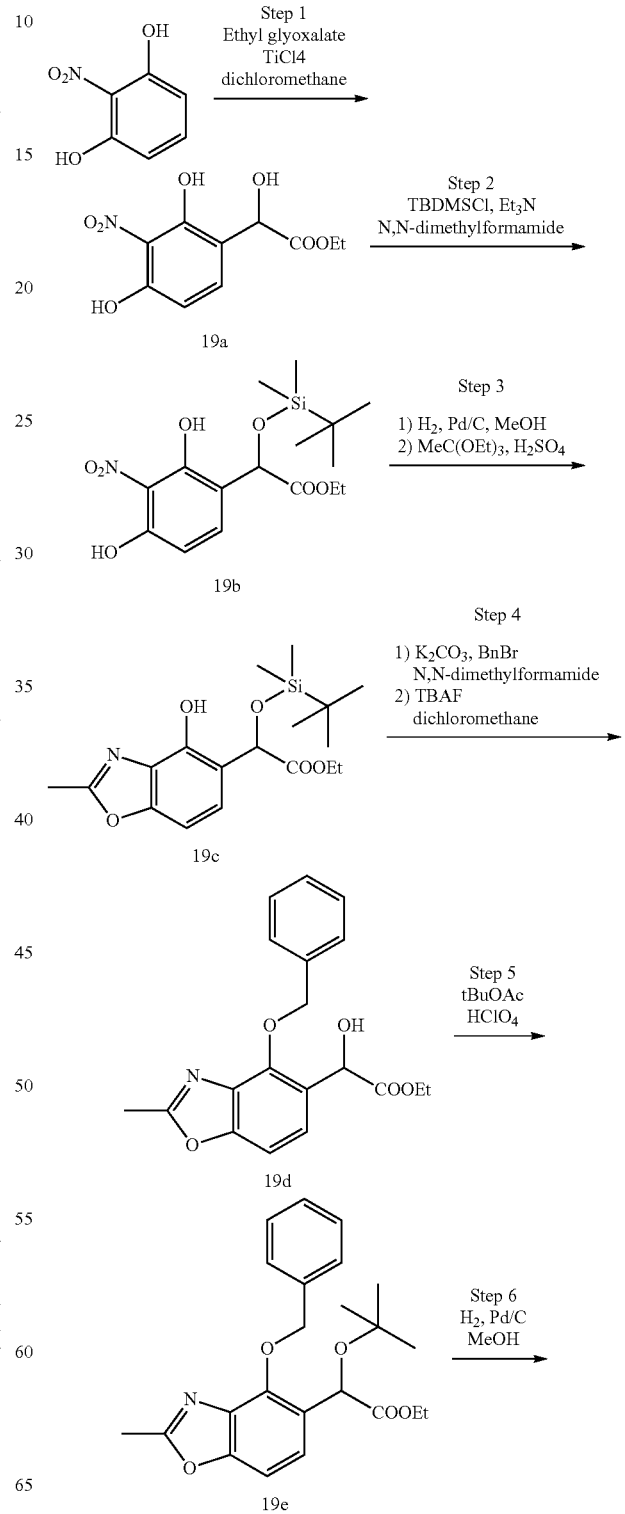

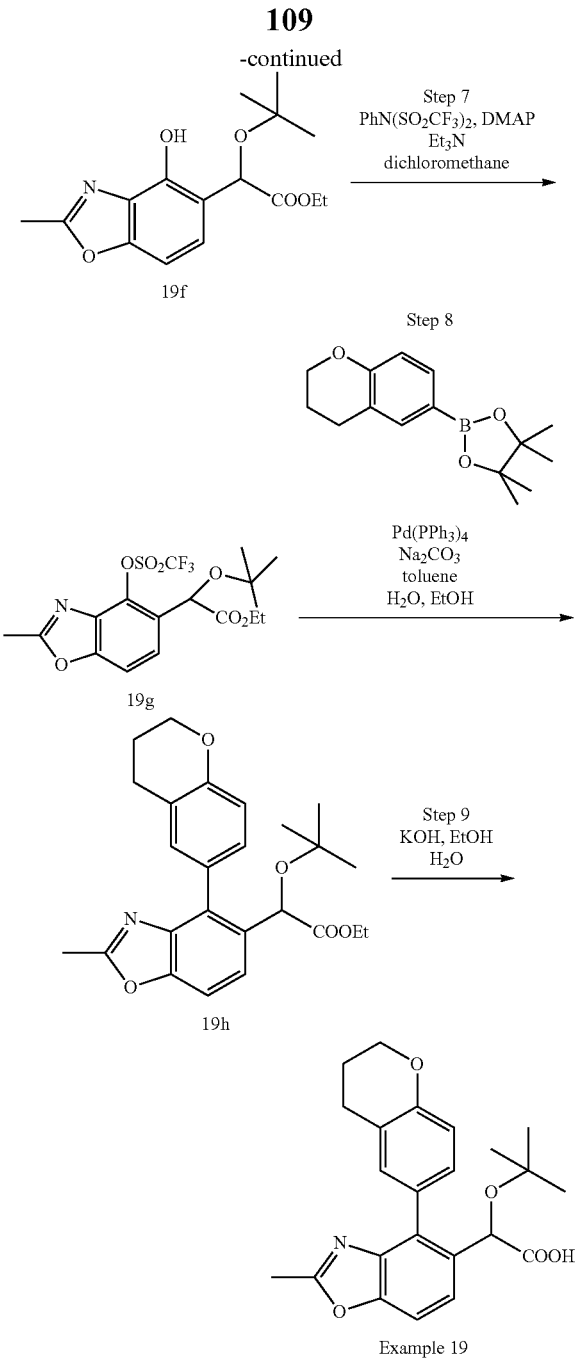

Step 7
PhN(SO₂CF₃)₂, DMAP
Et₃N
dichloromethane

19f

Step 8

Pd(PPh₃)₄
Na₂CO₃
toluene
H₂O, EtOH

19g

Step 9
KOH, EtOH
H₂O

19h

Example 19

Step 1: Preparation of intermediate ethyl 2-(2,4-dihydroxy-3-nitrophenyl)-2-hydroxyacetate (19a)

To a solution 2-nitroresorcinol (2.95 g, 19 mmol) and ethyl glyoxalate 50% in toluene (4.9 mL, 24.7 mmol) in anhydrous dichloromethane (40 mL) at 0° C., under nitrogen atmosphere was dropwise added titanium chloride (2.5 mL, 22.8 mmol). The black mixture was stirred at 0° C. for 20 minutes then poured in a mixture of ice (100 mL) and water (100 mL). The mixture was stirred for 20 minutes. The aqueous layer was extracted with dichloromethane (2×40 mL). The organic layers were washed with brine (50 mL), dried over sodium sulfate and concentrated in vacuo. The residue was purified by flash chromatography on silica gel (cyclohexane/ethyl acetate 70/30 then 50/50) to provide ethyl 2-(2,4-dihydroxy-3-nitrophenyl)-2-hydroxyacetate (19a) (3.64 g, 14.1 mmol, 74%) as an orange solid.

¹H NMR (300 MHz, CDCl₃) δ 1.24 (t, J=7.1 Hz, 3H), 3.54 (d, J=4.5 Hz, 1H), 4.15-4.34 (m, 2H), 5.34 (d, J=3.8 Hz, 1H), 6.66 (d, J=8.7 Hz, 1H), 7.52 (d, J=8.7 Hz, 1H), 10.68 (s, 1H), 11.11 (s, 1H).

MS m/z ([M−H]⁻) 256.

Step 2: Preparation of intermediate ethyl 2-[(tert-butyldimethylsilyl)oxy]-2-(2,4-dihydroxy-3-nitrophenyl)acetate (19b)

To a solution of ethyl 2-(2,4-dihydroxy-3-nitrophenyl)-2-hydroxyacetate (19a) (2.0 g, 7.78 mmol) in anhydrous N,N-dimethylformamide (20 mL) under nitrogen atmosphere were added at 0° C. tert-butyl(chloro)dimethylsilane (1.41 g, 9.33 mmol) and triethylamine (1.30 mL, 9.33 mmol). The mixture was stirred at room temperature for 2.5 hours then poured in a saturated solution of ammonium chloride (100 mL). The aqueous layer was extracted with ethyl acetate (3×60 mL). The organic layers were washed with brine (2×50 mL), dried over sodium sulfate and concentrated in vacuo. The residue was purified by flash chromatography on silica gel (cyclohexane/ethyl acetate 90/10) to provide ethyl 2-[(tert-butyldimethylsilyl)oxy]-2-(2,4-dihydroxy-3-nitrophenyl)acetate (19b) (1.68 g, 4.52 mmol, 58%) as an orange solid.

¹H NMR (300 MHz, CDCl₃) δ 0.06 (s, 3H), 0.14 (s, 3H), 0.90 (s, 9H), 1.24 (t, J=7.1 Hz, 3H), 4.13-4.21 (m, 2H), 5.54 (s, 1H), 6.68 (d, J=8.8 Hz, 1H), 7.75 (d, J=8.8 Hz, 1H), 10.68 (s, 1H), 11.03 (s, 1H).

MS m/z ([M−H]⁻) 370.

Step 3: Preparation of intermediate ethyl 2-[(tert-butyldimethylsilyl)oxy]-2-(4-hydroxy-2-methyl-1,3-benzoxazol-5-yl)acetate (19c)

A mixture of ethyl 2-[(tert-butyldimethylsilyl)oxy]-2-(2,4-dihydroxy-3-nitrophenyl)acetate (19b) (0.60 g, 1.62 mmol) and palladium on charcoal (60 mg) in methanol (10 mL) was stirred at room temperature under hydrogen atmosphere for 40 minutes. The mixture was then filtered on Millipore and the filtrate concentrated in vacuo. The residue was dissolved in trimethyl orthoacetate (6 mL) and a drop of sulfuric acid was added. The mixture was stirred at room temperature overnight before being concentrated in vacuo. Water (10 mL) was added to the residue. The aqueous layer was extracted with ethyl acetate (2×15 mL). The organic layer was washed with brine (10 mL), dried over sodium sulfate and concentrate in vacuo. The residue was purified by flash chromatography on silica gel (cyclohexane/ethyl acetate 80/20) to provide ethyl 2-[(tert-butyldimethylsilyl)oxy]-2-(4-hydroxy-2-methyl-1,3-benzoxazol-5-yl)acetate (19c) (162 mg, 0.44 mmol, 27%) as a white solid and ethyl 2-[(tert-butyldimethylsilyl)oxy]-2-(4-hydroxy-2-methyl-1,3-benzoxazol-7-yl)acetate (227 mg, 0.62 mmol, 38%) as a white solid.

¹H NMR (300 MHz, CDCl₃) δ 0.05 (s, 3H), 0.15 (s, 3H), 0.92 (s, 9H), 1.21 (t, J=7.2 Hz, 3H), 2.63 (s, 3H), 4.10-4.21 (m, 2H), 5.46 (s, 1H),), 6.98 (d, J=8.4 Hz, 1H), 7.21 (d, J=8.4 Hz, 1H), 8.86 (broad s, 1H).

MS m/z ([M+H]⁺) 366.
MS m/z ([M−H]⁻) 364.

Step 4: Preparation of intermediate ethyl 2-hydroxy-2-(4-benzyloxy-2-methyl-1,3-benzoxazol-5-yl)acetate (19d)

To a solution of ethyl 2-[(tert-butyldimethylsilyl)oxy]-2-(4-hydroxy-2-methyl-1,3-benzoxazol-5-yl)acetate (19c) (123 mg, 0.34 mmol) in anhydrous N,N-dimethylformamide (4 mL) under nitrogen atmosphere were successively added potassium carbonate (84 mg, 0.61 mmol) and benzyl bromide (58 µL, 0.49 mmol). The mixture was stirred at room temperature for 1 hour then poured in water (10 mL). The aqueous layer was extracted with ethyl acetate (3×10 mL). The organic layers were washed with brine (2×5 mL), dried over sodium sulfate and concentrated in vacuo. The residue was dissolved in anhydrous tetrahydrofuran under nitrogen atmosphere and a 1M solution of tetrabutylammonium fluoride in tetrahydrofuran (0.40 mL, 0.4 mmol) was dropwise added. The mixture was stirred at room temperature for 30 minutes and concentrated in vacuo. The residue was purified by flash chromatography on silica gel (cyclohexane/ethyl acetate 70/30) to provide intermediate ethyl 2-hydroxy-2-(4-benzyloxy-2-methyl-1,3-benzoxazol-5-yl)acetate (19d) (96 mg, 0.28 mmol, 83%) as a colorless oil.

$^1$H NMR (300 MHz, CDCl$_3$) δ 1.13 (t, J=7.2 Hz, 3H), 2.63 (s, 3H), 3.48 (d, J=6.0 Hz, 1H), 4.02-4.21 (m, 2H), 5.44 (d, J=6.0 Hz, 1H), 5.75 (d, J=11.7 Hz, 1H), 5.80 (d, J=11.7 Hz, 1H), 7.12 (d, J=8.4 Hz, 1H), 7.21 (d, J=8.4 Hz, 1H), 7.32-7.41 (m, 3H), 7.51 (d, J=8.1 Hz, 2H).

MS m/z ([M+H]$^+$) 342.
MS m/z ([M−H]$^−$) 340.

Step 5: Preparation of intermediate ethyl 2-(4-benzyloxy-2-methyl-1,3-benzoxazol-5-yl)-2-(tert-butoxy)acetate (19e)

To a solution of ethyl 2-hydroxy-2-(4-benzyloxy-2-methyl-1,3-benzoxazol-5-yl)acetate (19d) (96 mg, 0.28 mmol) in tert-butyl acetate (4.6 mL) at −20° C. was added perchloric acid (0.6 mL). The mixture was stirred at −20° C. for 1.25 hours before being poured into a saturated aqueous solution of sodium bicarbonate (10 mL). Water (15 mL) was added. The layers were separated and the aqueous layer was extracted with ethyl acetate (2×10 mL). The organic layers were dried over sodium sulfate and concentrated in vacuo. The residue was purified by flash chromatography on silica gel (cyclohexane/ethyl acetate 90/10) to provide ethyl 2-(4-benzyloxy-2-methyl-1,3-benzoxazol-5-yl)-2-(tert-butoxy)acetate (19e) (70 mg, 0.17 mmol, 62%) as a colorless oil.

$^1$H NMR (400 MHz, CDCl$_3$) δ 1.15 (t, J=7.1 Hz, 3H), 1.17 (s, 9H), 2.62 (s, 3H), 4.00-4.17 (m, 2H), 5.58 (s, 1H), 5.69 (d, J=11.8 Hz, 1H), 5.85 (d, J=11.8 Hz, 1H), 7.12 (d, J=8.4 Hz, 1H), 7.30-7.40 (m, 3H), 7.49 (d, J=8.4 Hz, 1H), 7.53-7.55 (m, 2H).

MS m/z ([M+H]$^+$) 398.
MS m/z ([M−H]$^−$) 396.

Step 6: Preparation of intermediate ethyl 2-(tert-butoxy)-2-(4-hydroxy-2-methyl-1,3-benzoxazol-5-yl)acetate (19f)

A mixture of ethyl 2-(4-benzyloxy-2-methyl-1,3-benzoxazol-5-yl)-2-(tert-butoxy)acetate (19e) (80 mg, 0.20 mmol) and palladium on charcoal (13 mg) in methanol (4 mL) was stirred at room temperature under hydrogen atmosphere for 1 hour. The mixture was filtered on millipore and the filtrate was concentrated in vacuo. to provide intermediate ethyl 2-(tert-butoxy)-2-(4-hydroxy-2-methyl-1,3-benzoxazol-5-yl)acetate (19f) (62 mg, 0.20 mmol, 100%) as a colorless oil.

$^1$H NMR (300 MHz, CDCl$_3$) δ 1.20 (t, J=7.1 Hz, 3H), 1.27 (s, 9H), 2.64 (s, 3H), 4.09-4.21 (m, 2H), 5.45 (s, 1H), 6.98 (d, J=8.4 Hz, 1H), 7.29 (d, J=8.4 Hz, 1H), 9.76 (broad s, 1H).

MS m/z ([M+H]$^+$) 308.
MS m/z ([M−H]$^−$) 306.

Step 7: Preparation of intermediate ethyl 2-(tert-butoxy)-2-[2-methyl-4-(trifluoromethane)sulfonyloxy)-1,3-benzoxazol-5-yl]acetate (19g)

To a solution of ethyl 2-(tert-butoxy)-2-(4-hydroxy-2-methyl-1,3-benzoxazol-5-yl)acetate (19f) (62 mg, 0.20 mmol), N-phenyl-trifluoromethanesulfonimide (108 mg, 0.30 mmol) and 4-(dimethylamino)pyridine (2 mg, 0.016 mmol) in anhydrous dichloromethane (5 mL) at 0° C. under nitrogen atmosphere was added triethylamine (56 µL, 0.40 mmol). The mixture was stirred at room temperature for 4 hours. N-phenyl-trifluoromethanesulfonimide (54 mg, 0.15 mmol) and triethylamine (56 µL, 0.40 mmol) were added and the mixture stirred overnight. Water (5 mL) was added. The aqueous layer was extracted with dichloromethane (2×5 mL). The organic layers were dried over sodium sulfate and concentrated in vacuo. The residue was purified by flash chromatography on silica gel (cyclohexane/ethyl acetate 90/10) to provide ethyl 2-(tert-butoxy)-2-[2-methyl-4-(trifluoromethane)sulfonyloxy)-1,3-benzoxazol-5-yl]acetate (19g) (86 mg, 0.195 mmol, 96%) as a colorless oil.

$^1$H NMR (300 MHz, CDCl$_3$) J 1.18 (t, J=7.1 Hz, 3H), 1.24 (s, 9H), 2.67 (s, 3H), 4.04-4.22 (m, 2H), 5.48 (s, 1H), 7.50 (d, J=8.4 Hz, 1H), 7.71 (d, J=8.4 Hz, 1H).

MS m/z ([M+H]$^+$) 440.

Step 8: Preparation of intermediate ethyl 2-(tert-butoxy)-2-[4-(3,4-dihydro-2H-1-benzopyran-6-yl)-2-methyl-1,3-benzoxazol-5-yl]acetate (19h)

To a solution of ethyl 2-(tert-butoxy)-2-[2-methyl-4-(trifluoromethane)sulfonyloxy)-1,3-benzoxazol-5-yl]acetate (19g) (86 mg, 0.195 mmol), sodium carbonate (83 mg, 0.78 mmol), 6-(4,4,5,5-tetramethyl-1,3,2-dioxaborolan-2-yl) chroman (92 mg, 0.35 mmol) and palladium tetrakis(triphenylphosphine) (23 mg, 0.02 mmol) in a mixture of toluene (1.1 mL), water (0.55 mL) and ethanol (0.48 mL) was heated at 110° C. for 4 hours. After cooling to room temperature, the mixture was poured into water (10 mL). The aqueous layer was extracted with ethyl acetate (2×5 mL). The organic layer was washed with brine (10 mL), dried over sodium sulfate and concentrated in vacuo. The residue was purified by flash chromatography on silica gel (cyclohexane/ethyl acetate 90/10) then by preparative TLC to provide ethyl 2-(tert-butoxy)-2-[4-(3,4-dihydro-2H-1-benzopyran-6-yl)-2-methyl-1,3-benzoxazol-5-yl]acetate (19h) (12 mg, 0.028 mmol, 14%) as a colorless oil.

$^1$H NMR (300 MHz, CDCl$_3$) δ 1.00 (s, 9H), 1.21 (t, J=7.1 Hz, 3H), 2.01-2.10 (m, 2H), 2.58 (s, 3H), 2.75-2.94 (m, 2H), 4.06-4.19 (m, 2H), 4.22-4.26 (m, 2H), 5.20 (s, 1H), 6.91 (d, J=8.4 Hz, 1H), 7.16-7.20 (m, 2H), 7.43 (d, J=8.6 Hz, 1H), 7.65 (d, J=8.6 Hz, 1H).

MS m/z ([M+H]$^+$) 424.

Step 9: Preparation of ethyl 2-(tert-butoxy)-2-[4-(3,4-dihydro-2H-1-benzopyran-6-yl)-2-methyl-1,3-benzoxazol-5-yl]acetic acid A mixture of ethyl 2-(tert-butoxy)-2-[4-(3,4-dihydro-2H-1-benzopyran-6-yl)-2-methyl-1,3-benzoxazol-5-yl]acetate (19h) (12 mg, 0.028 mmol) and potassium hydroxide (6 mg, 0.11 mmol) in a mixture of ethanol (3 mL) and water (1 mL) was refluxed for 2 hours. The mixture was concentrated in vacuo. Water (1 mL) was added to the residue. The aqueous layer was acidified with 1M hydrochloric acid until pH 3 and extracted with ethyl acetate (2×5 mL). The organic layer was dried over sodium sulfate and concentrated in vacuo. The residue was triturated in pentane and concentrated in vacuo to provide the desired acid (example 19) (11 mg, 0.027 mmol, 96%) as a white solid.

$^1$H NMR (300 MHz, CDCl$_3$) δ 0.99 (s, 9H), 2.01-2.06 (m, 2H), 2.60 (s, 3H), 2.77-2.93 (m, 2H), 4.23 (t, J=5.2 Hz, 2H), 5.30 (s, 1H), 6.91 (d, J=8.4 Hz, 1H), 7.20-7.38 (broad s, 2H), 7.41 (d, J=8.5 Hz, 1H), 7.44 (d, J=8.5 Hz, 1H).

MS m/z ([M+H]$^+$) 396.

MS m/z ([M−H]$^−$) 394.

Example 20: Synthesis of 2-(tert-butoxy)-2-[16-(3,4-dihydro-2H-1-benzopyran-6-yl)quinolin-5-yl]acetic acid

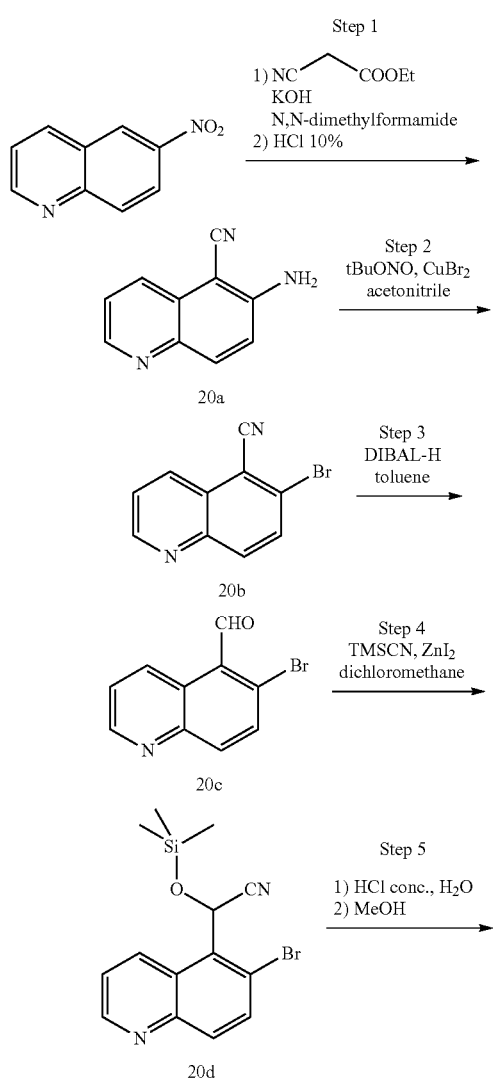
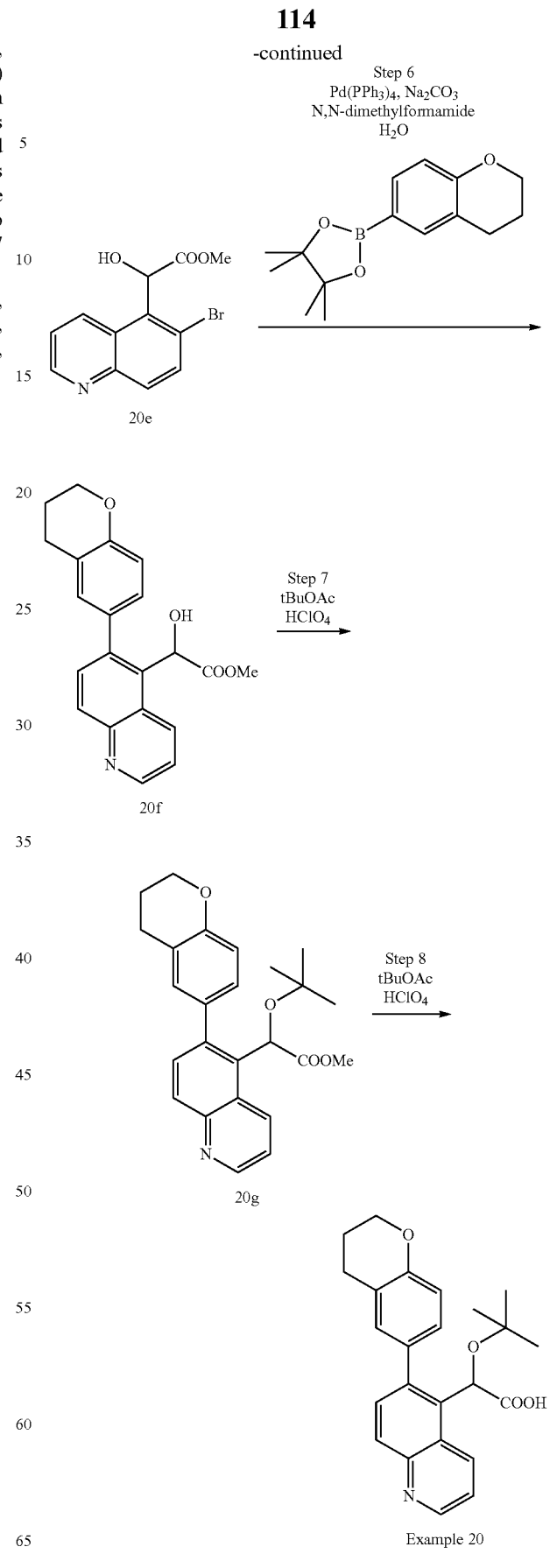

Step 1: Preparation of intermediate 6-aminoquinoline-5-carbonitrile (20a)

Nitroquinoline (5 g, 28.71 mmol) was added to a stirred solution of ethyl cyanoacetate (9.74 g, 86.13 mmol) and potassium hydroxide (4.83 g, 86.13 mmol) in N,N-dimethylformamide (87 mL). The mixture was stirred at room temperature for 22 hours. Then the solvent was removed in vacuo and the residue was hydrolyzed with hydrochloric acid 10%, at reflux for 3 hours. The mixture was basified with aqueous sodium hydroxide 10% and extracted three times with chloroform. The organic layer was washed with brine, dried over sodium sulfate, filtered and evaporated under reduced pressure. The residue was purified by flash chromatography on silica gel (dichloromethane/methanol 95/5), to give 6-aminoquinoline-5-carbonitrile (20a) (3.4 g, 20.1 mmol, 70%).

$^1$H NMR (400 MHz, CDCl$_3$) δ 4.92 (broad s, 2H), 7.14 (d, J=9.2 Hz, 1H), 7.46 (dd, J=4.3 and 8.4 Hz, 1H), 8.04 (d, J=9.2 Hz, 1H), 8.22 (dd, J=1.6 and 8.4 Hz, 1H), 8.73 (dd, J=1.6 and 4.3 Hz, 1H).

MS m/z ([M+H]$^+$) 170.

Step 2: Preparation of intermediate 6-bromoquinoline-5-carbonitrile (20b)

Under argon, cupper bromide (1.58 g, 7.09 mmol) was added to a solution of 6-aminoquinoline-5-carbonitrile (20a) (1 g, 5.91 mmol) in acetonitrile (25 mL). After 10 minutes at room temperature, tert-butyl nitrite (920 µL, 7.68 mmol) was added to the mixture which was heated at 60° C. for 8 hours. The mixture was stirred at room temperature for 10 hours more. Hydrochloric acid 1N was added to the mixture which was stirred for 4 hours and extracted three times with ethyl acetate. The organic layer was washed with hydrochloric acid 1N, brine, dried over sodium sulfate and evaporated under reduced pressure to give 6-bromoquinoline-5-carbonitrile (20b) as a beige solid (1.34 g, 5.75 mmol, 98%).

$^1$H NMR (400 MHz, CDCl$_3$) b 7.65 (dd, J=4.2 and 8.5 Hz, 1H), 7.94 (d, J=9.1 Hz, 1H), 8.21 (d, J=9.1 Hz, 1H), 8.53 (d, J=8.5 Hz, 1H), 9.05 (d, J=4.2 Hz, 1H).

MS m/z ([M+H]$^+$) 233/235.

Step 3: Preparation of intermediate 6-bromoquinoline-5-carbaldehyde (20c)

Under nitrogen atmosphere at −10° C., a solution of diisobutylaluminium hybride (1M in toluene, 11.15 mL, 11.15 mmol) was added slowly to a solution of 6-bromoquinoline-5-carbonitrile (20b) in toluene (105 mL). The mixture was stirred at −5° C. for 50 minutes. At −5° C., a solution of sulfuric acid 5% was added to the mixture which was stirred at room temperature for 1 hour. Then the mixture was basified with saturated solution of hydrogencarbonate and extracted three times with ethyl acetate. The organic layer was washed with brine, dried over sodium sulfate and evaporated under reduced pressure. The residue was purified by flash chromatography on silica gel (dichloromethane/methanol 95/5), to give 6-bromoquinoline-5-carbaldehyde (20c) (900 mg, 3.81 mmol, 68%).

$^1$H NMR (400 MHz, CDCl$_3$) δ 7.58 (dd, J=4.2 and 8.8 Hz, 1H), 7.94 (d, J=9.0 Hz, 1H), 8.16 (d, J=9.0 Hz, 1H), 8.98 (dd, J=1.6 and 4.2 Hz, 1H), 9.45-9.48 (m, 1H), 10.72 (s, 1H).

MS m/z ([M+H]$^+$) 236/238.

Step 4: Preparation of intermediate 2-(6-bromoquinolin-5-yl)-2-[(trimethylsilyl)oxy]acetonitrile (20d)

Under a nitrogen atmosphere, trimethylsilylcyanide (255 µL, 2.03 mmol) was added at 0° C. to a solution of 6-bromoquinoline-5-carbaldehyde (20c) (400 mg, 1.69 mmol) and zinc iodide (II) (54 mg, 0.17 mmol) in dichloromethane (33 mL). After 7 hours, trimethylsilylcyanide (255 µL, 2.03 mmol) and zinc iodide (II) (54 mg, 0.17 mmol) were added to the mixture to complete the reaction. After stirring 15 hours more, the reaction mixture was quenched with a saturated aqueous solution of sodium carbonate and extracted twice with dichloromethane. The organic layer was washed with brine, dried over sodium sulfate, filtered, and evaporated under reduced pressure to provide 2-(6-bromoquinolin-5-yl)-2-[(trimethylsilyl)oxy]acetonitrile (20d) (529 mg, 1.58 mmol, 93%) which was used without further purification.

MS m/z ([M+H]$^+$) 335/337.

Step 5: Preparation of intermediate methyl 2-(6-bromoquinolin-5-yl)-2-hydroxyacetate (20e)

hydrochloric acid 37% (8 mL) was added to a solution of 2-(6-bromoquinolin-5-yl)-2-[(trimethylsilyl)oxy]acetonitrile (20d) (529 mg, 2.24 mmol) in water (2 mL). The mixture was warmed at 70° C. for 4 hours, at 50° C. for 14 hours and finally at 90° C. for 2 hours. At room temperature methanol (11 mL) and hydrochloric acid 37% (1 mL) were added to the mixture which was warmed at 90° C. for 5 hours. It was stirred at room temperature for 48 hours more. The reaction mixture was quenched with a saturated aqueous solution of sodium carbonate. Methanol was evaporated and the mixture was extracted twice with ethyl acetate. The organic layer was washed with brine, dried over sodium sulfate, filtered, and evaporated under reduced pressure. The crude material was purified by preparative TLC (cyclohexane/ethyl acetate 60/40) to provide methyl 2-(6-bromoquinolin-5-yl)-2-hydroxyacetate (20e) as a beige powder (329 mg, 1.11 mmol, 49%).

$^1$H NMR (400 MHz, DMSO-d$_6$) δ 3.57 (s, 3H), 6.09 (s, 1H), 7.59 (dd, J=4.2 and 8.8 Hz, 1H), 7.92 (d, J=9.1 Hz, 1H), 7.96 (d, J=9.0 Hz, 1H), 8.69-8.71 (m, 1H), 8.93 (dd, J=1.6 and 4.2 Hz, 1H).

MS m/z ([M+H]$^+$) 296/298.

Step 6: Preparation of intermediate methyl 2-[6-(3,4-dihydro-2H-1-benzopyran-6-yl)quinolin-5-yl]-2-hydroxyacetate (20f)

Under argon atmosphere, sodium carbonate (88.6 mg, 0.84 mmol), water (5 mL), and 2-(6-bromoquinolin-5-yl)-2-hydroxyacetate (20e) (225 mg, 0.76 mmol) were added to a solution of 6-(4,4,5,5-tetramethyl-1,3,2-dioxaborolan-2-yl)chroman (217 mg, 0.84 mmol) in N,N-dimethylformamide (15 mL). The solution was degassed under argon and palladium tetrakis(triphenylphosphine) (263 mg, 0.23 mmol) was added. The mixture was heated at 100° C. for 4 hours. The mixture was then cooled at room temperature, water was added and the aqueous layer was extracted three times with ethyl acetate. The organic layer was washed with brine, dried over sodium sulfate, filtered and evaporated under reduced pressure. The residue was purified by flash chromatography on silica gel (cyclohexane/ethyl acetate 95/5 to 6/4), to give methyl 2-[6-(3,4-dihydro-2H-1-benzopyran-6-yl)quinolin-5-yl]-2-hydroxyacetate (20f) (105 mg, 0.30 mmol, 39%).

$^1$H NMR (400 MHz, CDCl$_3$) 2.04-2.10 (m, 2H), 2.84-2.87 (m, 2H), 3.66 (s, 3H), 4.24-4.26 (m, 2H), 5.76 (s, 1H), 6.88 (d, J=8.3 Hz, 1H), 7.16-7.23 (m, 2H), 7.53-7.58 (m,

1H), 7.84-7.90 (m, 1H), 8.15-8.19 (m, 1H), 8.52-8.57 (m, 1H), 8.90-8.92 (m, 1H).
MS m/z ([M+H]$^+$) 350.

Step 7: Preparation of intermediate methyl 2-(tert-butoxy)-2-[6-(3,4-dihydro-2H-1-benzopyran-6-yl)quinolin-5-yl]acetate (20g)

To a suspension of methyl 2-[6-(3,4-dihydro-2H-1-benzopyran-6-yl)quinolin-5-yl]-2-hydroxyacetate (20f) (105 mg, 0.30 mmol) in tert-butylacetate (8.6 mL) at −10° C. was added perchloric acid (70%, 144 μL). The mixture was stirred at 0° C. for 1 hour and was warmed at room temperature for 1 hour more. The mixture was then basified with a saturated aqueous solution of sodium bicarbonate until pH 8. The aqueous layer was extracted with ethyl acetate. The organic layer was washed with brine, dried over sodium sulfate, filtered and concentrated in vacuo. The residue was purified by preparative TLC (cyclohexane/ethyl acetate 60/40) to afford methyl 2-(tert-butoxy)-2-[6-(3,4-dihydro-2H-1-benzopyran-6-yl)quinolin-5-yl]acetate (20g) (30 mg, 0.07 mmol, 24%).
$^1$H NMR (400 MHz, CDCl$_3$) δ 0.94-0.95 (m, 9H), 2.07-2.11 (m, 2H), 2.79-2.87 (m, 2H), 3.67-3.69 (m, 3H), 4.26-4.29 (m, 2H), 5.60-5.64 (m, 1H), 6.89 (d, J=8.3 Hz, 1H), 7.40-7.75 (m, 5H), 7.85-8.08 (m, 2H).
MS m/z ([M+H]$^+$) 406.

Step 8: Preparation of 2-(tert-butoxy)-2-[6-(3,4-dihydro-2H-1-benzopyran-6-yl)quinolin-5-yl]acetic acid Potassium hydroxide (12 mg, 0.21 mmol) is added to a solution of methyl 2-(tert-butoxy)-2-[6-(3,4-dihydro-2H-1-benzopyran-6-yl)quinolin-5-yl]acetate (20g) (29 mg, 0.07 mmol) in a mixture of ethanol (0.8 mL) and water (1.77 mL). The reaction was warmed to 85° C. until complete conversion. Ethanol was then concentrated. Water was added to the reaction mixture which was washed with dichloromethane. The aqueous layer was acidified with an aqueous solution of hydrochloric acid 1N and extracted with ethyl acetate three times. The organic layer was washed with brine, dried over sodium sulfate, filtered and evaporated under reduced pressure. The residue was purified by preparative TLC (dichloromethane/methanol 90/10) to afford the desired acid (example 20) (6 mg, 0.02 mmol, 21%).
$^1$H NMR (400 MHz, CDCl$_3$) δ 0.91 (s, 9H), 2.04-2.07 (m, 2H), 2.81-2.85 (m, 2H), 4.24-4.26 (m, 2H), 5.75 (s, 1H), 6.88-7.60 (m, 5H), 8.05-8.07 (m, 1H), 8.70-8.71 (m, 1H), 8.84-8.86 (m, 1H).
MS m/z ([M+H]$^+$) 392.

Example 21: Synthesis of 2-(tert-butoxy)-2-[2-(3,4-dihydro-2H-1-benzopyran-6-yl)-3-trifluoromethylphenyl]acetic acid

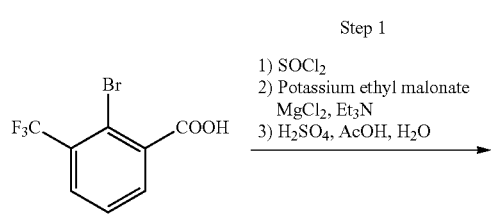

Step 1
1) SOCl$_2$
2) Potassium ethyl malonate MgCl$_2$, Et$_3$N
3) H$_2$SO$_4$, AcOH, H$_2$O

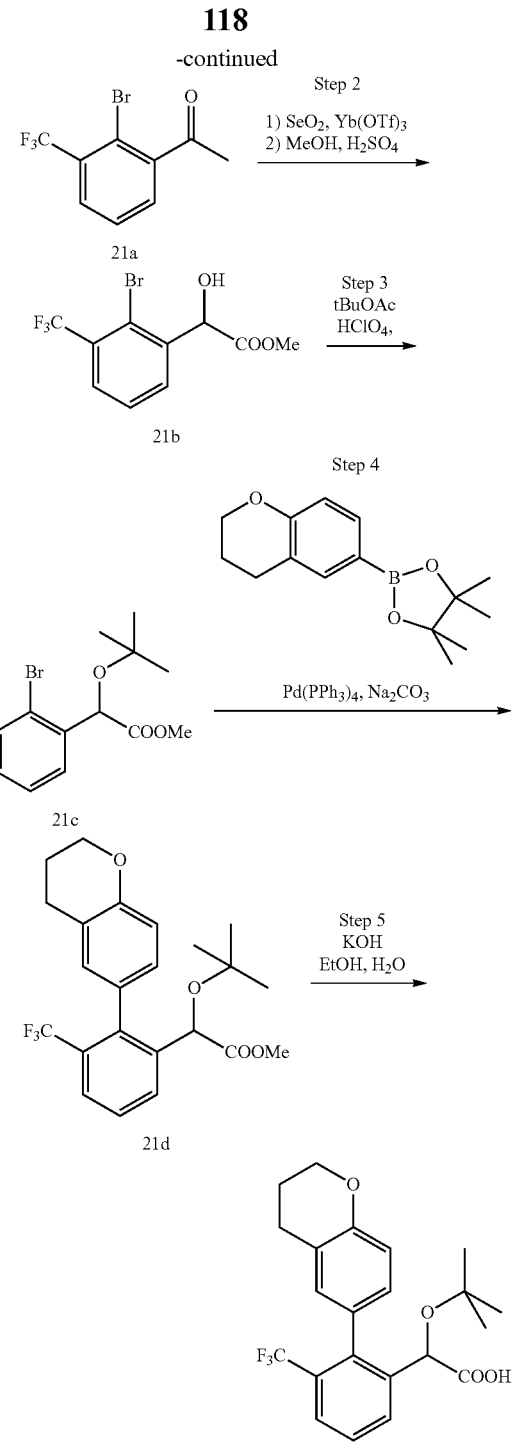

Step 1: Preparation of intermediate 1-(2-bromo-3-trifluoromethylphenyl)ethan-1-one (21a)

A solution of 2-bromo-3-trifluoromethylbenzoic acid (500 mg, 1.86 mmol) in thionyl chloride (10 mL) was refluxed for 2 hours. After cooling to room temperature, the mixture was concentrated in vacuo. Toluene (2×10 mL) was added and the mixture was concentrated again to provide acyl chloride. To a suspension of potassium ethyl malonate (664 mg, 3.9 mmol) in anhydrous acetonitrile (5 mL) under nitrogen atmosphere at 0° C. were successively added triethylamine (0.83 mL, 5.94 mmol) and magnesium chloride (407 mg, 4.27 mmol). The mixture was stirred at room temperature for 2.5 hours and re-cooled before adding dropwise a solution of acyl chloride in acetonitrile (5 mL). The mixture was stirred at room temperature overnight, cooled at 0° C. and a 13% hydrochloric acid aqueous solution (4 mL) was added. Layers were separated. The aqueous layer was extracted with ethyl acetate (2×10 mL). The combined organic layers extracts were washed with a saturated solution of sodium bicarbonate (10 mL), brine (10 mL), dried over sodium sulfate and concentrated in vacuo. The residue was then refluxed in a mixture of acetic acid (3.2 mL), water (2 mL) and sulfuric acid (0.4 mL) for 3 hours. After cooling to room temperature, the mixture was concentrated in vacuo. The residue was poured into ice water (20 mL) and extracted with ethyl acetate (2×15 mL). The organic layer was washed with a saturated solution of sodium bicarbonate (10 mL), brine (10 mL), dried over sodium sulfate and evaporated to dryness to provide 1-(2-bromo-3-trifluoromethylphenyl) ethan-1-one (21b) (382 mg, 1.43 mmol, 77%) as a yellow oil which was used without further purification.

$^1$H NMR (400 MHz, CDCl$_3$) δ 2.63 (s, 3H), 7.45-7.49 (m, 2H), 7.76 (d, J=8.0 Hz, 1H).

Step 2: Preparation of intermediate methyl 2-(2-bromo-3-trifluoromethylphenyl)-2-hydroxyacetate (21b)

A mixture of 1-(2-bromo-3-trifluoromethylphenyl)ethan-1-one (21a) (382 mg, 1.43 mmol), selenium dioxide (317 mg, 2.86 mmol) and ytterbium(III) trifluoromethanesulfonate (89 mg, 0.143 mmol) in a mixture of 1,4-dioxane (5 mL) and water (1.5 mL) was stirred at 90° C. overnight. After cooling to room temperature, the mixture was filtered on Celite®. The filtrate was concentrated in vacuo. The residue was dissolved in ethyl acetate (30 mL) and washed with 0.5M NaOH (3×15 mL). The aqueous layer was acidified with 37% hydrochloric acid until pH 3 and extracted with ethyl acetate (2×20 mL). The organic layer was dried over sodium sulfate and concentrated in vacuo. The residue was refluxed in methanol (10 mL) in the presence of five drops of sulfuric acid for 1 hour. The mixture was concentrated in vacuo. The residue was dissolved in ethyl acetate (20 mL) washed with a saturated aqueous solution of sodium bicarbonate (10 mL), brine (10 mL), dried over sodium sulfate and evaporated to dryness to provide methyl 2-(2-bromo-3-trifluoromethylphenyl)-2-hydroxyacetate (21b) (296 mg, 1.14 mmol, 42%) as a yellow oil which was used without further purification.

$^1$H NMR (400 MHz, CDCl$_3$) δ 3.79 (s, 3H), 5.77 (s, 1H), 7.45 (t, J=8.0 Hz, 1H), 7.56 (d, J=8.0 Hz, 1H), 7.69 (d, J=8.0 Hz, 1H).

Step 3: Preparation of intermediate methyl 2-(2-bromo-3-trifluoromethylphenyl)-2-(tert-butoxy)acetate (21c)

To a solution of methyl 2-(2-bromo-3-trifluoromethylphenyl)-2-hydroxyacetate (21b) (330 mg, 1.05 mmol) in tert-butyl acetate (20 mL) at −15° C. was added perchloric acid (3 mL). The mixture was stirred at −15° C. for 2 hours before being poured into a saturated aqueous solution of sodium bicarbonate (50 mL). The layers were separated and the aqueous layer was extracted with ethyl acetate (20 mL). The organic layers were dried over sodium sulfate and concentrated in vacuo. The residue was purified by flash chromatography on silica gel (cyclohexane/ethyl acetate 90/10) to provide methyl 2-(2-bromo-3-trifluoromethylphenyl)-2-(tert-butoxy)acetate (21c) (210 mg, 0.56 mmol, 54%) as a yellow oil.

$^1$H NMR (400 MHz, CDCl$_3$) δ 1.22 (s, 9H), 3.68 (s, 3H), 5.82 (s, 1H), 7.02 (t, J=8.0 Hz, 1H), 7.06 (d, J=8.0 Hz, 1H), 7.37 (d, J=8.0 Hz, 1H).

Step 4: Preparation of intermediate methyl 2-(tert-butoxy)-2-[2-(3,4-dihydro-2H-1-benzopyran-6-yl)-3-trifluoromethylphenyl]acetate (21d)

A mixture of methyl 2-(2-bromo-3-trifluoromethylphenyl)-2-(tert-butoxy)acetate (21c) (137 mg, 0.37 mmol), sodium carbonate (157 mg, 1.48 mmol), 6-(4,4,5,5-tetramethyl-1,3,2-dioxaborolan-2-yl)chroman (145 mg, 0.56 mmol) and palladium tetrakis(triphenylphosphine) (21 mg, 0.02 mmol) in dioxane (3 mL) and water (1.5 mL) was irradiated (200 W, 80° C.) for 1 hour. The mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate 95/5) to provide methyl 2-(tert-butoxy)-2-[2-(3,4-dihydro-2H-1-benzopyran-6-yl)-3-trifluoromethylphenyl]acetate (21d) (114 mg, 0.26 mmol, 70%) as a yellow oil.

$^1$H NMR (400 MHz, CDCl$_3$) δ 1.03 and 1.05 (s, 9H), 2.05-2.08 (m, 2H), 2.79-2.83 (m, 2H), 3.61 (s, 3H), 4.24-4.26 (m, 2H), 4.83 and 4.84 (s, 1H), 6.82-6.94 (m, 3H), 7.43-7.50 (m, 1H), 7.68 (d, J=8.0 Hz, 1H), 7.87-7.93 (m, 1H).

Step 5: Preparation of 2-(tert-butoxy)-2-[2-(3,4-dihydro-2H-1-benzopyran-6-yl)-3-trifluoro methylphenyl]acetic acid To a solution of methyl 2-(tert-butoxy)-2-[2-(3,4-dihydro-2H-1-benzopyran-6-yl)-3-trifluoromethylphenyl]acetate (21d) (114 mg, 0.27 mmol) in tetrahydrofuran (4 mL) and water (0.3 mL) was added a 2 M solution of sodium hydroxide (0.16 mL, 0.33 mmol). The mixture was stirred at room temperature overnight. Supplementary sodium hydroxide solution was added (1 mL, 2.1 mmol) and stirring was maintained for 24 hours. The solution was then acidified with sodium phosphate monobasic solution and extracted with ethyl acetate (2×5 mL). The organic layer was dried over sodium sulfate and concentrated in vacuo. The residue was first purified by flash chromatography on silica gel (cyclohexane/ethyl acetate 10/90) then triturated in a mixture of acetonitrile and water to provide the desired acid (57 mg, 0.14 mmol, 52%) as a white solid.

$^1$H NMR (400 MHz, DMSO-d$_6$) δ 0.95 (s, 9H), 1.94-1.97 (m, 2H), 2.68-2.74 (m, 2H), 4.19-4.21 (m, 2H), 4.63 (s, 1H), 6.78-6.95 (m, 3H), 7.62 (t, J=8.0 Hz, 1H), 7.74-7.82 (m, 2H), 12.65 (s, 1H).

MS m/z ([M−H]$^−$) 407.

Example 22: Synthesis of 2-(tert-butoxy)-2-[2-(3,4-dihydro-2H-1-benzopyran-6-yl)-6-methylphenyl]acetic acid

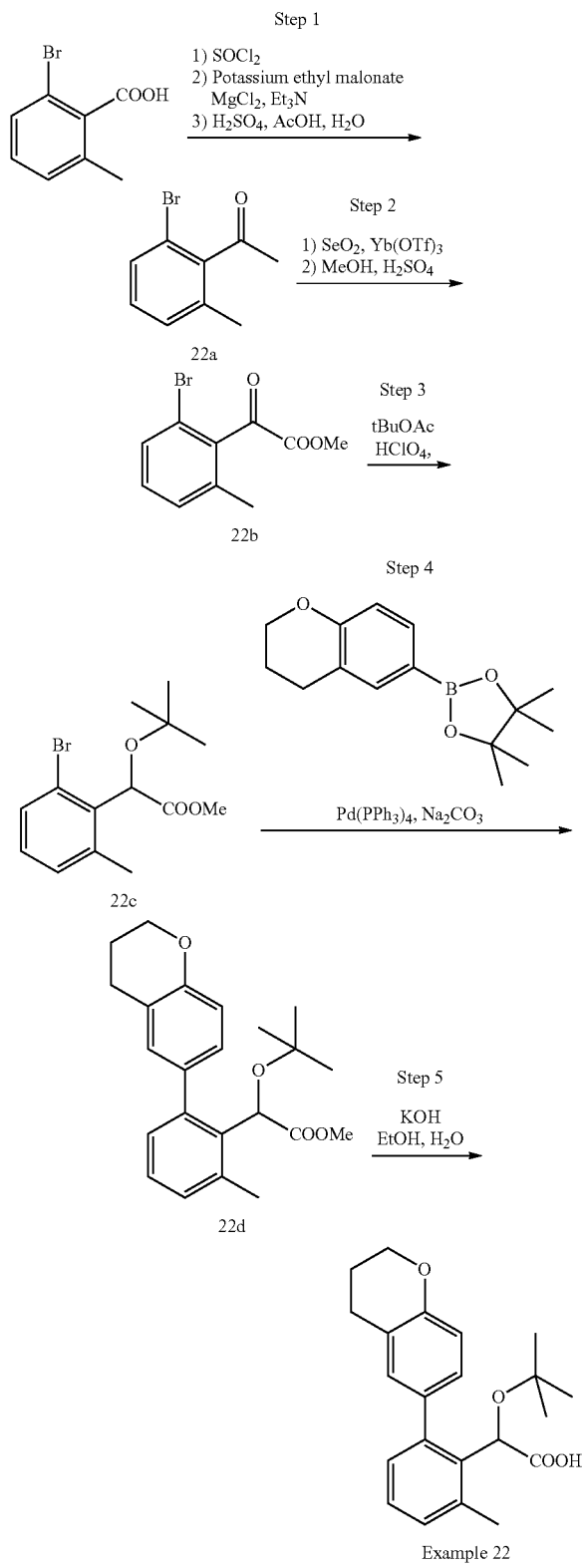

Step 1: Preparation of intermediate 1-(2-bromo-6-methylphenyl)ethan-1-one (22a)

Using the procedure described in example 21, step 1, 2-bromo-6-methylbenzoic acid (1 g, 4.65 mmol) is converted to 1-(2-bromo-6-methylphenyl)ethan-1-one (22a) (684 mg, 3.21 mmol, 69%) as an orange oil which was used without further purification.

$^1$H NMR (400 MHz, CDCl$_3$) δ 2.27 (s, 3H), 2.55 (s, 3H), 7.12-7.14 (m, 2H), 7.38 (d, J=8.0 Hz, 1H).

Step 2: Preparation of intermediate methyl 2-(2-bromo-6-methylphenyl)-2-hydroxyacetate (22b)

Using the procedure described in example 21, step 2, 1-(2-bromo-3-methylphenyl)ethan-1-one (22a) (684 mg, 3.21 mmol), is converted to methyl 2-(2-bromo-6-methylphenyl)-2-hydroxyacetate (22b) (757 mg, 2.92 mmol, 91%) as an orange oil which was used without further purification.

$^1$H NMR (400 MHz, CDCl$_3$) δ 2.39 (s, 3H), 3.43 (broad s, 1H), 3.79 (s, 3H), 5.81 (s, 1H), 7.10 (t, J=8.0 Hz, 1H), 7.14 (d, J=8.0 Hz, 1H), 7.44 (d, J=8.0 Hz, 1H).

Step 3: Preparation of intermediate methyl 2-(2-bromo-6-methylphenyl)-2-(tert-butoxy)acetate (22c)

Using the procedure described in example 21, step 3, methyl 2-(2-bromo-6-methylphenyl)-2-hydroxyacetate (22b) (756 mg, 2.92 mmol), is converted, after purification by flash chromatography on silica gel (cyclohexane/ethyl acetate 80/20), to methyl 2-(2-bromo-6-methylphenyl)-2-(tert-butoxy)acetate (22c) (248 mg, 0.78 mmol, 27%) as a beige solid.

$^1$H NMR (400 MHz, CDCl$_3$) δ 1.22 (s, 9H), 2.42 (s, 3H), 3.68 (s, 3H), 5.82 (s, 1H), 7.02 (t, J=8.0 Hz, 1H), 7.09 (d, J=8.0 Hz, 1H), 7.40 (d, J=8.0 Hz, 1H).

Step 4: Preparation of intermediate methyl 2-(tert-butoxy)-2-[2-(3,4-dihydro-2H-1-benzopyran-6-yl)-6-methylphenyl]acetate (22d)

Using the procedure described in example 21, step 4, methyl 2-(2-bromo-6-methylphenyl)-2-(tert-butoxy)acetate (22c) (124 mg, 0.39 mmol), is converted, after purification by flash chromatography on silica gel (cyclohexane/ethyl acetate 90/10), to methyl 2-(tert-butoxy)-2-[2-(3,4-dihydro-2H-1-benzopyran-6-yl)-6-methylphenyl]acetate (22d) (73 mg, 0.2 mmol, 64%) as a yellow oil.

$^1$H NMR (400 MHz, CDCl$_3$) δ 0.91 (s, 9H), 2.03-2.07 (m, 2H), 2.41 (s, 3H), 2.75-2.85 (m, 2H), 3.74 (s, 3H), 4.22-4.25 (m, 2H), 5.34 (s, 1H), 6.82 (d, J=8.0 Hz, 1H), 7.06-7.20 (m, 5H).

Step 5: Preparation of 2-(tert-butoxy)-2-[2-(3,4-dihydro-2H-1-benzopyran-6-yl)-6-methylphenyl]acetic acid Using the procedure described in example 21, step 5, methyl 2-(tert-butoxy)-2-[2-(3,4-dihydro-2H-1-benzopyran-6-yl)-6-methylphenyl]acetate (22d) (269 mg, 0.73 mmol), is converted, after purification by flash chromatography on silica gel (cyclohexane/ethyl acetate 10/90) and recrystallization in a mixture of acetonitrile and water, to recristallised in a mixture of acetonitrile and water to 2-(tert-butoxy)-2-[2-(3,4-dihydro-2H-1-benzopyran-6-yl)-6-methyl phenyl] acetic acid (example 22) (60 mg, 0.17 mmol, 23%) as a white solid.

$^1$H NMR (400 MHz, DMSO-d$_6$) δ 0.82 (s, 9H), 1.93-1.97 (m, 2H), 2.35 (s, 3H), 2.68-2.78 (m, 2H), 4.18 (t, J=5.0 Hz, 2H), 5.24 (s, 1H), 6.81 (d, J=8.0 Hz, 1H), 7.00-7.20 (m, 5H).

MS m/z ([M–H]$^−$) 353.

Example 23: Synthesis of 2-(tert-butoxy)-2-[2-(3,4-dihydro-2H-1-benzopyran-6-yl)-4-phenyl-phenyl] acetic acid

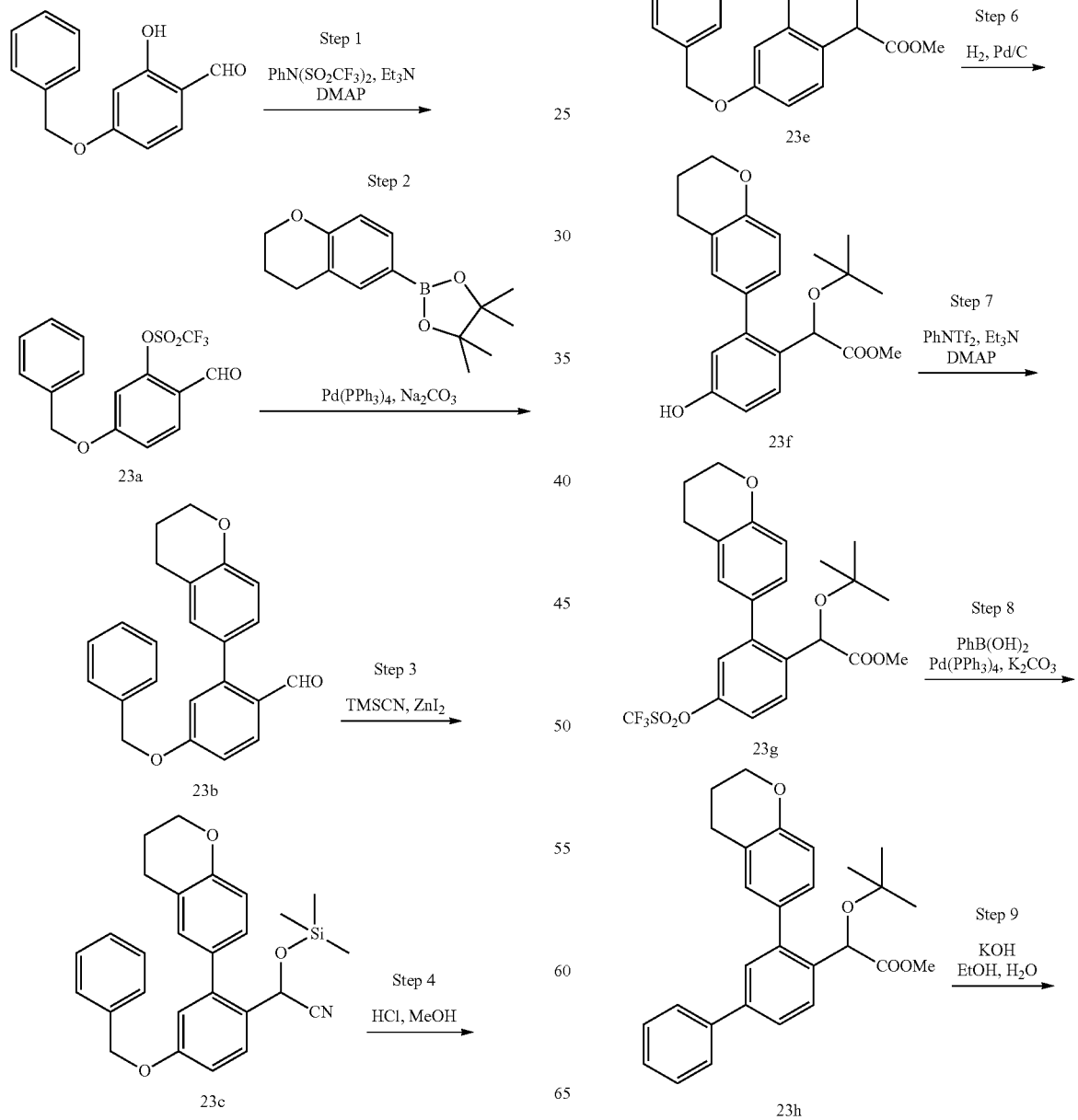

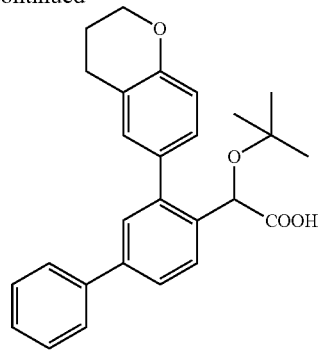

Example 23

Step 1: Preparation of intermediate 5-(benzyloxy)-2-formylphenyl trifluoromethanesulfonate (23a)

To a solution of 4-(benzyloxy)-2-hydroxybenzaldehyde (1 g, 4.38 mmol) in anhydrous N,N-dimethylformamide (20 mL) at 0° C. under nitrogen atmosphere were added N-phenyl-bis(trifluoromethanesulfonimide) (2.35 g, 8.76 mmol), 4-(dimethylamino)pyridine (53 mg, 0.44 mmol) and triethylamine (1.25 mL, 8.76 mmol). The mixture was stirred at room temperature overnight and poured in water (100 mL). The aqueous layer was extracted with dichloromethane (2×30 mL). The organic layers were dried over sodium sulfate and concentrated in vacuo. The residue was purified by flash chromatography on silica gel (cyclohexane/ethyl acetate 40/60) to provide 5-(benzyloxy)-2-formylphenyl trifluoromethane sulfonate (23a) (1.47 g, 4.08 mmol, 93%) as a colorless oil.

$^1$H NMR (400 MHz, CDCl$_3$) δ 5.16 (s, 2H), 6.95 (d, J=1.0 Hz, 1H), 7.09 (dd, J=1.0 Hz, J=8.0 Hz, 1H), 7.33-7.43 (m, 5H), 7.95 (d, J=8.0 Hz, 1H), 10.13 (s, 1H).

Step 2: Preparation of intermediate 4-(benzyloxy)-2-(3,4-dihydro-2H-1-benzopyran-6-yl)benzaldehyde (23b)

A mixture of 5-(benzyloxy)-2-formylphenyl trifluoromethanesulfonate (23a) (1.45 g, 4.02 mmol), sodium carbonate (1.70 g, 16.08 mmol), 6-(4,4,5,5-tetramethyl-1,3,2-dioxaborolan-2-yl)chroman (1.57 g, 6.04 mmol) and palladium tetrakis(triphenylphosphine) (232 mg, 0.20 mmol) in a mixture of toluene (19 mL) ethanol (8 mL) and water (10 mL) was refluxed overnight. The mixture was poured into water (20 mL). The aqueous layer was extracted with ethyl acetate (2×20 mL). The organic layer was washed with brine (20 mL), dried over sodium sulfate and concentrated in vacuo. The residue was purified by flash chromatography on silica gel (cyclohexane/ethyl acetate 95/5) to provide methyl 4-(benzyloxy)-2-(3,4-dihydro-2H-1-benzopyran-6-yl)benzaldehyde (23b) (1.18 g, 3.42 mmol, 85%) as a white solid.

$^1$H NMR (400 MHz, CDCl$_3$) δ 2.03-2.07 (m, 2H), 2.84 (t, J=8.0 Hz, 2H), 4.23-4.26 (m, 2H), 5.16 (s, 2H), 6.87 (d, J=8.0 Hz, 1H), 6.95 (d, J=1.0 Hz, 1H), 7.01-7.04 (m, 2H), 7.09 (dd, J=1.0 Hz, J=8.0 Hz, 1H), 7.35-7.45 (m, 5H), 7.99 (d, J=8.0 Hz, 1H), 10.13 (s, 1H).

Step 3: Preparation of intermediate 2-[4-(benzyloxy)-2-(3,4-dihydro-2H-1-benzopyran-6-yl)phenyl]-2-[(trimethylsilyl)oxy]acetonitrile (23c)

To a solution of 4-(benzyloxy)-2-(3,4-dihydro-2H-1-benzopyran-6-yl)benzaldehyde (23b) (1.30 g, 3.43 mmol) in anhydrous dichloromethane (13 mL) at 0° C. under nitrogen atmosphere were successively added zinc iodide (109 mg, 0.34 mmol) and trimethylsilyl cyanide (0.54 mL, 4.29 mmol). The mixture was stirred at room temperature overnight. A saturated solution of sodium hydrogenocarbonate (10 mL) was added. Layers were separated and the aqueous layer was extracted with dichloromethane (10 mL). The organic layers were dried over sodium sulfate and concentrated in vacuo to provide 2-[4-(benzyloxy)-2-(3,4-dihydro-2H-1-benzopyran-6-yl)phenyl]-2-[(trimethylsilyl)oxy]acetonitrile (23c) (1.50 g, 3.38 mmol, 98%).

$^1$H NMR (400 MHz, CDCl$_3$) δ 0.06 (s, 9H), 2.04-2.07 (m, 2H), 2.80-2.86 (m, 2H), 4.23-4.26 (m, 2H), 5.08 (s, 2H), 5.42 (s, 1H), 6.84-6.86 (m, 2H), 6.98-7.05 (m, 3H), 7.33-7.44 (m, 5H), 7.69 (d, J=8.0 Hz, 1H).

Step 4: Preparation of intermediate methyl 2-[4-(benzyloxy)-2-(3,4-dihydro-2H-1-benzopyran-6-yl)phenyl]-2-hydroxyacetate (23d)

2-[4-(benzyloxy)-2-(3,4-dihydro-2H-1-benzopyran-6-yl)phenyl]-2-[(trimethylsilyl)oxy] acetonitrile (23c) (4.8 g, 11.24 mmol) was dissolved in a 3M hydrochloric acid solution in methanol (37 mL, 111 mmol) and stirred at for 10 days adding 3 M hydrochloric acid solution in methanol (18 mL, 54 mmol) everyday. The mixture was concentrated in vacuo. The residue was dissolved in dichloromethane (50 mL), washed with a saturated aqueous solution of sodium bicarbonate (30 mL), brine (30 mL), dried over sodium sulfate and concentrated in vacuo. The residue was purified by flash chromatography on silica gel (cyclohexane/ethyl acetate 90/10 then 80/20) to provide methyl 2-[4-(benzyloxy)-2-(3,4-dihydro-2H-1-benzopyran-6-yl)phenyl]-2-hydroxyacetate (23d) (1.39 g, 3.43 mmol, 30%) as an orange solid.

$^1$H NMR (400 MHz, CDCl$_3$) δ 2.03-2.06 (m, 2H), 2.83 (t, J=8.0 Hz, 2H), 3.71 (s, 3H), 4.21-4.24 (m, 2H), 5.07 (s, 2H), 5.23 (s, 1H), 6.83 (d, J=8.0 Hz, 1H), 6.90 (d, J=1.0 Hz, 1H), 6.95 (dd, J=1.0 Hz, J=8.0 Hz, 1H), 7.11 (s, 1H), 7.16 (d, J=8.0 Hz, 1H), 7.25-7.43 (m, 6H).

Step 5: Preparation of intermediate methyl 2-[4-(benzyloxy)-2-(3,4-dihydro-2H-1-benzopyran-6-yl)phenyl]-2-(tert-butoxy)acetate (23e)

To a solution of methyl 2-[4-(benzyloxy)-2-(3,4-dihydro-2H-1-benzopyran-6-yl)phenyl]-2-hydroxyacetate (23d) (1.36 g, 3.37 mmol) in tert-butyl acetate (64 mL) at −10° C. was added perchloric acid (10 mL). The mixture was stirred at −10° C. for 1 hour then 0° C. for 1 hour before being poured into a saturated aqueous solution of sodium bicarbonate (200 mL). The layers were separated and the aqueous layer was extracted with ethyl acetate (50 mL). The organic layers were dried over sodium sulfate and concentrated in vacuo. The residue was purified by flash chromatography on silica gel (cyclohexane/ethyl acetate 85/15) to provide methyl 2-[4-(benzyloxy)-2-(3,4-dihydro-2H-1-benzopyran-6-yl)phenyl]-2-(tert-butoxy)acetate (23e) (467 mg, 1.01 mmol, 30%) as colorless oil.

$^1$H NMR (400 MHz, CDCl$_3$) b 0.98 (s, 9H), 2.03-2.07 (m, 2H), 2.80-2.85 (m, 2H), 3.69 (s, 3H), 4.23-4.26 (m, 2H), 5.05 (s, 2H), 5.14 (s, 1H), 6.83-6.86 (m, 2H), 6.97 (dd, J=1.0

Hz, J=8.0 Hz, 1H), 7.07 (s, 1H), 7.13 (d, J=8.0 Hz, 1H), 7.32-7.43 (m, 5H), 7.57 (d, J=8.0 Hz, 1H).

Step 6: Preparation of intermediate methyl 2-[2-(3, 4-dihydro-2H-1-benzopyran-6-yl)-4-hydroxy phenyl]-2-(tert-butoxy)acetate (23f)

A solution of methyl 2-[4-(benzyloxy)-2-(3,4-dihydro-2H-1-benzopyran-6-yl)phenyl]-2-(tert-butoxy)acetate (23e) (417 mg, 0.90 mmol) in 2-propanol (80 mL) was hydrogenated (H-cube) overnight in the presence of Pd/C. The solution was then concentrated in vacuo. The residue was purified by flash chromatography on silica gel (cyclohexane/ethyl acetate 85/15 then 75/25) to provide methyl 2-[2-(3, 4-dihydro-2H-1-benzopyran-6-yl)-4-hydroxy phenyl]-2-(tert-butoxy)acetate (23f) (314 mg, 0.84 mmol, 94%) as a white foam.

$^1$H NMR (400 MHz, CDCl$_3$) 50.97 (s, 9H), 2.04-2.06 (m, 2H), 2.79-2.85 (m, 2H), 3.69 (s, 3H), 4.23-4.25 (m, 2H), 5.12 (s, 1H), 6.67 (d, J=1.0 Hz, 1H), 6.80 (dd, J=1.0 Hz, J=8.0 Hz, 1H), 6.84 (d, J=8.0 Hz, 1H), 7.06 (s, 1H), 7.11 (d, J=8.0 Hz, 1H), 7.53 (d, J=8.0 Hz, 1H).

Step 7: Preparation of intermediate methyl 2-(tert-butoxy)-2-[2-(3,4-dihydro-2H-1-benzopyran-6-yl)-4-[(trifluoromethane)sulfonyloxy]phenyl]acetate (23g)

A mixture of methyl 2-[2-(3,4-dihydro-2H-1-benzopyran-6-yl)-4-hydroxy phenyl]-2-(tert-butoxy)acetate (23f) (300 mg, 0.81 mmol) in anhydrous dichloromethane (4 mL) at 0° C. under nitrogen atmosphere were added N-phenyl-bis(trifluoromethanesulfonimide) (433 mg, 1.21 mmol), 4-(dimethylamino)pyridine (10 mg, 0.08 mmol) and triethylamine (230 µL, 1.62 mmol). The mixture was stirred at room temperature overnight. Water (10 mL) was added. The aqueous layer was extracted with dichloromethane (2×10 mL). The organic layers were dried over sodium sulfate and concentrated in vacuo. The residue was purified by flash chromatography on silica gel (cyclohexane/ethyl acetate 90/10) to provide methyl 2-(tert-butoxy)-2-[2-(3,4-dihydro-2H-1-benzopyran-6-yl)-4-[(trifluoromethane)sulfonyloxy] phenyl] acetate (23g) (470 mg) as a colorless oil.

$^1$H NMR (400 MHz, CDCl$_3$) δ 0.99 (s, 9H), 2.05-2.08 (m, 2H), 2.80-2.86 (m, 2H), 3.70 (s, 3H), 4.24-4.27 (m, 2H), 5.17 (s, 1H), 6.87 (d, J=8.0 Hz, 1H), 7.03-7.12 (m, 3H), 7.23 (dd, J=1.0 Hz, J=8.0 Hz, 1H), 7.75 (d, J=8.0 Hz, 1H).

Step 8: Preparation of intermediate methyl 2-(tert-butoxy)-2-[2-(3,4-dihydro-2H-1-benzopyran-6-yl)-4-phenyl-phenyl]acetate (23h)

A mixture of methyl 2-(tert-butoxy)-2-[2-(3,4-dihydro-2H-1-benzopyran-6-yl)-4-[(trifluoromethane)sulfonyloxy] phenyl]acetate (23g) (110 mg, 0.21 mmol), potassium carbonate (116 mg, 0.86 mmol), phenylboronic acid (37 mg, 0.30 mmol) and palladium tetrakis(triphenylphosphine) (12 mg, 0.01 mmol) in dioxane (1.2 mL) and water (0.4 mL) was irradiated (200 W, 80° C.) for 1 hour. The mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate: 90/10) to provide methyl 2-(tert-butoxy)-2-[2-(3,4-dihydro-2H-1-benzopyran-6-yl)-4-phenylphenyl]acetate (23h) (37 mg, 0.086 mmol, 41%) as a colorless oil.

$^1$H NMR (400 MHz, CDCl$_3$) δ 1.03 (s, 9H), 2.03-2.10 (m, 2H), 2.79-2.89 (m, 2H), 3.71 (s, 3H), 4.24-4.27 (m, 2H), 5.25 (s, 1H), 6.88 (d, J=8.0 Hz, 1H), 7.12 (s, 1H), 7.18 (d, J=8.0 Hz, 1H), 7.33 (t, J=8.0 Hz, 1H), 7.40-7.46 (m, 3H), 7.57-7.62 (m, 3H), 7.73 (d, J=8.0 Hz, 1H).

Step 9: Preparation of 2-(tert-butoxy)-2-[2-(3,4-dihydro-2H-1-benzopyran-6-yl)-4-phenyl-phenyl] acetic acid A solution of methyl 2-(tert-butoxy)-2-[2-(3,4-dihydro-2H-1-benzopyran-6-yl)-4-phenyl-phenyl]acetate (23h) (34 mg, 0.077 mmol) and potassium hydroxide (18 mg, 0.31 mmol) in a mixture of ethanol (2.1 mL) and water (0.8 mL) was stirred at 95° C. for 24 hours. Potassium hydroxide (10 mg, 0.18 mmol) was added and the mixture was stirred for 6 hours. Ethanol was evaporated in vacuo and an aqueous solution of monosodium phosphate 10% was added until acidic pH. The solid was filtered, dissolved in ethyl acetate (5 mL), dried over sodium sulfate and concentrated in vacuo. The residue was purified by flash chromatography on silica gel (cyclohexane/ethyl acetate 10/90) to provide the desired acid (example 23) (18 mg, 0.043 mmol, 56%) as a white solid.

$^1$H NMR (400 MHz, CDCl$_3$) δ 1.02 (s, 9H), 2.05-2.07 (m, 2H), 2.80-2.88 (m, 2H), 4.25 (t, J=4.0 Hz, 2H), 5.29 (s, 1H), 6.88 (d, J=8.0 Hz, 1H), 7.34-7.62 (m, 10H).

MS m/z ([M+NH$_4$]$^+$) 434.

MS m/z ([M−H]$^−$) 415.

Example 24: Synthesis of 2-(tert-butoxy)-2-[2-(3,4-dihydro-2H-1-benzopyran-6-yl)-4-(1-methyl-1H-pyrazol-4-yl)phenyl]acetic acid

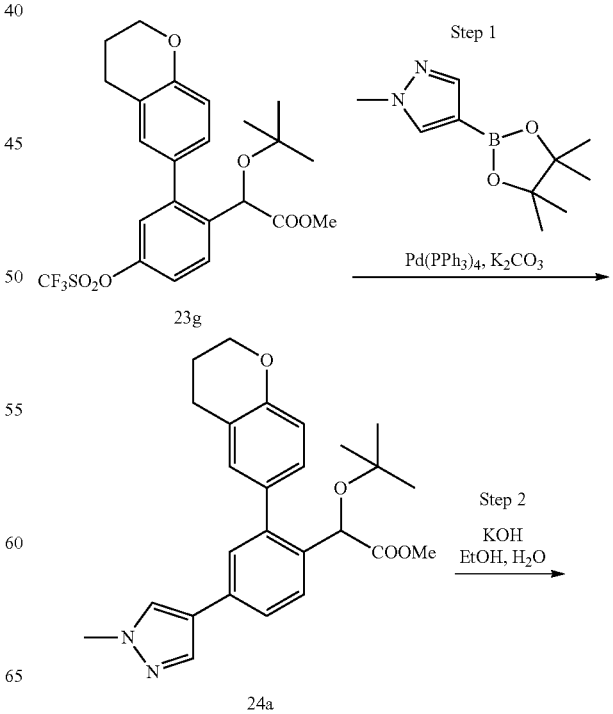

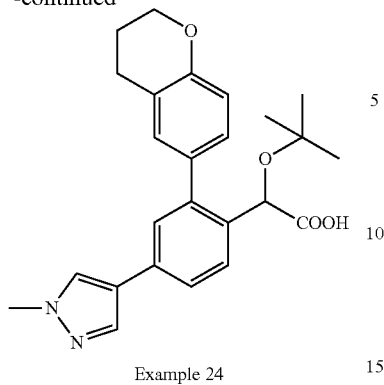

Example 24

Step 1: Preparation of intermediate methyl 2-(tert-butoxy)-2-[2-(3,4-dihydro-2H-1-benzopyran-6-yl)-4-(1-methyl-1H-pyrazol-4-yl)phenyl]acetate (24a)

A mixture of methyl 2-(tert-butoxy)-2-[2-(3,4-dihydro-2H-1-benzopyran-6-yl)-4-[(trifluoromethane)sulfonyloxy]phenyl]acetate (23g) (110 mg, 0.21 mmol), potassium carbonate (116 mg, 0.86 mmol), 1-methyl-4-(4,4,5,5-tetramethyl-1,3,2-dioxoborolan-2-yl)-1H-pyrazole (62 mg, 0.30 mmol) and palladium tetrakis(triphenylphosphine) (12 mg, 0.01 mmol) in a mixture of dioxane (1.2 mL) and water (0.4 mL) was irradiated (200 W, 80° C.) for 1 hour. The mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate: 90/10 then 50/50) to provide methyl 2-(tert-butoxy)-2-[2-(3,4-dihydro-2H-1-benzopyran-6-yl)-4-(1-methyl-1H-pyrazol-4-yl)phenyl]acetate (24a) (46 mg, 0.10 mmol, 50%) as a colorless oil.

$^1$H NMR (400 MHz, CDCl$_3$) δ 1.00 (s, 9H), 2.05-2.10 (m, 2H), 2.79-2.89 (m, 2H), 3.69 (s, 3H), 3.92 (s, 3H), 4.23-4.26 (m, 2H), 5.18 (s, 1H), 6.86 (d, J=8.0 Hz, 1H), 7.09 (s, 1H), 7.15 (d, J=8.0 Hz, 1H), 7.31 (d, J=1.0 Hz, 1H), 7.43 (dd, J=1.0 Hz, J=8.0 Hz, 1H), 7.60 (s, 1H), 7.64 (d, J=8.0 Hz, 1H), 7.75 (s, 1H).

Step 2: Preparation of 2-(tert-butoxy)-2-[2-(3,4-dihydro-2H-1-benzopyran-6-yl)-4-(1-methyl-1H-pyrazol-4-yl)phenyl]acetic acid A solution of methyl 2-(tert-butoxy)-2-[2-(3,4-dihydro-2H-1-benzopyran-6-yl)-4-(1-methyl-1H-pyrazol-4-yl)phenyl]acetate (24a) (46 mg, 0.10 mmol) and potassium hydroxide (24 mg, 0.42 mmol) in a mixture of ethanol (2.9 mL) and water (1.1 mL) was stirred at 95° C. for 24 hours. Potassium hydroxide (12 mg, 0.21 mmol) was added and the mixture was stirred for 6 hours. Ethanol was evaporated in vacuo and an aqueous solution of monosodium phosphate 10% was added until acidic pH. The solid was filtered, dissolved in ethyl acetate (5 mL), dried over sodium sulfate and concentrated in vacuo. The residue was purified by flash chromatography on silica gel (cyclohexane/ethyl acetate 10/90 then dichloromethane/methanol 90/10) to provide the desired acid (example 24) (22 mg, 0.052 mmol, 52%) as a white solid.

$^1$H NMR (400 MHz, DMSO-d$_6$) δ 0.90 (s, 9H), 1.95-2.00 (m, 2H), 2.75-2.81 (m, 2H), 3.84 (s, 3H), 4.18 (t, J=4.0 Hz, 2H), 5.03 (s, 1H), 6.83 (d, J=8.0 Hz, 1H), 7.13-7.18 (m, 2H), 7.36 (d, J=1.0 Hz, 1H), 7.45-7.52 (m, 2H), 7.86 (s, 1H), 8.16 (s, 1H).

MS m/z ([M+H]$^+$) 421.

MS m/z ([M−H]$^-$) 419.

Example 25: Synthesis of 2-[4-benzyl-6-(3,4-dihydro-2H-1-benzopyran-6-yl)-5-oxo-2,3,4,5-tetrahydro-1,4-benzoxazepin-7-yl]-2-(tert-butoxy)acetic acid

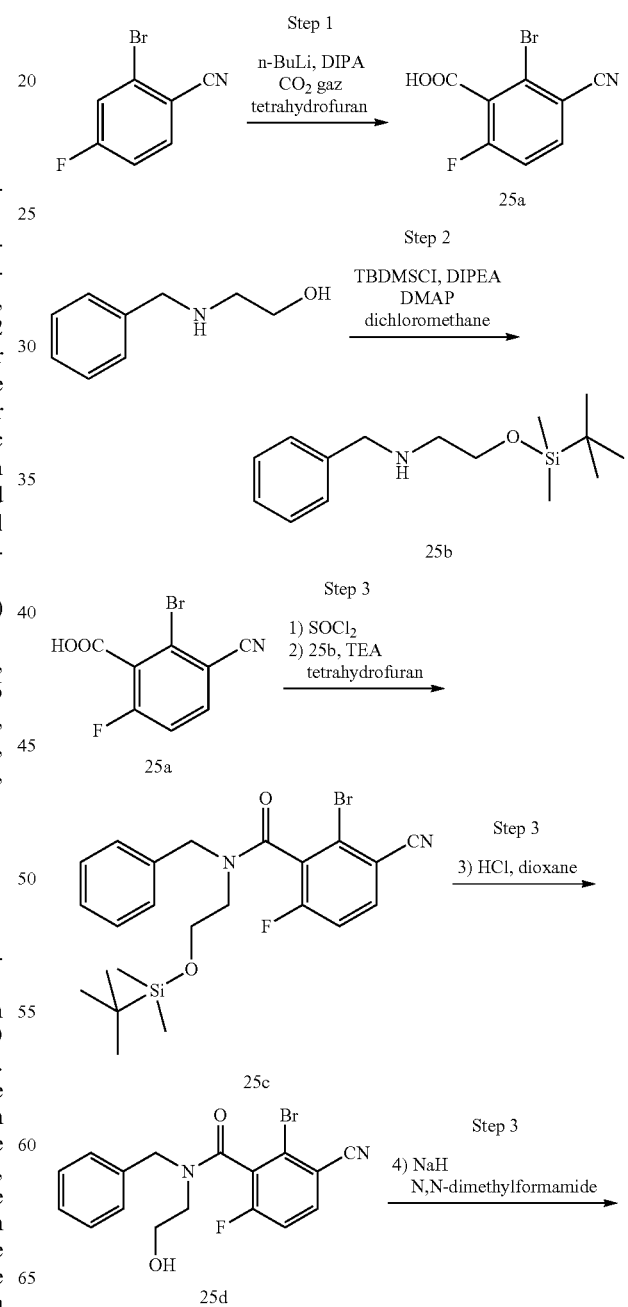

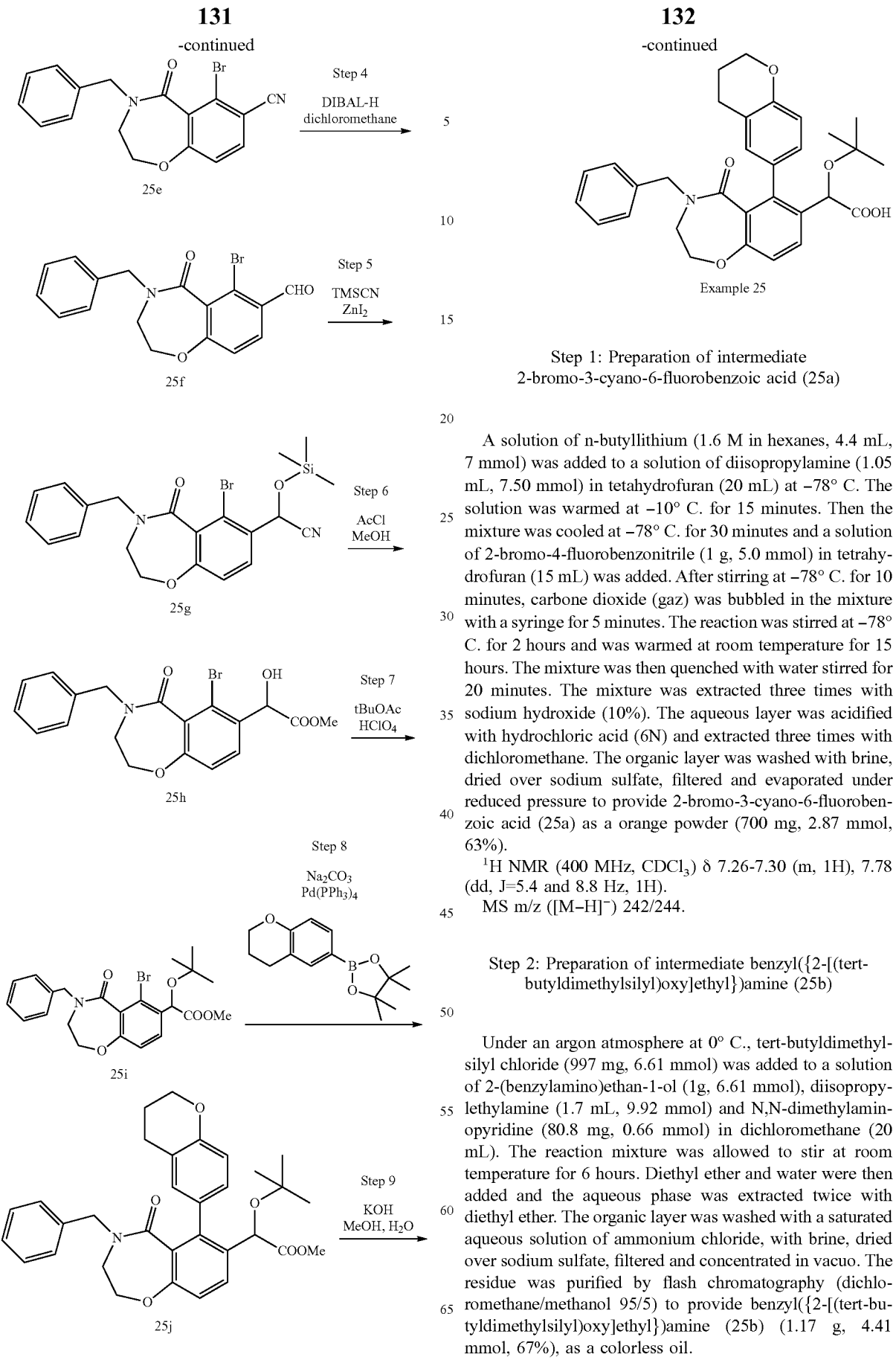

Example 25

Step 1: Preparation of intermediate
2-bromo-3-cyano-6-fluorobenzoic acid (25a)

A solution of n-butyllithium (1.6 M in hexanes, 4.4 mL, 7 mmol) was added to a solution of diisopropylamine (1.05 mL, 7.50 mmol) in tetahydrofuran (20 mL) at −78° C. The solution was warmed at −10° C. for 15 minutes. Then the mixture was cooled at −78° C. for 30 minutes and a solution of 2-bromo-4-fluorobenzonitrile (1 g, 5.0 mmol) in tetrahydrofuran (15 mL) was added. After stirring at −78° C. for 10 minutes, carbone dioxide (gaz) was bubbled in the mixture with a syringe for 5 minutes. The reaction was stirred at −78° C. for 2 hours and was warmed at room temperature for 15 hours. The mixture was then quenched with water stirred for 20 minutes. The mixture was extracted three times with sodium hydroxide (10%). The aqueous layer was acidified with hydrochloric acid (6N) and extracted three times with dichloromethane. The organic layer was washed with brine, dried over sodium sulfate, filtered and evaporated under reduced pressure to provide 2-bromo-3-cyano-6-fluorobenzoic acid (25a) as a orange powder (700 mg, 2.87 mmol, 63%).

$^1$H NMR (400 MHz, CDCl$_3$) δ 7.26-7.30 (m, 1H), 7.78 (dd, J=5.4 and 8.8 Hz, 1H).

MS m/z ([M−H]$^−$) 242/244.

Step 2: Preparation of intermediate benzyl({2-[(tert-butyldimethylsilyl)oxy]ethyl})amine (25b)

Under an argon atmosphere at 0° C., tert-butyldimethylsilyl chloride (997 mg, 6.61 mmol) was added to a solution of 2-(benzylamino)ethan-1-ol (1g, 6.61 mmol), diisopropylethylamine (1.7 mL, 9.92 mmol) and N,N-dimethylaminopyridine (80.8 mg, 0.66 mmol) in dichloromethane (20 mL). The reaction mixture was allowed to stir at room temperature for 6 hours. Diethyl ether and water were then added and the aqueous phase was extracted twice with diethyl ether. The organic layer was washed with a saturated aqueous solution of ammonium chloride, with brine, dried over sodium sulfate, filtered and concentrated in vacuo. The residue was purified by flash chromatography (dichloromethane/methanol 95/5) to provide benzyl({2-[(tert-butyldimethylsilyl)oxy]ethyl})amine (25b) (1.17 g, 4.41 mmol, 67%), as a colorless oil.

¹H NMR (400 MHz, CDCl₃) δ 0.05 (s, 6H), 0.89 (s, 9H), 2.74 (t, J=5.3 Hz, 2H), 3.75 (t, J=5.3 Hz, 2H), 3.82 (s, 2H), 7.24-7.33 (m, 5H).

MS m/z ([M+H]⁺) 266.

Step 3: Preparation of intermediate 4-benzyl-6-bromo-5-oxo-2,3,4,5-tetrahydro-1,4-benzoxazepine-7-carbonitrile (25e) (three steps)

A solution of 2-bromo-3-cyano-6-fluorobenzoic acid (25a) (993 mg, 4.07 mmol) in thionyl chloride (20 mL) was heated at 85° C. for 3 hours. The mixture was coevaporated two times with toluene. The residue was diluted in tetrahydrofuran (15 mL) and was added at 0° C. to a solution of triethylamine (851 μL, 6.10 mmol) and benzyl-({2-[(tert-butyldimethylsilyl)oxy]ethyl})amine (25b) (1.08 g, 4.07 mmol) in tetrahydrofuran (15 mL). The mixture was slowly warmed at room temperature for 15 hours. Water was added to the mixture which was extracted twice with ethyl acetate. The organic layer was washed with a saturated aqueous solution of ammonium chloride, with brine, dried over sodium sulfate, filtered and concentrated in vacuo. The residue was purified by flash chromatography (cyclohexane/ethyl acetate: 85/15) to provide the protected intermediate (25c) (1.76 g, 3.58 mmol, 88%).

Under a nitrogen atmosphere, the resultant product (25c) was dissolved in dioxane and treated with hydrochloric acid (4M in dioxane, 2.5 mL, 10 mmol) at room temperature for 18 hours and at 50° C. for 2 hours more. The solvent was then removed in vacuo and the residue was basified with aqueous sodium hydroxide (1N) and extracted twice with ethyl acetate. The organic layer was washed with brine, dried over sodium sulfate, filtered, and evaporated under reduced pressure. The residue was filtered on silica gel to give a crude product N-benzyl-2-bromo-3-cyano-6-fluoro-N-(2-hydroxyethyl)benzamide (25d) (875 mg, 2.31 mmol, 58%).

MS m/z ([M+H]⁺) 377/379.

Under nitrogen atmosphere, at 0° C., sodium hydride (60% dispersion in mineral oil, 120.5 mg, 3.01 mmol) was added to a solution of (25b) (874 mg, 2.32 mmol) in dimethylformamide (11.4 mL). After 1 hour, the mixture was warmed at room temperature for 5 hours. The mixture was then hydrolyzed at 0° C. with water and the aqueous layer was extracted twice with ethyl acetate. The organic layer was washed with brine, dried over sodium sulfate, filtered, and evaporated under reduced pressure. The residue was purified by flash chromatography (dichloromethane/ethyl acetate 95/5) to provide 4-benzyl-6-bromo-5-oxo-2,3,4,5-tetrahydro-1,4-benzoxazepine-7-carbonitrile (25e) (348 mg, 0.97 mmol, 24%), as a white solid.

¹H NMR (400 MHz, CDCl₃) δ 3.42 (t, J=5.6 Hz, 2H), 4.09 (t, J=5.6 Hz, 2H), 4.86 (s, 2H), 7.10 (d, J=8.4 Hz, 1H), 7.31-7.39 (m, 5H), 7.67 (d, J=8.4 Hz, 1H).

MS m/z ([M+H]⁺) 357/359.

Step 4: Preparation of intermediate 4-benzyl-6-bromo-5-oxo-2,3,4,5-tetrahydro-1,4-benzoxazepine-7-carbaldehyde (25f)

Under nitrogen atmosphere at −78° C., a solution of diisobutylaluminium hydride (1 M in toluene, 2 mL, 2 mmol) was dropped to a solution of 4-benzyl-6-bromo-5-oxo-2,3,4,5-tetrahydro-1,4-benzoxazepine-7-carbonitrile (25e) (210 mg, 0.59 mmol) in dichloromethane (25 mL). The mixture was stirred at −78° C. for 1.5 hours. The mixture was then hydrolyzed with hydrochloric acid (1N) and warmed at room temperature. After extraction with dichloromethane, the organic layer was washed with brine, dried over sodium sulfate and evaporated under reduced pressure. The residue was purified by preparative TLC (cyclohexane/ethyl acetate 60/40) to provide 4-benzyl-6-bromo-5-oxo-2,3,4,5-tetrahydro-1,4-benzoxazepine-7-carbaldehyde (25f) (74 mg, 0.20 mmol, 35%) as a white solid.

¹H NMR (400 MHz, CDCl₃) δ 3.43-3.45 (m, 2H), 4.09 (t, J=5.6 Hz, 2H), 4.89 (s, 2H), 7.13 (d, J=8.4 Hz, 1H), 7.24-7.42 (m, 5H), 8.01 (d, J=8.4 Hz, 1H), 10.47 (s, 1H).

MS m/z ([M+H]⁺) 360/362.

Step 5: Preparation of intermediate 2-(4-benzyl-6-bromo-5-oxo-2,3,4,5-tetrahydro-1,4-benzoxazepin-7-yl)-2-[(trimethylsilyl)oxy]acetonitrile (25g)

Under a nitrogen atmosphere, trimethylsilylcyanide (46 μL, 0.366 mmol) was added at 0° C. to a solution of 4-benzyl-6-bromo-5-oxo-2,3,4,5-tetrahydro-1,4-benzoxazepine-7-carbaldehyde (25f) (110 mg, 0.305 mmol) and zinc iodide (II) (10 mg, 0.03 mmol) in dichloromethane (5.9 mL). After 4 hours at room temperature, the reaction mixture was quenched with a saturated aqueous solution of sodium carbonate and extracted twice with dichloromethane. The organic layer was washed with brine, dried over sodium sulfate, filtered and evaporated under reduced pressure to provide 2-(4-benzyl-6-bromo-5-oxo-2,3,4, 5-tetrahydro-1,4-benzoxazepin-7-yl)-2-[(trimethylsilyl)oxy]acetonitrile (25g) (131 mg, 0.28 mmol, 93.5%) which was used without further purification.

¹H NMR (400 MHz, CDCl₃) δ 0.28 (s, 9H), 3.29-3.35 (m, 1H), 3.46-3.54 (m, 1H), 3.98-4.10 (m, 2H), 4.84 (d, J=14.8 Hz, 1H), 4.92 (d, J=14.8 Hz, 1H), 5.84 (s, 1H), 7.11 (d, J=8.5 Hz, 1H), 7.30-7.41 (m, 5H), 7.77 (d, J=8.5 Hz, 1H).

MS m/z ([M+H]⁺) 459/461.

Step 6: Preparation of intermediate methyl 2-(4-benzyl-6-bromo-5-oxo-2,3,4,5-tetrahydro-1,4-benzoxazepin-7-yl)-2-hydroxyacetate (25h)

Under nitrogen atmosphere, acetyl chloride (406 μL, 5.70 mmol) was added at −10° C. in anhydrous methanol (0.7 mL). The mixture was stirred for 30 minutes. A solution of 2-(4-benzyl-6-bromo-5-oxo-2,3,4,5-tetrahydro-1, 4-benzoxazepin-7-yl)-2-[(trimethylsilyl)oxy] acetonitrile (25g) in a mixture of methanol (0.4 mL) and dichloromethane (0.5 mL) was added to the mixture which was stirred at 0° C. for 4 hours and then at room temperature for 2 hours more. After being concentrated, the mixture was quenched with a saturated aqueous solution of sodium carbonate and extracted twice with dichloromethane. The organic layer was washed with aqueous sodium hydroxide (1N), with brine, dried over sodium sulfate, filtered and evaporated under reduced pressure. The residue was purified by preparative TLC (dichloromethane/methanol 98/2) to provide methyl 2-(4-benzyl-6-bromo-5-oxo-2,3,4,5-tetrahydro-1,4-benzoxazepin-7-yl)-2-hydroxyacetate (25h) (52 mg, 0.12 mmol, 43%).

¹H NMR (400 MHz, CDCl₃) 53.33-3.50 (m, 1H), 3.51-3.60 (m, 1H), 3.79 (s, 3H), 3.97-4.01 (m, 2H), 4.88 (s, 2H), 5.71-5.72 (m, 1H), 7.03 (d, J=8.4 Hz, 1H), 7.31-7.43 (m, 6H).

MS m/z ([M+H]⁺) 420/422.

Step 7: Preparation of intermediate methyl 2-(4-benzyl-6-bromo-5-oxo-2,3,4,5-tetrahydro-1,4-benzoxazepin-7-yl)-2-(tert-butoxy)acetate (25i)

To a suspension of methyl 2-(4-benzyl-6-bromo-5-oxo-2, 3,4,5-tetrahydro-1,4-benzoxazepin-7-yl)-2-hydroxyacetate (25h) (52 mg, 0.12 mmol) in tert-butylacetate (737 µL) at −10° C. was added perchloric acid (70%, 22 µL). The mixture was stirred at −10° C. for 1 hour. The mixture was then basified with a saturated aqueous solution of sodium bicarbonate until pH 8. The aqueous layer was extracted twice with ethyl acetate. The organic layer was washed with brine, dried over sodium sulfate, filtered and concentrated in vacuo. The residue was purified by preparative TLC (cyclohexane/ethyl acetate 60/40) to afford methyl 2-(4-benzyl-6-bromo-5-oxo-2,3,4,5-tetrahydro-1,4-benzoxazepin-7-yl)-2-(tert-butoxy)acetate (25i) (49 mg, 0.10 mmol, 83%) as a white solid.

$^1$H NMR (400 MHz, CDCl$_3$) δ 1.24 (s, 9H), 3.30-3.48 (m, 2H), 3.70 (s, 3H), 3.96-4.01 (m, 2H), 4.82-4.91 (m, 2H), 5.58 (s, 1H), 7.03-7.05 (d, J=8.5 Hz, 1H), 7.31-7.41 (m, 5H), 7.71-7.73 (d, J=8.5 Hz, 1H).

MS m/z ([M+H]$^+$) 476/478.

Step 8: Preparation of intermediate methyl 2-[4-benzyl-6-(3,4-dihydro-2H-1-benzopyran-6-yl)-5-oxo-2,3,4,5-tetrahydro-1,4-benzoxazepin-7-yl]-2-(tert-butoxy)acetate (25j)

Under argon atmosphere, methyl 2-(4-benzyl-6-bromo-5-oxo-2,3,4,5-tetrahydro-1,4-benzoxazepin-7-yl)-2-(tert-butoxy)acetate (25i) (49 mg, 0.10 mmol), 6-(4,4,5,5-tetramethyl-1,3,2-dioxaborolan-2-yl)chroman (28.1 mg, 0.11 mmol) and sodium carbonate (11.4 mg, 0.11 mmol) were dissolved in N,N-dimethylformamide/H$_2$O (2.3 mL/0.7 mL). The solution was degassed under Argon and palladium tetrakis(triphenylphosphine)palladium (24 mg, 0.02 mmol) was added. The mixture was heated at 100° C. for 16 hours. The mixture was then cooled at room temperature, water was added and the aqueous layer was extracted with ethyl acetate. The organic layer was washed with brine, dried over sodium sulfate, filtered, and evaporated under reduced pressure. The residue was purified by preparative TLC (cyclohexane/ethyl acetate 60/40) to afford methyl 2-[4-benzyl-6-(3,4-dihydro-2H-1-benzopyran-6-yl)-5-oxo-2,3,4,5-tetrahydro-1,4-benzoxazepin-7-yl]-2-(tert-butoxy)acetate (25j) (20 mg, 0.04 mmol, 36%).

$^1$H NMR (400 MHz, CDCl$_3$) δ 0.98 and 1.01 (s, 9H), 2.02-2.11 (m, 2H), 2.69-2.93 (m, 2H), 3.28-3.61 (m, 2H), 3.63 and 3.66 (s, 3H), 4.00-4.17 (m, 2H), 4.22-4.26 (m, 2H), 4.51-4.58 (m, 1H), 4.80-4.86 (m, 1H), 5.07 and 5.08 (s, 1H), 6.81-6.84 (m, 1H), 6.88 (d, J=8.5 Hz, 1H), 7.03 (d, J=8.1 Hz, 1H), 7.16-7.21 (m, 1H), 7.22-7.34 (m, 5H), 7.70 (dd, J=8.6 and 9.7 Hz, 1H).

MS m/z ([M+H]$^+$) 530.

Step 9: Preparation of 2-[4-benzyl-6-(3,4-dihydro-2H-1-benzopyran-6-yl)-5-oxo-2,3,4,5-tetrahydro-1,4-benzoxazepin-7-yl]-2-(tert-butoxy)acetic acid A solution of methyl 2-[4-benzyl-6-(3,4-dihydro-2H-1-benzopyran-6-yl)-5-oxo-2,3,4,5-tetrahydro-1,4-benzoxazepin-7-yl]-2-(tert-butoxy)acetate (25j) (20 mg, 0.04 mmol) and potassium hydroxide (4.2 mg, 0.08 mmol) in ethanol/water (0.45 mL/1 mL) was warmed to 85° C. for 5 hours. Ethanol was evaporated and water was added to the reaction mixture which was washed with dichloromethane. The aqueous layer was acidified with an aqueous solution of chlorhydric acid 1N until pH 2 and extracted with dichloromethane three times. The organic layer was washed with brine, dried over sodium sulfate, filtered and evaporated under reduced pressure to afford the desired acid (example 25) (13 mg, 0.02 mmol, 65%) as a white powder.

$^1$H NMR (400 MHz, CDCl$_3$) δ 1.03 and 1.07 (s, 9H), 2.01-2.09 (m, 2H), 2.69-2.91 (m, 2H), 3.32-3.56 (m, 2H), 4.02-4.17 (m, 2H), 4.22-4.25 (m, 2H), 4.48-4.56 (m, 1H), 4.81-4.89 (m, 1H), 5.07 and 5.08 (s, 1H), 6.78-6.89 (m, 2H), 7.03 (d, J=8.4 Hz, 1H), 7.20-7.37 (m, 6H), 7.50 (d, J=8.4 Hz, 1H).

MS m/z ([M−H]$^−$) 514.

Example 26: Synthesis of 2-(tert-butoxy)-2-[14-(3,4-dihydro-2H-1-benzopyran-6-yl)-2-methyl-5,6,7,8-tetrahydroquinolin-3-yl]acetic acid

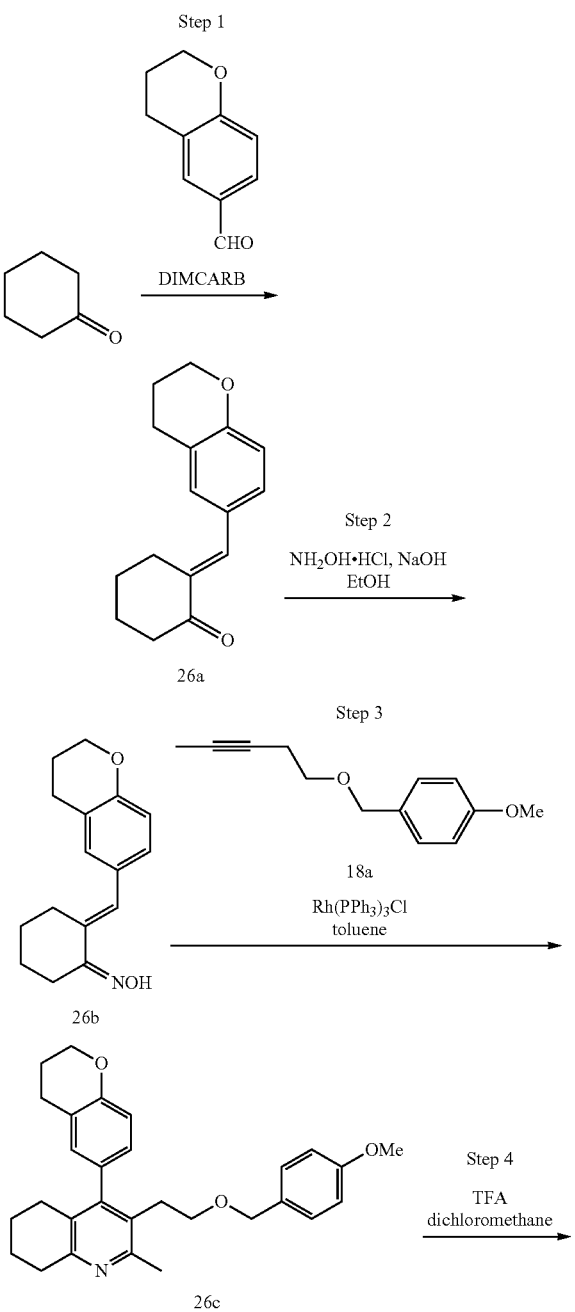

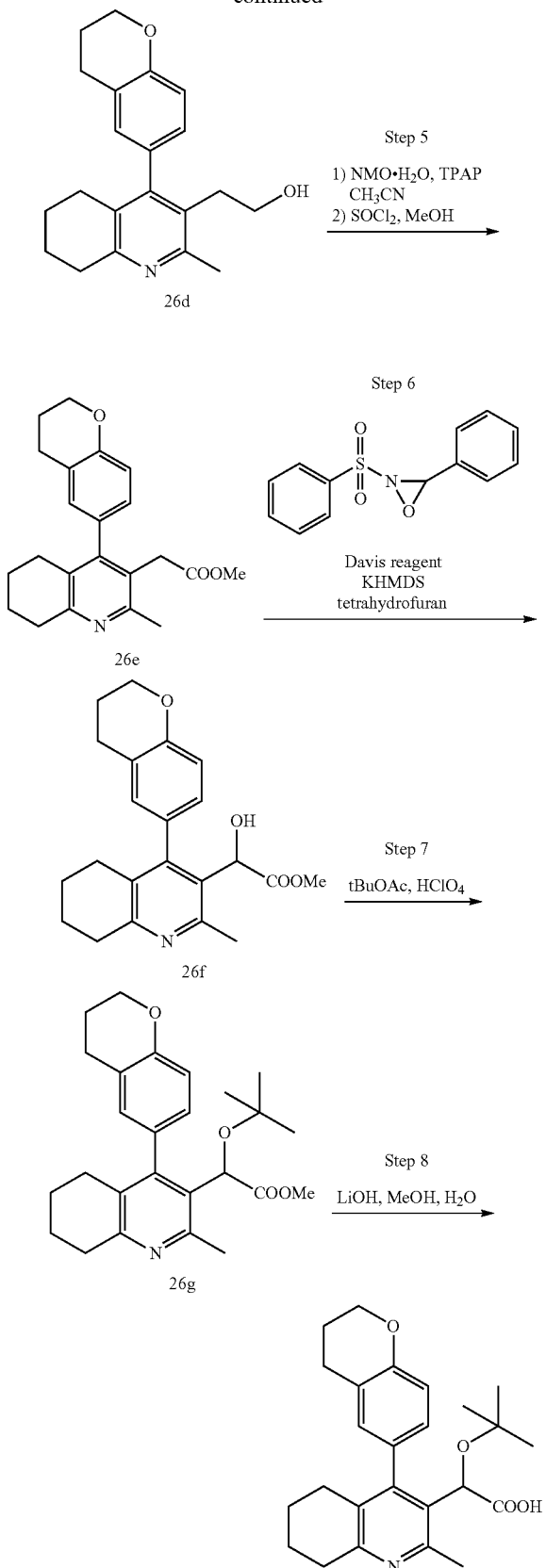

Step 1: Preparation of intermediate (2E)-2-(3,4-dihydro-2H-1-benzopyran-6-ylmethylidene) cyclohexan-1-one (26a)

Chroman-6-carbaldehyde (0.865 g, 5.33 mmol) was added to dimethylammonium dimethylcarbamate (DIMCARB, 3 mL) at room temperature with stirring. Gas evolved. The solution was heated to 50° C. and cyclohexanone (1.10 mL, 10.67 mmol) was added in one portion. After 4H00 at 50° C., the reaction mixture was acidified with 0.5M sulfuric acid (30 mL) and extracted with dichloromethane (3×30 mL). The combined organic extracts were dried over sodium sulfate and evaporated to dryness. The residue was purified by flash chromatography on silica gel (cyclohexane/diethyl ether: 90/10 to 80/20) to provide (2E)-2-(3,4-dihydro-2H-1-benzopyran-6-ylmethylidene) cyclohexan-1-one (26a) (1.05 g, 4.37 mmol, 82%) as a yellow solid.

$^1$H NMR (300 MHz, CDCl$_3$) δ 1.73-1.81 (m, 2H), 1.87-1.95 (m, 2H), 1.98-2.06 (m, 2H), 2.51 (t, J=6.7 Hz, 2H), 2.75-2.88 (m, 4H), 4.21 (t, J=5.2 Hz, 2H), 6.79 (d, J=8.5 Hz, 1H), 7.13 (d, J=1.7 Hz, 1H), 7.20 (dd, J=1.7, 8.5 Hz, 1H), 7.46 (s, 1H).

MS m/z ([M+H]$^+$) 243.

Step 2: Preparation of intermediate N-[(2E)-2-(3,4-dihydro-2H-1-benzopyran-6-ylmethylidene)cyclohexylidene] hydroxylamine (26b)

(2E)-2-(3,4-dihydro-2H-1-benzopyran-6-ylmethylidene) cyclohexan-1-one (26a) (1.92 g, 7.92 mmol) was dissolved in ethanol (10 mL) followed by the addition of hydroxylamine hydrochloride (1.10 g, 15.83 mmol). The reaction mixture was heated to reflux, 10N sodium hydroxide (1.0 mL) was added dropwise and the reflux was continued for 2H30. The precipitate that formed during the reaction was removed by filtration. The filtrate was evaporated, the residue was taken up with ethyl acetate (80 mL) and washed with water (2×100 mL). The organic layer was dried over sodium sulfate, evaporated to dryness to afford N-[(2E)-2-(3,4-dihydro-2H-1-benzopyran-6-ylmethylidene)cyclohexylidene]hydroxylamine (26b) (1.83 g, 7.11 mmol, 90%) as a white solid.

$^1$H NMR (300 MHz, CDCl$_3$) δ 1.58-1.76 (m, 4H), 1.95-2.06 (m, 2H), 2.59-2.70 (m, 4H), 2.77 (t, J=6.5 Hz, 2H), 4.19 (t, J=5.2 Hz, 2H), 6.72-6.83 (m, 2H), 7.00 (s, 1H), 7.06 (dd, J=1.9, 8.4 Hz, 1H).

MS m/z ([M+H]$^+$) 258.

Step 3: Preparation of intermediate 4-(3,4-dihydro-2H-1-benzopyran-6-yl)-3-{2-[(4-methoxy phenyl)methoxy]ethyl}-2-methyl-5,6,7,8-tetrahydroquinoline (26c)

Using the procedure described in example 18, step 2, a mixture of 1-methoxy-4-[(pent-3-yn-1-yloxy)methyl]benzene (18a) (1.50 g, 7.34 mmol) and N-[(2E)-2-(3,4-dihydro-2H-1-benzopyran-6-ylmethylidene)cyclohexylidene] hydroxylamine (26b) (1.72 g, 6.67 mmol) led to 4-(3,4-dihydro-2H-1-benzopyran-6-yl)-3-{2-[(4-methoxyphenyl) methoxy]ethyl}-2-methyl-5,6,7,8-tetrahydroquinoline (26c) (0.932 g, 2.10 mmol, 31%) as a brown oil.

$^1$H NMR (400 MHz, CDCl$_3$) δ 1.60-1.70 (m, 2H), 1.76-1.85 (m, 2H), 1.98-2.08 (m, 2H), 2.23 (t, J=6.3 Hz, 2H), 2.57 (s, 3H), 2.66-2.79 (m, 4H), 2.91 (t, J=6.3 Hz, 2H), 3.28-3.38 (m, 2H), 3.80 (s, 3H), 4.22 (t, J=5.1 Hz, 2H), 4.28 (s, 2H), 6.64 (d, J=1.7 Hz, 1H), 6.68 (dd, J=1.7, 8.2 Hz, 2H), 6.80 (d, J=8.2 Hz, 1H), 6.83 (d, J=8.6 Hz, 2H), 7.12 (d, J=8.6 Hz, 2H).

MS m/z ([M+H]$^+$) 444.

Step 4: Preparation of intermediate 2-[4-(3,4-dihydro-2H-1-benzopyran-6-yl)-2-methyl-5,6,7,8-tetrahydroquinolin-3-yl]ethan-1-ol (26d)

Using the procedure described in example 18, step 3, the intermediate 4-(3,4-dihydro-2H-1-benzopyran-6-yl)-3-{2-[(4-methoxyphenyl)methoxy]ethyl}-2-methyl-5,6,7,8-tetrahydro quinoline (26c) (0.907 g, 2.04 mmol) is converted, after purification by flash chromatography on silica gel (dichloromethane/methanol 100/0 to 90/10), to 2-[4-(3,4-dihydro-2H-1-benzopyran-6-yl)-2-methyl-5,6,7,8-tetrahydroquinolin-3-yl]ethan-1-ol (26d) (0.662 g, 2.04 mmol, 100%) as a beige meringue.

$^1$H NMR (400 MHz, CDCl$_3$) δ 1.65-1.74 (m, 2H), 1.79-1.88 (m, 2H), 2.01-2.11 (m, 2H), 2.31 (t, J=6.3 Hz, 2H), 2.70-2.85 (m, 7H), 3.11 (t, J=6.2 Hz, 2H), 3.57 (t, J=7.0 Hz, 2H), 4.24 (t, J=5.3 Hz, 2H), 6.72 (d, J=2.0 Hz, 1H), 6.76 (dd, J=2.0, 8.2 Hz, 1H), 6.87 (d, J=8.2 Hz, 1H).

MS m/z ([M+H]$^+$) 324.

Step 5: Preparation of intermediate methyl 2-[4-(3,4-dihydro-2H-1-benzopyran-6-yl)-2-methyl-5,6,7,8-tetrahydroquinolin-3-yl]acetate (26e)

2-[4-(3,4-Dihydro-2H-1-benzopyran-6-yl)-2-methyl-5,6,7,8-tetrahydroquinolin-3-yl]ethan-1-ol (26d) (0.665 g, 2.06 mmol) and N-methyl morpholine N-oxide (NMO) monohydrate (2.78 g, 20.56 mmol) were dissolved in acetonitrile (7.5 mL). Tetra-n-propylammonium perruthenate (TPAP, 0.072 g, 0.204 mmol) was added and the mixture was stirred at room temperature for 40 minutes. The reaction mixture was quenched with an excess of 2-propanol (3 mL) and concentrated in vacuo. Water (10 mL) was added and the pH adjusted to 4-5 by addition of hydrochloric acid 1N solution. The aqueous phase was extracted with ethyl acetate (2×30 mL) and dichloromethane (2×30 mL). The combined organic extracts were dried over sodium sulfate and concentrated in vacuo. This material was dissolved in methanol (15 mL), the mixture was cooled to 0° C. and thionyl chloride (0.365 mL, 5.01 mmol) was added dropwise. The mixture was allowed to stir at room temperature for 16 hours and was concentrated to dryness. The residue was taken up in ethyl acetate (30 mL) and washed with sodium hydroxide 2N aqueous solution (20 mL) and water (2×20 mL). The organic layer was dried over sodium sulfate and evaporated to dryness. The residue was purified by flash chromatography on silica gel (cyclohexane/ethyl acetate 70/30) to provide methyl 2-[4-(3,4-dihydro-2H-1-benzopyran-6-yl)-2-methyl-5,6,7,8-tetrahydroquinolin-3-yl]acetate (26e) (0.232 g, 0.660 mmol, 32%) as a beige solid.

$^1$H NMR (300 MHz, CDCl$_3$) δ 1.62-1.73 (m, 2H), 1.77-1.89 (m, 2H), 1.98-2.10 (m, 2H), 2.31 (t, J=6.2 Hz, 2H), 2.49 (s, 3H), 2.77 (td, J=2.2, 6.4 Hz, 2H), 2.96 (t, J=6.4 Hz, 2H), 3.41 (s, 2H), 3.62 (s, 3H), 4.22 (t, J=5.2 Hz, 2H), 6.71 (d, J=2.0 Hz, 1H), 6.75 (dd, J=2.0, 8.2 Hz, 1H), 6.82 (d, J=8.2 Hz, 1H).

MS m/z ([M+H]$^+$) 352.

Step 6: Preparation of intermediate methyl 2-[4-(3,4-dihydro-2H-1-benzopyran-6-yl)-2-methyl-5,6,7,8-tetrahydroquinolin-3-yl]-2-hydroxyacetate (26f)

Using the procedure described in example 18, step 5, the intermediate methyl 2-[4-(3,4-dihydro-2H-1-benzopyran-6-yl)-2-methyl-5,6,7,8-tetrahydroquinolin-3-yl]acetate (26e) (0.216 g, 0.61 mmol) is converted, after purification by flash chromatography on silica gel (cyclohexane/ethyl acetate 50/50), to methyl 2-[4-(3,4-dihydro-2H-1-benzopyran-6-yl)-2-methyl-5,6,7,8-tetrahydroquinolin-3-yl]-2-hydroxyacetate (26f) (0.221 g, 0.60 mmol, 98%), as a yellow oil.

$^1$H NMR (300 MHz, CDCl$_3$) δ 1.63-1.76 (m, 2H), 1.78-1.90 (m, 2H), 2.00-2.11 (m, 2H), 2.31 (t, J=6.2 Hz, 2H), 2.52 and 2.54 (s, 3H), 2.75-3.84 (m, 2H), 2.94-3.04 (m, 2H), 3.09 and 3.13 (d, J=2.4 Hz, 1H), 3.70 and 3.71 (s, 3H), 4.23 (t, J=5.2 Hz, 2H), 5.09-5.15 (m, 1H), 6.79-6.86 (m, 3H).

MS m/z ([M+H]$^+$) 368.

Step 7: Preparation of intermediate methyl 2-(tert-butoxy)-2-[4-(3,4-dihydro-2H-1-benzopyran-6-yl)-2-methyl-5,6,7,8-tetrahydroquinolin-3-yl]acetate (26g)

Using the procedure described in example 18, step 6, the intermediate methyl 2-[4-(3,4-dihydro-2H-1-benzopyran-6-yl)-2-methyl-5,6,7,8-tetrahydroquinolin-3-yl]-2-hydroxyacetate (26f) (0.221 g, 0.60 mmol) is converted, after purification by flash chromatography on silica gel (cyclohexane/ethyl acetate 80/20), to methyl 2-(tert-butoxy)-2-[4-(3,4-dihydro-2H-1-benzopyran-6-yl)-2-methyl-5,6,7,8-tetrahydro quinolin-3-yl]acetate (26g) (0.140 g, 0.60 mmol, 55%), as a colorless oil.

$^1$H NMR (400 MHz, CDCl$_3$) δ 0.98 (s, 9H), 1.46-1.94 (m, 4H), 1.98-2.28 (m, 3H), 2.34-2.49 (m, 1H), 2.64 (broad s, 3H), 2.70-2.87 (m, 2H), 2.93-3.05 (m, 2H), 3.67 and 3.69 (s, 3H), 4.24 (t, J=5.1 Hz, 2H), 4.96 and 4.97 (s, 1H), 6.75-6.98 (m, 3H).

MS m/z ([M+H]$^+$) 424.

Step 8: Preparation of 2-(tert-butoxy)-2-[4-2-methyl-5,6,7,8-tetrahydroquinolin-3-yl]acetic acid Using the procedure described in example 18, step 7, the intermediate methyl 2-(tert-butoxy)-2-[4-(3,4-dihydro-2H-1-benzopyran-6-yl)-2-methyl-5,6,7,8-tetrahydro quinolin-3-yl]acetate (26g) (0.140 g, 0.33 mmol) is converted to 2-(tert-butoxy)-2-[4-(3,4-dihydro-2H-1-benzopyran-6-yl)-2-methyl-5,6,7,8-tetrahydroquinolin-3-yl]acetic acid (Example 26) (0.082 g, 0.20 mmol, 60%), as a yellow oil.

$^1$H NMR (400 MHz, CDCl$_3$) δ 0.99 (s, 9H), 1.51-1.63 (m, 1H), 1.70-1.93 (m, 3H), 1.99-2.10 (m, 2H), 2.13-2.26 (m, 1H), 2.41-2.53 (m, 1H), 2.64 and 2.65 (s, 3H), 2.69-2.88 (m, 2H), 2.98-3.08 (m, 2H), 4.24 (t, J=5.1 Hz, 2H), 5.04 and 5.05 (s, 1H), 6.77-6.90 (m, 2H), 7.20 and 7.22 (broad s, 1H).

MS m/z ([M+H]$^+$) 410.

MS m/z ([M–H]$^-$) 408.

Example 27: Synthesis of 2-(tert-butoxy)-2-[2-(3,4-dihydro-2H-1-benzopyran-6-yl)-3,6-dimethylphenyl]acetic acid

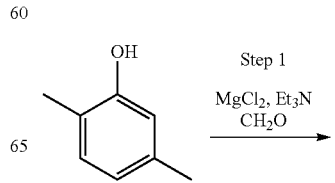

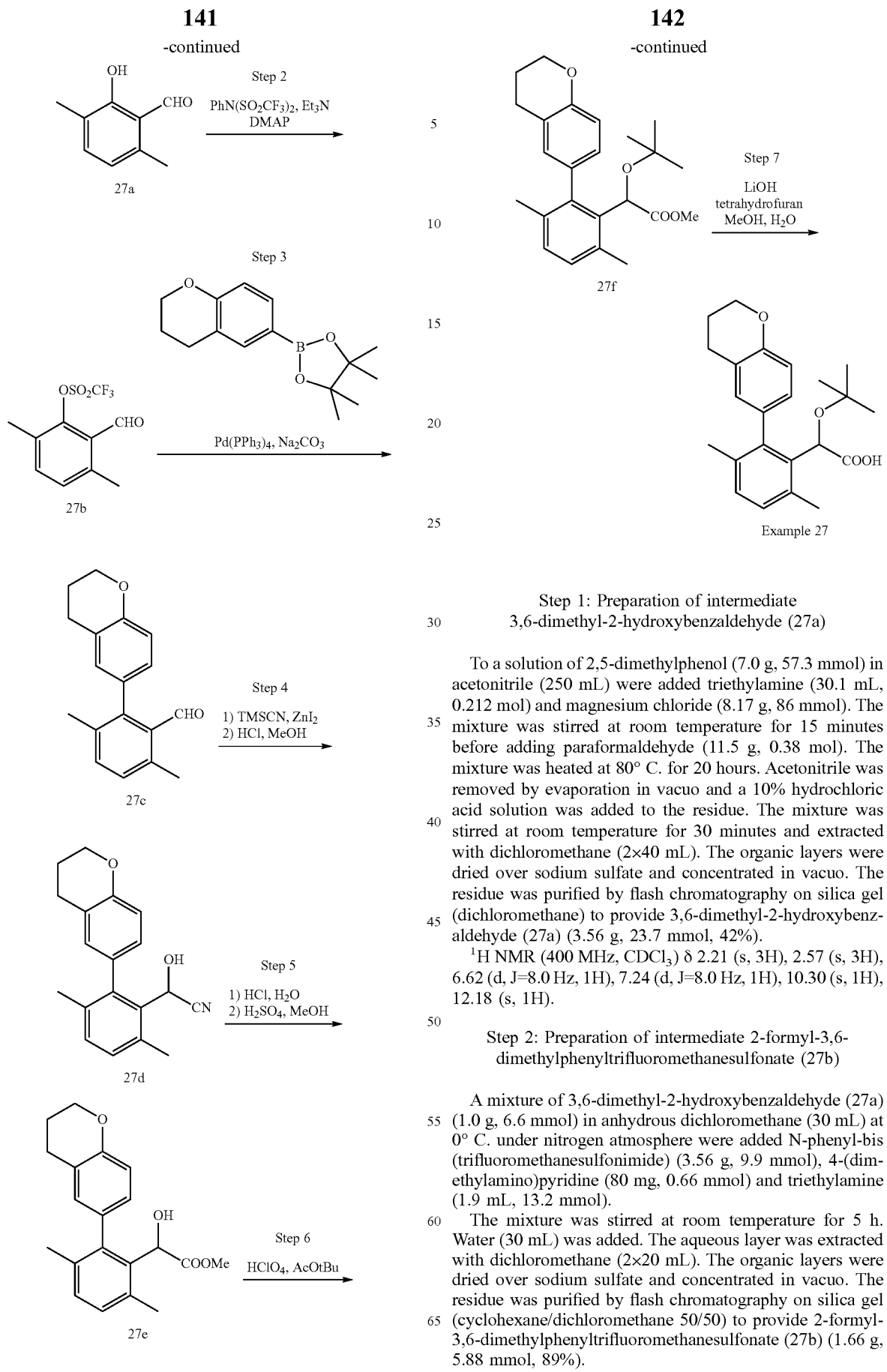

Step 1: Preparation of intermediate
3,6-dimethyl-2-hydroxybenzaldehyde (27a)

To a solution of 2,5-dimethylphenol (7.0 g, 57.3 mmol) in acetonitrile (250 mL) were added triethylamine (30.1 mL, 0.212 mol) and magnesium chloride (8.17 g, 86 mmol). The mixture was stirred at room temperature for 15 minutes before adding paraformaldehyde (11.5 g, 0.38 mol). The mixture was heated at 80° C. for 20 hours. Acetonitrile was removed by evaporation in vacuo and a 10% hydrochloric acid solution was added to the residue. The mixture was stirred at room temperature for 30 minutes and extracted with dichloromethane (2×40 mL). The organic layers were dried over sodium sulfate and concentrated in vacuo. The residue was purified by flash chromatography on silica gel (dichloromethane) to provide 3,6-dimethyl-2-hydroxybenzaldehyde (27a) (3.56 g, 23.7 mmol, 42%).

$^1$H NMR (400 MHz, CDCl$_3$) δ 2.21 (s, 3H), 2.57 (s, 3H), 6.62 (d, J=8.0 Hz, 1H), 7.24 (d, J=8.0 Hz, 1H), 10.30 (s, 1H), 12.18 (s, 1H).

Step 2: Preparation of intermediate 2-formyl-3,6-dimethylphenyltrifluoromethanesulfonate (27b)

A mixture of 3,6-dimethyl-2-hydroxybenzaldehyde (27a) (1.0 g, 6.6 mmol) in anhydrous dichloromethane (30 mL) at 0° C. under nitrogen atmosphere were added N-phenyl-bis(trifluoromethanesulfonimide) (3.56 g, 9.9 mmol), 4-(dimethylamino)pyridine (80 mg, 0.66 mmol) and triethylamine (1.9 mL, 13.2 mmol).

The mixture was stirred at room temperature for 5 h. Water (30 mL) was added. The aqueous layer was extracted with dichloromethane (2×20 mL). The organic layers were dried over sodium sulfate and concentrated in vacuo. The residue was purified by flash chromatography on silica gel (cyclohexane/dichloromethane 50/50) to provide 2-formyl-3,6-dimethylphenyltrifluoromethanesulfonate (27b) (1.66 g, 5.88 mmol, 89%).

¹H NMR (400 MHz, CDCl₃) δ 2.42 (s, 3H), 2.60 (s, 3H), 7.21 (d, J=8.0 Hz, 1H), 7.41 (d, J=8.0 Hz, 1H), 10.41 (s, 1H).

Step 3: Preparation of intermediate 2-(3,4-dihydro-2H-1-benzopyran-6-yl)-3,6-dimethyl benzaldehyde (27c)

A mixture of 2-formyl-3,6-dimethylphenyltrifluoromethanesulfonate (27b) (300 mg, 1.06 mmol), sodium carbonate (449 mg, 4.2 mmol), 6-(4,4,5,5-tetramethyl-1,3,2-dioxaborolan-2-yl)chroman (359 mg, 1.38 mmol) and palladium tetrakis(triphenylphosphine) (62 mg, 0.053 mmol) in a mixture of toluene (3 mL), ethanol (1 mL) and water (1.5 mL) was irradiated (200 W, 80° C.) for 1 hour. The mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate 95/5) to provide 2-(3,4-dihydro-2H-1-benzopyran-6-yl)-3,6-dimethylbenzaldehyde (27c) (160 mg, 0.60 mmol, 57%) as a yellow oil.

¹H NMR (400 MHz, CDCl₃) δ 1.98-2.05 (m, 2H), 2.10 (s, 3H), 2.58 (s, 3H), 2.78-2.82 (m, 2H), 4.20-4.24 (m, 2H), 6.83-6.90 (m, 3H), 7.14 (d, J=8.0 Hz, 1H), 7.31 (d, J=8.0 Hz, 1H), 9.80 (s, 1H).

Step 4: Preparation of intermediate 2-[2-(3,4-dihydro-2H-1-benzopyran-6-yl)-3,6-dimethylphenyl]-2-hydroxyacetonitrile (27d)

To a solution of 2-(3,4-dihydro-2H-1-benzopyran-6-yl)-3,6-dimethylbenzaldehyde (27c) (800 mg, 3.00 mmol) in anhydrous dichloromethane (10 mL) at 0° C. under nitrogen atmosphere were successively added zinc iodide (96 mg, 0.30 mmol) and trimethylsilyl cyanide (372 mg, 3.75 mmol). The mixture was stirred at room temperature overnight. A saturated solution of sodium hydrogenocarbonate (10 mL) was added. Layers were separated and the aqueous layer was extracted with dichloromethane (10 mL). The organic layers were dried over sodium sulfate and concentrated in vacuo. The residue was dissolved in 3N hydrochloric acid in methanol (4 mL) and stirred overnight at room temperature then concentrated in vacuo. The residue was purified by flash chromatography on silica gel (cyclohexane/ethyl acetate 80/20) to provide 2-[2-(3,4-dihydro-2H-1-benzopyran-6-yl)-3,6-dimethylphenyl]-2-hydroxy acetonitrile (27d) (700 mg, 2.38 mmol, 79%) as a yellow oil.

¹H NMR (400 MHz, CDCl₃) δ 2.00 (s, 3H), 2.02-2.06 (m, 2H), 2.63 and 2.65 (s, 3H), 2.78-2.82 (m, 2H), 4.23-4.26 (m, 2H), 5.56 (d, J=1.0 Hz, 1H), 6.80-6.88 (m, 3H), 7.15 (d, J=8.0 Hz, 1H), 7.19 (d, J=8.0 Hz, 1H).

Step 5: Preparation of intermediate methyl 2-[2-(3,4-dihydro-2H-1-benzopyran-6-yl)-3,6-dimethylphenyl]-2-hydroxyacetate (27e)

A solution of 2-[2-(3,4-dihydro-2H-1-benzopyran-6-yl)-3,6-dimethylphenyl]-2-hydroxy acetonitrile (27d) (700 mg, 2.39 mmol) in 12N hydrochloric acid (10 mL) was heated at 80° C. for 16 hours. The mixture was extracted with dichloromethane (2×10 mL). The organic layers were dried over sodium sulfate and concentrated in vacuo. The residue was dissolved methanol (20 mL), sulfuric acid (0.5 mL) was added and the mixture was refluxed for 16 hours. Methanol was evaporated in vacuo. The residue was dissolved in dichloromethane (20 mL) and washed with a saturated solution of sodium hydrogenocarbonate (20 mL), brine (20 mL), dried over sodium sulfate and concentrated in vacuo. The residue was purified by flash chromatography on silica gel (cyclohexane/ethyl acetate 80/20) to provide methyl 2-[2-(3,4-dihydro-2H-1-benzopyran-6-yl)-3,6-dimethylphenyl]-2-hydroxyacetate (27e) (160 mg, 0.49 mmol, 20%) as a brown solid.

¹H NMR (400 MHz, CDCl₃) δ 1.99 (s, 3H), 2.02-2.06 (m, 2H), 2.29 and 2.31 (s, 3H), 2.78-2.80 (m, 2H), 3.70 and 3.71 (s, 3H), 4.21-4.25 (m, 2H), 5.18 (d, J=1.0 Hz, 1H), 6.82-6.90 (m, 3H), 7.06 (d, J=8.0 Hz, 1H), 7.13 (d, J=8.0 Hz, 1H).

Step 6: Preparation of intermediate methyl 2-(tert-butoxy)-2-[2-(3,4-dihydro-2H-1-benzopyran-6-yl)-3,6-dimethylphenyl]acetate (27f)

To a solution of methyl 2-[2-(3,4-dihydro-2H-1-benzopyran-6-yl)-3,6-dimethylphenyl]-2-hydroxyacetate (27e) (160 mg, 0.49 mmol) in tert-butyl acetate (10 mL) at −15° C. was added perchloric acid (1.45 mL). The mixture was stirred at −15° C. for 2 hours before being poured into a saturated aqueous solution of sodium bicarbonate (30 mL). The layers were separated and the aqueous layer was extracted with ethyl acetate (20 mL). The organic layers were dried over sodium sulfate and concentrated in vacuo. The residue was purified by flash chromatography on silica gel (cyclohexane/ethyl acetate 97/3 then (90/10) to provide methyl 2-(tert-butoxy)-2-[2-(3,4-dihydro-2H-1-benzopyran-6-yl)-3,6-dimethylphenyl]acetate (27f) (16 mg, 0.042 mmol, 8%).

¹H NMR (400 MHz, CDCl₃) δ 0.99 (s, 9H), 1.98 and 1.99 (s, 3H), 2.02-2.08 (m, 2H), 2.40 (s, 3H), 2.75-2.82 (m, 2H), 3.65 and 3.67 (s, 3H), 4.24-4.26 (m, 2H), 5.05 and 5.07 (s, 1H), 6.79-6.90 (m, 2H), 6.97-7.04 (m, 2H), 7.08 (d, J=8.0 Hz, 1H).

Step 7: Preparation of 2-(tert-butoxy)-2-[2-(3,4-dihydro-2H-1-benzopyran-6-yl)-3,6-dimethylphenyl] acetic acid A solution of methyl 2-(tert-butoxy)-2-[2-(3,4-dihydro-2H-1-benzopyran-6-yl)-3,6-dimethylphenyl] acetate (27f) (16 mg, 0.042 mmol) in a mixture of tetrahydrofuran (2 mL), methanol (0.7 mL), water (2 mL) and 1 M lithium hydroxide solution (0.44 mL, 0.44 mmol) was stirred at 60° C. for 20 hours. 2M hydrochloric acid was added until pH 3. The solid was filtered and washed with water to provide the desired acid (13 mg, 0.035 mmol, 84%) as a yellow solid.

¹H NMR (400 MHz, CDCl₃) δ 1.00 (s, 9H), 2.00-2.05 (m, 5H), 2.36 (s, 3H), 2.75-2.85 (m, 2H), 4.22-4.24 (m, 2H), 5.19 (s, 1H), 6.79-6.90 (m, 2H), 7.03 (d, J=8.0 Hz, 1H), 7.11 (d, J=8.0 Hz, 1H), 7.18 (s, 1H).

MS m/z ([M−H]⁻) 367.

Example 28: Synthesis of 2-(tert-butoxy)-2-[2-(3,4-dihydro-2H-1-benzopyran-6-yl)-3-(hydroxymethyl)phenyl]acetic acid

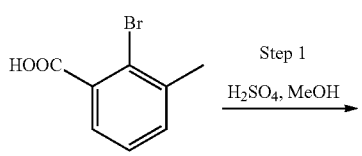

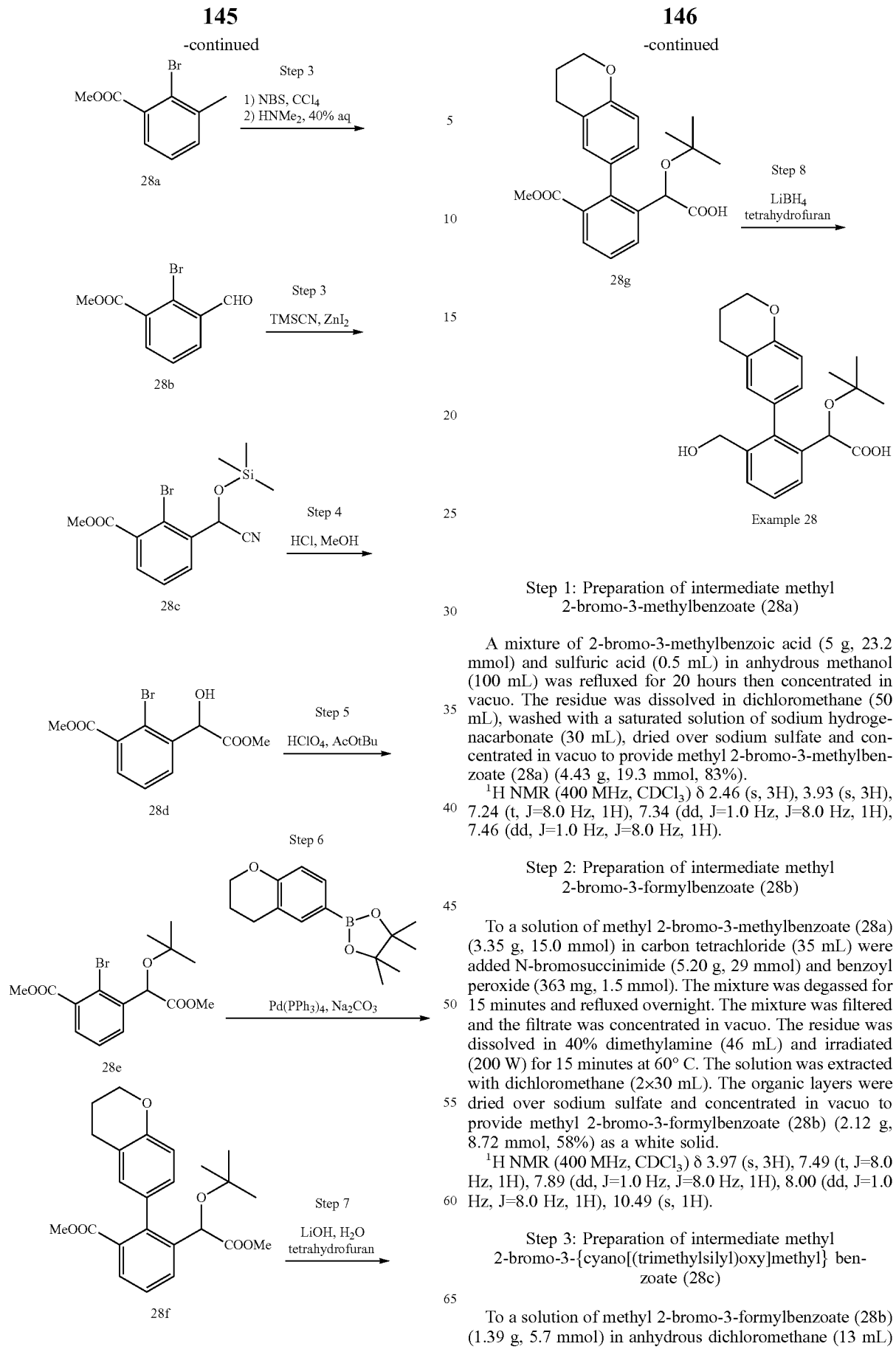

Step 1: Preparation of intermediate methyl 2-bromo-3-methylbenzoate (28a)

A mixture of 2-bromo-3-methylbenzoic acid (5 g, 23.2 mmol) and sulfuric acid (0.5 mL) in anhydrous methanol (100 mL) was refluxed for 20 hours then concentrated in vacuo. The residue was dissolved in dichloromethane (50 mL), washed with a saturated solution of sodium hydrogenacarbonate (30 mL), dried over sodium sulfate and concentrated in vacuo to provide methyl 2-bromo-3-methylbenzoate (28a) (4.43 g, 19.3 mmol, 83%).

$^1$H NMR (400 MHz, CDCl$_3$) δ 2.46 (s, 3H), 3.93 (s, 3H), 7.24 (t, J=8.0 Hz, 1H), 7.34 (dd, J=1.0 Hz, J=8.0 Hz, 1H), 7.46 (dd, J=1.0 Hz, J=8.0 Hz, 1H).

Step 2: Preparation of intermediate methyl 2-bromo-3-formylbenzoate (28b)

To a solution of methyl 2-bromo-3-methylbenzoate (28a) (3.35 g, 15.0 mmol) in carbon tetrachloride (35 mL) were added N-bromosuccinimide (5.20 g, 29 mmol) and benzoyl peroxide (363 mg, 1.5 mmol). The mixture was degassed for 15 minutes and refluxed overnight. The mixture was filtered and the filtrate was concentrated in vacuo. The residue was dissolved in 40% dimethylamine (46 mL) and irradiated (200 W) for 15 minutes at 60° C. The solution was extracted with dichloromethane (2×30 mL). The organic layers were dried over sodium sulfate and concentrated in vacuo to provide methyl 2-bromo-3-formylbenzoate (28b) (2.12 g, 8.72 mmol, 58%) as a white solid.

$^1$H NMR (400 MHz, CDCl$_3$) δ 3.97 (s, 3H), 7.49 (t, J=8.0 Hz, 1H), 7.89 (dd, J=1.0 Hz, J=8.0 Hz, 1H), 8.00 (dd, J=1.0 Hz, J=8.0 Hz, 1H), 10.49 (s, 1H).

Step 3: Preparation of intermediate methyl 2-bromo-3-{cyano[(trimethylsilyl)oxy]methyl} benzoate (28c)

To a solution of methyl 2-bromo-3-formylbenzoate (28b) (1.39 g, 5.7 mmol) in anhydrous dichloromethane (13 mL)

at 0° C. under nitrogen atmosphere were successively added zinc iodide (181 mg, 0.57 mmol) and trimethylsilyl cyanide (0.89 mL, 7.13 mmol). The mixture was stirred at room temperature overnight. A saturated solution of sodium hydrogenocarbonate (10 mL) was added. Layers were separated and the aqueous layer was extracted with dichloromethane (10 mL). The organic layers were dried over sodium sulfate and concentrated in vacuo to provide methyl 2-bromo-3-{cyano[(trimethylsilyl)oxy]methyl} benzoate (28c) (1.84 g, 5.37 mmol, 94%).

$^1$H NMR (400 MHz, CDCl$_3$) δ 0.27 (s, 9H), 3.95 (s, 3H), 5.86 (s, 1H), 7.48 (t, J=8.0 Hz, 1H), 7.73 (dd, J=1.0 Hz, J=8.0 Hz, 1H), 7.86 (dd, J=1.0 Hz, J=8.0 Hz, 1H).

Step 4: Preparation of intermediate methyl 2-bromo-3-(1-hydroxy-2-methoxy-2-oxoethyl) benzoate (28d)

Methyl 2-bromo-3-{cyano[(trimethylsilyl)oxy]methyl}benzoate (28c) (1.8 g, 5.3 mmol) was dissolved in a 3M hydrochloric acid solution in methanol (35 mL, 105 mmol) and stirred at room temperature for 2 days. 3M Hydrochloric acid solution in methanol (18 mL, 54 mmol) was added every day until completion (10 days). The mixture was concentrated in vacuo. The residue was dissolved in dichloromethane (50 mL), washed with a saturated aqueous solution of sodium bicarbonate (30 mL), brine (30 mL), dried over sodium sulfate and concentrated in vacuo. The residue was purified by flash chromatography on silica gel (cyclohexane/ethyl acetate 75/25 then 60/40) to provide methyl 2-bromo-3-(1-hydroxy-2-methoxy-2-oxoethyl)benzoate (28d) (1.12 g, 3.69 mmol, 70%) as a yellow oil.

$^1$H NMR (400 MHz, CDCl$_3$) δ 3.77 (s, 3H), 3.95 (s, 3H), 5.73 (s, 1H), 7.37 (t, J=8.0 Hz, 1H), 7.51 (dd, J=1.0 Hz, J=8.0 Hz, 1H), 7.62 (dd, J=1.0 Hz, J=8.0 Hz, 1H).

Step 5: Preparation of intermediate methyl 2-bromo-3-[1-(tert-butoxy)-2-methoxy-2-oxoethyl] benzoate (28e)

To a solution of methyl 2-bromo-3-(1-hydroxy-2-methoxy-2-oxoethyl)benzoate (28d) (1.70 g, 5.61 mmol) in tert-butyl acetate (107 mL) at −10° C. was added perchloric acid (17 mL). The mixture was stirred at −10° C. for 1 hour then 0° C. for 1 hour before being poured into a saturated aqueous solution of sodium bicarbonate (200 mL). The layers were separated and the aqueous layer was extracted with ethyl acetate (50 mL). The organic layers were dried over sodium sulfate and concentrated in vacuo. The residue was purified by flash chromatography on silica gel (cyclohexane/ethyl acetate 80/20 then 65/35) to provide methyl 2-bromo-3-[1-(tert-butoxy)-2-methoxy-2-oxoethyl]benzoate (28e) (1.43 g, 3.98 mmol, 71%) as a colorless oil.

$^1$H NMR (400 MHz, CDCl$_3$) δ 1.22 (s, 9H), 3.68 (s, 3H), 3.93 (s, 3H), 5.60 (s, 1H), 7.38 (t, J=8.0 Hz, 1H), 7.60 (dd, J=1.0 Hz, J=8.0 Hz, 1H), 7.80 (dd, J=1.0 Hz, J=8.0 Hz, 1H).

Step 6: Preparation of intermediate methyl 3-[1-(tert-butoxy)-2-methoxy-2-oxoethyl]-2-(3,4-dihydro-2H-1-benzopyran-6-yl)benzoate (28f)

A mixture of methyl 2-bromo-3-[1-(tert-butoxy)-2-methoxy-2-oxoethyl]benzoate (28e) (300 mg, 0.835 mmol), sodium carbonate (354 mg, 3.54 mmol), 6-(4,4,5,5-tetramethyl-1,3,2-dioxaborolan-2-yl)chroman (304 mg, 1.17 mmol) and palladium tetrakis(triphenylphosphine) (48 mg, 0.041 mmol) in dioxane (3.6 mL) and water (1.4 mL) was irradiated (200 W, 80° C.) for 3×1 hour. The mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate 90/10) to provide methyl 3-[1-(tert-butoxy)-2-methoxy-2-oxoethyl]-2-(3,4-dihydro-2H-1-benzopyran-6-yl)benzoate (28f) (339 mg, 0.821 mmol, 98%) as a yellow oil.

$^1$H NMR (400 MHz, CDCl$_3$) δ 1.00 (s, 9H), 1.95-2.10 (m, 2H), 2.60-2.85 (m, 2H), 3.59 and 3.60 (s, 3H), 3.62 and 3.64 (s, 3H), 4.22-4.25 (m, 2H), 4.98 and 5.01 (s, 1H), 6.78-6.88 (m, 2H), 6.97-7.08 (m, 1H), 7.38-7.43 (m, 1H), 7.72 (d, J=8.0 Hz, 1H), 7.80-87 (m, 1H).

Step 7: Preparation of intermediate 2-(tert-butoxy)-2-[2-(3,4-dihydro-2H-1-benzopyran-6-yl)-3-(methoxycarbonyl)phenyl]acetic acid (28g)

A solution of methyl 3-[1-(tert-butoxy)-2-methoxy-2-oxoethyl]-2-(3,4-dihydro-2H-1-benzopyran-6-yl)benzoate (28f) (200 mg, 0.48 mmol) in tetrahydrofurane (6 mL) and water (2 mL) was added a 1M lithium hydroxide aqueous solution (0.67 mL, 0.67 mmol). The mixture was stirred at room temperature for 4 hours. 1M Hydrochloric acid (1.2 mL, 1.2 mmol) and brine (10 mL) were added. The aqueous layer was extracted with ethyl acetate (2×5 mL). The organic layer was dried over sodium sulfate and concentrated in vacuo. The residue was purified by flash chromatography on silica gel (cyclohexane/ethyl acetate 30/70) to provide 2-(tert-butoxy)-2-[2-(3,4-dihydro-2H-1-benzopyran-6-yl)-3-(methoxycarbonyl)phenyl]acetic acid (28g) (172 mg, 0.43 mmol, 89%) as a yellow oil.

$^1$H NMR (400 MHz, CDCl$_3$) δ 1.00 and 1.01 (s, 9H), 1.95-2.08 (m, 2H), 2.74-2.86 (m, 2H), 3.57 and 3.59 (s, 3H), 4.23-4.25 (m, 2H), 5.06 and 5.09 (s, 1H), 6.75-6.88 (m, 2H), 7.28-7.42 (m, 2H), 7.58-7.60 (m, 1H), 7.72-7.74 (m, 1H).

Step 8: Preparation of 2-(tert-butoxy)-2-[2-(3,4-dihydro-2H-1-benzopyran-6-yl)-3-(hydroxymethyl) phenyl]acetic acid To a solution 2-(tert-butoxy)-2-[2-(3,4-dihydro-2H-1-benzopyran-6-yl)-3-(methoxycarbonyl) phenyl]acetic acid (28g) (270 mg, 0.677 mmol) in anhydrous tetrahydrofuran (20 mL) in the presence of a drop of cyclohexylamine at 0° C. under nitrogen atmosphere was added a 3 M solution of lithium borohydride in tetrahydrofuran (1.36 mL, 2.71 mmol). The mixture was stirred at room temperature for 7 hours before adding 3M solution of lithium borohydride in tetrahydrofuran (0.90 mL, 2.7 mmol). The mixture was stirred overnight and a saturated solution of ammonium chloride (20 mL) was added. The aqueous layer was extracted with ethyl acetate (3×15 mL). The organic layers were dried over sodium sulfate and concentrated in vacuo. The residue was purified by flash chromatography on silica gel (ethyl acetate/methanol 95/5 then 80/20) to provide 2-(tert-butoxy)-2-[2-(3,4-dihydro-2H-1-benzopyran-6-yl)-

3-(hydroxymethyl)phenyl]acetic acid (example 28) (126 mg, 0.34 mmol, 50%) as a white solid.

$^1$H NMR (400 MHz, CDCl$_3$) δ 1.06 (s, 9H), 2.04-2.06 (m, 2H), 2.77-2.87 (m, 2H), 4.23-4.25 (m, 2H), 4.37-4.53 (m, 2H), 4.92 and 4.94 (s, 1H), 6.81-6.90 (m, 2H), 7.27 (s, 1H), 7.35-7.42 (m, 2H), 7.49-7.51 (m, 1H).

MS m/z ([M−H]$^-$) 369.

Example 29: Synthesis of 2-(tert-butoxy)-2-[2-(3,4-dihydro-2H-1-benzopyran-6-yl)-3-(methoxymethyl)phenyl]acetic acid

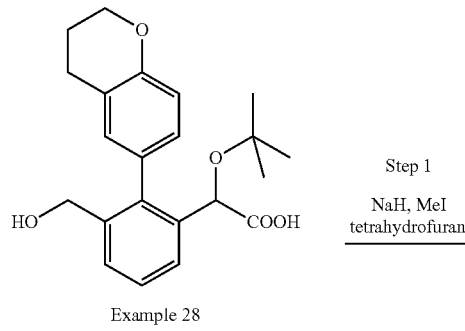

Example 28

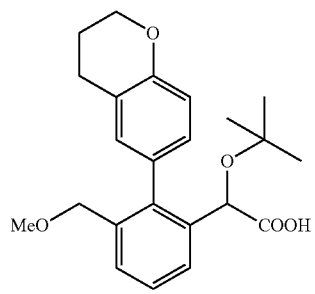

Example 29

Step 1: Preparation of 2-(tert-butoxy)-2-[2-(3,4-dihydro-2H-1-benzopyran-6-yl)-3-(methoxy methyl)phenyl]acetic acid To a solution 2-(tert-butoxy)-2-[2-(3,4-dihydro-2H-1-benzopyran-6-yl)-3-(hydroxymethyl) phenyl]acetic acid (example 28) (121 mg, 0.326 mmol) in anhydrous tetrahydrofuran (5 mL) in at 0° C. under nitrogen atmosphere was added sodium hydride 60% in oil (39 mg, 0.98 mmol). The mixture was stirred for 5 minutes and iodomethane was added (0.03 mL, 0.359 mmol). The mixture was then stirred at room temperature for 24 hours before adding a saturated solution of ammonium chloride (5 mL). Na2HPO4 was added until pH 3 and the aqueous layer was extracted with ethyl acetate (3×5 mL). The organic layers were dried over sodium sulfate and concentrated in vacuo. The residue was purified by flash chromatography on silica gel (dichloromethane/methanol 99/1 then 95/5) to provide 2-(tert-butoxy)-2-[2-(3,4-dihydro-2H-1-benzopyran-6-yl)-3-(methoxymethyl) phenyl]acetic acid (example 29) (40 mg, 0.10 mmol, 32%) as colorless oil.

$^1$H NMR (400 MHz, CDCl$_3$) δ 1.03 (s, 9H), 2.04-2.07 (m, 2H), 2.76-2.86 (m, 2H), 3.27 (s, 3H), 4.07-4.16 (m, 2H), 4.23-4.26 (m, 2H), 4.93 and 4.95 (s, 1H), 6.79-6.91 (m, 2H), 7.23 (s, 1H), 7.35 (t, J=8.0 Hz, 1H), 7.42 (d, J=8.0 Hz, 1H), 7.47 (d, J=8.0 Hz, 1H).

MS m/z ([M−H]$^-$) 383.

Example 30: Synthesis of methyl 2-(tert-butoxy)-2-[2-(3,4-dihydro-2H-1-benzopyran-6-yl)-4-[3-(pyridin-3-yl)phenyl]phenyl]acetic acid Step 1

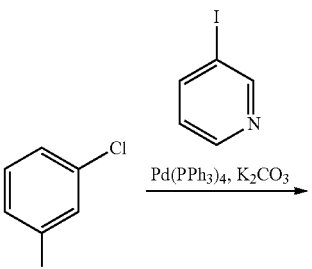

Step 2

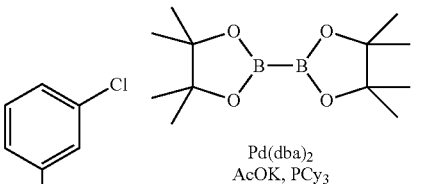

30a

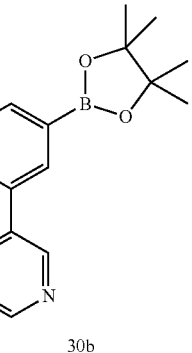

30b

Step 3

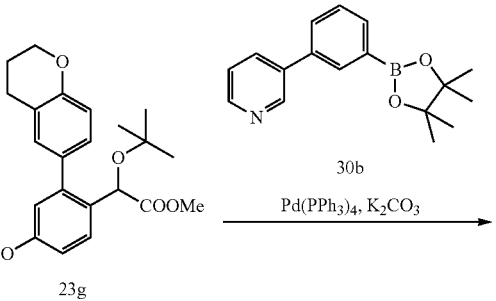

23g

151

-continued

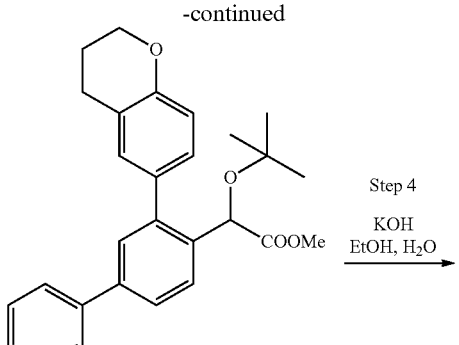

30c

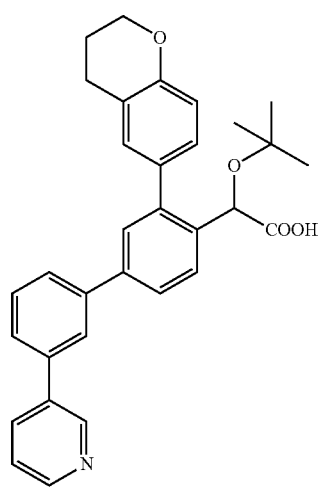

Example 30

Step 1: Preparation of intermediate
3-(3-chlorophenyl)pyridine (30a)

A mixture of 3-chlorophenylboronic acid (239 mg, 1.53 mmol), 3-iodopyridine (285 mg, 1.39 mmol) and potassium carbonate (768 mg, 5.56 mmol) and palladium tetrakis (triphenylphosphine) (60 mg, 0.06 mmol) in a mixture of toluene (7.5 mL), ethanol (2.5 mL) and water (2.8 mL) was stirred at 80° C. overnight. Toluene (10 mL) and water (10 mL) were added. The layers were separated and the aqueous layer was extracted with toluene (10 mL). The organic layers dried over sodium sulfate and concentrated in vacuo. The residue was purified by flash chromatography on silica gel (cyclohexane/ethyl acetate 75/25) to provide 3-(3-chlorophenyl)pyridine (30a) (238 mg, 1.25 mmol, 90%).

$^1$H NMR (400 MHz, CDCl$_3$) δ 7.38-7.47 (m, 4H), 7.57 (s, 1H), 7.87-7.90 (m, 1H), 8.63 (d, J=1.0 Hz, 1H), 8.83 (s, 1H).

Step 2: Preparation of intermediate 3-[3-(4,4,5,5-tetramethyl-1,3,2-dioxoborolan-2-yl)phenyl] pyridine (30b)

A mixture of 3-(3-chlorophenyl)pyridine (30a) (130 mg, 0.68 mmol), bipinacolatodiboron (209 mg, 0.82 mmol), tricyclohexylphosphine (38 mg, 0.14 mmol), potassium acetate (67 mg, 2.05 mmol) and bis(dibenzylideneacetone) palladium (24 mg, 0.04 mmol) in dioxane (3.6 mL) was irradiated (200 W, 80° C.) for 1 hour. The mixture was diluted in ethyl acetate (10 mL) and filtered on celite. Water (10 mL) was added to the filtrate. The aqueous layer was extracted with ethyl acetate (10 mL). The organic layers were dried over sodium sulfate and concentrated in vacuo. The residue was purified by flash chromatography on silica gel (dichloromethane/ethyl acetate 85/15) to provide 3-[3-(4,4,5,5-tetramethyl-1,3,2-dioxoborolan-2-yl)phenyl]pyridine (30b) (100 mg, 0.35 mmol, 52%) as a lightly yellow solid.

$^1$H NMR (400 MHz, CDCl$_3$) δ 1.37 (s, 12H), 7.38-7.41 (m, 1H), 7.50 (t, J=8.0 Hz, 1H), 7.67-7.70 (m, 1H), 7.86 (d, J=8.0 Hz, 1H), 7.95-7.97 (m, 1H), 8.03 (s, 1H), 8.60 (d, J=1.0 Hz, 1H), 8.88 (s, 1H).

Step 3: Preparation of intermediate methyl 2-(tert-butoxy)-2-[2-(3,4-dihydro-2H-1-benzopyran-6-yl)-4-[3-(pyridin-3-yl)phenyl]phenyl]acetate (30c)

A mixture of methyl 2-(tert-butoxy)-2-[2-(3,4-dihydro-2H-1-benzopyran-6-yl)-4-[(trifluoromethane)sulfonyloxy] phenyl]acetate (23g) (170 mg, 0.33 mmol), potassium carbonate (183 mg, 1.35 mmol), 3-[3-(4,4,5,5-tetramethyl-1,3,2-dioxoborolan-2-yl)phenyl] pyridine (30b) (100 mg, 0.35 mmol) and palladium tetrakis(triphenylphosphine) (20 mg, 0.01 mmol) in a mixture of dioxane (1.9 mL) and water (0.6 mL) was irradiated (200 W, 80° C.) for 1 hour. The mixture was poured into water (10 mL). The aqueous layer was extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate 90/10 then 65/45) to provide methyl 2-(tert-butoxy)-2-[2-(3,4-dihydro-2H-1-benzopyran-6-yl)-4-[3-(pyridin-3-yl) phenyl]phenyl]acetate (30c) (151 mg, 0.30 mmol, 90%) as a colorless oil.

$^1$H NMR (400 MHz, CDCl$_3$) δ 1.03 (s, 9H), 2.05-2.10 (m, 2H), 2.80-2.90 (m, 2H), 3.72 (s, 3H), 4.24-4.27 (m, 2H), 5.25 (s, 1H), 6.86 (d, J=8.0 Hz, 1H), 7.12 (s, 1H), 7.19 (d, J=8.0 Hz, 1H), 7.48-7.69 (m, 6H), 7.76-7.79 (m, 2H), 8.03-8.06 (m, 1H), 8.63 (dd, J=1.0 Hz, J=4.0 Hz, 1H), 8.91 (s, 1H).

Step 4: Preparation of methyl 2-(tert-butoxy)-2-[2-(3,4-dihydro-2H-1-benzopyran-6-yl)-4-[3-(pyridin-3-yl)phenyl]phenyl]acetic acid A solution of methyl 2-(tert-butoxy)-2-[2-(3,4-dihydro-2H-1-benzopyran-6-yl)-4-[3-(pyridin-3-yl)phenyl]phenyl] acetate (30c) (164 mg, 0.32 mmol) and potassium hydroxide (100 mg, 1.78 mmol) in a mixture of ethanol (8.7 mL) and water (3.3 mL) was stirred at 95° C. for 16 hours. Potassium hydroxide (20 mg, 0.35 mmol) was added and the mixture was stirred for 8 hours. Ethanol was evaporated in vacuo and an aqueous solution of monosodium phosphate 10% was added until acidic pH. The solid was filtered, dissolved in ethyl acetate (5 mL), dried over sodium sulfate and concentrated in vacuo. The residue was purified by flash chromatography on silica gel (dichloromethane/methanol 95/5) to provide the desired acid (example 30) (70 mg, 0.14 mmol, 44%) as an orange solid.

¹H NMR (400 MHz, DMSO-d₆) δ 0.94 (s, 9H), 1.94-1.98 (m, 2H), 2.75-2.83 (m, 2H), 4.19 (t, J=4.0 Hz, 2H), 5.13 (s, 1H), 6.85 (d, J=8.0 Hz, 1H), 7.20-7.24 (m, 2H), 7.48-7.51 (m, 1H), 7.58-7.62 (m, 3H), 7.72-7.77 (m, 3H), 8.01 (s, 1H), 8.19 (d, J=4.0 Hz, 1H), 8.60 (d, J=1.0 Hz, 1H), 9.00 (s, 1H), 12.70 (s, 1H).

MS m/z ([M+H]⁺) 494.

MS m/z ([M−H]⁻) 492.

Example 31: Synthesis of 2-(terf-butoxy)-2-[3-(diethylcarbamoyl)-2-(3,4-dihydro-2H-1-benzopyran-6-yl)phenyl]acetic acid

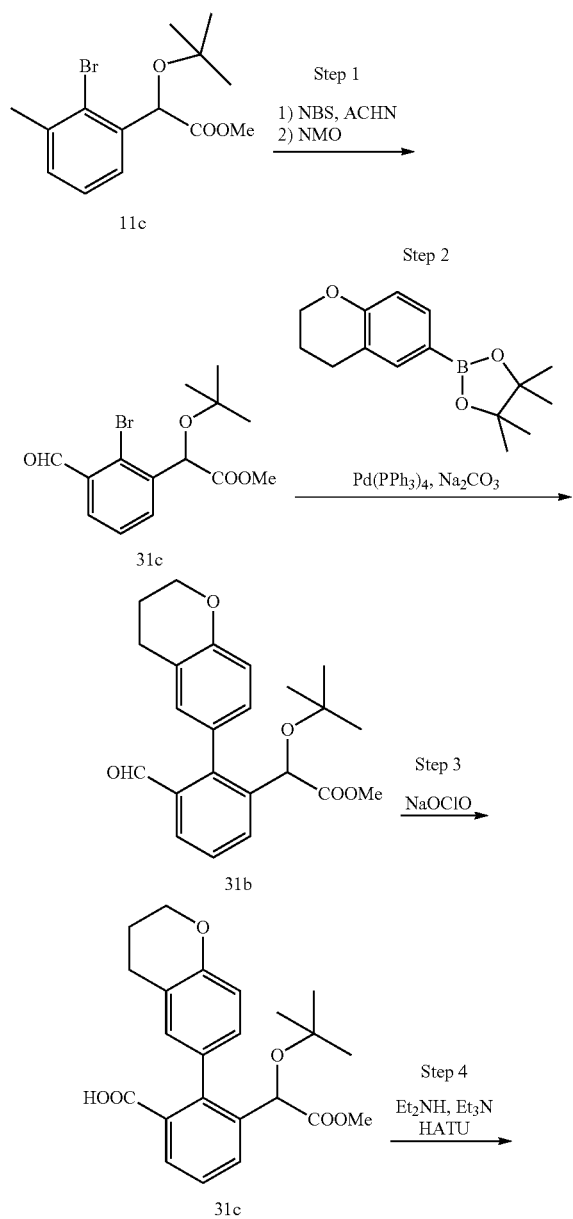

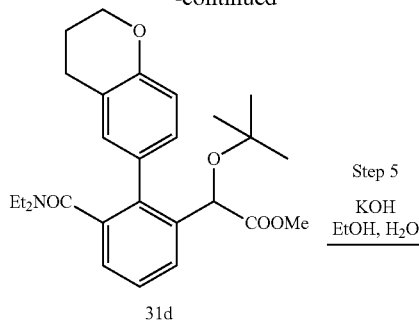

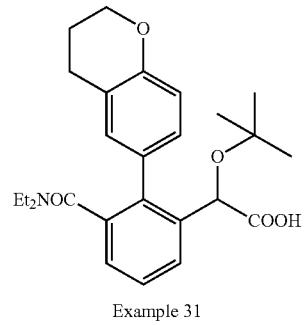

Example 31

Step 1: Preparation of intermediate methyl 2-(2-bromo-3-formylphenyl)-2-(tert-butoxy) acetate (31a)

To a solution of methyl 2-(2-bromo-3-methylphenyl)-2-(tert-butoxy)acetate (11c) (200 mg, 0.63 mmol) in carbon tetrachloride (3 mL) were added N-bromosuccinimide (136 mg, 0.76 mmol) and 1,1'-azobis(cyclohexanecarbonitrile) (16 mg, 0.06 mmol). Further 1,1'-azobis(cyclohexanecarbonitrile) (16 mg, 0.06 mmol) was added and the reflux maintained for 2 hours. The mixture was diluted with dichloromethane (10 mL), washed with a saturated solution of sodium carbonate (20 mL) dried over sodium sulfate and concentrated in vacuo. The residue was dissolved in dioxane (6 mL) and 4-methylmorpholine-N-oxide (257 mg, 1.90 mmol) was added. The mixture was refluxed overnight then concentrated in vacuo. The residue was dissolved in ethyl acetate (5 mL), washed with a saturated solution of ammonium chloride (5 mL), water (5 mL), brine (5 mL), dried over sodium sulfate and concentrated in vacuo. The residue was purified by flash chromatography on silica gel (cyclohexane/ethyl acetate 90/10) to provide methyl 2-(2-bromo-3-formylphenyl)-2-(tert-butoxy)acetate (31a) (126 mg, 0.38 mmol, 60%) as a colorless oil.

¹H NMR (400 MHz, CDCl₃) δ 1.24 (s, 9H), 3.70 (s, 3H), 5.62 (s, 1H), 7.46 (t, J=7.6 Hz, 1H), 7.86 (dd, J=2.0 Hz, J=7.6 Hz, 2H), 7.92 (dd, J=2.0 Hz, J=7.6 Hz, 1H), 10.44 (s, 1H).

Step 2: Preparation of intermediate methyl 2-(tert-butoxy)-2-[2-(3,4-dihydro-2H-1-benzopyran-6-yl)-3-formylphenyl]acetate (31b)

A mixture of methyl 2-(2-bromo-3-formylphenyl)-2-(tert-butoxy)acetate (31a) (126 mg, 0.38 mmol), sodium carbonate (162 mg, 1.53 mmol), 6-(4,4,5,5-tetramethyl-1,3,2-dioxaborolan-2-yl)chroman (149 mg, 0.57 mmol) and palladium tetrakis(triphenylphosphine) (44 mg, 0.04 mmol) in a mixture of dioxane (2 mL) and water (1 mL) was heated at 85° C. overnight. The mixture was poured into water (5 mL) and extracted with ethyl acetate (2×10 mL). The organic layer was washed with brine (10 mL), dried over sodium sulfate and concentrated in vacuo. The residue was purified by flash chromatography on silica gel (cyclohexane/ethyl acetate 90/10) to provide methyl 2-(tert-butoxy)-2-[2-(3,4-dihydro-2H-1-benzopyran-6-yl)-3-formylphenyl]acetate (31b) (103 mg, 0.27 mmol, 70%) as a yellow oil.

$^1$H NMR (300 MHz, CDCl$_3$) 1.01-1.05 (m, 9H), 2.02-2.10 (m, 2H), 2.70-2.85 (m, 2H), 3.65 and 3.66 (s, 3H), 4.24-4.28 (m, 2H), 5.01-5.04 (m, 1H), 6.84-7.14 (m, 3H), 7.46-7.50 (m, 1H), 7.90-7.96 (m, 2H), 9.71 (s, 1H).

Step 3: Preparation of intermediate 3-[1-(tert-butoxy)-2-methoxy-2-oxoethyl]-2-(3,4-dihydro-2H-1-benzopyran-6-yl)benzoic acid (31c)

To a solution of methyl 2-(tert-butoxy)-2-[2-(3,4-dihydro-2H-1-benzopyran-6-yl)-3-formyl phenyl]acetate (31b) (95 mg, 0.25 mmol) and dimethylsulfoxide (21 µL, 0.30 mmol), in a mixture of acetonitrile (200 µL) and water (50 µL) was added a solution of sodium chlorite (56 mg, 0.50 mmol) in water (270 µL). The mixture was heated at 55° C. for 3 days. A saturated solution of sodium sulfite (2 mL) and a saturated solution of sodium bicarbonate (2 mL) were added. The mixture was stirred for 10 minutes at room temperature and extracted with diethyl ether (2×5 mL). The aqueous layer was acidified with 1M hydrochloric acid and extracted with diethyl ether (2×5 mL). The organic layer was dried over sodium sulfate and concentrated in vacuo to provide 3-[1-(tert-butoxy)-2-methoxy-2-oxoethyl]-2-(3,4-dihydro-2H-1-benzopyran-6-yl)benzoic acid (31c) (35 mg, 0.088 mmol, 35%) as a yellow oil.

$^1$H NMR (400 MHz, CDCl$_3$) δ 1.00 (s, 9H), 2.00-2.08 (m, 2H), 2.67-2.85 (m, 1H), 3.62 and 3.63 (s, 3H), 4.21-4.25 (m, 2H), 4.96 and 4.98 (s, 1H), 6.76-7.04 (m, 3H), 7.39-7.44 (m, 1H), 7.84-7.90 (m, 2H).

MS m/z ([M−H]$^-$) 397.

Step 4: Preparation of intermediate methyl 2-(tert-butoxy)-2-[3-(diethylcarbamoyl)-2-(3,4-dihydro-2H-1-benzopyran-6-yl)phenyl]acetate (31d)

To a solution of 3-[1-(tert-butoxy)-2-methoxy-2-oxoethyl]-2-(3,4-dihydro-2H-1-benzopyran-6-yl)benzoic acid (31c) (34 mg, 0.09 mmol) and diethylamine (17 µL, 0.13 mmol) in anhydrous N,N-dimethylformamide (1 mL) under nitrogen atmosphere were added triethylamine (24 µL, 0.17 mmol) and O-(7-azabenzotriazol-1-yl)-N,N,N',N'-tetramethyluronium hexafluoro phosphate (36 mg, 0.09 mmol). The mixture was stirred at room temperature for 2.5 hours and poured in water (5 mL). The aqueous layer was extracted with ethyl acetate (2×5 mL). The organic layer was washed with a saturated solution of sodium bicarbonate (5 mL), dried over sodium sulfate and concentrated in vacuo. The residue was purified by preparative TLC (cyclohexane/ethyl acetate 50/50) to provide methyl 2-(tert-butoxy)-2-[3-(diethylcarbamoyl)-2-(3,4-dihydro-2H-1-benzopyran-6-yl)phenyl]acetate (31d) (35 mg, 0.077 mmol, 89%) as a yellow oil.

$^1$H NMR (300 MHz, CDCl$_3$) δ 0.61-0.71 (m, 3H), 0.82-0.97 (m, 9H), 1.10-1.12 (m, 3H), 1.94-2.02 (m, 2H), 2.54-2.85 (m, 4H), 2.94-3.19 (m, 1H), 3.52 and 3.54 (s, 3H), 3.71 and 3.72 (s, 2H), 3.72-3.83 (m, 1H), 4.17-4.22 (m, 2H), 4.97-5.05 (m, 1H), 6.71-7.14 (m, 3H), 7.20-7.27 (m, 1H), 7.34-3.39 (m, 1H), 7.64-7.74 (m, 1H).

Step 5: Preparation of 2-(tert-butoxy)-2-[3-(diethylcarbamoyl)-2-(3,4-dihydro-2H-1-benzopyran-6-yl)phenyl]acetic acid A solution of methyl 2-(tert-butoxy)-2-[3-(diethylcarbamoyl)-2-(3,4-dihydro-2H-1-benzopyran-6-yl)phenyl]acetate (31d) (35 mg, 0.08 mmol) and potassium hydroxide (22 mg, 0.31 mmol) in a mixture of ethanol (3 mL) and water (1 mL) was stirred at 90° C. for 90 minutes. Ethanol was evaporated in vacuo. The residue was diluted with water (2 mL) and washed with diethyl ether (5 mL). The aqueous layer was acidified with 1M hydrochloric acid was added until pH 2 and extracted with diethyl ether (2×5 mL). The organic layer was dried over sodium sulfate and concentrated in vacuo. The residue was triturated in pentane and concentrated in vacuo to provide the desired acid (example 31) (15 mg, 0.034 mmol, 44%) as a white solid.

$^1$H NMR (300 MHz, CDCl$_3$) δ 0.64 (t, J=7.1 Hz, 3H), 0.82 (t, J=7.1 Hz, 3H), 0.96 and 0.98 (s, 8H), 1.08 and 1.09 (s, 1H), 1.96-2.05 (m, 2H), 2.50-2.86 (m, 4H), 2.92-3.04 (m, 1H), 3.71-3.88 (m, 1H), 4.13-4.25 (m, 2H), 4.88 and 4.91 and 5.06 and 5.11 (s, 1H), 6.66-6.83 1 (m, 1H), 7.10-7.13 (m, 1H), 7.22-7.50 (m, 4H).

MS m/z ([M+H]$^+$) 440.

MS m/z ([M−H]$^-$) 438.

Example 32: Synthesis of (2-1-benzopyran-6-yl-3,3-dimethyl-cyclohex-1-enyl)-tert-butoxy-acetic acid

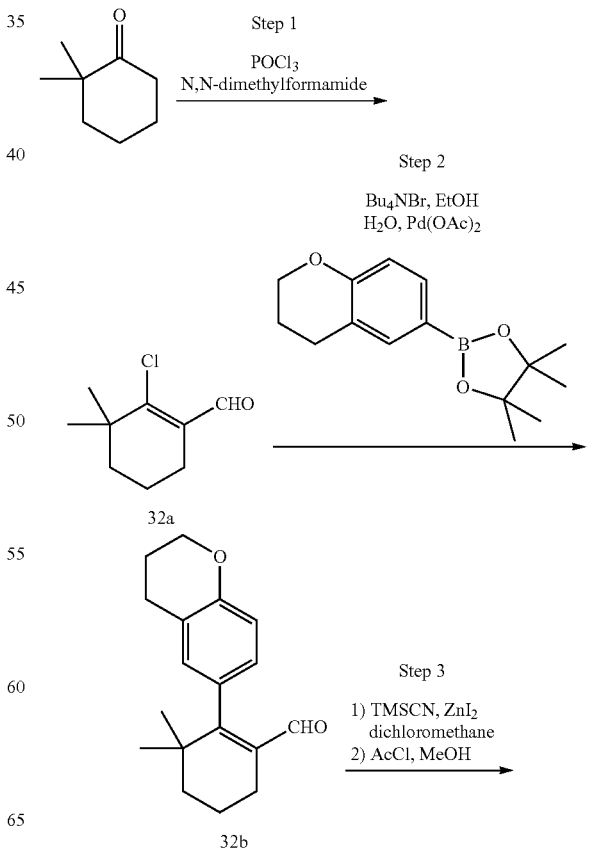

-continued

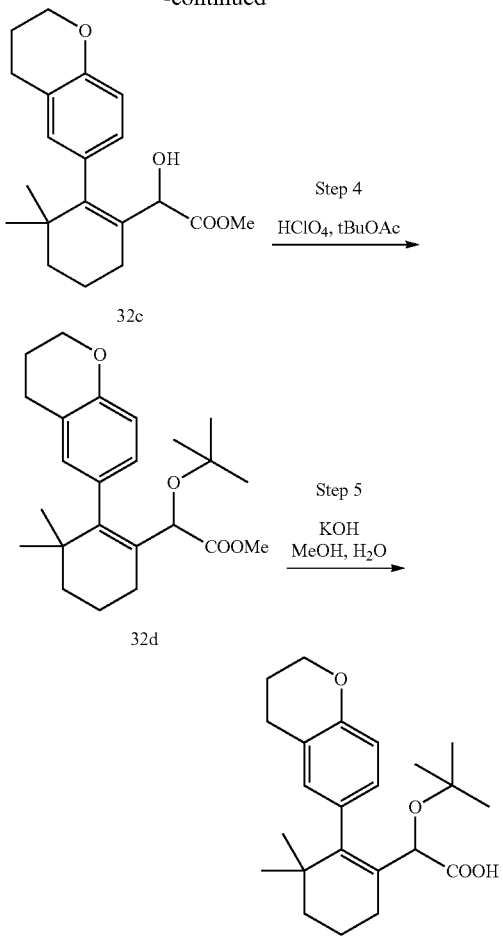

Example 32

Step 1: Preparation of intermediate 2-chloro-3,3-dimethyl-cyclohex-1-enecarbaldehyde (32a)

At 0° C., N,N-dimethylformamide (525 μL, 7.1 mmol) was added to a solution of 2,2-dimethylcyclohexanone (450 mg, 3.55 mmol) in phosphorus oxychloride (1 mL, 10.65 mmol). The mixture was stirred at 110° C. for 3 hours, cooled to room temperature and quenched with a mixture of ice and ethyl acetate. The organic layer was washed with water (30 mL), brine (30 mL), dried over sodium sulfate, filtered and evaporated under reduced pressure to give 2-chloro-3,3-dimethyl-cyclohex-1-enecarbaldehyde (32a) (520 mg, 3.01 mmol, 85%).

$^1$H NMR (400 MHz, CDCl$_3$) δ 1.25 (s, 6H), 1.62-1.71 (m, 4H), 2.27 (t, J=6 Hz, 2H), 10.20 (s, 1H).

Step 2: Preparation of intermediate 2-1-benzopyran-6-yl-3,3-dimethyl-cyclohex-1-ene carbaldehyde (32b)

Under a nitrogen atmosphere, a solution of 2-chloro-3,3-dimethyl-cyclohex-1-enecarbaldehyde (32a) (520 mg, 3.01 mmol), potassium carbonate (416 mg, 3.01 mmol), palladium diacetate (107 mg, 0.51 mmol), 6-(4,4,5,5-tetramethyl-1,3,2-dioxaborolan-2-yl)chroman (781 mg, 3.01 mmol) and tetrabutylammonium bromide (965 mg, 3.01 mmol) in ethanol (7 mL) and water (10 mL) was stirred at 70° C. for 3 hours. The mixture was then cooled at room temperature and diluted with ethyl acetate (30 mL) and water (30 mL). The organic layer was washed with water (30 mL), brine (30 mL), dried over sodium sulfate, filtered, and evaporated under reduced pressure. The residue was purified by flash chromatography on silica gel (dichloromethane) to provide 2-1-benzopyran-6-yl-3,3-dimethyl-cyclohex-1-enecarbaldehyde (32b) (400 mg, 1.48 mmol, 49%).

$^1$H NMR (400 MHz, CDCl$_3$) δ 1.03 (s, 3H), 1.04 (s, 3H), 1.60-1.66 (m, 2H), 1.69-1.77 (m, 2H), 1.98-2.06 (m, 2H), 2.25-2.30 (m, 2H), 2.75-2.79 (m, 2H), 4.18-4.22 (m, 2H), 6.72-6.82 (m, 3H), 9.22 (s, 1H).

MS m/z ([M+H]$^+$) 271.

Step 3: Preparation of intermediate methyl (2-1-Benzopyran-6-yl-3,3-dimethyl-cyclohex-1-enyl)-hydroxy-acetate (32c)

Using the procedure described in example 25, step 5 and step 6, the intermediate 2-1-benzopyran-6-yl-3,3-dimethyl-cyclohex-1-enecarbaldehyde (32b) (400 mg, 1.48 mmol) was converted, after purification by flash chromatography on silica gel (dichloromethane/ethyl acetate 95/5), to methyl (2-1-benzopyran-6-yl-3,3-dimethyl-cyclohex-1-enyl)-hydroxy-acetate (32c) (200 mg, 0.605 mmol, 41%).

$^1$H NMR (400 MHz, CDCl$_3$) δ 0.93-0.97 (4s, 6H), 1.51-1.75 (m, 5H), 1.97-2.03 (m, 2H), 2.24-2.30 (m, 1H), 2.71-2.82 (m, 2H), 3.74 and 3.75 (s, 3H), 4.16-4.19 (m, 2H), 4.43 and 4.44 (s, 1H), 6.69-6.81 (m, 3H).

MS m/z ([M+Na]$^+$) 353.

Step 4: Preparation of intermediate methyl (2-1-Benzopyran-6-yl-3,3-dimethyl-cyclohex-1-enyl)-tert-butoxy-acetate (32d)

Under a nitrogen atmosphere, perchloric acid (70%, 0.25 mL) was added at −10° C. to a solution of methyl (2-1-benzopyran-6-yl-3,3-dimethyl-cyclohex-1-enyl)-hydroxy-acetate (32c) (200 mg, 0.605 mmol) in tert-butyl acetate (6.3 mL). After 1 hour, the reaction was quenched with a saturated solution of sodium bicarbonate and extracted with dichloromethane. The organic layer was washed with brine (20 mL), dried over sodium sulfate, filtered and evaporated under reduced pressure. The residue was purified by preparative TLC (cyclohexane/ethyl acetate 85/15) to afford methyl (2-1-benzopyran-6-yl-3,3-dimethyl-cyclohex-1-enyl)-tert-butoxy-acetate (32d) as a white solid (160 mg, 0.414 mmol, 68%).

$^1$H NMR (400 MHz, CDCl$_3$) s 0.85 and 0.87 (s, 3H), 0.97 and 0.98 (s, 3H), 1.00 and 1.01 (s, 9H), 1.48-1.60 (m, 2H), 1.65-1.71 (m, 2H), 1.87-2.06 (m, 3H), 2.33-2.41 (m, 1H), 2.63-2.82 (m, 2H), 3.65 and 3.66 (s, 3H), 4.18-4.21 (m, 2H), 4.31 and 4.33 (s, 1H), 6.68-6.82 (m, 3H).

MS m/z ([M+Na]$^+$) 409.

Step 5: Preparation of (2-1-benzopyran-6-yl-3,3-dimethyl-cyclohex-1-enyl)-tert-butoxy-acetic acid Using the procedure described in example 25, step 9, the intermediate methyl (2-1-Benzopyran-6-yl-3,3-di methyl-cyclohex-1-enyl)-tert-butoxy-acetate (32d) (160 mg, 0.414 mmol) was converted, after purification by preparative TLC (cyclohexane/ethyl acetate 70/30), to (2-1-benzopyran-6-yl-3,3-dimethyl-cyclohex-1-enyl)-tert-butoxy-acetic acid (example 32) (51 mg, 0.137 mmol, 33%).

¹H NMR (400 MHz, CDCl₃) δ 0.84 (s, 3H), 1.04 and 1.05 (s, 3H), 1.08 and 1.09 (s, 9H), 1.52-1.57 (m, 2H), 1.66-1.85 (m, 3H), 1.97-2.04 (m, 2H), 2.25-2.33 (m, 1H), 2.64-2.83 (m, 2H), 4.16-4.23 (m, 2H), 4.42 and 4.44 (s, 1H), 6.68-6.81 (m, 2H), 7.07-7.11 (m, 1H).

MS m/z ([M–H]⁻) 371.

Example 33: Synthesis of 2-(tert-butoxy)-2-[2-(3,4-dihydro-2H-1-benzopyran-6-yl)-6-(trifluoromethyl)phenyl]acetic acid

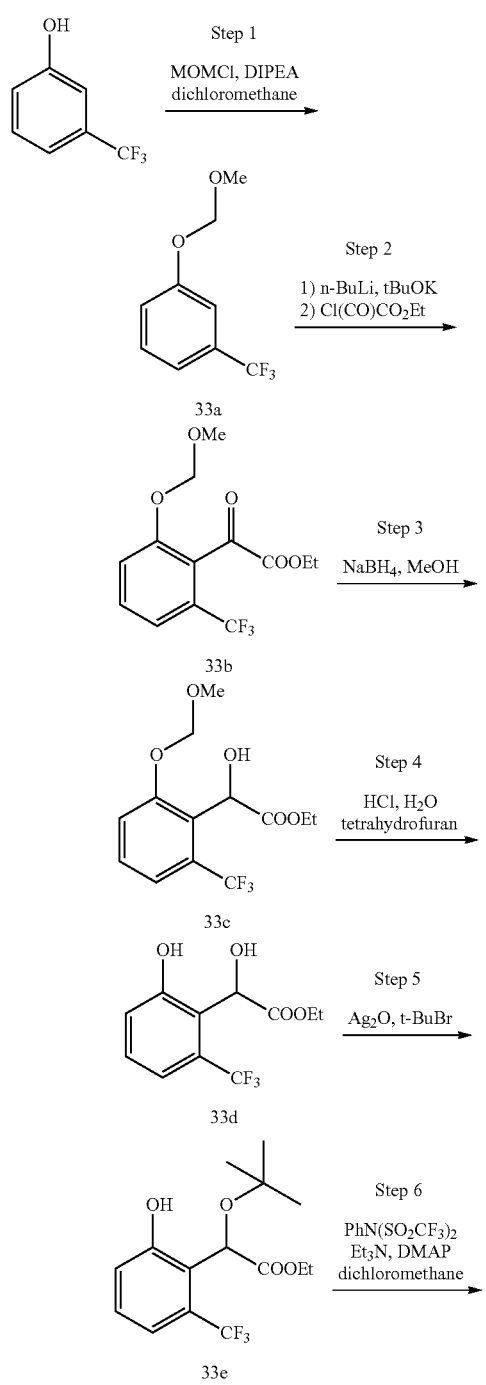

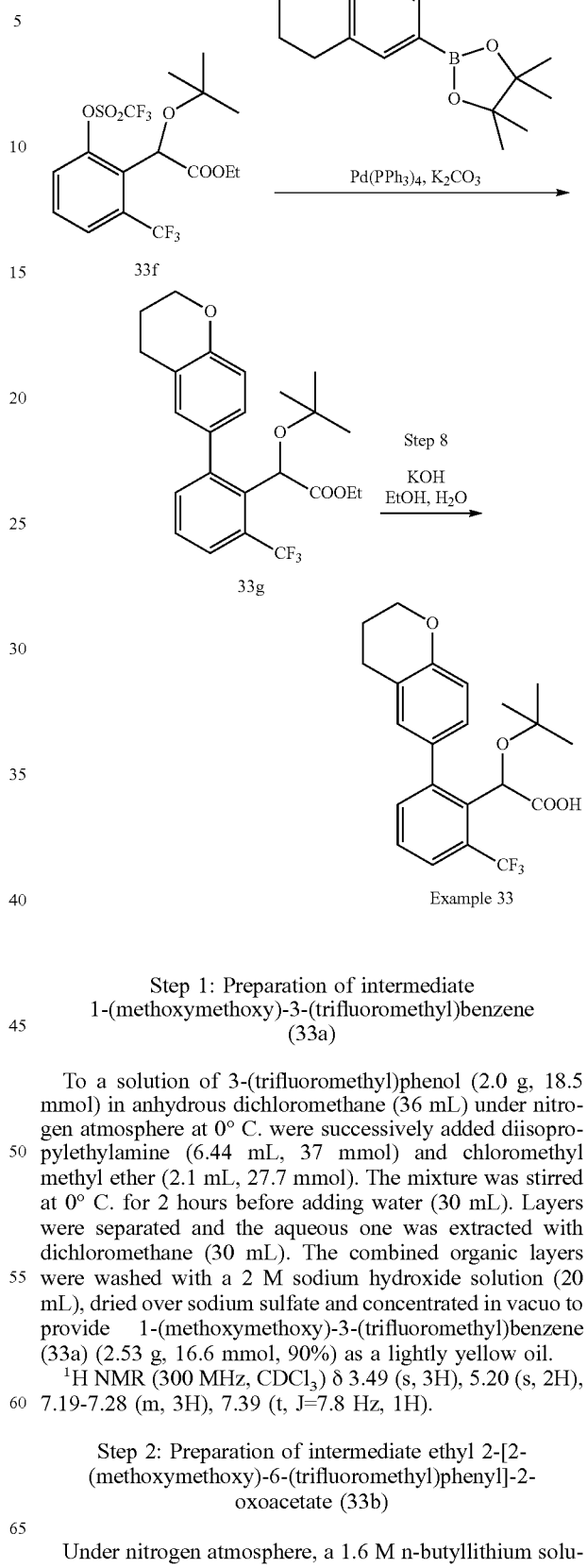

Step 1: Preparation of intermediate 1-(methoxymethoxy)-3-(trifluoromethyl)benzene (33a)

To a solution of 3-(trifluoromethyl)phenol (2.0 g, 18.5 mmol) in anhydrous dichloromethane (36 mL) under nitrogen atmosphere at 0° C. were successively added diisopropylethylamine (6.44 mL, 37 mmol) and chloromethyl methyl ether (2.1 mL, 27.7 mmol). The mixture was stirred at 0° C. for 2 hours before adding water (30 mL). Layers were separated and the aqueous one was extracted with dichloromethane (30 mL). The combined organic layers were washed with a 2 M sodium hydroxide solution (20 mL), dried over sodium sulfate and concentrated in vacuo to provide 1-(methoxymethoxy)-3-(trifluoromethyl)benzene (33a) (2.53 g, 16.6 mmol, 90%) as a lightly yellow oil.

¹H NMR (300 MHz, CDCl₃) δ 3.49 (s, 3H), 5.20 (s, 2H), 7.19-7.28 (m, 3H), 7.39 (t, J=7.8 Hz, 1H).

Step 2: Preparation of intermediate ethyl 2-[2-(methoxymethoxy)-6-(trifluoromethyl)phenyl]-2-oxoacetate (33b)

Under nitrogen atmosphere, a 1.6 M n-butyllithium solution in hexanes (1.9 mL, 3.04 mmol) and a 1M potassium tert-butoxide solution in tetrahydrofuran (3.04 mL, 3.04 mmol) were added to anhydrous tetrahydrofuran (20 mL) at −78° C. The mixture was stirred for 15 minutes before adding dropwise a solution of 1-(methoxymethoxy)-3-(trifluoromethyl)benzene (33a) (500 mg, 2.43 mmol) in tetrahydrofuran (5 mL). The mixture was stirred at −78° C. for 90 minutes and was added via cannulation to a solution of ethyl oxalyl chloride (0.75 mL, 4.85 mmol) in tetrahydrofuran (15 mL) at −78° C. The mixture was stirred at −78° C. for 45 minutes and water (40 mL) was added. Layers were separated and the aqueous layer was extracted with ethyl acetate (2×20 mL). The combined organic layers were washed with a saturated solution of sodium hydrogenocarbonate (20 mL), brine (20 mL), dried over sodium sulfate and concentrated in vacuo. The residue was purified by flash chromatography on silica gel (cyclohexane/ethyl acetate 80/20) to provide ethyl 2-[2-(methoxymethoxy)-6-(trifluoromethyl) phenyl]-2-oxoacetate (33b) (278 mg, 0.90 mmol, 37%) as a yellow oil.

$^1$H NMR (300 MHz, CDCl$_3$) δ 1.36 (t, J=7.2 Hz, 3H), 3.43 (s, 3H), 4.37 (q, J=7.2 Hz, 2H), 5.17 (s, 2H), 7.35-7.40 (m, 2H), 7.53 (t, J=7.8 Hz, 1H).

Step 3: Preparation of intermediate ethyl 2-hydroxy-2-[2-(methoxymethoxy)-6-(trifluoro methyl) phenyl]acetate (33c)

To a solution of ethyl 2-[2-(methoxymethoxy)-6-(trifluoromethyl)phenyl]-2-oxoacetate (33b) (278 mg, 0.91 mmol) in anhydrous methanol (5 mL) under nitrogen atmosphere at 0° C. was added portionwise sodium borohydride (69 mg, 1.82 mmol). The mixture was stirred at 0° C. for 30 minutes. Water (2 mL) was added. Methanol was evaporated in vacuo. The resulting solution was extracted with ethyl acetate (2×10 mL). The organic layer was washed with brine (10 mL), dried over sodium sulfate and concentrated in vacuo to provide ethyl 2-hydroxy-2-[2-(methoxymethoxy)-6-(trifluoromethyl)phenyl]acetate (33c) (267 mg, 0.86 mmol, 95%) as a white solid which was used without further purification.

$^1$H NMR (400 MHz, CDCl$_3$) δ 1.20 (t, J=7.2 Hz, 3H), 3.45 (s, 3H), 3.67 (broad s, 1H), 4.13-4.30 (m, 2H), 5.15-5.19 (m, 2H), 5.40 (s, 1H), 7.33-7.41 (m, 3H).

MS m/z ([M+Na]$^+$) 331.

Step 4: Preparation of intermediate ethyl 2-hydroxy-2-[2-hydroxy-6-(trifluoromethyl)phenyl] acetate (33d)

A mixture of ethyl 2-hydroxy-2-[2-(methoxymethoxy)-6-(trifluoromethyl)phenyl]acetate (33c) (554 mg, 1.80 mmol), 3N hydrochloric acid (2 mL) and tetrahydrofuran (10 mL) was heated at 65° C. for 3 h 30. Tetrahydrofuran was removed in vacuo. Water (10 mL) was added to the residue and this solution was extracted with ethyl acetate (2×10 mL). The organic layer was washed with a saturated solution of sodium hydrogenocarbonate (10 mL), brine (10 mL), dried over sodium sulfate and concentrated in vacuo to provide ethyl 2-hydroxy-2-[2-hydroxy-6-(trifluoromethyl) phenyl]acetate (33d) (387 mg, 1.46 mmol, 81%) as a white solid which was used without further purification.

$^1$H NMR (400 MHz, CDCl$_3$) δ 1.18 (t, J=7.2 Hz, 3H), 3.72 (broad s, 1H), 4.14-4.30 (m, 2H), 5.59 (s, 1H), 7.09 (d, J=8.0 Hz, 1H), 7.28-7.35 (m, 2H), 7.40 (broad s, 1H).

MS m/z ([M−H]$^-$) 263.

Step 5: Preparation of intermediate ethyl 2-(tert-butoxy)-2-[2-hydroxy-6-(trifluoromethyl) phenyl] acetate (33e)

To a solution of ethyl 2-hydroxy-2-[2-hydroxy-6-(trifluoromethyl)phenyl]acetate (33d) (247 mg, 0.93 mmol) in dichloromethane were added silver oxide (867 mg, 3.74 mmol) and tert-butylbromide (0.84 mL, 7.48 mmol). The mixture was stirred at room temperature for 24 hours. Further silver oxide (867 mg, 3.74 mmol) and tert-butylbromide (0.84 mL, 7.48 mmol) were added and the stirring was maintained for 24 supplementary hours. The mixture was filtered and the filtrate was concentrated in vacuo. The residue was purified by flash chromatography on silica gel (cyclohexane/ethyl acetate 90/10) to provide ethyl 2-(tert-butoxy)-2-[2-hydroxy-6-(trifluoromethyl)phenyl]acetate (33e) (223 mg, 0.69 mmol, 74%) as a lightly yellow oil.

$^1$H NMR (300 MHz, CDCl$_3$) δ 1.20 (t, J=7.2 Hz, 3H), 1.29 (s, 9H), 4.10-4.22 (m, 2H), 5.55 (s, 1H), 7.09 (d, J=8.1 Hz, 1H), 7.18 (d, J=6.9 Hz, 1H), 7.26-7.31 (m, 1H), 8.71 (s, 1H).

MS m/z ([M−H]$^-$) 319.

Step 6: Preparation of intermediate ethyl 2-(tert-butoxy)-2-{2-[(trifluoromethane)sulfonyloxy]-6-(trifluoromethyl)phenyl}acetate (33f)

Using the procedure described in example 27, step 2, the intermediate ethyl 2-(tert-butoxy)-2-[2-hydroxy-6-(trifluoromethyl)phenyl]acetate (33e) (222 mg, 0.69 mmol) is converted, after purification by flash chromatography on silica gel (cyclohexane/ethyl acetate 80/20), to ethyl 2-(tert-butoxy)-2-{2-[(trifluoromethane)sulfonyloxy]-6-(trifluoromethyl)phenyl}acetate (33f) (314 mg, 0.69 mmol, 100%) as a yellow oil.

$^1$H NMR (300 MHz, CDCl$_3$) δ 1.19 (t, J=7.2 Hz, 3H), 1.22 (s, 9H), 4.18 (q, J=7.2 Hz, 2H), 5.54 (s, 1H), 7.42-7.52 (m, 2H), 7.72 (dd, J=2.1 Hz, J=6.9 Hz, 1H).

Step 7: Preparation of intermediate ethyl 2-(tert-butoxy)-2-[2-(3,4-dihydro-2H-1-benzopyran-6-yl)-6-(trifluoromethyl)phenyl]acetate (33g)

A degassed solution of ethyl 2-(tert-butoxy)-2-{2-[(trifluoromethane)sulfonyloxy]-6-(trifluoromethyl) phenyl}acetate (33f) (70 mg, 0.15 mmol), potassium carbonate (86 mg, 0.62 mmol), 6-(4,4,5,5-tetramethyl-1,3,2-dioxaborolan-2-yl)chroman (52 mg, 0.20 mmol) and palladium tetrakis(triphenylphosphine) (18 mg, 0.02 mmol) in dioxane (1 mL) and water (0.25 mL) was heated at 85° C. for 16 hours. Water (3 mL) was added and the mixture was extracted with ethyl acetate (2×5 mL). The organic layer was washed with brine (5 mL), dried over sodium sulfate and concentrated in vacuo. The residue was purified twice by preparative TLC (cyclohexane/ethyl acetate 95/5 then 80/20) to provide ethyl 2-(tert-butoxy)-2-[2-(3,4-dihydro-2H-1-benzopyran-6-yl)-6-(trifluoromethyl)phenyl]acetate (33g) (49 mg, 0.11 mmol, 72%) as a colorless oil.

$^1$H NMR (300 MHz, CDCl$_3$) δ 0.93 (s, 9H), 1.25 (t, J=7.2 Hz, 3H), 2.02-2.07 (m, 2H), 2.78 (t, J=6.4 Hz, 2H), 4.17-4.25 (m, 4H), 5.23 (s, 1H), 6.81 (d, J=8.4 Hz, 1H), 7.04-7.09 (m, 2H), 7.36-7.43 (m, 2H), 7.69 (dd, J=2.1 Hz, J=7.3 Hz, 1H).

Step 8: Preparation of 2-(tert-butoxy)-2-[2-(3,4-dihydro-2H-1-benzopyran-6-yl)-6-(trifluoro methyl)phenyl]acetic acid A solution of ethyl 2-(tert-butoxy)-2-[2-(3,4-dihydro-2H-1-benzopyran-6-yl)-6-(trifluoro methyl)phenyl]acetate (33g) (49 mg, 0.11 mmol) and potassium hydroxide (61 mg, 1.08 mmol) in a mixture of ethanol (3 mL) and water (1 mL) was stirred at 90° C. for 24 hours. Further potassium hydroxide (40 mg, 0.71 mmol) was added. The mixture was refluxed for 24 supplementary hours. Ethanol was evaporated in vacuo. The residue was diluted with water (2 mL) and acidified with 1M hydrochloric acid was added until pH 2 and extracted with ethyl acetate (2×5 mL). The organic layer was washed with brine (5 mL), dried over sodium sulfate and concentrated in vacuo. The residue was triturated in pentane and concentrated in vacuo to provide the desired acid (example 33) (30 mg, 0.073 mmol, 68%) as a white solid.

$^1$H NMR (400 MHz, CDCl$_3$) δ 0.95 (s, 9H), 2.02-2.08 (m, 2H), 2.75-2.88 (m, 2H), 4.22-4.25 (m, 2H), 5.40 (s, 1H), 6.85 (d, J=8.4 Hz, 1H), 6.98 (broad s, 1H), 7.42-7.48 (m, 3H), 7.71 (dd, J=2.2 Hz, J=7.2 Hz, 1H).

MS m/z ([M−H]$^−$) 407.

Example 34: Synthesis of 2-(tert-butoxy)-2-[2-(3,4-dihydro-2H-1-benzopyran-6-yl)-3-fluoro-6-(trifluoromethyl)phenyl]acetic acid

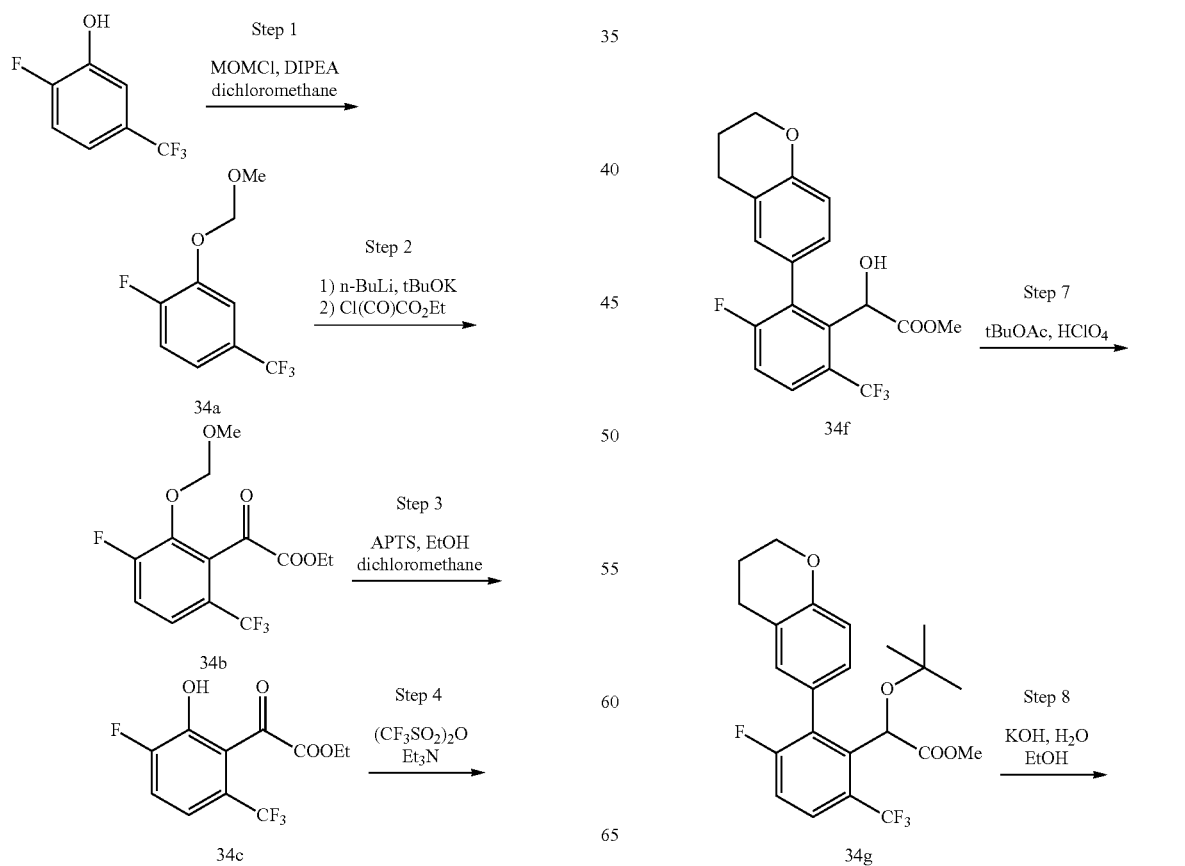

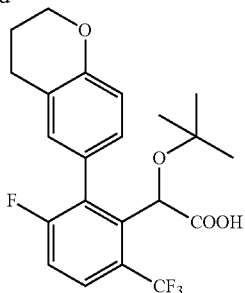

Example 34

Step 1: Preparation of intermediate 1-fluoro-2-(methoxymethoxy)-4-(trifluoromethyl)benzene (34a)

To a solution of 2-fluoro-5-(trifluoromethyl)phenol (2.0 g, 11.1 mmol) in anhydrous dichloromethane (20 mL) under nitrogen atmosphere at 0° C. were successively added diisopropylethylamine (3.87 mL, 22.2 mmol) and chloromethyl methyl ether (1.26 mL, 16.6 mmol). The mixture was stirred at 0° C. for 45 minutes before adding water (20 mL). Layers were separated and the aqueous one was extracted with dichloromethane (30 mL). The combined organic layers were washed with a 2 M sodium hydroxide solution (20 mL), dried over sodium sulfate and concentrated in vacuo to provide 1-fluoro-2-(methoxymethoxy)-4-(trifluoromethyl)benzene (34a) (2.49 g, 11.1 mmol, 100%) as a lightly yellow oil.

$^1$H NMR (400 MHz, CDCl$_3$) δ 3.53 (s, 3H), 5.25 (s, 2H), 7.16-7.20 (m, 1H), 7.24-7.27 (m, 1H), 7.46 (dd, J=1.8 Hz, J=7.4 Hz, 1H).

Step 2: Preparation of intermediate ethyl 2-[3-fluoro-2-(methoxymethoxy)-6-(trifluoromethyl)phenyl]-2-oxoacetate (34b)

Under nitrogen atmosphere, a 1.6 M n-butyllithium solution in hexanes (3.5 mL, 5.6 mmol) and a 1M potassium tert-butoxide solution in tetrahydrofuran (5.6 mL, 5.6 mmol) were added to anhydrous tetrahydrofuran (30 mL) at −78° C. The mixture was stirred for 15 minutes before adding dropwise a solution of 1-fluoro-2-(methoxymethoxy)-4-(trifluoromethyl)benzene (34a) (1.0 g, 4.46 mmol) in tetrahydrofuran (10 mL). The mixture was stirred at −78° C. for 2 hours and was added via cannulation to a solution of ethyl oxalyl chloride (1.4 mL, 9.0 mmol) in tetrahydrofuran (20 mL) at −78° C. The mixture was stirred at −78° C. for 45 minutes and water (50 mL) was added. Layers were separated and the aqueous layer was extracted with ethyl acetate (2×30 mL). The combined organic layers were washed with a saturated solution of sodium hydrogenocarbonate (30 mL), brine (30 mL), dried over sodium sulfate and concentrated in vacuo. The residue was purified by flash chromatography on silica gel (cyclohexane/ethyl acetate 90/10) to provide ethyl 2-[3-fluoro-2-(methoxymethoxy)-6-(trifluoromethyl)phenyl]-2-oxoacetate (34b) (840 mg, 2.59 mmol, 58%) as a yellow oil.

$^1$H NMR (300 MHz, CDCl$_3$) δ 1.36 (t, J=7.2 Hz, 3H), 3.45 (s, 3H), 4.38 (q, J=7.2 Hz, 2H), 5.16 (s, 2H), 7.28-7.34 (m, 1H), 7.43 (dd, J=4.4 Hz, J=8.8 Hz, 1H).

Step 3: Preparation of intermediate ethyl 2-[3-fluoro-2-hydroxy-6-(trifluoromethyl)phenyl]-2-oxoacetate (34c)

To a solution of ethyl 2-[3-fluoro-2-(methoxymethoxy)-6-(trifluoromethyl)phenyl]-2-oxoacetate (34b) (500 mg, 1.54 mmol) and p-toluenesulfonic acid (59 mg, 0.31 mmol) in dichloromethane (7.5 mL) and ethanol (1.5 mL) was heated at 50° C. overnight. The mixture was concentrated in vacuo. The residue was purified by flash chromatography on silica gel (cyclohexane/ethyl acetate 60/40) to provide ethyl 2-[3-fluoro-2-hydroxy-6-(trifluoromethyl) phenyl]-2-oxoacetate (34c) (394 mg, 1.40 mmol, 91%) as a yellow oil.

$^1$H NMR (300 MHz, CDCl$_3$) δ 1.38 (t, J=7.2 Hz, 3H), 4.38 (q, J=7.2 Hz, 2H), 6.91 (d, J=2.7 Hz), 7.26-7.35 (m, 2H).

Step 4: Preparation of intermediate ethyl 2-{3-fluoro-2-[(trifluoromethane)sulfonyloxy]-6-(trifluoromethyl)phenyl}-2-oxoacetate (34d)

To a solution of ethyl 2-[3-fluoro-2-hydroxy-6-(trifluoromethyl)phenyl]-2-oxoacetate (34c) (394 mg, 1.41 mmol) in anhydrous dichloromethane (5 mL) under nitrogen atmosphere at −78° C. were successively added triethylamine (0.24 mL, 1.69 mmol) and triflic anhydride (0.26 mL, 1.55 mmol). The mixture was stirred at −78° C. for 45 minutes before adding water (10 mL). Layers were separated. The aqueous layer was extracted with dichloromethane (10 mL). The combined organic layers were washed with a saturated solution of sodium hydrogenocarbonate (10 mL), dried over sodium sulfate and concentrated in vacuo to ethyl 2-{3-fluoro-2-[(trifluoromethane)sulfonyloxy]-6-(trifluoromethyl)phenyl}-2-oxoacetate (34d) (548 mg, 1.32 mmol, 94%) as a yellow oil which was used without further purification.

$^1$H NMR (300 MHz, CDCl$_3$) δ 1.37 (t, J=7.2 Hz, 3H), 4.42 (q, J=7.2 Hz, 2H), 7.55 (t, J=8.7 Hz), 7.78 (dd, J=4.5 Hz, J=8.7 Hz, 1H).

Step 5: Preparation of intermediate methyl 2-[2-(3,4-dihydro-2H-1-benzopyran-6-yl)-3-fluoro-6-(trifluoromethyl)phenyl]-2-oxoacetate (34e)

A degassed solution of ethyl 2-{3-fluoro-2-[(trifluoromethane)sulfonyloxy]-6-(trifluoromethyl)phenyl}-2-oxoacetate (34d) (478 mg, 1.16 mmol), potassium carbonate (641 mg, 4.64 mmol), 6-(4,4,5,5-tetramethyl-1,3,2-dioxaborolan-2-yl)chroman (392 mg, 1.51 mmol) and palladium tetrakis(triphenylphosphine) (134 mg, 0.12 mmol) in dioxane (10 mL) and water (2 mL) was heated at 85° C. overnight. Water (10 mL) was added and dioxane was evaporated in vacuo. Diethyl ether (10 mL) was added and the layers were separated. The organic layer was washed with a saturated solution of sodium hydrogenocarbonate (10 mL). The combined aqueous layers were acidified with 37% hydrochloric acid until pH 2 then extracted with diethyl ether (2×20 mL). The organic layer was dried over sodium sulfate and concentrated in vacuo. The residue was dissolved in cyclohexane (5 mL) and methanol (2.5 mL) at 0° C. and a 2M solution of trimethylsilyldiazomethane in diethyl ether (4 mL, 8 mmol) was added. The mixture was stirred at room temperature for 15 minutes, cooled at 0° C. and acetic acid was added until the end of bubbling. The mixture was concentrated in vacuo. The residue was dissolved in ethyl acetate (10 mL), washed with a saturated solution of sodium hydrogenocarbonate (10 mL), brine (10 mL), dried over sodium sulfate and concentrated in vacuo to provide methyl 2-[2-(3,4-dihydro-2H-1-benzopyran-6-yl)-3-fluoro-6-(trifluoromethyl) phenyl]-2-oxoacetate (34e) (343 mg, 0.90 mmol, 77%) as a yellow solid which was used without further purification.

¹H NMR (400 MHz, CDCl₃) δ 1.98-2.04 (m, 2H), 2.77 (t, J=6.4 Hz, 2H), 3.57 (s, 3H), 4.19-4.22 (m, 2H), 6.81 (d, J=8.4 Hz, 1H), 6.86 (d, J=1.0 Hz, 1H), 6.95 (dd, J=1.0 Hz, J=8.4 Hz, 1H), 7.35 (t, J=8.6 Hz, 1H), 7.73 (dd, J=4.8 Hz, J=8.6 Hz, 1H).

Step 6: Preparation of intermediate methyl 2-[2-(3,4-dihydro-2H-1-benzopyran-6-yl)-3-fluoro-6-(trifluoromethyl)phenyl]-2-hydroxyacetate (34f)

To a solution of methyl 2-[2-(3,4-dihydro-2H-1-benzopyran-6-yl)-3-fluoro-6-(trifluoromethyl) phenyl]-2-oxoacetate (34e) (100 mg, 0.26 mmol) in anhydrous 1,2-dimethoxyethane (2 mL) at 0° C. was portionwise added sodium borohydride (12 mg, 0.31 mmol). The mixture was stirred at room temperature for 1 hour. Water (5 mL) was added. 1,2-Dimethoxyethane was evaporated in vacuo. The resulting solution was extracted with ethyl acetate (2×5 mL). The organic layer was washed with brine (5 mL) and dried over sodium sulfate to provide methyl 2-[2-(3,4-dihydro-2H-1-benzopyran-6-yl)-3-fluoro-6-(trifluoromethyl)phenyl]-2-hydroxyacetate (34f) (84 mg, 0.22 mmol, 83%) as a white solid.

¹H NMR (300 MHz, CDCl₃) δ 2.00-2.08 (m, 2H), 2.75-2.82 (m, 2H), 3.57 and 3.60 (s, 3H), 4.22-4.25 (m, 2H), 5.40 (s, 1H), 6.80-6.85 (m, 2H), 7.06-7.10 (m, 1H), 7.22 (t, J=8.6 Hz, 1H), 7.73 (dd, J=5.2 Hz, J=8.6 Hz, 1H).

Step 7: Preparation of intermediate methyl 2-(tert-butoxy)-2-[2-(3,4-dihydro-2H-1-benzopyran-6-yl)-3-fluoro-6-(trifluoromethyl)phenyl]acetate (34g)

Using the procedure described in example 28, step 5, the intermediate methyl 2-[2-(3,4-dihydro-2H-1-benzopyran-6-yl)-3-fluoro-6-(trifluoromethyl)phenyl]-2-hydroxyacetate (34f) (84 mg, 0.22 mmol) is converted, after purification by preparative TLC (cyclohexane/ethyl acetate 80/20), to methyl 2-(tert-butoxy)-2-[2-(3,4-dihydro-2H-1-benzopyran-6-yl)-3-fluoro-6-(trifluoro methyl)phenyl]acetate (34g) (28 mg, 0.06 mmol, 29%) as a colorless oil.

¹H NMR (400 MHz, CDCl₃) δ 0.97 and 0.98 (s, 9H), 2.03-2.07 (m, 2H), 2.72-2.89 (m, 2H), 3.70 (s, 3H), 4.22-4.26 (m, 2H), 5.14 (s, 1H), 6.83-6.87 (m, 1H), 6.94-6.98 (m, 1H), 7.04-7.09 (m, 1H), 7.17 (t, J=8.6 Hz, 1H), 7.70 (dd, J=5.6 Hz, J=8.6 Hz, 1H).

Step 8: Preparation of 2-(tert-butoxy)-2-[2-(3,4-dihydro-2H-1-benzopyran-6-yl)-3-fluoro-6-(trifluoromethyl)phenyl]acetic acid A solution of methyl 2-(tert-butoxy)-2-[2-(3,4-dihydro-2H-1-benzopyran-6-yl)-3-fluoro-6-(trifluoromethyl)phenyl]acetate (34g) (28 mg, 0.063 mmol) and potassium hydroxide (36 mg, 0.64 mmol) in a mixture of ethanol (3 mL) and water (1 mL) was stirred at 90° C. for 18 hours. Ethanol was evaporated in vacuo. The residue was diluted with water (2 mL) and acidified with 1M hydrochloric acid was added until pH 2 and extracted with diethyl ether (2×5 mL). The organic layer was dried over sodium sulfate and concentrated in vacuo. The residue was triturated in pentane and concentrated in vacuo to provide the desired acid (example 34) (21 mg, 0.049 mmol, 78%) as a white solid.

¹H NMR (400 MHz, CDCl₃) δ 1.00 (s, 9H), 2.01-2.07 (m, 2H), 2.75-2.85 (m, 2H), 4.23-4.26 (m, 2H), 5.24 and 5.28 (s, 1H), 6.86-6.99 (m, 2H), 7.22 (t, J=8.6 Hz, 1H), 7.35 (broad s, 1H), 7.72 (dd, J=5.6 Hz, J=8.6 Hz, 1H).

MS m/z ([M−H]⁻) 425.

Example 35: Synthesis of 2-[3-(benzyloxy)-2-(3,4-dihydro-2H-1-benzopyran-6-yl)-6-(trifluoromethyl)phenyl]-2-(tert-butoxy)acetic acid

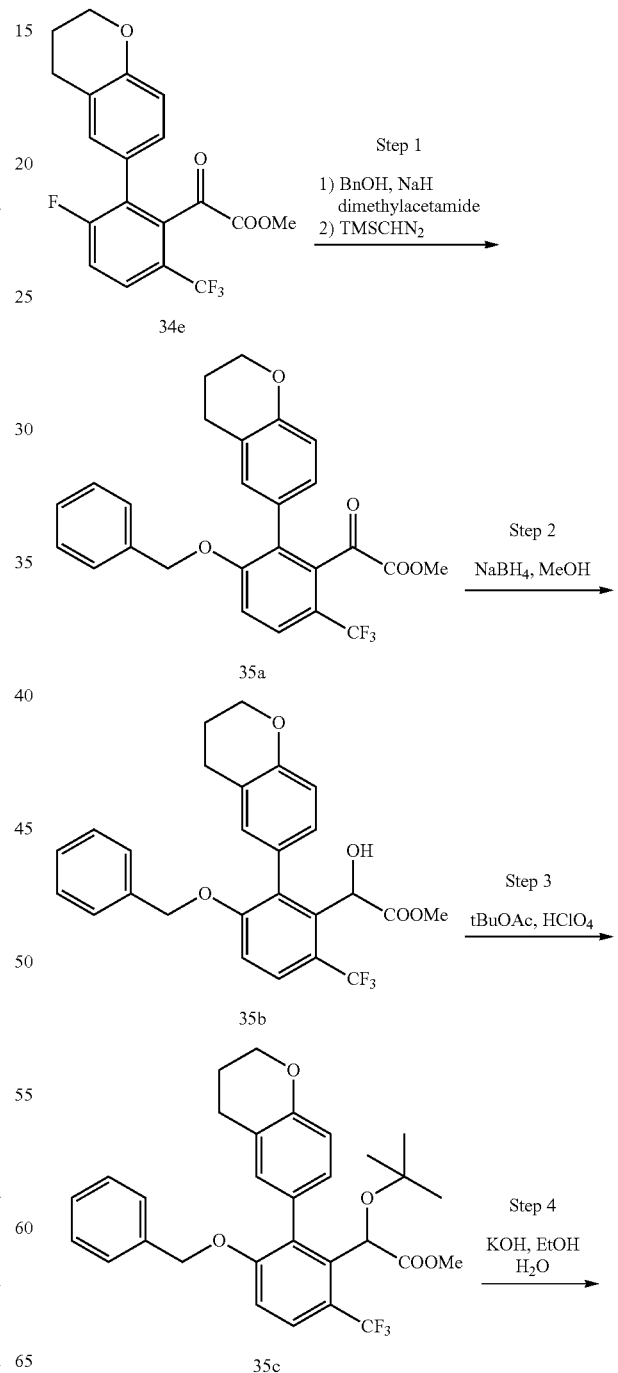

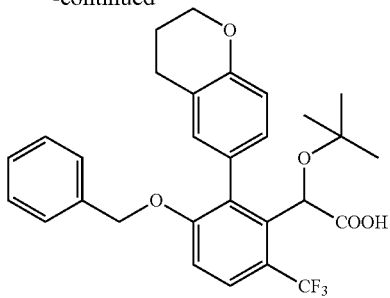

Example 35

Step 1: Preparation of intermediate methyl 2-[3-(benzyloxy)-2-(3,4-dihydro-2H-1-benzopyran-6-yl)-6-(trifluoromethyl)phenyl]-2-oxoacetate (35a)

To a suspension of sodium hydride 60% in oil (21 mg, 0.52 mmol) in anhydrous dimethylacetamide (1 mL) at 0° C. under nitrogen atmosphere, was dropsise added anhydrous benzyl alcohol (54 µL, 0.52 mmol). The mixture was stirred at room temperature for 30 minutes before adding dropwise a solution of methyl 2-[2-(3,4-dihydro-2H-1-benzopyran-6-yl)-3-fluoro-6-(trifluoromethyl)phenyl]-2-oxoacetate (34e) (100 mg, 0.26 mmol) in anhydrous dimethylacetamide (1 mL). The mixture was stirred for 1 hour at room temperature then sodium hydride 60% in oil (10 mg, 0.25 mmol) and benzyl alcohol (25 µL, 0.24 mmol) were added. The stirring was maintained for 3 hours. The mixture was poured in brine (5 mL) and 1M hydrochloric acid was added until pH 2. The mixture was extracted with ethyl acetate (2×10 mL). The organic layer was washed with brine (5 mL), dried over sodium sulfate and concentrated in vacuo. The residue was dissolved in cyclohexane (3 mL) and methanol (1.5 mL) at 0° C. and a 2 M solution of trimethylsilyldiazomethane in diethyl ether (0.3 mL, 0.6 mmol) was added. The mixture was stirred at room temperature for 20 minutes before adding a few drops of acetic acid. The residue was dissolved in ethyl acetate (10 mL), washed with a saturated solution of sodium hydrogenocarbonate (10 mL), brine (10 mL), dried over sodium sulfate and concentrated in vacuo The residue was purified by flash chromatography on silica gel (cyclohexane/ethyl acetate 75/25) to provide methyl 2-[3-(benzyloxy)-2-(3,4-dihydro-2H-1-benzopyran-6-yl)-6-(trifluoromethyl)phenyl]-2-oxoacetate (35a) (76 mg, 0.16 mmol, 62%) as a colorless oil.

$^1$H NMR (300 MHz, CDCl$_3$) δ 1.97-2.05 (m, 2H), 2.75 (t, J=6.4 Hz, 2H), 3.55 (s, 3H), 4.19-4.22 (m, 2H), 5.15 (s, 2H), 6.80 (d, J=8.4 Hz, 1H), 6.85 (d, J=2.1 Hz, 1H), 6.99 (dd, J=2.1 Hz, J=8.4 Hz, 1H), 7.11 (d, J=8.7 Hz, 1H), 7.23-7.36 (m, 5H), 7.65 (d, J=8.7 Hz, 1H).

Step 2: Preparation of intermediate methyl 2-[3-(benzyloxy)-2-(3,4-dihydro-2H-1-benzopyran-6-yl)-6-(trifluoromethyl)phenyl]-2-hydroxyacetate (35b)

To a solution of methyl 2-[3-(benzyloxy)-2-(3,4-dihydro-2H-1-benzopyran-6-yl)-6-(trifluoromethyl)phenyl]-2-oxoacetate (35a) (76 mg, 0.16 mmol) in anhydrous methanol (2 mL) at 0° C. was portionwise added sodium borohydride (12 mg, 0.32 mmol). The mixture was stirred at room temperature for 30 minutes before adding another portion of sodium borohydride (12 mg, 0.32 mmol). After 30 minutes stirring, water (5 mL) was added. Methanol was evaporated in vacuo. The resulting solution was extracted with ethyl acetate (2×5 mL). The organic layer was washed with brine (5 mL) and dried over sodium sulfate to provide methyl 2-[3-(benzyloxy)-2-(3,4-dihydro-2H-1-benzopyran-6-yl)-6-(trifluoromethyl) phenyl]-2-hydroxyacetate (35b) (76 mg, 0.16 mmol, 100%) as a white solid.

$^1$H NMR (300 MHz, CDCl$_3$) δ 2.01-2.09 (m, 2H), 2.75-2.82 (m, 2H), 3.58 and 3.61 (s, 3H), 4.22-4.26 (m, 2H), 5.07 (s, 2H), 5.38 and 5.39 (s, 1H), 6.79-6.85 (m, 2H), 6.97-7.14 (m, 4H), 7.24-7.31 (m, 3H), 7.65 (d, J=9.0 Hz, 1H).

Step 3: Preparation of intermediate methyl 2-[3-(benzyloxy)-2-(3,4-dihydro-2H-1-benzopyran-6-yl)-6-(trifluoromethyl)phenyl]-2-(tert-butoxy)acetate (35c)

To a solution of methyl 2-[3-(benzyloxy)-2-(3,4-dihydro-2H-1-benzopyran-6-yl)-6-(trifluoromethyl)phenyl]-2-hydroxyacetate (35b) (76 mg, 0.12 mmol) in tert-butyl acetate (3 mL) at 0° C. was added perchloric acid (0.4 mL). The mixture was stirred at 0° C. for 30 minutes hours then for 30 minutes at room temperature before being poured into a saturated aqueous solution of sodium hydrogenocarbonate (20 mL). The layers were separated and the aqueous layer was extracted with ethyl acetate (2×10 mL). The organic layers were washed with brine, dried over sodium sulfate and concentrated in vacuo. The residue was purified by preparative TLC (cyclohexane/ethyl acetate 80/20) to provide methyl 2-[3-(benzyloxy)-2-(3,4-dihydro-2H-1-benzopyran-6-yl)-6-(trifluoromethyl)phenyl]-2-(tert-butoxy)acetate (35c) (17 mg, 0.032 mmol, 20%) as a colorless oil.

$^1$H NMR (300 MHz, CDCl$_3$) δ 0.99 and 1.36 and 1.37 (s, 9H), 2.00-2.09 (m, 2H), 2.70-2.85 (m, 2H), 3.59 and 3.61 and 3.69 and 3.70 (s, 3H), 4.22-4.27 (m, 2H), 5.00-5.41 (m, 3H), 6.81-7.32 (m, 9H), 7.63-7.70 (m, 1H).

Step 4: Preparation of 2-[3-(benzyloxy)-2-(3,4-dihydro-2H-1-benzopyran-6-yl)-6-(trifluoro methyl) phenyl]-2-(tert-butoxy)acetic acid Using the procedure described in example 33, step 8, the intermediate methyl 2-[3-(benzyloxy)-2-(3,4-dihydro-2H-1-benzopyran-6-yl)-6-(trifluoromethyl)phenyl]-2-(tert-butoxy)acetate (35c) (17 mg, 0.032 mmol) is converted to 2-[3-(benzyloxy)-2-(3,4-dihydro-2H-1-benzopyran-6-yl)-6-(trifluoromethyl)phenyl]-2-(tert-butoxy)acetic acid (example 35) (12 mg, 0.023 mmol, 70%) as a white solid.

$^1$H NMR (400 MHz, CDCl$_3$) δ 1.01 and 1.33 and 1.35 (s, 9H), 1.96-2.08 (m, 2H), 2.69-2.83 (m, 2H), 4.17-4.25 (m, 2H), 5.00-5.12 (m, 2H), 5.24 and 5.29 and 5.46 and 5.48 (s, 1H), 6.72-7.06 (m, 3H), 7.10-7.16 (m, 2H), 7.23-7.32 (m, 4H), 7.64-7.69 (m, 1H).

MS m/z ([M−H]$^−$) 513.

Example 36: Synthesis of 2-(tert-butoxy)-2-[2-(4,4-dimethylcyclohex-1-en-1-yl)-6-(trifluoromethyl)phenyl]acetic acid

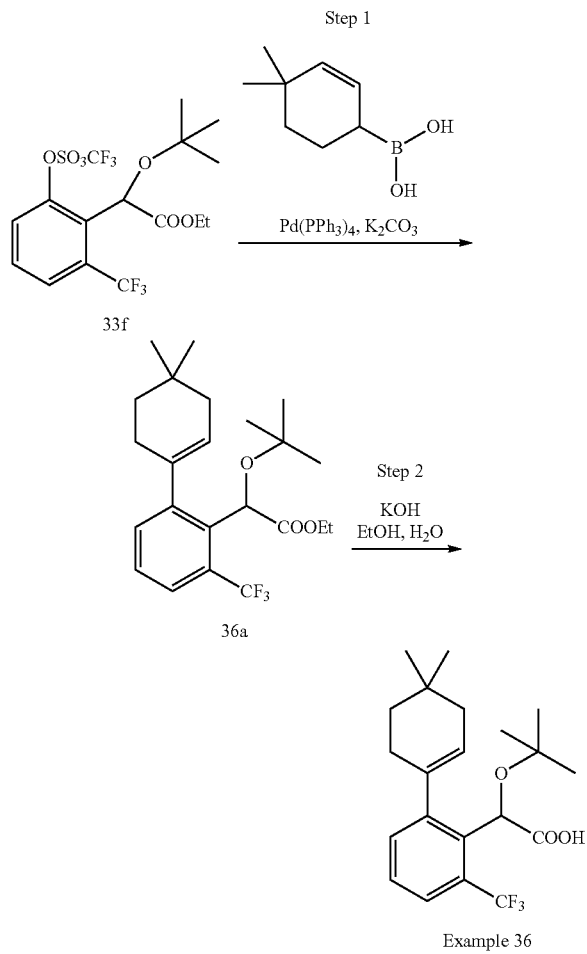

Example 36

Step 1: Preparation of intermediate ethyl 2-(tert-butoxy)-2-[2-(4,4-dimethylcyclohex-1-en-1-yl)-6-(trifluoromethyl)phenyl]acetate (36a)

A degassed solution of ethyl 2-(tert-butoxy)-2-{2-[(trifluoromethane)sulfonyloxy]-6-(trifluoromethyl)phenyl}acetate (33f) (80 mg, 0.18 mmol), potassium carbonate (98 mg, 0.71 mmol), 4,4-dimethylcyclohexen-1-ylboronic acid (41 mg, 0.27 mmol) and palladium tetrakis (triphenylphosphine) (20 mg, 0.02 mmol) in dioxane (1 mL) and water (0.25 mL) was heated at 85° C. for 16 hours. Water (3 mL) was added and the mixture was extracted with ethyl acetate (2×5 mL). The organic layer was washed with a saturated solution of sodium hydrogenocarbonate (5 mL), brine (5 mL), dried over sodium sulfate and concentrated in vacuo. The residue was purified by preparative TLC (cyclohexane/ethyl acetate 95/5) to provide ethyl 2-(tert-butoxy)-2-[2-(4,4-dimethylcyclohex-1-en-1-yl)-6-(trifluoromethyl)phenyl] acetate (36a) (45 mg, 0.11 mmol, 61%) as a colorless oil.

$^1$H NMR (400 MHz, CDCl$_3$) δ 1.00 (s, 3H), 1.02 (s, 3H), 1.14 (s, 9H), 1.19 (t, J=7.1 Hz, 3H), 1.43-1.56 (m, 2H), 1.90-1.92 (m, 2H), 2.12-2.20 (m, 1H), 2.42-2.50 (m, 1H), 4.13 (q, J=7.1 Hz, 2H), 5.45 (broad s, 2H), 7.24-7.27 (m, 1H) 7.33 (t, J=7.8 Hz, 1H), 7.58 (dd, J=1.2, J=7.8 Hz, 1H).

Step 2: Preparation of 2-(tert-butoxy)-2-[2-(4,4-dimethylcyclohex-1-en-1-yl)-6-(trifluoro methyl)phenyl]acetic acid Using the procedure described in example 33, step 8, the intermediate ethyl 2-(tert-butoxy)-2-[2-(4,4-dimethylcyclohex-1-en-1-yl)-6-(trifluoromethyl)phenyl]acetate (36a) (45 mg, 0.11 mmol) is converted, after purification by preparative TLC (cyclohexane/ethyl acetate 70/30), to 2-(tert-butoxy)-2-[2-(4,4-dimethylcyclohex-1-en-1-yl)-6-(trifluoromethyl)phenyl]acetic acid (example 36) (15 mg, 0.039 mmol, 36%) as a colorless oil.

$^1$H NMR (300 MHz, CDCl$_3$) δ 1.00 (s, 3H), 1.01 (s, 3H), 1.18 (s, 9H), 1.48-1.52 (m, 2H), 1.95 (broad s, 2H), 2.16-2.25 (m, 1H), 2.47-2.57 (m, 1H), 5.60 (broad s, 2H), 7.29-7.32 (m, 1H) 7.39 (t, J=7.7 Hz, 1H), 7.58 (dd, J=1.0, J=7.7 Hz, 1H), 9.73 (broad s, 1H).

MS m/z ([M−H]$^−$) 383.

Antiviral Activity

The antiviral activity, particularly against HIV, of compounds according to the invention is evaluated by the protocol described below.

Preparation of Virus stock of the NL4-3 strain of HIV-1 (Adachi et al, J Virol, 1986, 59(2):284-91).

The virus was prepared as described in Lopez et al (Lopez et al, Proc Natl Acad Sci USA., 2006, 103(40):14947-52, by transfecting 2×10$^6$ 293 T cells (CRL-1573, ATCC) with following modifications: 6 μg of NL4-3 proviral DNA molecular clone were mixed with Fugene 6 transfection reagent from Roche, and used according to manufacturer's instructions. Forty eight hours later, transfected cell supernatants were harvested, filtered through 0.45-μm-pore-size filters, quantified for HIV-1 p24 antigen by using a Innotest HIV antigen mAb assay (Ingen) according to manufacturer's instructions, and used in infection experiments.

Preparation of Compounds:

Serial dilutions of compounds to be tested were prepared in complete RPMI medium from 10 mM DMSO stock solutions, and distributed in a volume of 20 μl in 96 well Falcon 353072 Microtest™ tissue culture plate, in order to get 0.5% DMSO final concentration in each well, after the addition of infected cells. Control wells contained also 0.5% DMSO final concentration but no compound.

Infection of Cells:

MT4 cells (from the NIH AIDS Research and Reference Reagent Program) in RPMI complete medium were counted (10×10$^6$ cells per well in Falcon 353047 Multiwell™ 24 well) and infected for 2 hours at 37°, at a multiplicity of infection (moi) of 0.0001-0.00001. Cells were then centrifuged 3 min at 3000 rpm, and washed two times in 1 ml PBS to remove viruses that have not entered in cells. Infected cells were resuspended in complete RPMI at 1.25×10$^6$ cells/ml, and 80 μl of infected cells were distributed in each well containing compounds to be tested or control wells. The plates were then incubated at 37° for 5 days.

Assay used to measure the inhibition of HIV replication by the compounds (according to Gregg S. Jones et al., Antimicrobial Agents and Chemotherapy, 2009, 53 (3): 1194-1203).

After 5 days of incubation, 50 μl of CellTiter-Glo reagent (Promega Biosciences, Inc., Madison Wis., USA) were added to each well. Cell lysis was carried out at room temperature during 10 min, 150 μl of lysates were transferred in Packard Optiplate 96 well, and luminescence was read on a Fluoroskan (Thermo Scientific).

The EC50, or effective concentration 50, is the concentration of compound leading to 50% of cyto-protection in a Cell-Titer-Glo® viability assay based on MT4 cells infected with NL4-3 virus.

| Example number | EC50 (µM) |
|---|---|
| 2 | 2.0 |
| 11 | 48 |
| 15 | 16 |
| 17 | 3.3 |
| 18 | 3.4 |
| 20 | 3.8 |
| 21 | 9.7 |
| 22 | 26 |
| 26 | 0.54 |
| 27 | 1.6 |
| 30 | 4.2 |
| 33 | 25 |
| 34 | 14 |
| 35 | 3.2 |
| 36 | 4.5 |

The results show that the compounds according to the invention can inhibit the HIV replication and thus can be used as anti-HIV compounds.

The invention claimed is:
1. A compound of formula (5A)

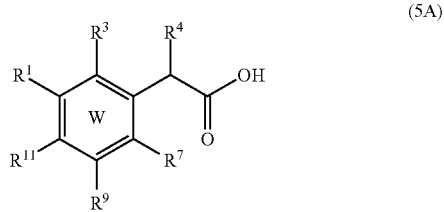

wherein:
(a) W is a substituted aromatic carbocycle;
(b) $R^1$, $R^9$, and $R^{11}$ are each independently hydrogen, —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COOH, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, and are non-substituted or substituted by at least one T$^1$;
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form CO═O, C═S, N═O, N═S, S═O or S(O)$_2$;
wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one carbocycle or heterocycle; and
wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, or heterocyclyl-alkynyl group can include one or more heteroatoms, selected from O, S and N, in the alkyl, alkenyl, or alkynyl moiety;
(c) $R^3$ is C$_4$-C$_{20}$ alkyl, C$_4$-C$_{20}$ alkenyl, C$_4$-C$_{20}$ alkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, and is non-substituted or substituted by at least one T$^1$;
wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form C═O, C═S, N═O, N═S, S═O or S(O)$_2$;
wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be fused with at least one carbocycle or heterocycle; and
wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, or heterocyclyl-alkynyl group can include one or more heteroatoms, selected from O, S and N, in the alkyl, alkenyl, or alkynyl moiety;
(d) $R^4$ is —O-alkyl;
(e) $R^7$ is —CN, —OH, —O-cycloalkyl, —O-cycloalkenyl, —O-cycloalkynyl, —NH$_2$, —NR$^{13}$-cycloalkyl, —NR$^{13}$-cycloalkenyl, —NR$^{13}$-cycloalkynyl, —S-cycloalkyl, —S-cycloalkenyl, —S-cycloalkynyl, —COON, —C(O)NH$_2$, —CF$_3$, —SO$_2$NH$_2$, —NHSO$_2$NH$_2$, —NHC(O)NH$_2$, —OC(O)NH$_2$, halogen, alkyl, alkenyl, alkynyl, heteroalkyl, heteroalkenyl, heteroalkynyl, aryl, —O-aryl, —NR$^{13}$-aryl, —S-aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, —O-heterocycle, —NR$^{13}$-heterocycle, —S-heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl, and is non-substituted or substituted by at least one T$^1$;
wherein a carbon atom or a heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form C=O, C=S, N=O, N=S, S=O or S(O)$_2$;

wherein the aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl group can be fused with at least one carbocycle or heterocycle; and wherein the alkyl, alkenyl, alkynyl, arylalkyl, arylalkenyl, arylalkynyl, cycloalkyl, cycloalkenyl, cycloalkynyl, heterocyclyl-alkyl, heterocyclyl-alkenyl, or heterocyclyl-alkynyl group can include one or more heteroatoms, selected from O, S and N, in the alkyl, alkenyl, or alkynyl moiety;

(f) $R^{13}$ is hydrogen, alkyl, aryl or arylalkyl,
wherein a carbon atom of said alkyl or aryl can be oxidized to form C=O or C=S;

each $T^1$ is independently hydrogen, halogen, —OT$^3$, —OCF$_3$, =O, —ST$^3$, =S, —S(O)T$^4$, —S(O)$_2$T$^4$, —S(O)$_2$NT$^5$T$^6$, —CF$_3$, —NO$_2$, —NT$^5$T$^6$, —NT$^3$S(O)$_2$T$^4$, CN, —NT$^3$C(O)T$^4$, —NT$^3$C(O)NT$^5$T$^6$, —C(O)OT$^3$, —C(O)NT$^5$T$^6$, —C(O)T$^4$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl is non-substituted or substituted with at least one $T^7$;

wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form C=O, C=S, N=O, N=S, S=O or S(O)$_2$;

(g) each $T^2$ is independently hydrogen, halogen, —OT$^8$, —OCF$_3$, =O, —ST$^8$, =S, —S(O)T$^8$, —S(O)$_2$T$^9$, —S(O)$_2$NT$^{10}$T$^{11}$, —CF$_3$, —NO$_2$, —NT$^{10}$T$^{11}$, —NT$^8$S(O)$_2$T$^9$, —CN, —NT$^8$C(O)T$^9$, —NT$^8$C(O)NT$^{10}$T$^{11}$, —C(O)OT$^8$, —C(O)NT$^{10}$T$^{11}$, —C(O)T$^9$, alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl;

wherein said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl is non-substituted or substituted with at least one $T^7$; and wherein a carbon atom or heteroatom of said alkyl, alkenyl, alkynyl, heteroalkyl, heteroalkenyl, heteroalkynyl, aryl, arylalkyl, arylalkenyl, arylalkynyl, arylheteroalkyl, arylheteroalkenyl, arylheteroalkynyl, cycloalkyl, cycloalkenyl, cycloalkynyl, heterocycle, heterocyclyl-alkyl, heterocyclyl-alkenyl, heterocyclyl-alkynyl, heterocyclyl-heteroalkyl, heterocyclyl-heteroalkenyl, or heterocyclyl-heteroalkynyl can be oxidized to form C=O, C=S, N=O, N=S, S=O or S(O)$_2$;

(h) $T^3$ is hydrogen, alkyl, alkenyl, alkynyl, heteroalkyl, heteroalkenyl, heteroalkynyl, aryl, or heterocycle;

wherein said alkyl, alkenyl, alkynyl, heteroalkyl, heteroalkenyl, heteroalkynyl, aryl, or heterocycle is non-substituted or substituted with at least one substituent independently selected from —OH, =O, halogen, —SH, =S, —CF$_3$, —O-alkyl, —OCF$_3$, —CN, —NO$_2$, —C(O)OH, —NH$_2$ and —C(O)NH$_2$; and wherein a carbon atom or heteroatom of said alkyl, alkenyl, alkynyl, heteroalkyl, heteroalkenyl, heteroalkynyl, aryl, or heterocycle can be oxidized to form C=O, C=S, N=O, N=S, S=O or S(O)$_2$;

(i) $T^4$ is —OH, alkyl, alkenyl, alkynyl, heteroalkyl, heteroalkenyl, heteroalkynyl, aryl, or heterocycle;

wherein said alkyl, alkenyl, alkynyl, heteroalkyl, heteroalkenyl, heteroalkynyl, aryl, or heterocycle is non-substituted or substituted with at least one substituent independently selected from —OH, =O, halogen, —SH, =S, —CF$_3$, —O-alkyl, —OCF$_3$, —CN, —NO$_2$, —C(O)OH, —NH$_2$ and —C(O)NH$_2$; and wherein a carbon atom or heteroatom of said alkyl, alkenyl, alkynyl, heteroalkyl, heteroalkenyl, heteroalkynyl aryl, or heterocycle can be oxidized to form CO=O, C=S, N=O, N=S, S=O or S(O)$_2$;

(j) $T^5$ and $T^6$:
are each independently hydrogen, alkyl, alkenyl, alkynyl, heteroalkyl, heteroalkenyl, heteroalkynyl, aryl, or heterocycle;

wherein said alkyl, alkenyl, alkynyl, heteroalkyl, heteroalkenyl, heteroalkynyl, aryl, or heterocycle is non-substituted or substituted with at least one substituent independently selected from —OH, =O, halogen, —SH, =S, —CF$_3$, —O-alkyl, —OCF$_3$, —CN, —NO$_2$, —C(O)OH, —NH$_2$ and —C(O)NH$_2$; and wherein a carbon atom or heteroatom of said alkyl, alkenyl, alkynyl, heteroalkyl, heteroalkenyl, heteroalkynyl aryl, or heterocycle can be oxidized to form C=O, C=S, N=O, N=S, S=O or S(O)$_2$; or together form a 4, 5, 6 or 7 membered heterocycle that is non-substituted or substituted with an alkyl, alkenyl, alkynyl, heteroalkyl, heteroalkenyl, heteroalkynyl, —OH, halogen, —SH, —CF$_3$, —O-alkyl, —OCF$_3$, —CN, —NO$_2$, —C(O)OH, —NH$_2$ or —C(O)NH$_2$;

(k) each $T^7$ is independently an alkyl, alkenyl, alkynyl, heteroalkyl, heteroalkenyl, heteroalkynyl, —OH, =O, halogen, —SH, =S, —CF$_3$, —CN, —NO$_2$, —COOH, —NH$_2$, or —C(O)NH$_2$;

(l) $T^8$ is hydrogen, alkyl, alkenyl, alkynyl, heteroalkyl, heteroalkenyl, or heteroalkynyl;

wherein said alkyl, alkenyl, alkynyl, heteroalkyl, heteroalkenyl, or heteroalkynyl is non-substituted or substituted with at least one substitutent independently selected from —OH, =O, halogen, —SH, =S, —CF$_3$, —O-alkyl, —OCF$_3$, —CN, —NO$_2$, —C(O)OH, —NH$_2$ and —C(O)NH$_2$; and wherein a carbon atom or heteroatom of said alkyl, alkenyl, alkynyl, heteroalkyl, heteroalkenyl, or heteroalkynyl can be oxidized to form C=O, C=S, N=O, N=S, S=O or S(O)$_2$;

(m) $T^9$ is —OH, alkyl, alkenyl, alkynyl, heteroalkyl, heteroalkenyl, or heteroalkynyl, wherein said alkyl, alkenyl, alkynyl, heteroalkyl, heteroalkenyl, or heteroalkynyl can be substituted or non substituted with one or more —OH, =O, halogen, —SH, =S, —CF$_3$, —O-alkyl, —OCF$_3$, —CN, —NO$_2$, —C(O)OH, —NH$_2$ or —C(O)NH$_2$, wherein a carbon atom or heteroatom of said alkyl, alkenyl, alkynyl, heteroalkyl, heteroalkenyl, or heteroalkynyl can be oxidized to form C=O, C=S, N=O, N=S, S=O or S(O)$_2$; and (n) $T^{10}$ and $T^{11}$:

are each independently hydrogen, alkyl, alkenyl, alkynyl, heteroalkyl, heteroalkenyl, or heteroalkynyl;

wherein said alkyl, alkenyl, alkynyl, heteroalkyl, heteroalkenyl, or heteroalkynyl is non-substituted or substituted with at least one substitutent independently selected from —OH, =O, halogen, —SH, =S, —CF$_3$, —O-alkyl, —OCF$_3$, —CN, —NO$_2$, —C(O)OH, —NH$_2$ and —C(O)NH$_2$; and wherein a carbon atom or heteroatom of said alkyl, alkenyl, alkynyl, heteroalkyl, heteroalkenyl, or heteroalkynyl can be oxidized to form C=O, C=S, N=O, N=S, S=O or S(O)$_2$; or together form a 4, 5, 6 or 7 membered heterocycle that is non-substituted or substituted with an alkyl, alkenyl, alkynyl, heteroalkyl, heteroalkenyl, heteroalkynyl, —OH, halogen, —SH, —CF$_3$, O-alkyl, —OCF$_3$, —CN, —NO$_2$, —C(O)OH, —NH$_2$ or —C(O)NH$_2$.

2. A compound of claim 1, wherein: $R^1$ is hydrogen, halogen, —O-aryl, or alkyl; $R^3$ is 3,4-hydro-2H-1-benopyran, aryl, or cycloalkenyl, non-substituted or substituted by at least one $T^1$; and $R^{11}$ is hydrogen or non-substituted or substituted by at least one $T^1$.

3. A compound of claim 1, wherein: $R^1$ is hydrogen; $R^3$ is 3,4-hydro-2H-1-benopyran; and $R^{11}$ is hydrogen.

4. A pharmaceutical composition comprising a compound according to claim 1 as an active ingredient and at least a pharmaceutically acceptable carrier.

5. A pharmaceutical composition according to claim 4 further comprising a further antiviral agent.

6. A method of treatment of a viral infection comprising administering a compound according to claim 1 to a patient in need thereof.

7. The method according to claim 6 wherein said viral infection is a retroviral infection.

8. The method according to claim 7 wherein said retroviral infection is HIV.

9. A method for the treatment of an HIV infection in a mammal being infected or having a risk to be infected by the HIV comprising administering the pharmaceutical composition according to claim 4.

10. A method of inhibiting the replication of HIV comprising exposing said HIV to an effective amount of a compound according to claim 1 under conditions where replication of HIV is inhibited.

* * * * *